US012529087B2

(12) United States Patent
Wichmann et al.

(10) Patent No.: US 12,529,087 B2

(45) Date of Patent: Jan. 20, 2026

(54) ABC TRANSPORTERS FOR THE HIGH EFFICIENCY PRODUCTION OF REBAUDIOSIDES

(71) Applicant: AMYRIS, INC., Emeryville, CA (US)

(72) Inventors: Gale A. Wichmann, Emeryville, CA (US); Sean Lund, Emeryville, CA (US); Joshua Lerman, Emeryville, CA (US); Hanxiao Jiang, Emeryville, CA (US); Yi Xiong, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 1070 days.

(21) Appl. No.: 17/425,634

(22) PCT Filed: Jan. 23, 2020

(86) PCT No.: PCT/US2020/014859

§ 371 (c)(1),
(2) Date: Jul. 23, 2021

(87) PCT Pub. No.: WO2020/154549

PCT Pub. Date: Jul. 30, 2020

(65) Prior Publication Data

US 2022/0106619 A1 Apr. 7, 2022

Related U.S. Application Data

(60) Provisional application No. 62/796,228, filed on Jan. 24, 2019.

(51) Int. Cl.
*C12P 19/56* (2006.01)
*C12N 9/02* (2006.01)
(Continued)

(52) U.S. Cl.
CPC ............ *C12P 19/56* (2013.01); *C12N 9/0042* (2013.01); *C12N 9/0071* (2013.01);
(Continued)

(58) Field of Classification Search
CPC .......... C12P 19/56; C12P 7/40; C12N 9/0042; C12N 9/0071; C12N 9/0073;
(Continued)

(56) References Cited

U.S. PATENT DOCUMENTS

2020/0347425 A1 * 11/2020 Philippe .................... A23L 2/60

FOREIGN PATENT DOCUMENTS

WO WO 2008/034648 A1 3/2008
WO WO 2014/122328 A1 8/2014
(Continued)

OTHER PUBLICATIONS

Christian M. Paumi, Matthew Chuk, Jamie Snider, Igor Stagljar and Susan Michaelis, ABC Transporters in *Saccharomyces cerevisiae* and Their Interactors: New Technology Advances the Biology of the ABCC (MRP) Subfamily, 2009, Microbiology and Molecular Biology Reviews, vol. 73, No. 4, p. 577-593 (Year: 2009).*
(Continued)

*Primary Examiner* — David W Berke-Schlessel
*Assistant Examiner* — Trent R Clarke
(74) *Attorney, Agent, or Firm* — Squire Patton Boggs (US) LLP

(57) ABSTRACT

Provided herein are genetically modified host cells, compositions, and methods for improved production of steviol glycosides. In some embodiments, the host cell is genetically modified to comprise a heterologous nucleic acid expression cassette that expresses an ABC-transporter capable of transporting steviol glycosides to the extracellular space or to the luminal space of an intracellular organelle. In some embodiments, the host cell further comprises one or more heterologous nucleotide sequence encoding further enzymes of a pathway capable of producing one or more steviol glycosides in the host cell. The host cells, compositions, and methods described herein provide an efficient
(Continued)

| Parent Strain | Standard Well | | | | | | | |
|---|---|---|---|---|---|---|---|---|
| None | CEN.PK BPT1 | T4_Fungal_1 | T4_Fungal_10 | T4_Fungal_2 | T4_Fungal_3 | T4_Fungal_4 | T4_Fungal_5 | T4_Fungal_8 |
| 39.3 | 29.1 | 32.3 | 32.1 | 31.8 | 34.2 | 35.7 | 99.0 | 47.4 |

route for the heterologous production of steviol glycosides, including but not limited to, rebaudioside D and rebaudioside M.

20 Claims, 11 Drawing Sheets

Specification includes a Sequence Listing.

(51) Int. Cl.

| | |
|---|---|
| ***C12N 9/10*** | (2006.01) |
| ***C12N 9/88*** | (2006.01) |
| ***C12N 9/90*** | (2006.01) |
| ***C12P 5/00*** | (2006.01) |
| ***C12P 7/40*** | (2006.01) |

(52) U.S. Cl.
CPC ......... *C12N 9/0073* (2013.01); *C12N 9/1051* (2013.01); *C12N 9/1085* (2013.01); *C12N 9/88* (2013.01); *C12N 9/90* (2013.01); *C12P 5/007* (2013.01); *C12P 7/40* (2013.01); *C12Y 106/02004* (2013.01); *C12Y 114/13079* (2013.01); *C12Y 204/01017* (2013.01); *C12Y 205/01001* (2013.01); *C12Y 402/03019* (2013.01); *C12Y 505/01013* (2013.01)

(58) Field of Classification Search
CPC ...... C12N 9/1051; C12N 9/1085; C12N 9/88; C12N 9/90; C12Y 106/02004; C12Y 114/13079; C12Y 204/01017; C12Y 205/01001; C12Y 402/03019; C12Y 505/01013
See application file for complete search history.

(56) References Cited

FOREIGN PATENT DOCUMENTS

| | | | |
|---|---|---|---|
| WO | WO 2016/023844 | A1 | 2/2016 |
| WO | WO 2017/025362 | A1 | 2/2017 |
| WO | WO 2017/025648 | A1 | 2/2017 |
| WO | WO 2017/025649 | A1 | 2/2017 |
| WO | WO 2018/211032 | A1 | 11/2018 |

OTHER PUBLICATIONS

Sinisa Petrovic et al., The products of YCF1 and YLL015w (BPT1) cooperate for the ATP-dependent vacuolar transport of unconjugated bilirubin in *Saccharomyces cerevisiae*, 2000, Yeast , vol. 16, pp. 561-571 (Year: 2000).*

International Search Report and Written Opinion of PCT/US2020/014859 dated Aug. 27, 2020; 21 pages.

Office Action of Japanese Patent Application No. 2021-542445 dated Nov. 15, 2023, and its English translation; 9 pages.

* cited by examiner farnesyl pyrophosphate (FPP)

geranylgeranyl pyrophosphate synthase (GGPPS)

geranylgeranyl pyrophosphate (GGPP)

ent-copalyl pyrophosphate synthase (CPS)

ent-copalyl pyrophosphate (CPP)

ent-kaurene synthase (KS)

ent-kaurene ent-kaurene 19-oxidase (KO)

ent-kaurenoic acid ent-kaurenoic acid 13-hydroxylase (KAH)

steviol steviol 19-glycoside rubusoside steviolmonoside steviolbioside

| Parent Strain | Standard Well | | | | | | | |
|---|---|---|---|---|---|---|---|---|
| None | CEN.PK BPT1 | T4_Fungal_1 | T4_Fungal_10 | T4_Fungal_2 | T4_Fungal_3 | T4_Fungal_4 | T4_Fungal_5 | T4_Fungal_8 |
| 20.4 | 13.7 | 16.4 | 18.1 | 15.2 | 16.9 | 17.8 | 97.7 | 20.1 |

| Parent Strain | Standard Well | | | | | | | |
|---|---|---|---|---|---|---|---|---|
| None | CEN.PK BPT1 | T4_Fungal_1 | T4_Fungal_10 | T4_Fungal_2 | T4_Fungal_3 | T4_Fungal_4 | T4_Fungal_5 | T4_Fungal_8 |
| 1.00 | 1.86 | 1.62 | 1.26 | 1.89 | 1.64 | 1.81 | 2.05 | 1.20 |

| Parent Strain | Standard Well | | | | | | | |
|---|---|---|---|---|---|---|---|---|
| None | CEN.PK BPT1 | T4_Fungal_1 | T4_Fungal_10 | T4_Fungal_2 | T4_Fungal_3 | T4_Fungal_4 | T4_Fungal_5 | T4_Fungal_8 |
| 1.00 | 2.01 | 1.57 | 1.36 | 2.02 | 1.57 | 1.87 | 1.64 | 0.89 |

| Parent Strain | Standard Well | | | | | | | |
|---|---|---|---|---|---|---|---|---|
| None | CEN.PK BPT1 | T4_Fungal_1 | T4_Fungal_10 | T4_Fungal_2 | T4_Fungal_3 | T4_Fungal_4 | T4_Fungal_5 | T4_Fungal_8 |
| 1.00 | 1.37 | 1.36 | 1.03 | 1.55 | 1.42 | 1.67 | 5.14 | 1.43 |

ABC TRANSPORTERS FOR THE HIGH EFFICIENCY PRODUCTION OF REBAUDIOSIDES

1. CROSS-REFERENCE TO RELATED APPLICATION

The present application is 35 U.S.C. 371 national phase filing of PCT/US2020/014859, filed on Jan. 23, 2020, which claims the benefit of provisional U.S. Patent Application Ser. No. 62/796,228 filed Jan. 24, 2019, entitled "ABC TRANSPORTERS FOR THE HIGH EFFICIENCY PRODUCTION OF REBAUDIOSIDES," the disclosures of both of which are hereby incorporated fully by reference into the present application.

INCORPORATION-BY-REFERENCE

The present application contains a Sequence Listing which has been submitted in ASCII format via EFS-Web and is hereby incorporated by reference in its entirety. Said ASCII copy having been modified on Jul. 22, 2021, is named "107345_00779_ST25.txt," and is 246,580 bytes in size.

2. FIELD OF THE INVENTION

The present disclosure relates to particular ABC-transporters, host cells comprising the same, and methods of their use for the production of steviol and/or rebaudiosides including rebaudioside D and rebaudioside M.

3. BACKGROUND

Reduced-calorie sweeteners derived from natural sources are desired to limit the health effects of high-sugar consumption. The *stevia* plant (*Stevia rebaudiana* Bertoni) produces a variety of sweet-tasting glycosylated diterpenes termed steviol glycosides. Of all the known steviol glycosides, Reb M has the highest potency (~200-300× sweeter than sucrose) and has the most appealing flavor profile. However, Reb M is only produced in minute quantities by the *stevia* plant and is a small fraction of the total steviol glycoside content (<1.0%), making the isolation of Reb M from *stevia* leaves impractical. Alternative methods of obtaining Reb M are needed. One such approach is the application of synthetic biology to design microorganisms (e.g. yeast) that produce large quantities of Reb M from sustainable feedstock sources.

To economically produce a product using synthetic biology, each step in the bioconversion from feedstock to product needs to have a high conversion efficiency (ideally >90%). In our engineering of yeast to produce Reb M, we noted that cytosolic accumulation of Reb M repressed the steviol glycoside metabolic pathway engineered into the yeast, thereby limiting the total yield of a fermentation run. This repression is likely due to product inhibition or end-product inhibition of one or more enzymes involved in steviol glycoside biosynthesis. Accordingly, novel mechanisms of relieving the product inhibition are needed to increase the conversion efficiency of biosynthetic Reb M production.

4. SUMMARY OF THE INVENTION

Provided herein are genetically modified host cells, compositions, and methods for the improved production of Reb M. These compositions and methods are based in part on the expression of certain heterologous ABC-transporters in host cells that have been genetically modified to produce steviol glycosides such as Reb M. These ABC-transporters are capable of transporting certain steviol glycosides, preferably Reb M and/or the related high molecular weight steviol glycoside rebaudioside D (Reb D), out of the cytosol either into the extracellular space or into the lumen of subcellular organelles, for example the yeast vacuole. The sequestration of certain steviol glycosides like Reb D and Reb M increases the efficiency of the steviol glycoside metabolic pathway by relieving the product inhibition caused by the accumulation of steviol glycosides.

In one aspect of the invention, provided herein are genetically modified host cells and methods of their use for the production of industrially useful compounds. In one aspect, provided herein is a genetically modified host cell capable of producing one or more steviol glycosides where the host cell contains a heterologous nucleic acid encoding an ABC-transporter having an amino acid sequence having at least 80% sequence identity to an amino acid sequence selected from the sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID: 28, SEQ ID NO: 29, and SEQ ID NO: 30.

In one embodiment of the invention the ABC-transporter has an amino acid sequence having a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 28, SEQ ID NO: 29, and SEQ ID NO: 30. In another embodiment the genetically modified host cells of the invention contain nucleic acids encoding geranylgeranyl pyrophosphate synthase (GGPPS), ent-copalyl pyrophosphate synthase (CPS), ent-kaurene synthase (KS), ent-kaurene 19-oxidase (KO), ent-kaurenoic acid 13-hydroxylase (KAH), cytochrome p450 reductase (CPR), and one or more UDP-glucosyltransferases (UGT). In a further embodiment the one or more UDP-glucosyltransferases (UGT) are selected from EUGT11, UGT85C2, UGT74G1, UGT91D like3, UGT76G1, and UGT40087. In a further embodiment of the invention the geranylgeranyl pyrophosphate synthase (GGPPS) has an amino acid sequence having at least 80% sequence identity to SEQ ID NO: 9, the ent-copalyl pyrophosphate synthase (CPS) has an amino acid sequence having at least 80% sequence identity to SEQ ID NO: 10, the ent-kaurene synthase (KS) has an amino acid sequence having at least 80% sequence identity to SEQ ID NO: 11, the ent-kaurene 19-oxidase (KO) has an amino acid sequence having at least 80% sequence identity to SEQ ID NO: 12, the ent-kaurenoic acid 13-hydroxylase (KAH) has an amino acid sequence having at least 80% sequence identity to SEQ ID NO: 13, the cytochrome p450 reductase (CPR) has an amino acid sequence having at least 80% sequence identity to SEQ ID NO: 14, and the one or more UDP-glucosyltransferases (UGT) has an amino acid sequence having at least 80% sequence identity to an amino acid sequence selected from the group consisting of SEQ ID NO: 15, SEQ ID NO: 16, SEQ ID NO: 17, SEQ ID NO:18, SEQ ID NO: 19, SEQ ID NO: 27.

In a particular embodiment of the invention the geranylgeranyl pyrophosphate synthase (GGPPS) has an amino acid sequence of SEQ ID NO: 9, the ent-copalyl pyrophosphate synthase (CPS) has an amino acid sequence of SEQ ID NO: 10, the ent-kaurene synthase (KS) has an amino acid sequence of SEQ ID NO: 11, the ent-kaurene 19-oxidase (KO) comprises an amino acid sequence of SEQ ID NO: 12, the ent-kaurenoic acid 13-hydroxylase (KAH) comprises an amino acid sequence of SEQ ID NO: 13, the cytochrome p450 reductase (CPR) comprises an amino acid sequence of SEQ ID NO: 14, and the one or more UDP-glucosyltransferases (UGT) comprise an amino acid sequence selected from the group consisting of SEQ ID NO: 15, SEQ ID NO: 16, SEQ ID NO: 17, SEQ ID NO:18, SEQ ID NO: 19, and SEQ ID NO: 27.

In an embodiment the host cell is selected from a bacterial cell, a fungal cell, an algal cell, an insect cell, and a plant cell. In another embodiment the host cell is a *Saccharomyces cerevisiae* cell.

In an embodiment of the invention the ABC-transporter has an amino acid sequence having the sequence of SEQ ID NO: 1.

In another embodiment the ABC-transporter has an amino acid sequence having the sequence of SEQ ID NO: 2.

In a further embodiment the ABC-transporter has an amino acid sequence having the sequence of SEQ ID NO: 3.

In yet another embodiment the ABC-transporter has an amino acid sequence having the sequence of SEQ ID NO: 4.

In additional embodiment the ABC-transporter has an amino acid sequence having the sequence of SEQ ID NO: 5.

In an embodiment the ABC-transporter has an amino acid sequence having the sequence of SEQ ID NO: 6.

In another embodiment the ABC-transporter has an amino acid sequence having the sequence of SEQ ID NO: 7.

In yet another embodiment the ABC-transporter has an amino acid sequence having the sequence of SEQ ID NO: 8

In yet another embodiment the ABC-transporter has an amino acid sequence having the sequence of SEQ ID NO: 28.

In yet another embodiment the ABC-transporter has an amino acid sequence having the sequence of SEQ ID NO: 29.

In yet another embodiment the ABC-transporter has an amino acid sequence having the sequence of SEQ ID NO: 30.

In an embodiment of the invention the one or more steviol glycosides is selected from rebaudioside A (Reb A), rebaudioside B (Reb B), Reb D, rebaudioside E (Reb E), or Reb M. In another embodiment the one or more steviol glycosides comprises Reb M.

In one embodiment a majority of the one or more steviol glycosides accumulate within a lumen of an organelle. In another embodiment a majority of the one or more steviol glycosides accumulate extracellularly.

In another aspect the invention provides a nucleic acid sequence of a heterologous nucleic acid expression cassette that expresses an ABC-transporter. In an embodiment the nucleotide sequence of the heterologous nucleic acid expression cassette has a coding sequence of SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27, where the coding sequence is operably linked to a heterologous promoter.

In another aspect the invention provides for a method for producing steviol or one or more steviol glycosides involving: culturing a population of the host cells of the invention in a medium with a carbon source under conditions suitable for making steviol or one or more steviol glycosides to yield a culture broth; and recovering the steviol or one or more steviol glycosides from the culture broth.

In another aspect the invention provides for a method for producing Reb D involving: culturing a population of the host cells of the invention in a medium with a carbon source under conditions suitable for making Reb D to yield a culture broth; and recovering said Reb D compound from the culture broth.

In another aspect the invention provides for a method for producing Reb M involving: culturing a population of the host cells of the invention in a medium with a carbon source under conditions suitable for making Reb M to yield a culture broth; and recovering said Reb M compound from the culture broth.

5. BRIEF DESCRIPTION OF THE FIGURES

Figure 3:
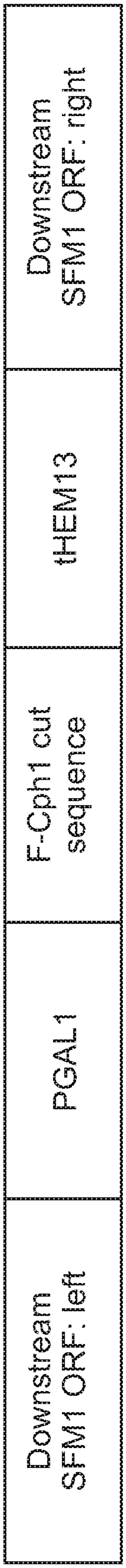

FIG. 3 is a schematic of the landing pad DNA construct used to insert transporters into Reb M strains. Each end of the construct contains 500 bp of DNA sequence from downstream of the yeast SFM1 gene to facilitate homologous recombination at this locus. Insertion of the landing pad at this locus does not delete any gene. The landing pad contains a full length GAL1 promoter followed by a recognition site for the F-CphI endonuclease and the terminator from the native yeast gene HEM13.

Figure 4:
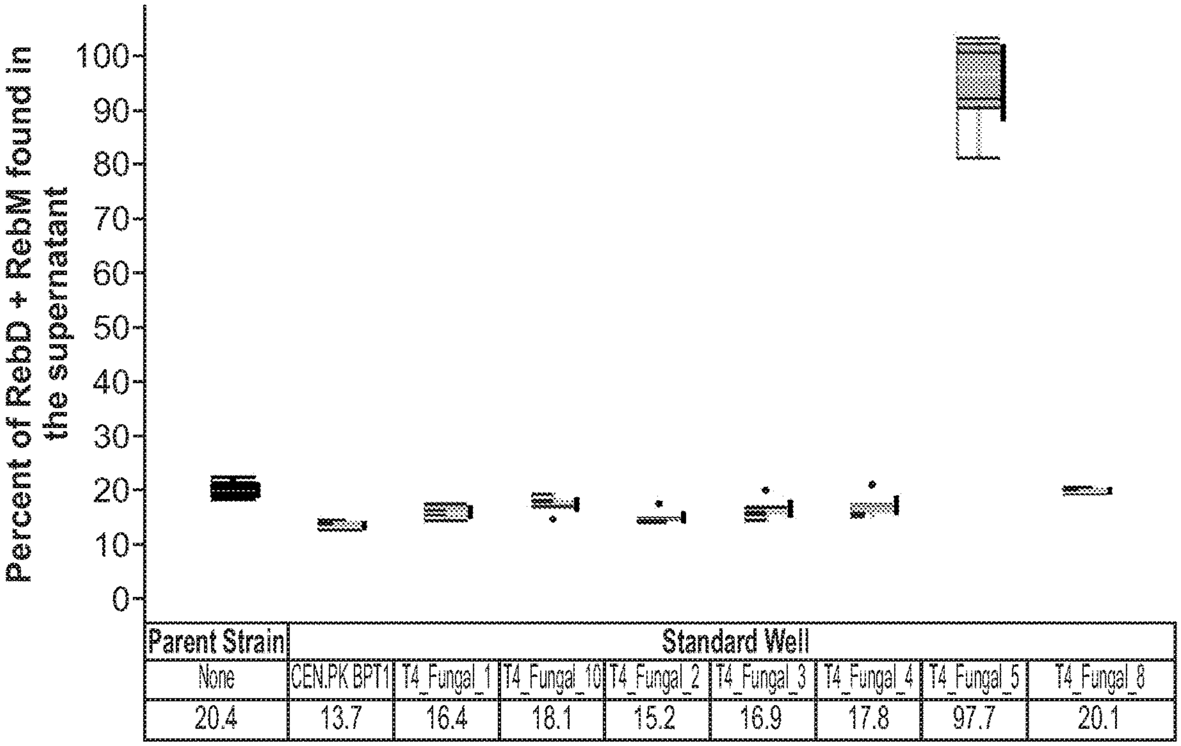

FIG. 4 is a graph of the percent of Reb D+Reb M found in the supernatant. Yeast strains with different overexpressed transporters were grown in microtiter plates. This figure reports the percent of Reb D+Reb M (measured in μmoles) that is detected in the supernatant after the cells have been removed. The parent strain does not contain an overexpressed transporter. The amount of Reb D+Reb M measured in the supernatant is divided by the amount of Reb D+Reb M measured in the whole cell broth to obtain the percent of Reb D+Reb M in the supernatant.

Figure 5:
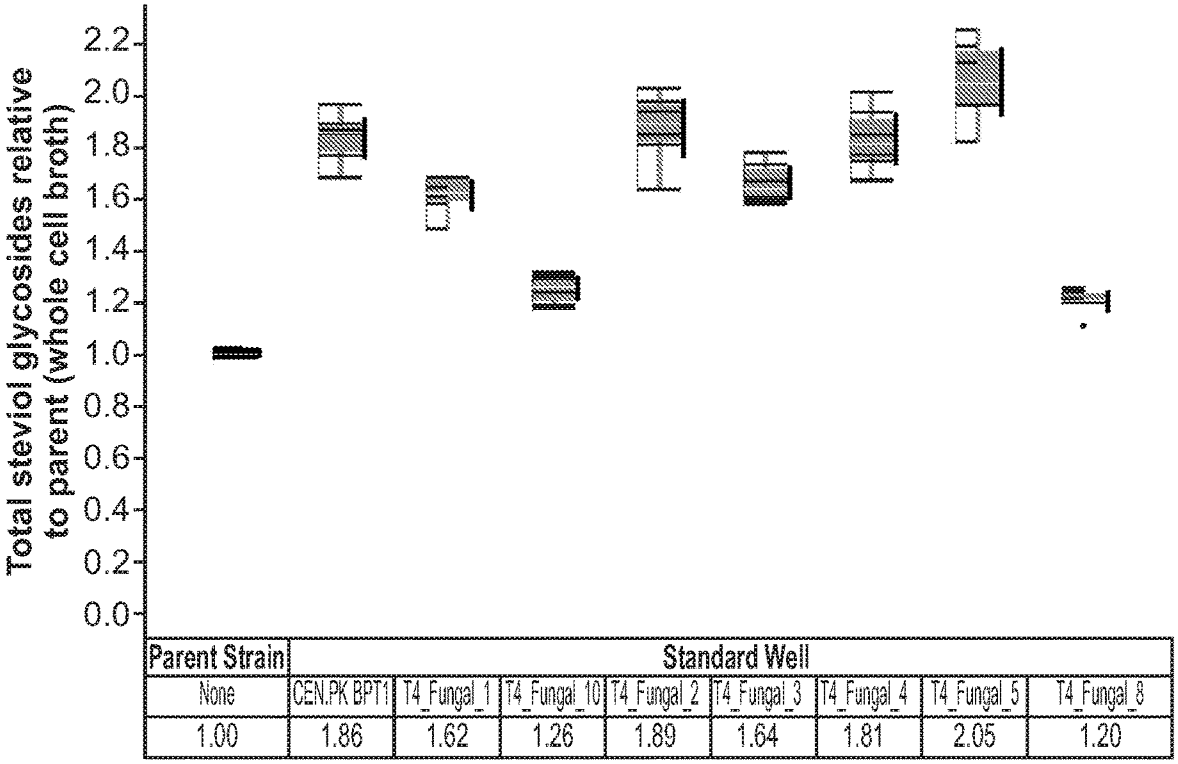

FIG. 5 is a graph of total steviol glycosides relative to parent in whole cell broth. Yeast strains with different overexpressed transporters were grown in microtiter plates. This figure reports the sum total of all steviol glycosides (measured in μmoles) that is detected in whole cell broth (both cells and supernatant) relative to the parent strain. The parent strain does not contain an overexpressed transporter.

Figure 6:
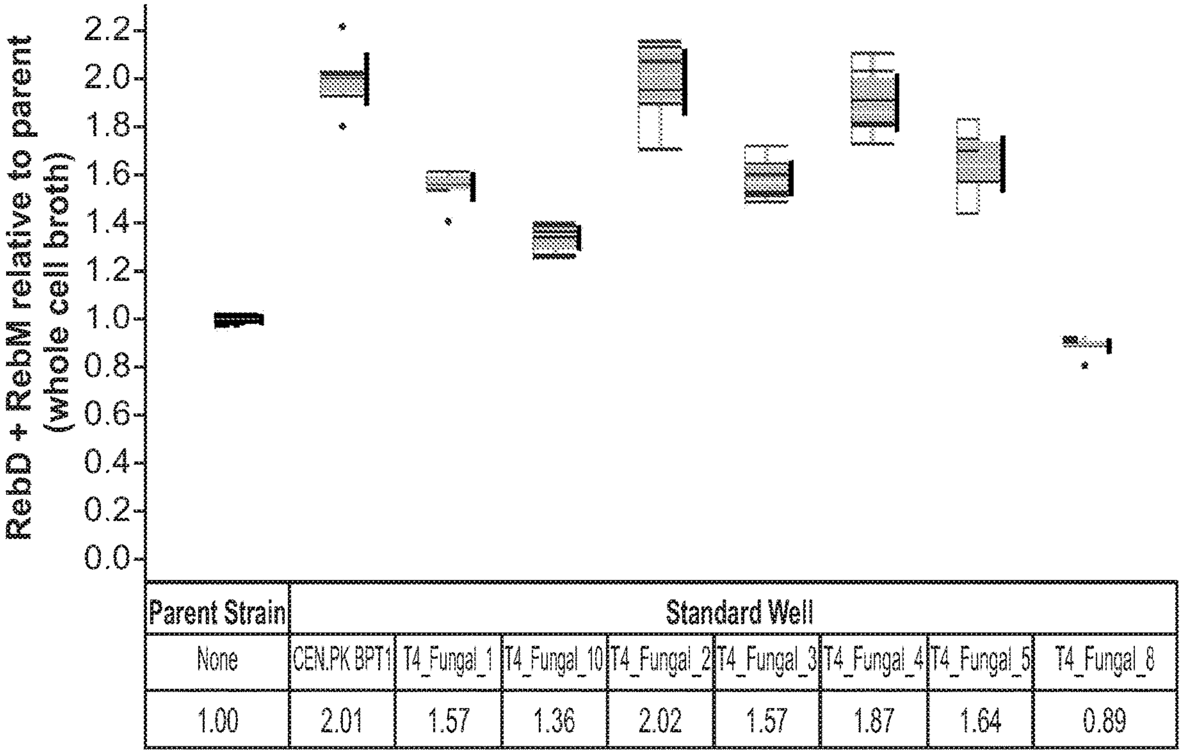

FIG. 6 is a graph of the amount of Reb D+Reb M relative to parent in whole cell broth. Yeast strains with different overexpressed transporters were grown in microtiter plates. This figure reports the sum of Reb D+Reb M (measured in μmoles) that is detected in whole cell broth (both cells and supernatant) relative to the parent strain. The parent strain does not contain an overexpressed transporter.

Figure 7:
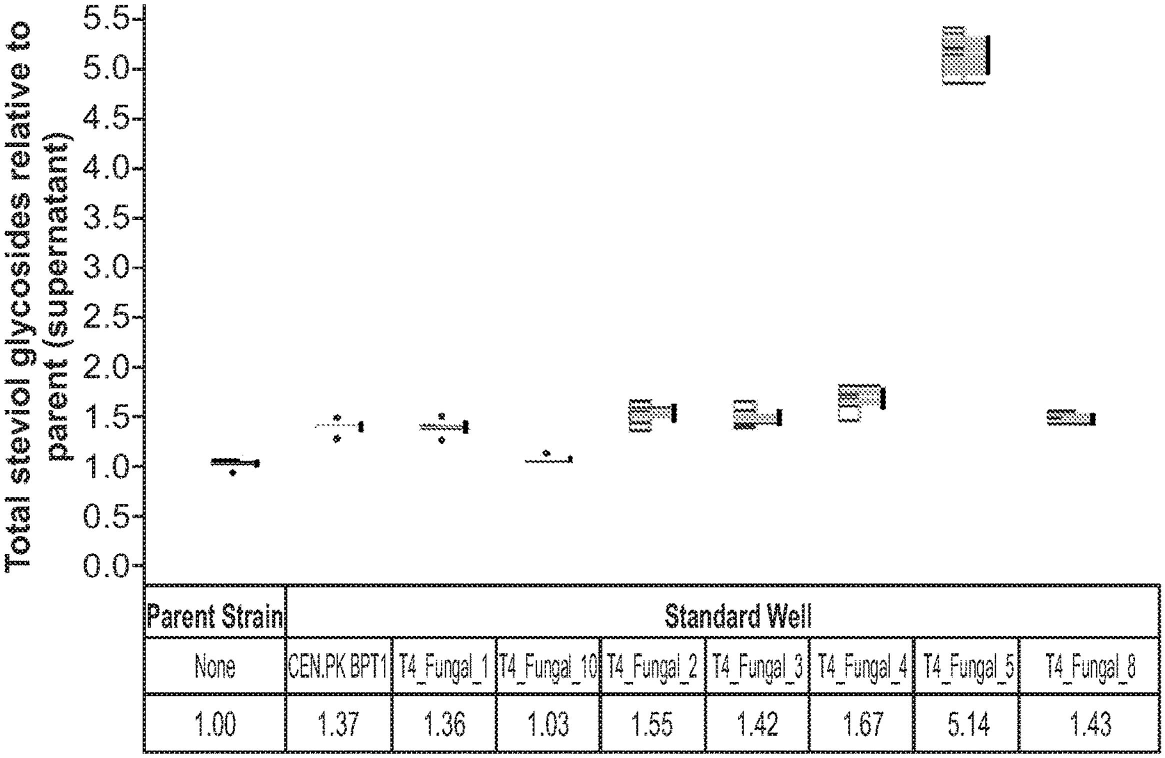

FIG. 7 is a graph of the total steviol glycosides relative to parent in the supernatant. Yeast strains with different overexpressed transporters were grown in microtiter plates. This figure reports the sum total of all steviol glycosides (measured in μmoles) that is detected in the supernatant after cells have been removed, relative to the parent strain. The parent strain does not contain an overexpressed transporter.

Figure 8:
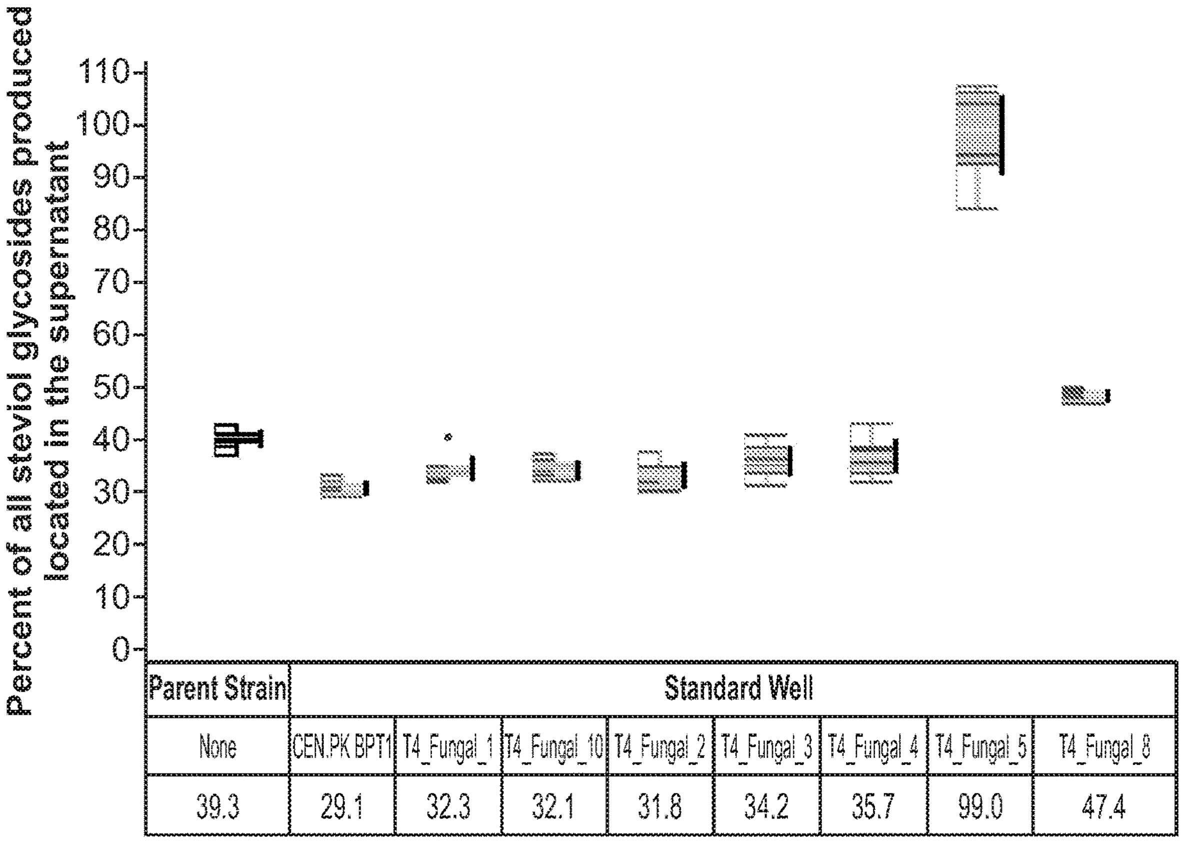

FIG. 8 shows the percent of all steviol glycosides produced located in the supernatant. Yeast strains with different overexpressed transporters were grown in microtiter plates. This figure reports the percent of all steviol glycosides produced by the cells (measured in μmoles) that is detected in the supernatant. The amount of total steviol glycosides measured in the supernatant is divided by the amount of total steviol glycosides measured in the whole cell broth to obtain the percent of total steviol glycosides in the supernatant.

Figure 9:
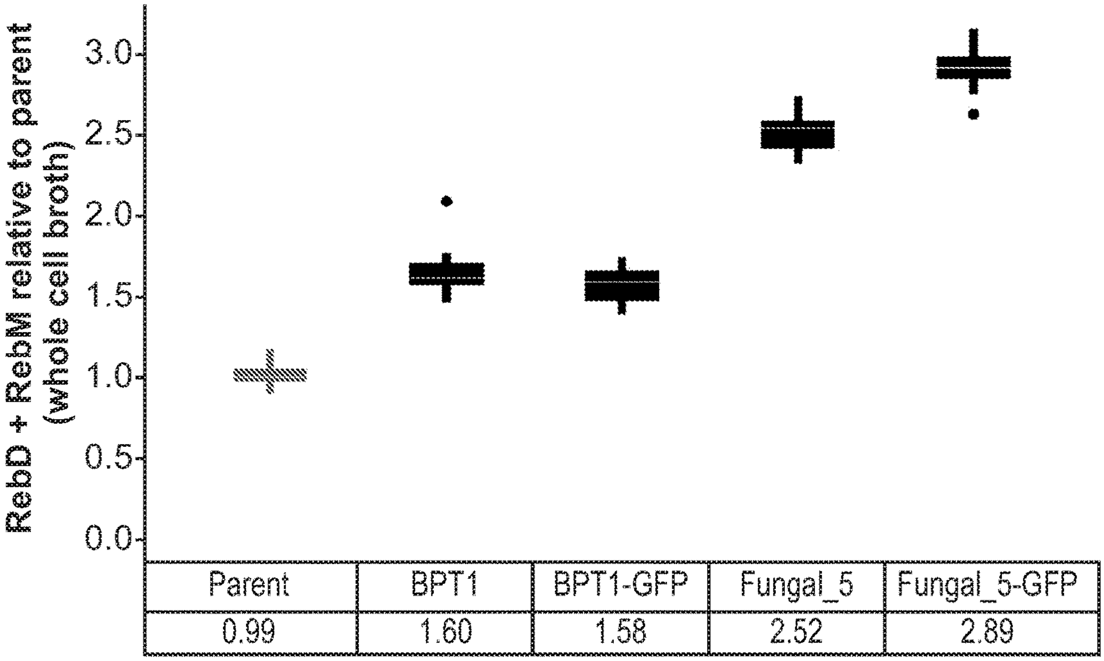

FIG. 9 is a graph of the amount of Reb D+Reb M relative to parent in whole cell broth. Yeast strains expressing GFP-tagged and untagged versions of BPT1 and T4_Fungal_5 Transporter were grown in microtiter plates. The relative activities of the GFP-tagged and untagged versions of the transporters were compared. The data demonstrates that the GFP-tagged versions behaved similarly to the untagged versions of the transporters.

Figure 10:
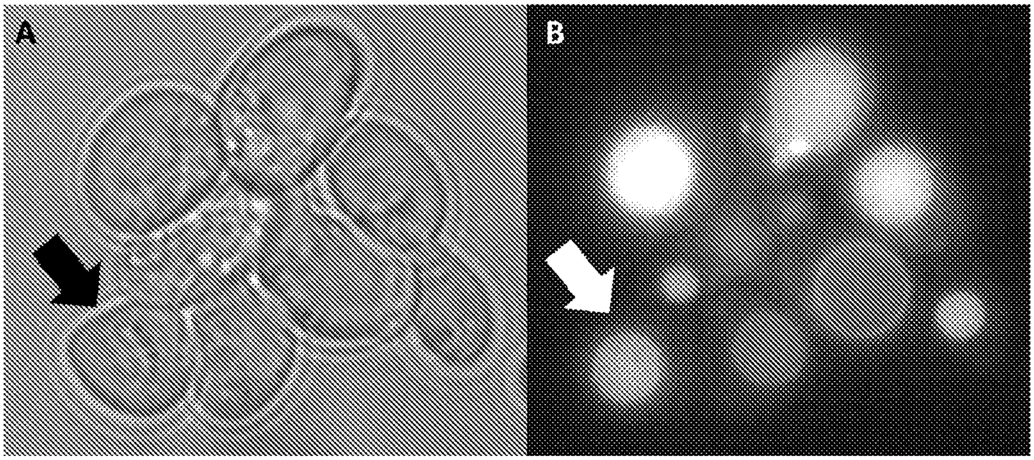

FIG. 10 is a set of photomicrographs of brightfield (A) and fluorescence (B) images of yeast expressing GFP-tagged BPT1.

Figure 11:
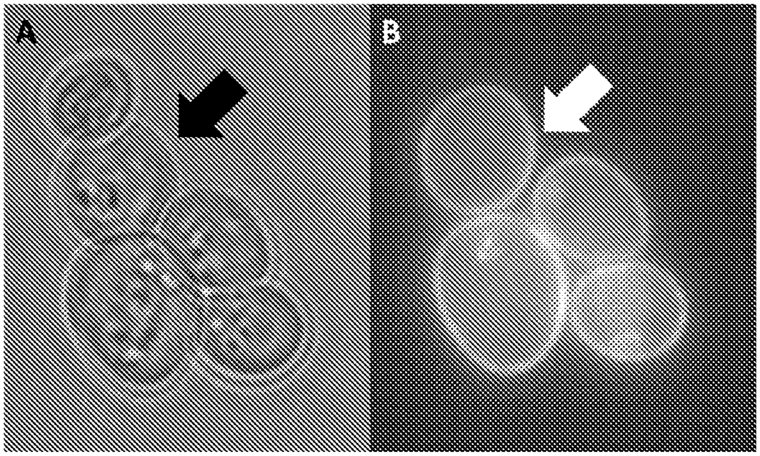

FIG. 11 is a set of photomicrographs of brightfield (A) and fluorescence (B) images of yeast expressing GFP-tagged T4_Fungal_5 transporter.

Figure 12:
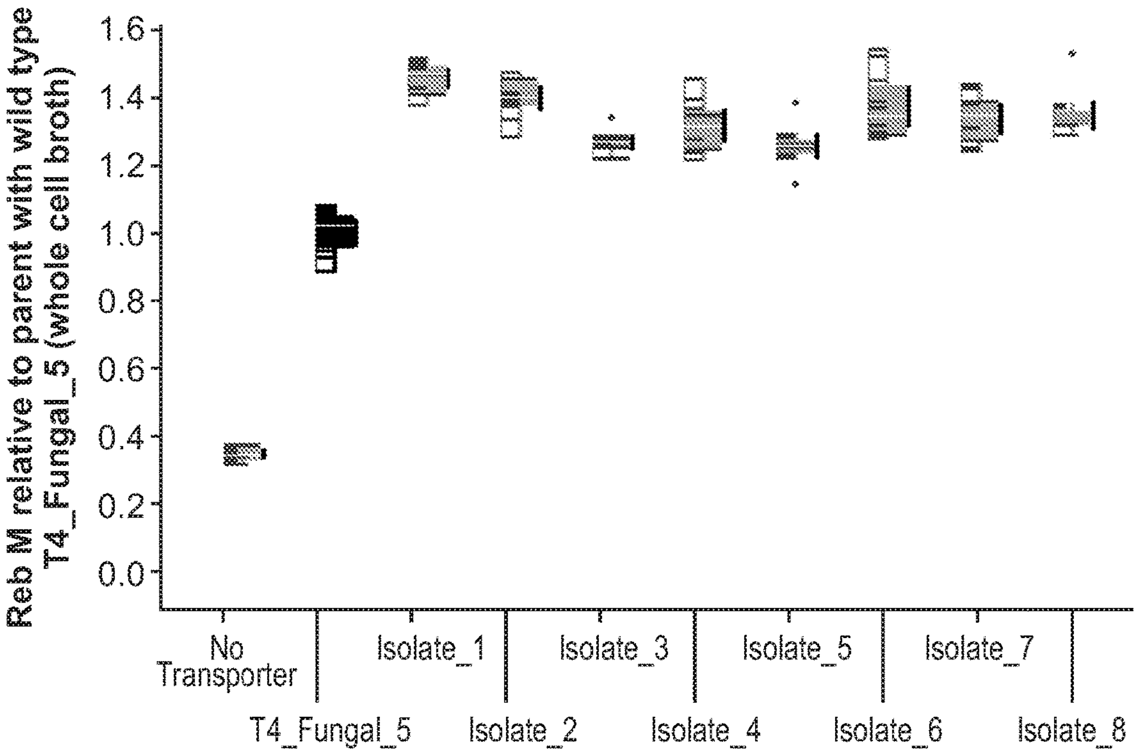

FIG. 12 is a graph of the amount of Reb M relative to parent with wild type T4_Fungal_5 in whole cell broth. Yeast strains expressing transporters T4_Fungal_5 and its variants (Isolate_1-8) derived via error prone PCR and selection were grown in microtiter plates. This figure reports the Reb M titer (measured in μmoles) that is detected in whole cell broth (both cells and supernatant) of yeast strains expressing mutagenized T4_Fungal_5 transporter variants (Isolate_1-8) relative to unmutagenized T4_Fungal_5. The data demonstrates that expression of Isolates_1-8 resulted in improved Reb M production by yeast strains in comparison to T4_Fungal_5.

Figure 13:
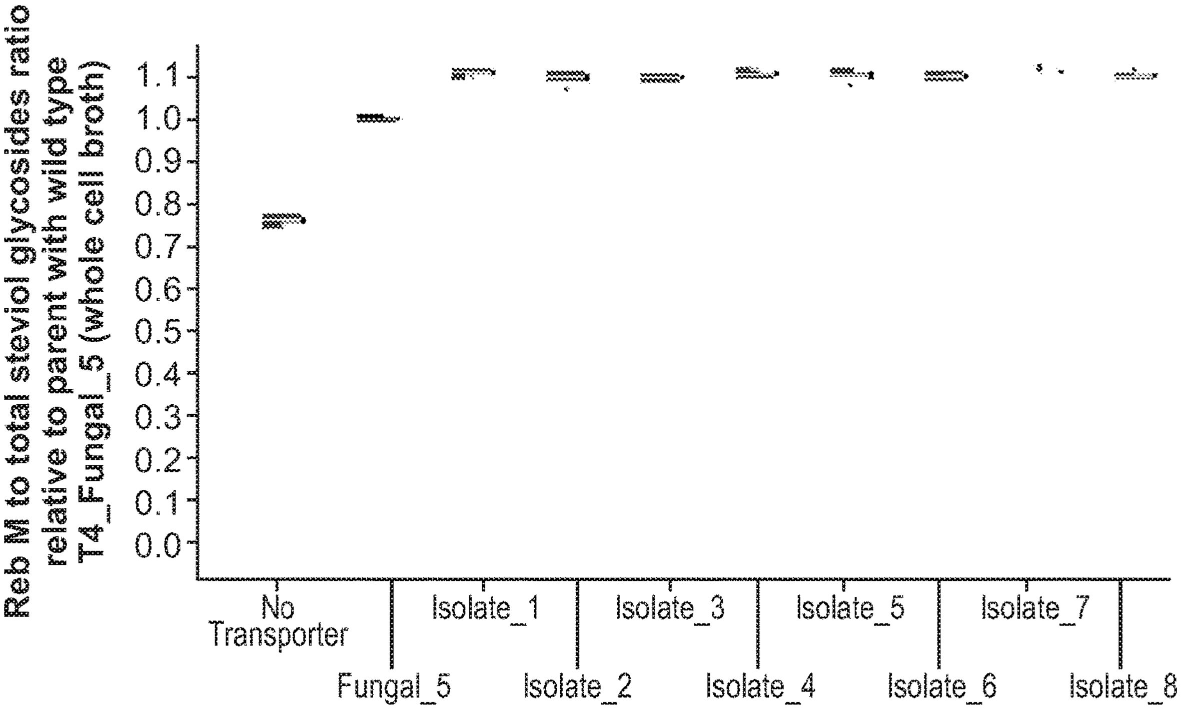

FIG. 13 is a graph of Reb M fraction of total steviol glycosides relative to parent with wild type T4_Fungal_5 in whole cell broth. Yeast strains expressing transporters T4_Fungal_5 and its variants (Isolate_1-8) derived via error prone PCR and selection were grown in microtiter plates. This figure reports the ratio of Reb M to the sum total of all steviol glycosides (measured in μmoles) that is detected in whole cell broth (both cells and supernatant) of yeast strains expressing mutagenized T4_Fungal_5 transporter variants (Isolate_1-8) relative to unmutagenized T4_Fungal_5. The data demonstrates that expression of Isolates_1-8 resulted in increased fraction of Reb M among all steviol glycosides in comparison to T4_Fungal_5 transporter. In other words, Isolates_1-8 display increased substrate preference for Reb M.

Figure 14:
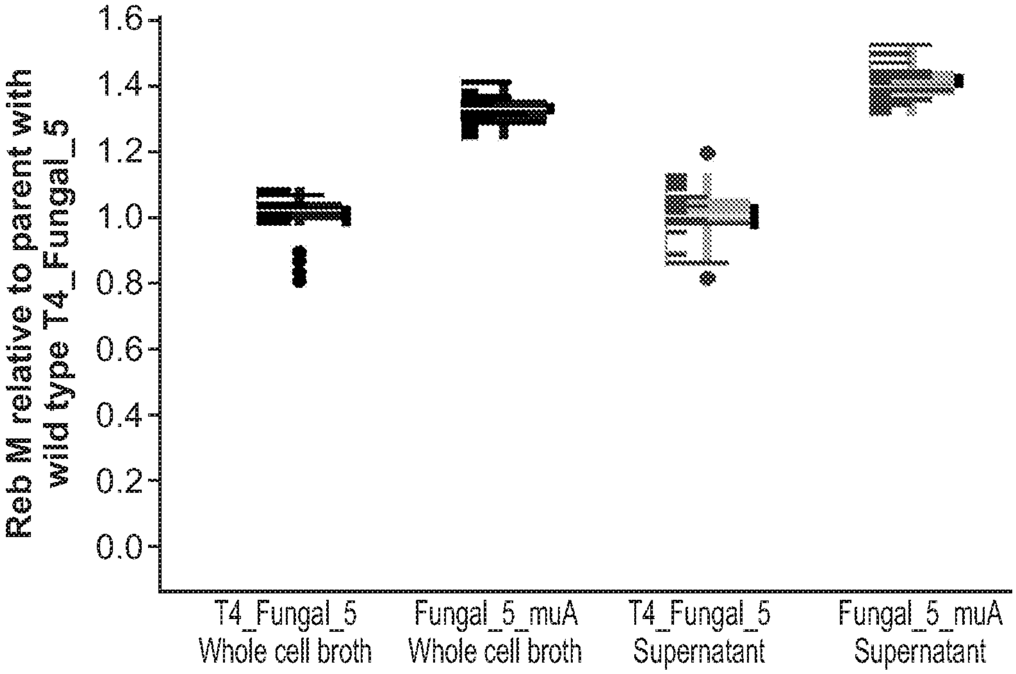

FIG. 14 is a graph of the amount of Reb M in whole cell broth and supernatant fraction produced by strains expressing either T4_Fungal_5 or Fungal_5_muA transporters. Yeast strains expressing T4_Fungal_5 or Fungal_5_muA under the control of PGAL3 (lower strength than PGAL1) were grown in microtiter plates. This figure reports the Reb M titer (measured in μmoles) that is detected in whole cell broth (both cells and supernatant) and supernatant fraction of yeast strains. The data confirms that Fungal_5_muA indeed confers improved performance when expressed in yeast strain: 30% more Reb M in whole cell broth and 40% more extracellular Reb M were produced by the strain with Fungal_5_muA than by the strain with the wild type T4_Fungal_5 when both transporters were expressed under lower promoter strength.

Figure 15:
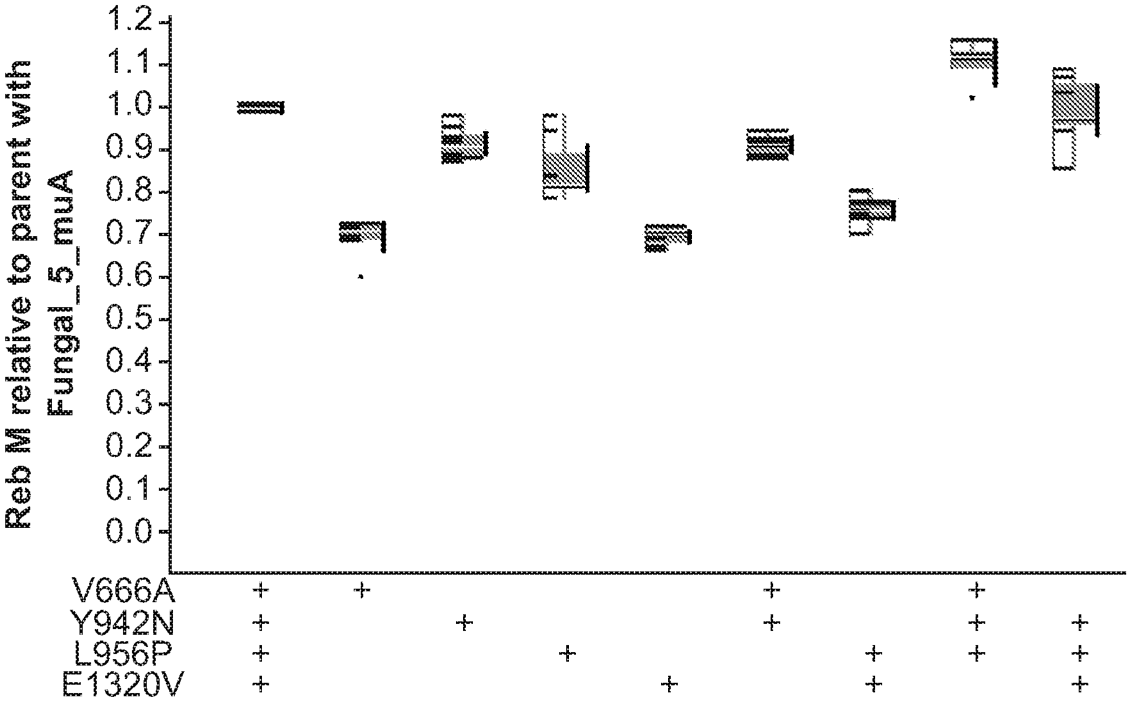

FIG. 15 is a graph of the amount of Reb M relative to parent with Fungal_5_muA in whole cell broth. Yeast strains expressing transporter Fungal_5_muA and eight of its variants where one, two, or three mutations were reverted to wild type T4_Fungal_5 sequence were grown in microtiter plates. This figure reports the Reb M titer (measured in μmoles) that is detected in whole cell broth (both cells and supernatant) of yeast strains expressing eight Fungal_5_muA variants relative to Fungal_5_muA. The data demonstrates the effect of different mutations on Reb M production, particularly interesting is the beneficial effect of E1320V reversion.

Figure 16:
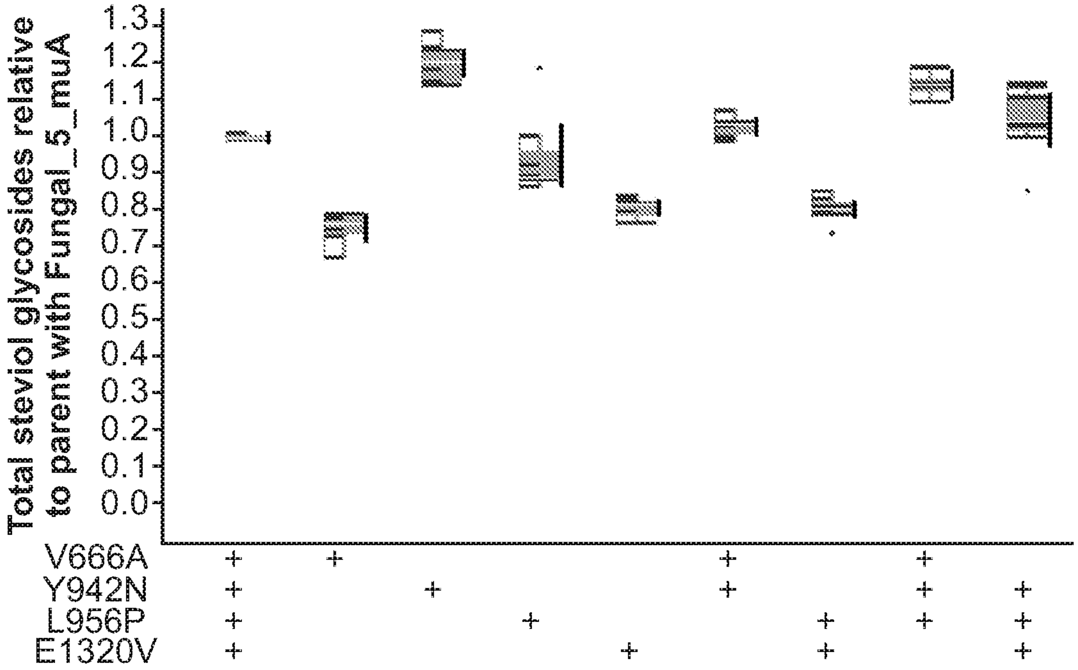

FIG. 16 is a graph of total steviol glycosides relative to parent with Fungal_5_muA in whole cell broth. Yeast strains expressing transporter Fungal_5_muA and eight of its variants where one, two, or three mutations were reverted to wild type T4_Fungal_5 sequence were grown in microtiter plates. This figure reports the sum total of all steviol glycosides (measured in μmoles) that is detected in whole cell broth (both cells and supernatant) of yeast strains expressing eight Fungal_5_muA variants relative to Fungal_5_muA. The data demonstrates the effect of different mutations on TSG production. Together with FIG. 15, it illustrates not only differences in activity but also substrate preference.

6. DETAILED DESCRIPTION OF THE EMBODIMENTS

6.1 Terminology

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

On the other hand, the term "native" or "endogenous" as used herein with reference to molecules, and in particular enzymes and nucleic acids, indicates molecules that are expressed in the organism in which they originated or are found in nature. It is understood that expression of native enzymes or polynucleotides may be modified in recombinant microorganisms.

As used herein, the term "heterologous nucleic acid expression cassette" refers to a nucleic acid sequence that comprises a coding sequence operably linked to one or more regulatory elements sufficient to expresses the coding sequence in a host cell. In an embodiment "ABC-transporter expression cassette" refers to a heterologous nucleic acid expression cassette in which the heterologous nucleic acid comprises the coding sequence for an ABC-transporter polypeptide. Non-limiting examples of regulatory elements include promoters, enhancers, silencers, terminators, and poly-A signals.

As used therein, the terms "ABC-transporter" and "ATP Binding Cassette Transporter" refer to a super-family of membrane associated polypeptides that couple adenosine triphosphate (ATP) hydrolysis to the translocation of various substrates across biological membranes.

```
As used herein, the term "CEN.PK.BPT1"
refers to an ABC-transporter having
the following amino acid sequence
(SEQ ID NO: 1):
MSSLEVVDGCPYGYRPYPDSGTNALNPCFISVISA

WQAVFFLLIGSYQLWKLYKNNKVPPRFKNFPTLPS

KINSRHLTHLTNVCFQSTLIICELALVSQSSDRVY

PFILKKALYLNLLFNLGISLPTQYLAYFKSTFSMG
```

-continued

NQLFYYMFQILLQLFLILQRYYHGSSNERLTVISG

QTAMILEVLLLFNSVAIFIYDLCIFEPINELSEYY

KKNGWYPPVHVLSYITFIWMNKLIVETYRNKKIKD

PNQLPLPPVDLNIKSISKEFKANWELEKWLNRNSL

WRAIWKSFGRTISVAMLYETTSDLLSVVQPQFLRI

FIDGLNPETSSKYPPLNGVFIALTLFVISVVSVFL

TNQFYIGIFEAGLGIRGSLASLVYQKSLRLTLAER

NEKSTGDILNLMSVDVLRIQRFFENAQTIIGAPIQ

IIVVLTSLYWLLGKAVIGGLVTMAIMMPINAFLSR

KVKKLSKTQMKYKDMRIKTITELLNAIKSIKLYAW

EEPMMARLNHVRNDMELKNFRKIGIVSNLIYFAWN

CVPLMVTCSTFGLFSLFSDSPLSPAIVFPSLSLFN

ILNSAIYSVPSMINTIIETSVSMERLKSFLLSDEI

DDSFIERIDPSADERALPAIEMNNITFLWKSKEVL

TSSQSGDNLRTDEESIIGSSQIALKNIDHFEAKRG

DLVCVVGRVGAGKSTFLKAILGQLPCMSGSRDSIP

PKLIIRSSSVAYCSQESWIMNASVRENILFGFIKF

DQDYYDLTIKACQLLPDLKILPDGDETLVGEKGIS

LSGGQKARLSLARAVYSRADIYLLDDILSAVDAEV

SKNIIEYVLIGKTALLKNKTIILTTNTVSILKFIS

QMIYALENGEIVEQGNYEDVMNRKNNTSKLKKLLE

EFDSPIDNGNESDVQTEHRSESEVDEPLQLKVTES

ETEDEVVTESELELIKANSRRASLATLRPRPFVGA

QLDSVKKTAQKAEKTEVGRVKTKIYLAYIKACGVL

GVVLFFLFMILTRVFDLAENFWLKYWSESNEKNGS

NERVWMFVGVYSLIGVASAAFNNLRSIMMLLYCSI

RGSKKLHESMAKSVIRSPMTFFETTPVGRIINRFS

SDMDAVDSNLQYIFSFFFKSILTYLVTVILVGYNM

PWFLVFNMFLVVIYIYYQTFYIVLSRELKRLISIS

YSPIMSLMSESLNGYSIIDAYDHFERFIYLNYEKI

QYNVDFVFNFRSTNRWLSVRLQTIGATIVLATAIL

ALATMNTKRQLSSGMVGLLMSYSLEVTGSLTWIVR

TTVTIETNIVSVERIVEYCELPPEAQSINPEKRPD

ENWPSKGGIEFKNYSTKYRENLDPVLNNINVKIEP

CEKVGIVGRTGAGKSTLSLALFRILEPTEGKIIID

GIDISDIGLFDLRSHLAIIPQDAQAFEGTVKTNLD

PFNRYSEDELKRAVEQAHLKPHLEKMLHSKPRGDD

SNEEDGNVNDILDVKINENGSNLSVGQRQLLCLAR

ALLNRSKILVLDEATASVDMETDKIIQDTIRREFK

-continued

DRTILTIAHRIDTVLDSDKIIVLDQGSVREFDSPS

KLLSDKTSIFYSLCEKGGYLK*;

and encoded by the following nucleic acid sequence (SEQ ID NO: 20):

ATGTCTTCACTAGAAGTGGTAGATGGGTGCCCCTA

TGGATACCGACCATATCCAGATAGTGGCACAAATG

CATTAAATCCATGTTTTATATCAGTAATATCCGCC

TGGCAAGCCGTCTTTTTCCTATTGATTGGTAGCTA

TCAATTGTGGAAACTTTATAAGAACAATAAAGTAC

CACCCAGATTTAAGAACTTTCCTACATTACCAAGT

AAAATCAACAGTCGACATCTAACGCATTTGACCAA

TGTTTGCTTTCAGTCCACGCTTATAATTTGTGAAC

TGGCCTTGGTATCCCAATCTAGCGATAGGGTTTAT

CCATTTATACTAAAGAAGGCTCTGTACTTGAATCT

CCTTTTCAATTTGGGTATTTCTCTCCCTACTCAAT

ACTTAGCTTATTTTAAAAGTACATTTTCAATGGGC

AACCAGCTTTTCTATTACATGTTTCAAATTCTTCT

ACAGCTCTTCTTGATATTGCAGAGGTACTATCATG

GTTCTAGTAACGAAAGGCTTACTGTTATTAGCGGA

CAAACTGCTATGATTTTAGAAGTGCTCCTTCTTTT

CAATTCTGTGGCAATTTTTATTTATGATCTATGCA

TTTTTGAGCCAATTAACGAATTATCTGAATACTAC

AAGAAAAATGGGTGGTATCCCCCCGTTCATGTACT

ATCCTATATTACATTTATCTGGATGAACAAACTGA

TTGTGGAAACTTACCGTAACAAGAAAATCAAAGAT

CCTAACCAGTTACCATTGCCGCCAGTAGATCTGAA

TATTAAGTCGATAAGTAAGGAATTTAAGGCTAACT

GGGAATTGGAAAAATGGTTGAATAGAAATTCTCTT

TGGAGGGCCATTTGGAAGTCATTTGGTAGGACTAT

TTCTGTGGCTATGCTGTATGAAACGACATCTGATT

TACTTTCTGTAGTACAGCCCCAGTTTCTACGGATA

TTCATAGATGGTTTGAACCCGGAAACATCTTCTAA

ATATCCTCCTTTAAATGGTGTATTTATTGCTCTAA

CCCTTTTCGTAATCAGCGTGGTTTCTGTGTTCCTC

ACCAATCAATTTTATATTGGAATTTTGAGGCTGGT

TTGGGGATAAGAGGCTCTTTAGCTTCTTTAGTGTA

TCAGAAGTCCTTAAGATTGACGCTAGCAGAGCGTA

ACGAAAAATCTACTGGTGACATCTTAAATTTGATG

TCTGTGGATGTGTTAAGGATCCAGCGGTTTTTCGA

AAATGCCCAAACCATTATTGGCGCTCCTATTCAGA

TTATTGTTGTATTAACTTCCCTGTACTGGTTGCTA

-continued

GGAAAGGCTGTTATTGGAGGGTTGGTTACTATGGC
TATTATGATGCCTATCAATGCCTTCTTATCTAGAA
AGGTAAAAAAGCTATCAAAAACTCAAATGAAGTAT
AAGGACATGAGAATCAAGACTATTACAGAGCTTTT
GAATGCTATAAAATCTATTAAATTATACGCCTGGG
AGGAACCTATGATGGCAAGATTGAATCATGTTCGT
AATGATATGGAGTTGAAAAATTTTCGGAAAATTGG
TATAGTGAGCAATCTGATATATTTTGCGTGGAATT
GTGTACCTTTAATGGTGACATGTTCCACATTTGGC
TTATTTTCTTTATTTAGTGATTCTCCGTTATCTCC
TGCCATTGTCTTCCCTTCATTATCTTTATTTAATA
TTTTGAACAGTGCCATCTATTCCGTTCCATCCATG
ATAAATACCATTATAGAGACAAGCGTTTCTATGGA
AAGATTAAAGTCATTCCTACTTAGTGACGAAATTG
ATGATTCGTTCATCGAACGTATTGATCCTTCAGCG
GATGAAAGAGCGTTACCTGCTATAGAGATGAATAA
TATTACATTTTTATGGAAATCAAAAGAAGTATTAA
CATCTAGCCAATCTGGAGATAATTTGAGGACAGAT
GAAGAGTCTATTATCGGATCTTCTCAAATTGCGTT
GAAGAATATCGATCATTTTGAAGCAAAAAGGGGTG
ATTTAGTTTGTGTTGTTGGTCGGGTAGGAGCTGGT
AAATCAACATTTTTGAAGGCAATTCTTGGTCAACT
TCCTTGCATGAGTGGTTCTAGGGACTCGATACCAC
CTAAACTGATCATTAGATCATCGTCTGTAGCCTAC
TGTTCACAAGAATCCTGGATAATGAACGCATCTGT
AAGAGAAAACATTCTATTTGGTCACAAGTTCGACC
AAGATTATTATGACCTCACTATTAAAGCATGTCAA
TTGCTACCCGATTTGAAAATACTACCAGATGGTGA
TGAAACTTTGGTAGGTGAAAAGGGCATTTCCCTAT
CAGGCGGTCAGAAGGCCCGTCTTTCATTAGCCAGA
GCGGTGTACTCGAGAGCAGATATTTATTTGTTGGA
TGACATTTTATCTGCTGTTGATGCAGAAGTTAGTA
AAAATATTATTGAATATGTTTTGATCGGAAAGACG
GCTTTATTAAAAAATAAAACAATTATTTTAACTAC
CAATACTGTATCAATTTTAAAACATTCGCAGATGA
TATATGCGCTAGAAAACGGTGAAATTGTTGAACAA
GGGAATTATGAGGATGTAATGAACCGTAAGAACAA
TACTTCAAAACTGAAAAAATTACTAGAGGAATTTG
ATTCTCCGATTGATAATGGAAATGAAAGCGATGTC
CAAACTGAACACCGATCCGAAAGTGAAGTGGATGA
ACCTCTGCAGCTTAAAGTAACTGAATCAGAAACTG

-continued

AGGATGAGGTTGTTACTGAGAGTGAATTAGAACTA
ATCAAAGCCAATTCTAGAAGAGCTTCTCTAGCTAC
GCTAAGACCTAGACCCTTTGTGGGAGCACAATTGG
ATTCCGTGAAGAAAACGGCGCAAAAGGCCGAGAAG
ACAGAGGTGGGAAGAGTCAAAACAAAGATTTATCT
TGCGTATATTAAGGCTTGTGGAGTTTTAGGTGTTG
TTTTATTTTTCTTGTTTATGATATTAACAAGGGTT
TTCGACTTAGCAGAGAATTTTTGGTTAAAGTACTG
GTCAGAATCTAATGAAAAAAATGGTTCAAATGAAA
GGGTTTGGATGTTTGTTGGTGTGTATTCCTTAATC
GGAGTAGCATCGGCCGCATTCAATAATTTACGGAG
TATTATGATGCTACTGTATTGTTCTATTAGGGGTT
CTAAGAAACTGCATGAAAGCATGGCCAAATCTGTA
ATTAGAAGTCCTATGACTTTCTTTGAGACTACACC
AGTTGGAAGGATCATAAACAGGTTCTCATCTGATA
TGGATGCAGTGGACAGTAATCTACAGTACATTTTC
TCCTTTTTTTTCAAATCAATACTAACCTATTTGGT
TACTGTTATATTAGTCGGGTACAATATGCCATGGT
TTTTAGTGTTCAATATGTTTTTGGTGGTTATCTAT
ATTTACTATCAAACATTTTACATTGTGCTATCTAG
GGAGCTAAAAAGATTGATCAGTATATCTTACTCTC
CGATTATGTCCTTAATGAGTGAGAGCTTGAACGGT
TATTCTATTATTGATGCATACGATCATTTTGAGAG
ATTCATCTATCTAAATTATGAAAAAATCCAATACA
ACGTTGATTTTGTCTTCAACTTTAGATCAACGAAT
AGATGGTTATCCGTGAGATTGCAAACTATTGGTGC
TACAATTGTTTTGGCTACTGCAATCTTAGCACTAG
CAACAATGAATACTAAAAGGCAACTAAGTTCGGGT
ATGGTTGGTCTACTAATGAGCTATTCATTAGAGGT
TACAGGTTCATTGACTTGGATTGTAAGGACAACTG
TGACGATTGAAACCAACATTGTATCAGTGGAGAGA
ATTGTTGAGTACTGCGAATTACCACCTGAAGCACA
GTCCATTAACCCTGAAAAGAGGCCAGATGAAAATT
GGCCATCAAAGGGTGGTATTGAATTCAAAAACTAT
TCCACAAAATACAGAGAAAATTTGGATCCAGTGCT
GAATAATATTAACGTGAAGATTGAGCCATGTGAAA
AGGTTGGGATTGTTGGCAGAACAGGTGCAGGGAAG
TCTACACTGAGCCTGGCATTATTTAGAATACTAGA
ACCTACCGAAGGTAAAATTATTATTGACGGCATTG
ATATATCCGACATAGGTCTGTTCGATTTAAGAAGC

-continued

CATTTGGCAATTATTCCTCAGGATGCACAAGCTTT
TGAAGGTACAGTAAAGACCAATTTGGACCCTTTCA
ATCGTTATTCAGAAGATGAACTTAAAAGGGCTGTT
GAGCAGGCACATTTAAAGCCTCATCTGGAAAAAAT
GCTGCACAGTAAACCAAGAGGTGATGATTCTAATG
AAGAGGATGGCAATGTTAATGATATTCTGGATGTC
AAGATTAATGAGAACGGTAGTAACTTGTCAGTGGG
GCAAAGACAACTACTATGTTTGGCAAGAGCGCTGC
TAAACCGTTCCAAAATATTGGTCCTTGATGAAGCA
ACGGCTTCTGTGGATATGGAAACCGATAAAATTAT
CCAAGACACTATAAGAAGAGAATTTAAGGACCGTA
CCATCTTAACAATTGCACATCGTATCGACACTGTA
TTGGACAGTGATAAGATAATTGTTCTTGACCAGGG
TAGTGTGAGGGAATTCGATTCACCCTCGAAATTGT
TATCCGATAAAACGTCTATTTTTTACAGTCTTTGT
GAGAAAGGTGGGTATTTGAAATAA.

As used herein, the term "T4_Fungal_1" refers to an ABC-transporter having the following amino acid sequence (SEQ ID NO. 2).

MSLELSNSTLCDSYWAVDDFTACGRQLVESWVSVP
LVLSALVVAFNLLRNSLASEKTDPYSKLDAEQQPL
LQNGHALYTSSIESDNTDIFQRHFDIALLKPVKDD
GKPIGVVRIVYRDTAEKLKVALEEILLISQTVLAF
LALSRLEDISESRFLLVKYINFSLWLYLTVITSAR
LLNVTKGFSANRVDLWYHCAILYNLQWFNSVMLFR
SALLHHVSGTYGYWFYVTQFVINTLLCLTNGLEKL
SDKPAIVYEEEGVIPSPETTSSLIDIMTYGYLDKM
VFSSYWKPITMEEVWGLRYDDYSHDVLIRFHKLKS
SIRFTLRLFLQFKKELALQTLCTCIEALLIFVPPL
CLKKILEYIESPHTKSRSMAWFYVLIMFGSGVIAC
SFSGRGLFLGRRICTRMRSILIGEIYSKALRRRLG
STDKEKTTEEEDDKSAKSKKEDEPS
NKELGGIINLMAVDAFKVSEIGGYLHYFPNSFVMA
AVAIYMLYKLLGWSSLIGTATLIAILPINYMLVEK
LSKYQKQMLLVTDKRIQKTNEAFQNIRIIKYFAWE
DKFADTIMKIREEELGYLVGRCVVWALLIFLWLVV
PTIVTLITFYAYTVIQGNPLTSPIAFTALSLFTLL
RGPLDALADMLSMVMQCKVSLDRVEDFLNEPETTK
YQQLSAPRGPNSPLIGFENATFYWSKNSKAEFALK
DLNIDFKVGKLNVVIGPTGSGKSSLLLALLGEMDL

-continued

DKGNVFLPGAIPRDDLTPNPVTGLMESVAYCSQTA
WLLNATVKDNIIFASPFNQERYDAVIHACGLTRDL
SILEAGDETEIGEKGITLSGGQKQRVSLARALYSS
ASYLLLDDCLSAVDSHTAVHIYDYCINGELMKGRT
CILVSHNVSLTVKEADFVVMMDNGRIKAQGSVDEL
MQEGLLNEEVVKSVMQSRSASTANLAALDDNSPIS
SEAIAEGLAKKTQKPEQSKKSKLIEDETKSDGSVK
PEIYYAYFRYFGNPALWIMIAFLFIGSQSVNVYQS
YWLRRWSAIEDKRDLSAFSNSNDMTLFLFPTFHSI
NWHRPLVNYALQPFGLAVEERSTMYYITIYTLIGL
AFATLGSSRVILTFIGGLNVSRKIFKDLLDKLLHA
KLRFFDQTPIGRIMNRFSKDIEAIDQELALYAEEF
VTYLISCLSTLVVVCAVTPAFLVAGVLILLVYYGV
GVLYLELSRDLKRFESITKSPIHQHFSETLVGMTT
IRAYGDERRFLKQNFEKIDVNNRPFWYVWVNNRWL
AYRSDMIGAFIIFFAAAFAVAYSDKIDAGLAGISL
SFSVSFRYTAV
WVVRMYAYVEMSMNSVERVQEYIEQTPQEPPKYLP
QDPVNSWPSNGVIDVQNICIRYSPELPRVIDNVSF
HVNAGEKIGVVGRTGAGKSTIITSFFRFVDLESGS
IKIDGLDISKIGLKPLRKGLTIIPQDPTLFSGTIR
SNLDIFGEYGDLQMFEALRRVNLISVDDYQRIVDG
NGAAVADETAQARGDNVNKFLDLDSTVSEGGGNLS
QGERQLLCLARSILKMPKILMLDEATASIDYESDA
KIQATIREEFSSSTVLTIAHRLKTIIDYDKILLLD
HGKVKEYDHPYKLITNKKSDFRKMCQDTGEFDDLV
NLAKQAYRK*;

and encoded by the following nucleic acid sequence (SEQ ID NO: 21):

ATGTCTTCACTAGAAGTGGTAGATGGGTGCCCCTA
TGGATACCGACCATATCCAGATAGTGGCACAAATG
CATTAAATCCATGTTTTATATCAGTAATATCCGCC
TGGCAAGCCGTCTTTTTCCTATTGATTGGTAGCTA
TCAATTGTGGAAACTTTATAAGAACAATAAAGTAC
CACCCAGATTTAAGAACTTTCCTACATTACCAAGT
AAAATCAACAGTCGACATCTAACGCATTTGACCAA
TGTTTGCTTTCAGTCCACGCTTATAATTTGTGAAC
TGGCCTTGGTATCCCAATCTAGCGATAGGGTTTAT
CCATTTATACTAAAGAAGGCTCTGTACTTGAATCT
CCTTTTCAATTTGGGTATTTCTCTCCCTACTCAAT
ACTTAGCTTATTTTAAAAGTACATTTTCAATGGGC

-continued

AACCAGCTTTTCTATTACATGTTTCAAATTCTTCT

ACAGCTCTTCTTGATATTGCAGAGGTACTATCATG

GTTCTAGTAACGAAAGGCTTACTGTTATTAGCGGA

CAAACTGCTATGATTTTAGAAGTGCTCCTTCTTTT

CAATTCTGTGGCAATTTTTATTTATGATCTATGCA

TTTTTGAGCCAATTAACGAATTATCTGAATACTAC

AAGAAAAATGGGTGGTATCCCCCCGTTCATGTACT

ATCCTATATTACATTTATCTGGATGAACAAACTGA

TTGTGGAAACTTACCGTAACAAGAAAATCAAAGAT

CCTAACCAGTTACCATTGCCGCCAGTAGATCTGAA

TATTAAGTCGATAAGTAAGGAATTTAAGGCTAACT

GGGAATTGGAAAAATGGTTGAATAGAAATTCTCTT

TGGAGGGCCATTTGGAAGTCATTTGGTAGGACTAT

TTCTGTGGCTATGCTGTATGAAACGACATCTGATT

TACTTTCTGTAGTACAGCCCCAGTTTCTACGGATA

TTCATAGATGGTTTGAACCCGGAAACATCTTCTAA

ATATCCTCCTTTAAATGGTGTATTTATTGCTCTAA

CCCTTTTCGTAATCAGCGTGGTTTCTGTGTTCCTC

ACCAATCAATTTTATATTGGAATTTTTGAGGCTGG

TTTGGGGATAAGAGGCTCTTTAGCTTCTTTAGTGT

ATCAGAAGTCCTTAAGATTGACGCTAGCAGAGCGT

AACGAAAAATCTACTGGTGACATCTTAAATTTGAT

GTCTGTGGATGTGTTAAGGATCCAGCGGTTTTTCG

AAAATGCCCAAACCATTATTGGCGCTCCTATTCAG

ATTATTGTTGTATTAACTTCCCTGTACTGGTTGCT

AGGAAAGGCTGTTATTGGAGGGTTGGTTACTATGG

CTATTATGATGCCTATCAATGCCTTCTTATCTAGA

AAGGTAAAAAAGCTATCAAAAACTCAAATGAAGTA

TAAGGACATGAGAATCAAGACTATTACAGAGCTTT

TGAATGCTATAAAATCTATTAAATTATACGCCTGG

GAGGAACCTATGATGGCAAGATTGAATCATGTTCG

TAATGATATGGAGTTGAAAAATTTTCGGAAAATTG

GTATAGTGAGCAATCTGATATATTTTGCGTGGAAT

TGTGTACCTTTAATGGTGACATGTTCCACATTTGG

CTTATTTTCTTTATTTAGTGATTCTCCGTTATCTC

CTGCCATTGTCTTCCCTTCATTATCTTTATTTAAT

ATTTTGAACAGTGCCATCTATTCCGTTCCATCCAT

GATAAATACCATTATAGAGACAAGCGTTTCTATGG

AAAGATTAAAGTCATTCCTACTTAGTGACGAAATT

GATGATTCGTTCATCGAACGTATTGATCCTTCAGC

GGATGAAAGAGCGTTACCTGCTATAGAGATGAATA

-continued

ATATTACATTTTTATGGAAATCAAAAGAAGTATTA

ACATCTAGCCAATCTGGAGATAATTTGAGGACAGA

TGAAGAGTCTATTATCGGATCTTCTCAAATTGCGT

TGAAGAATATCGATCATTTTGAAGCAAAAAGGGGT

GATTTAGTTTGTGTTGTTGGTCGGGTAGGAGCTGG

TAAATCAACATTTTTGAAGGCAATTCTTGGTCAAC

TTCCTTGCATGAGTGGTTCTAGGGACTCGATACCA

CCTAAACTGATCATTAGATCATCGTCTGTAGCCTA

CTGTTCACAAGAATCCTGGATAATGAACGCATCTG

TAAGAGAAAACATTCTATTTGGTCACAAGTTCGAC

CAAGATTATTATGACCTCACTATTAAAGCATGTCA

ATTGCTACCCGATTTGAAAATACTACCAGATGGTG

ATGAAACTTTGGTAGGTGAAAAGGGCATTTCCCTA

TCAGGCGGTCAGAAGGCCCGTCTTTCATTAGCCAG

AGCGGTGTACTCGAGAGCAGATATTTATTTGTTGG

ATGACATTTTATCTGCTGTTGATGCAGAAGTTAGT

AAAAATATTATTGAATATGTTTTGATCGGAAAGAC

GGCTTTATTAAAAAATAAAACAATTATTTTAACTA

CCAATACTGTATCAATTTTAAAACATTCGCAGATG

ATATATGCGCTAGAAAACGGTGAAATTGTTGAACA

AGGGAATTATGAGGATGTAATGAACCGTAAGAACA

ATACTTCAAAACTGAAAAAATTACTAGAGGAATTT

GATTCTCCGATTGATAATGGAAATGAAAGCGATGT

CCAAACTGAACACCGATCCGAAAGTGAAGTGGATG

AACCTCTGCAGCTTAAAGTAACTGAATCAGAAACT

GAGGATGAGGTTGTTACTGAGAGTGAATTAGAACT

AATCAAAGCCAATTCTAGAAGAGCTTCTCTAGCTA

CGCTAAGACCTAGACCCTTTGTGGGAGCACAATTG

GATTCCGTGAAGAAAACGGCGCAAAAGGCCGAGAA

GACAGAGGTGGGAAGAGTCAAAACAAAGATTTATC

TTGCGTATATTAAGGCTTGTGGAGTTTTAGGTGTT

GTTTTATTTTTCTTGTTTATGATATTAACAAGGGT

TTTCGACTTAGCAGAGAATTTTTGGTTAAAGTACT

GGTCAGAATCTAATGAAAAAAATGGTTCAAATGAA

AGGGTTTGGATGTTTGTTGGTGTGTATTCCTTAAT

CGGAGTAGCATCGGCCGCATTCAATAATTTACGGA

GTATTATGATGCTACTGTATTGTTCTATTAGGGGT

TCTAAGAAACTGCATGAAAGCATGGCCAAATCTGT

AATTAGAAGTCCTATGACTTTCTTTGAGACTACAC

CAGTTGGAAGGATCATAAACAGGTTCTCATCTGAT

-continued

ATGGATGCAGTGGACAGTAATCTACAGTACATTTT

CTCCTTTTTTTTCAAATCAATACTAACCTATTTGG

TTACTGTTATATTAGTCGGGTACAATATGCCATGG

TTTTTAGTGTTCAATATGTTTTTGGTGGTTATCTA

TATTTACTATCAAACATTTTACATTGTGCTATCTA

GGGAGCTAAAAAGATTGATCAGTATATCTTACTCT

CCGATTATGTCCTTAATGAGTGAGAGCTTGAACGG

TTATTCTATTATTGATGCATACGATCATTTTGAGA

GATTCATCTATCTAAATTATGAAAAAATCCAATAC

AACGTTGATTTTGTCTTCAACTTTAGATCAACGAA

TAGATGGTTATCCGTGAGATTGCAAACTATTGGTG

CTACAATTGTTTTGGCTACTGCAATCTTAGCACTA

GCAACAATGAATACTAAAAGGCAACTAAGTTCGGG

TATGGTTGGTCTACTAATGAGCTATTCATTAGAGG

TTACAGGTTCATTGACTTGGATTGTAAGGACAACT

GTGACGATTGAAACCAACATTGTATCAGTGGAGAG

AATTGTTGAGTACTGCGAATTACCACCTGAAGCAC

AGTCCATTAACCCTGAAAAGAGGCCAGATGAAAAT

TGGCCATCAAAGGGTGGTATTGAATTCAAAAACTA

TTCCACAAAATACAGAGAAAATTTGGATCCAGTGC

TGAATAATATTAACGTGAAGATTGAGCCATGTGAA

AAGGTTGGGATTGTTGGCAGAACAGGTGCAGGGAA

GTCTACACTGAGCCTGGCATTATTTAGAATACTAG

AACCTACCGAAGGTAAAATTATTATTGACGGCATT

GATATATCCGACATAGGTCTGTTCGATTTAAGAAG

CCATTTGGCAATTATTCCTCAGGATGCACAAGCTT

TTGAAGGTACAGTAAAGACCAATTTGGACCCTTTC

AATCGTTATTCAGAAGATGAACTTAAAAGGGCTGT

TGAGCAGGCACATTTAAAGCCTCATCTGGAAAAAA

TGCTGCACAGTAAACCAAGAGGTGATGATTCTAAT

GAAGAGGATGGCAATGTTAATGATATTCTGGATGT

CAAGATTAATGAGAACGGTAGTAACTTGTCAGTGG

GGCAAAGACAACTACTATGTTTGGCAAGAGCGCTG

CTAAACCGTTCCAAAATATTGGTCCTTGATGAAGC

AACGGCTTCTGTGGATATGGAAACCGATAAAATTA

TCCAAGACACTATAAGAAGAGAATTTAAGGACCGT

ACCATCTTAACAATTGCACATCGTATCGACACTGT

ATTGGACAGTGATAAGATAATTGTTCTTGACCAGG

GTAGTGTGAGGGAATTCGATTCACCCTCGAAATTG

TTATCCGATAAAACGTCTATTTTTTACAGTCTTTG

TGAGAAAGGTGGGTATTTGAAATAA.

As used herein, the term "T4_Fungal_10" refers to an ABC-transporter having the following amino acid sequence (SEQ ID NO: 3):

MGQSERAALIAFASRNTTECWLCRDKEGFGPISYY

GDFTVCFIDGVLLNFAALFMLIFGTYQVVKLSKKE

HPGIKYRRDWLLFSRITLVGCFLLFTSMAAYYSSE

KHESIALTSQYTLTLMSIFVALMLHWVEYHRSRIS

NGIVLFYWLFETLFQGSKWVNFSIRHAYNLNHEWP

VSYSVYILTIFQTISAFMILILEAGFEKPLPSYQR

VIESYSKQKRNPVDNSHIFQRLSFSWMTELMKTGY

KKYLTEQDLYKLPKSFGAKEISHKFSERWQYQLKH

KANPSLAWALLSTFGGKILLGGIFKVAYDILQFTQ

PQLLRILIKFVSDYTSTPEPQLPLVRGVMLSIAMF

VVSVVQTSILHQYFLNAFDTGMHIKSGMTSVIYQK

ALVLSSEASASSSTGDIVNLMSVDVQRLQDLTQWG

QIIWSGPFQIILCLVSLYKLLGPCMWVGVIIMIIM

IPINSVIVRIQKKLQKIQMKNKDERTRVTSEILNN

IKSLKVYGWEIPYKAKLDHVRNDKELKNLKKMGCT

LALASFQFNIVPFLVSCSTFAVFVFTEDRPLSTDL

VFPALTLFNLLSFPLAVVPNAISSFIEASVSVNRL

YAFLTNEELQTDAVHREPKVNNIGDEGVKVSDATF

LWQRKPEYKVALKNINFSAKKGELTCIVGKVGSGK

SALIQSLLGDLIRVKGYAAVHGSVAYVSQVAWIMN

GTVKDNIIFGHKYDPEFYELTIKACALAIDLSMLP

DGDQTLVGEKGISLSGGQKARLSLARAVYARADTY

LLDDPLAAVDEHVAKHLIEHVLGPHGLLHSKTKVL

ATNKISVLSIADSITLMENGEIIQQGTYEETNNTT

DSPLSKLISEFGKKGKATPSQSTTSLTKLATSDLG

SSSDSKVSDVSIDVSQLDTENLTEAEELKSLRRAS

MATLGSIGFDDDENIARREHREQGKVKWDIYMEYA

RACNPRSVCVFLFFIVLSMLLSVLGNFWLKHWSEV

NTGEGYNPHAARYLLIYFALGVGSALATLIQTIVL

WVFCTIHGSRYLHDAMATSVLKAPMSFFETTPIGR

ILNRFSNDIYKVDEVLGRTFSQFFANVVKVSFTII

VICMATWQFIFIILPLSVLYIYYQQYYLRTSR

ELRRLDSVTRSPIYA

HFQETLGGLTTIRGYSQQTRFVHINQTRVDNNMSA

FYPSVNANRWLAFRLEFIGSIIILGSSMLAVIRLG

NGTLTAGMIGLSLSFALQITQSLNWIVRMTVEVET

NIVSVERIKEYAELKSEAPYIIEDHRPPASWPEKG

DVKFVNYSTRYRPELELILKDINLHILPKEKIGIV

GRTGAGKSSLTLALFRIIEAASGHIIIDGIPIDSI

-continued

GLADLRHRLSIIPQDSQIFEGTIRENIDPSKQYTD

EQIWDALELSHLKNHVKNMGPDGLETMLSEGGGNL

SVGQRQLMCLARALLISSKILVLDEATAAVDVETD

QLIQKTIREAFKERTILTIAHRINTIMDSDRIIVL

DKGRVTEFDTPANLLNKKDSIFYSLCVEAGLAE*;

and encoded by the following nucleic acid sequence (SEQ ID NO: 22):

ATGTCTTCACTAGAAGTGGTAGATGGTGCCCCTA

TGGATACCGACCATATCCAGATAGTGGCACAAATG

CATTAAATCCATGTTTTATATCAGTAATATCCGCC

TGGCAAGCCGTCTTTTTCCTATTGATTGGTAGCTA

TCAATTGTGGAAACTTTATAAGAACAATAAAGTAC

CACCCAGATTTAAGAACTTTCCTACATTACCAAGT

AAAATCAACAGTCGACATCTAACGCATTTGACCAA

TGTTTGCTTTCAGTCCACGCTTATAATTTGTGAAC

TGGCCTTGGTATCCCAATCTAGCGATAGGGTTTAT

CCATTTATACTAAAGAAGGCTCTGTACTTGAATCT

CCTTTTCAATTTGGGTATTTCTCTCCCTACTCAAT

ACTTAGCTTATTTTAAAAGTACATTTTCAATGGGC

AACCAGCTTTTCTATTACATGTTTCAAATTCTTCT

ACAGCTCTTCTTGATATTGCAGAGGTACTATCATG

GTTCTAGTAACGAAAGGCTTACTGTTATTAGCGGA

CAAACTGCTATGATTTTAGAAGTGCTCCTTCTTTT

CAATTCTGTGGCAATTTTTATTTATGATCTATGCA

TTTTTGAGCCAATTAACGAATTATCTGAATACTAC

AAGAAAAATGGGTGGTATCCCCCCGTTCATGTACT

ATCCTATATTACATTTATCTGGATGAACAAACTGA

TTGTGGAAACTTACCGTAACAAGAAAATCAAAGAT

CCTAACCAGTTACCATTGCCGCCAGTAGATCTGAA

TATTAAGTCGATAAGTAAGGAATTTAAGGCTAACT

GGGAATTGGAAAAATGGTTGAATAGAAATTCTCTT

TGGAGGGCCATTTGGAAGTCATTTGGTAGGACTAT

TTCTGTGGCTATGCTGTATGAAACGACATCTGATT

TACTTTCTGTAGTACAGCCCCAGTTTCTACGGATA

TTCATAGATGGTTTGAACCCGGAAACATCTTCTAA

ATATCCTCCTTTAAATGGTGTATTTATTGCTCTAA

CCCTTTTCGTAATCAGCGTGGTTTCTGTGTTCCTC

ACCAATCAATTTTATATTGGAATTTTTGAGGCTGG

TTTGGGGATAAGAGGCTCTTTAGCTTCTTTAGTGT

ATCAGAAGTCCTTAAGATTGACGCTAGCAGAGCGT

AACGAAAAATCTACTGGTGACATCTTAAATTTGAT

-continued

GTCTGTGGATGTGTTAAGGATCCAGCGGTTTTTCG

AAAATGCCCAAACCATTATTGGCGCTCCTATTCAG

ATTATTGTTGTATTAACTTCCCTGTACTGGTTGCT

AGGAAAGGCTGTTATTGGAGGGTTGGTTACTATGG

CTATTATGATGCCTATCAATGCCTTCTTATCTAGA

AAGGTAAAAAAGCTATCAAAAACTCAAATGAAGTA

TAAGGACATGAGAATCAAGACTATTACAGAGCTTT

TGAATGCTATAAAATCTATTAAATTATACGCCTGG

GAGGAACCTATGATGGCAAGATTGAATCATGTTCG

TAATGATATGGAGTTGAAAAATTTTCGGAAAATTG

GTATAGTGAGCAATCTGATATATTTTGCGTGGAAT

TGTGTACCTTTAATGGTGACATGTTCCACATTTGG

CTTATTTTCTTTATTTAGTGATTCTCCGTTATCTC

CTGCCATTGTCTTCCCTTCATTATCTTTATTTAAT

ATTTTGAACAGTGCCATCTATTCCGTTCCATCCAT

GATAAATACCATTATAGAGACAAGCGTTTCTATGG

AAAGATTAAAGTCATTCCTACTTAGTGACGAAATT

GATGATTCGTTCATCGAACGTATTGATCCTTCAGC

GGATGAAAGAGCGTTACCTGCTATAGAGATGAATA

ATATTACATTTTTATGGAAATCAAAAGAAGTATTA

ACATCTAGCCAATCTGGAGATAATTTGAGGACAGA

TGAAGAGTCTATTATCGGATCTTCTCAAATTGCGT

TGAAGAATATCGATCATTTTGAAGCAAAAAGGGGT

GATTTAGTTTGTGTTGTTGGTCGGGTAGGAGCTGG

TAAATCAACATTTTTGAAGGCAATTCTTGGTCAAC

TTCCTTGCATGAGTGGTTCTAGGGACTCGATACCA

CCTAAACTGATCATTAGATCATCGTCTGTAGCCTA

CTGTTCACAAGAATCCTGGATAATGAACGCATCTG

TAAGAGAAAACATTCTATTTGGTCACAAGTTCGAC

CAAGATTATTATGACCTCACTATTAAAGCATGTCA

ATTGCTACCCGATTTGAAAATACTACCAGATGGTG

ATGAAACTTTGGTAGGTGAAAAGGGCATTTCCCTA

TCAGGCGGTCAGAAGGCCCGTCTTTCATTAGCCAG

AGCGGTGTACTCGAGAGCAGATATTTATTTGTTGG

ATGACATTTTATCTGCTGTTGATGCAGAAGTTAGT

AAAAATATTATTGAATATGTTTTGATCGGAAAGAC

GGCTTTATTAAAAAAATAAAACAATTATTTTAACTA

CCAATACTGTATCAATTTTAAAACATTCGCAGATG

ATATATGCGCTAGAAAACGGTGAAATTGTTGAACA

AGGGAATTATGAGGATGTAATGAACCGTAAGAACA

ATACTTCAAAACTGAAAAAATTACTAGAGGAATTT

-continued

GATTCTCCGATTGATAATGGAAATGAAAGCGATGT
CCAAACTGAACACCGATCCGAAAGTGAAGTGGATG
AACCTCTGCAGCTTAAAGTAACTGAATCAGAAACT
GAGGATGAGGTTGTTACTGAGAGTGAATTAGAACT
AATCAAAGCCAATTCTAGAAGAGCTTCTCTAGCTA
CGCTAAGACCTAGACCCTTTGTGGGAGCACAATTG
GATTCCGTGAAGAAAACGGCGCAAAAGGCCGAGAA
GACAGAGGTGGGAAGAGTCAAAACAAAGATTTATC
TTGCGTATATTAAGGCTTGTGGAGTTTTAGGTGTT
GTTTTATTTTTCTTGTTTATGATATTAACAAGGGT
TTTCGACTTAGCAGAGAATTTTTGGTTAAAGTACT
GGTCAGAATCTAATGAAAAAAATGGTTCAAATGAA
AGGGTTTGGATGTTTGTTGGTGTGTATTCCTTAAT
CGGAGTAGCATCGGCCGCATTCAATAATTTACGGA
GTATTATGATGCTACTGTATTGTTCTATTAGGGGT
TCTAAGAAACTGCATGAAAGCATGGCCAAATCTGT
AATTAGAAGTCCTATGACTTTCTTTGAGACTACAC
CAGTTGGAAGGATCATAAACAGGTTCTCATCTGAT
ATGGATGCAGTGGACAGTAATCTACAGTACATTTT
CTCCTTTTTTTTCAAATCAATACTAACCTATTTGG
TTACTGTTATATTAGTCGGGTACAATATGCCATGG
TTTTTAGTGTTCAATATGTTTTTGGTGGTTATCTA
TATTTACTATCAAACATTTTACATTGTGCTATCTA
GGGAGCTAAAAAGATTGATCAGTATATCTTACTCT
CCGATTATGTCCTTAATGAGTGAGAGCTTGAACGG
TTATTCTATTATTGATGCATACGATCATTTTGAGA
GATTCATCTATCTAAATTATGAAAAAATCCAATAC
AACGTTGATTTTGTCTTCAACTTTAGATCAACGAA
TAGATGGTTATCCGTGAGATTGCAAACTATTGGTG
CTACAATTGTTTTGGCTACTGCAATCTTAGCACTA
GCAACAATGAATACTAAAAGGCAACTAAGTTCGGG
TATGGTTGGTCTACTAATGAGCTATTCATTAGAGG
TTACAGGTTCATTGACTTGGATTGTAAGGACAACT
GTGACGATTGAAACCAACATTGTATCAGTGGAGAG
AATTGTTGAGTACTGCGAATTACCACCTGAAGCAC
AGTCCATTAACCCTGAAAAGAGGCCAGATGAAAAT
TGGCCATCAAAGGGTGGTATTGAATTCAAAAACTA
TTCCACAAAATACAGAGAAAATTTGGATCCAGTGC
TGAATAATATTAACGTGAAGATTGAGCCATGTGAA
AAGGTTGGGATTGTTGGCAGAACAGGTGCAGGGAA

-continued

GTCTACACTGAGCCTGGCATTATTTAGAATACTAG
AACCTACCGAAGGTAAAATTATTATTGACGGCATT
GATATATCCGACATAGGTCTGTTCGATTTAAGAAG
CCATTTGGCAATTATTCCTCAGGATGCACAAGCTT
TTGAAGGTACAGTAAAGACCAATTTGGACCCTTTC
AATCGTTATTCAGAAGATGAACTTAAAAGGGCTGT
TGAGCAGGCACATTTAAAGCCTCATCTGGAAAAAA
TGCTGCACAGTAAACCAAGAGGTGATGATTCTAAT
GAAGAGGATGGCAATGTTAATGATATTCTGGATGT
CAAGATTAATGAGAACGGTAGTAACTTGTCAGTGG
GGCAAAGACAACTACTATGTTTGGCAAGAGCGCTG
CTAAACCGTTCCAAAATATTGGTCCTTGATGAAGC
AACGGCTTCTGTGGATATGGAAACCGATAAAATTA
TCCAAGACACTATAAGAAGAGAATTTAAGGACCGT
ACCATCTTAACAATTGCACATCGTATCGACACTGT
ATTGGACAGTGATAAGATAATTGTTCTTGACCAGG
GTAGTGTGAGGGAATTCGATTCACCCTCGAAATTG
TTATCCGATAAAACGTCTATTTTTTACAGTCTTTG
TGAGAAAGGTGGGTATTTGAAATAA.

As used herein, the term “T4_Fungal_2” refers to an ABC-transporter having the following amino acid sequence (SEQ ID NO: 4):

MSSLEVVDGCPYGYRPYPDSGTNALNPCFISVISA
WQAVFFLLIGSYQLWKLYKNNKVPPRFKNFPTLPS
KINSRHLTHLTNVCFQSTLIICELALVSQSSDRVY
PFILKKALYLNLLFNLGISLPTQYLAYFKSTFSMG
NQLFYYMFQILLQLFLILQRYYHGSSNERLTVISG
QTAMILEVLLLFNSVAIFIYDLCIFEPINELSEYY
KKNGWYPPVHVLSYITFIWMNKLIVETYRNKKIKD
PNQLPLPPVDLNIKSISKEFKANWELEKWLNRNSL
WRAIWKSFGRTISVAMLYETTSDLLSVVQPQFLRI
FIDGFNPETSSKYPPLNGVFIALTLFVISVVSVFL
TNQFYIGIFEAGLGIRGSLASLVYQKSLRLTLAER
NEKSTGDILNLMSVDVLRIQRFFENAQTIIGAPIQ
IIVVLTSLYWLLGKAVVGGLVTMAIMMPINAFLSR
KVKKLSKTQMKYKDMRIKTITELLNAIKSIKLYAW
EEPMMARLNHVRNDMELKNFRKIGIVSNLIYFAWN
CVPLMVTCSTFGLFSLFSDSPLSPAIVFPSLSLFN
ILNSAIYSVPSMINTIIETSVSMERLKSFLLSDEI
DDSFIERIDPSADERALPAIEMNNITFLWKSKEVL

-continued

ASSQSGDNLRTDEESIIGSSQIALKNIDHFEAKRG

DLVCVVGRVGAGKSTFLKAILGQLPCMSGSRDSIP

PKLIIRSSSVAYCSQESWIMNASVRENILFGHKFD

QNYYDLTIKACQLLPDLKILPDGDETLVGEKGISL

SGGQKARLSLARAVYSRADIYLLDDILSAVDAEVS

KNIIEYVLIGKTALLKNKTIILTTNTVSILKHSQM

IYALENGEIVEQGNYEDVMNRKNNTSKLKKLLEEF

DSPIDNGNESDVQTEHRSESEVDEPLQLKVTESET

EDEVVTESELELIKANSRRASLATLRPRPFVGAQL

DSVKKTAQEAEKTEVGRVKTKVYLAYIKACGVLGV

VLFFLFMILTRVFDLAENFWLKYWSESNEKNGSNE

RVWMFVGVYSLIGVASAAFNNLRSIMMLLYCSIRG

SKKLHESMAKSVIRSPMTFFETTPVGRIINRFSSD

MDAVDSNLQYIFSFFFKSILTYLVTVILVGYNMPW

FLVFNMFLVVIYIYYQTFYIVLSRELKRLISISYS

PIMSLMSESLNGYSIIDAYDHFERFIYLNYEKIQY

NVDFVFNFRSTNRWLSVRLQTIGATIVLATAILAL

ATMNTKRQLSSGMVGLLMSYSLEVTGSLTWIVRTT

VMIETNIVSVERIVEYCELPPEAQSINPEKRPDEN

WPSKGGIEFKNYSTKYRENLDPVLNNINVKIEPCE

KVGIVGRTGAGKSTLSLALFRILEPTEGKIIIDGI

GISDIGLFDLRSHLAIIPQDAQAFEGTVKTNLDPF

NRYSEDELKRAVEQAHLKPHLEKMLHSKPRGDDSN

EEDGNVNDILDVKINENGSNLSVGQRQLLCLARAL

LNRSKILVLDEATASVDMETDKIIQDTIRREFKDR

TILTIAHRIDTVLDSDKIIVLDQGSVREFDSPSKL

LSDKTSIFYSLCEKGGYLK*;

and
encoded by the following nucleic
acid sequence (SEQ ID NO: 23):

ATGTCTTCACTAGAAGTGGTAGATGGGTGCCCCTA

TGGATACCGACCATATCCAGATAGTGGCACAAATG

CATTAAATCCATGTTTTATATCAGTAATATCCGCC

TGGCAAGCCGTCTTTTTCCTATTGATTGGTAGCTA

TCAATTGTGGAAACTTTATAAGAACAATAAAGTAC

CACCCAGATTTAAGAACTTTCCTACATTACCAAGT

AAAATCAACAGTCGACATCTAACGCATTTGACCAA

TGTTTGCTTTCAGTCCACGCTTATAATTTGTGAAC

TGGCCTTGGTATCCCAATCTAGCGATAGGGTTTAT

CCATTTATACTAAAGAAGGCTCTGTACTTGAATCT

CCTTTTCAATTTGGGTATTTCTCTCCCTACTCAAT

ACTTAGCTTATTTTAAAAGTACATTTTCAATGGGC

-continued

AACCAGCTTTTCTATTACATGTTTCAAATTCTTCT

ACAGCTCTTCTTGATATTGCAGAGGTACTATCATG

GTTCTAGTAACGAAAGGCTTACTGTTATTAGCGGA

CAAACTGCTATGATTTTAGAAGTGCTCCTTCTTTT

CAATTCTGTGGCAATTTTTATTTATGATCTATGCA

TTTTTGAGCCAATTAACGAATTATCTGAATACTAC

AAGAAAAATGGGTGGTATCCCCCCGTTCATGTACT

ATCCTATATTACATTTATCTGGATGAACAAACTGA

TTGTGGAAACTTACCGTAACAAGAAAATCAAAGAT

CCTAACCAGTTACCATTGCCGCCAGTAGATCTGAA

TATTAAGTCGATAAGTAAGGAATTTAAGGCTAACT

GGGAATTGGAAAAATGGTTGAATAGAAATTCTCTT

TGGAGGGCCATTTGGAAGTCATTTGGTAGGACTAT

TTCTGTGGCTATGCTGTATGAAACGACATCTGATT

TACTTTCTGTAGTACAGCCCCAGTTTCTACGGATA

TTCATAGATGGTTTGAACCCGGAAACATCTTCTAA

ATATCCTCCTTTAAATGGTGTATTTATTGCTCTAA

CCCTTTTCGTAATCAGCGTGGTTTCTGTGTTCCTC

ACCAATCAATTTTATATTGGAATTTTTGAGGCTGG

TTTGGGGATAAGAGGCTCTTTAGCTTCTTTAGTGT

ATCAGAAGTCCTTAAGATTGACGCTAGCAGAGCGT

AACGAAAAATCTACTGGTGACATCTTAAATTTGAT

GTCTGTGGATGTGTTAAGGATCCAGCGGTTTTTCG

AAAATGCCCAAACCATTATTGGCGCTCCTATTCAG

ATTATTGTTGTATTAACTTCCCTGTACTGGTTGCT

AGGAAAGGCTGTTATTGGAGGGTTGGTTACTATGG

CTATTATGATGCCTATCAATGCCTTCTTATCTAGA

AAGGTAAAAAAGCTATCAAAAACTCAAATGAAGTA

TAAGGACATGAGAATCAAGACTATTACAGAGCTTT

TGAATGCTATAAAATCTATTAAATTATACGCCTGG

GAGGAACCTATGATGGCAAGATTGAATCATGTTCG

TAATGATATGGAGTTGAAAAATTTTCGGAAAATTG

GTATAGTGAGCAATCTGATATATTTTGCGTGGAAT

TGTGTACCTTTAATGGTGACATGTTCCACATTTGG

CTTATTTTCTTTATTTAGTGATTCTCCGTTATCTC

CTGCCATTGTCTTCCCTTCATTATCTTTATTTAAT

ATTTTGAACAGTGCCATCTATTCCGTTCCATCCAT

GATAAATACCATTATAGAGACAAGCGTTTCTATGG

AAAGATTAAAGTCATTCCTACTTAGTGACGAAATT

GATGATTCGTTCATCGAACGTATTGATCCTTCAGC

GGATGAAAGAGCGTTACCTGCTATAGAGATGAATA

-continued

ATATTACATTTTTATGGAAATCAAAAGAAGTATTA
ACATCTAGCCAATCTGGAGATAATTTGAGGACAGA
TGAAGAGTCTATTATCGGATCTTCTCAAATTGCGT
TGAAGAATATCGATCATTTTGAAGCAAAAAGGGGT
GATTTAGTTTGTGTTGTTGGTCGGGTAGGAGCTGG
TAAATCAACATTTTTGAAGGCAATTCTTGGTCAAC
TTCCTTGCATGAGTGGTTCTAGGGACTCGATACCA
CCTAAACTGATCATTAGATCATCGTCTGTAGCCTA
CTGTTCACAAGAATCCTGGATAATGAACGCATCTG
TAAGAGAAAACATTCTATTTGGTCACAAGTTCGAC
CAAGATTATTATGACCTCACTATTAAAGCATGTCA
ATTGCTACCCGATTTGAAAATACTACCAGATGGTG
ATGAAACTTTGGTAGGTGAAAAGGGCATTTCCCTA
TCAGGCGGTCAGAAGGCCCGTCTTTCATTAGCCAG
AGCGGTGTACTCGAGAGCAGATATTTATTTGTTGG
ATGACATTTTATCTGCTGTTGATGCAGAAGTTAGT
AAAAATATTATTGAATATGTTTTGATCGGAAAGAC
GGCTTTATTAAAAAATAAAACAATTATTTTAACTA
CCAATACTGTATCAATTTTAAAACATTCGCAGATG
ATATATGCGCTAGAAAACGGTGAAATTGTTGAACA
AGGGAATTATGAGGATGTAATGAACCGTAAGAACA
ATACTTCAAAACTGAAAAAATTACTAGAGGAATTT
GATTCTCCGATTGATAATGGAAATGAAAGCGATGT
CCAAACTGAACACCGATCCGAAAGTGAAGTGGATG
AACCTCTGCAGCTTAAAGTAACTGAATCAGAAACT
GAGGATGAGGTTGTTACTGAGAGTGAATTAGAACT
AATCAAAGCCAATTCTAGAAGAGCTTCTCTAGCTA
CGCTAAGACCTAGACCCTTTGTGGGAGCACAATTG
GATTCCGTGAAGAAAACGGCGCAAAAGGCCGAGAA
GACAGAGGTGGGAAGAGTCAAAACAAAGATTTATC
TTGCGTATATTAAGGCTTGTGGAGTTTTAGGTGTT
GTTTTATTTTTCTTGTTTATGATATTAACAAGGGT
TTTCGACTTAGCAGAGAATTTTTGGTTAAAGTACT
GGTCAGAATCTAATGAAAAAAATGGTTCAAATGAA
AGGGTTTGGATGTTTGTTGGTGTGTATTCCTTAAT
CGGAGTAGCATCGGCCGCATTCAATAATTTACGGA
GTATTATGATGCTACTGTATTGTTCTATTAGGGGT
TCTAAGAAACTGCATGAAAGCATGGCCAAATCTGT
AATTAGAAGTCCTATGACTTTCTTTGAGACTACAC
CAGTTGGAAGGATCATAAACAGGTTCTCATCTGAT

-continued

ATGGATGCAGTGGACAGTAATCTACAGTACATTTT
CTCCTTTTTTTTCAAATCAATACTAACCTATTTGG
TTACTGTTATATTAGTCGGGTACAATATGCCATGG
TTTTTAGTGTTCAATATGTTTTTGGTGGTTATCTA
TATTTACTATCAAACATTTTACATTGTGCTATCTA
GGGAGCTAAAAAGATTGATCAGTATATCTTACTCT
CCGATTATGTCCTTAATGAGTGAGAGCTTGAACGG
TTATTCTATTATTGATGCATACGATCATTTTGAGA
GATTCATCTATCTAAATTATGAAAAAATCCAATAC
AACGTTGATTTTGTCTTCAACTTTAGATCAACGAA
TAGATGGTTATCCGTGAGATTGCAAACTATTGGTG
CTACAATTGTTTTGGCTACTGCAATCTTAGCACTA
GCAACAATGAATACTAAAAGGCAACTAAGTTCGGG
TATGGTTGGTCTACTAATGAGCTATTCATTAGAGG
TTACAGGTTCATTGACTTGGATTGTAAGGACAACT
GTGACGATTGAAACCAACATTGTATCAGTGGAGAG
AATTGTTGAGTACTGCGAATTACCACCTGAAGCAC
AGTCCATTAACCCTGAAAAGAGGCCAGATGAAAAT
TGGCCATCAAAGGGTGGTATTGAATTCAAAAACTA
TTCCACAAAATACAGAGAAAATTTGGATCCAGTGC
TGAATAATATTAACGTGAAGATTGAGCCATGTGAA
AAGGTTGGGATTGTTGGCAGAACAGGTGCAGGGAA
GTCTACACTGAGCCTGGCATTATTTAGAATACTAG
AACCTACCGAAGGTAAAATTATTATTGACGGCATT
GATATATCCGACATAGGTCTGTTCGATTTAAGAAG
CCATTTGGCAATTATTCCTCAGGATGCACAAGCTT
TTGAAGGTACAGTAAAGACCAATTTGGACCCTTTC
AATCGTTATTCAGAAGATGAACTTAAAAGGGCTGT
TGAGCAGGCACATTTAAAGCCTCATCTGGAAAAAA
TGCTGCACAGTAAACCAAGAGGTGATGATTCTAAT
GAAGAGGATGGCAATGTTAATGATATTCTGGATGT
CAAGATTAATGAGAACGGTAGTAACTTGTCAGTGG
GGCAAAGACAACTACTATGTTTGGCAAGAGCGCTG
CTAAACCGTTCCAAAATATTGGTCCTTGATGAAGC
AACGGCTTCTGTGGATATGGAAACCGATAAAATTA
TCCAAGACACTATAAGAAGAGAATTTAAGGACCGT
ACCATCTTAACAATTGCACATCGTATCGACACTGT
ATTGGACAGTGATAAGATAATTGTTCTTGACCAGG
GTAGTGTGAGGGAATTCGATTCACCCTCGAAATTG
TTATCCGATAAAACGTCTATTTTTTACAGTCTTTG
TGAGAAAGGTGGGTATTTGAAATAA.

As used herein, the term "T4_Fungal_3" refers to an ABC-transporter having the following amino acid sequence (SEQ ID NO: 5):

MNSYNESAPTGCSFWDNDDISPCIRKSLLDSYLPA

AIVVGSLLYLLLIGAQQIKTHRKLYAKDETQPLLE

PANGSPTDYSNTYGTIDYEEEQSTAELTTSQKHFD

ISRLEPLKDDGTPLGLVKYVQRDGWEKVKLILEFV

ILIFQLVIAVVALFVPSLNQEWEGYKLTPIVRVFV

WIFLFALGSIRALNKSGPFPLANISLLYYIVNIVP

SALSFRSVLIHPQNSQLVNYYYSFQFINNTLLFLL

LGSARVFDHPSVLFDTDDGVKPSPENNSNFFEIVT

YSWIDPLIFKAYKTPLQFNDIWGLRIDDYAYFLLR

RFKDLGFTRTFTYKIFYFSKGDLAAQALWASIDSM

LIFGPSLLLKRILEYVDNPGMTSRNMAWLYVLTMF

FIQISDSLVSGRSLYLGRRVCIRMKALIIGEVYAK

ALRRRMTSPEELIEEVDPKDGKAPIADQTSKEESK

STELGGIINLMAVDASKVSELCSYLHFFVNSFFMI

IVAVTLLYRLLGWSALAGSSSILILLPLNYKLASK

IGEFQKEMLGITDNRIQKLNEAFQSIRIIKFFAWE

ENFAKEIMKVRNEEIRYLRYRVIVWTCSAFVWFIT

PTLVTLISFYFYVVFQGKILTTPVAFTALSLFNLL

RSPLDQLSDMLSFMVQSKVSLDRVQKFLEEQESDK

YEQLTHTRGANSPEVGFENATLSWNKGSKNDFQLK

DIDIAFKVGKLNVIIGPTGSGKTSLLLGLLGEMQL

TNGKIFLPGSTPRDELIPNPETGMTEAVAYCSQIA

WLLNDTVKNNIVFAAPFNQQRYDAVIDACGLTRDL

KVLDAGDATEIGEKGITLSGGQKQRVSLARALYSN

ARHVLLDDCLSAVDSHTAAWIYENCITGPLMKDRT

CILVSHNVALTVRDAAWIVAMDNGRVLEQGTCEDL

LSSGSLGHDDLVSTVISSRSQSSVNLKQLNVSDTS

EIHQKLKKIAESDKADQLDEERLSPRGKLIEDETK

SSGAVSWEVYKFYGRAFGGVFIWFVFVAAFAASQG

SNIMQSVWLKIWAAANDKLVSPAFTMSIDRSLNAL

KEGFRASVASVEWSRPLGGEMFRVYGEESSHSSGY

YITIYALIGLSYALISAFRVYVVFMGGIVASNKIF

EDMLTKIFNAKLRFFDSTPIGRIMNRFSKDTESID

QELAPYAEGFIVSVLQCGATILLICIITPGFIVFA

AFIVIIYYYIGALYLASSRELKRYDSITVSPIHQH

FSETLVGVTTIRAYGDERRFMRQNLEKIDNNNRSF

FYLWVANRWLALRVDFVGALVSLLSAAFVMLSIGH

IDAGMAGLSLSYAIAFTQSALWVVRLYSVVEMNMN

SVERLEEYLNIDQEPDREIPDNKPPSSWPETGEIE

-continued

VDDVSLRYAPSLPKVIKNVSFKVEPRSKIGIVGRT

GAGKSTIITAFFRFVDPESGSIKIDGIDITSIGLK

DLRNAVTIIPQDPTLFTGTIRSNLDPFNQYSDAEI

FESLKRVNLVSTDEPTSGSSSDNIEDSNENVNKFL

NLNNTVSEGGSNLSQGQRQLTCLARSLLKSPKIIL

LDEATASIDYNTDSKIQTTIREEFSDSTILTIAHR

LRSIIDYDKILVMDAGRVVEYDDPYKLISDQNSLF

YSMCSNSGELDTLVKLAKEAFIAKRNKK*;

and encoded by the following nucleic acid sequence (SEQ ID NO: 24):

ATGTCTTCACTAGAAGTGGTAGATGGGTGCCCCTA

TGGATACCGACCATATCCAGATAGTGGCACAAATG

CATTAAATCCATGTTTTATATCAGTAATATCCGCC

TGGCAAGCCGTCTTTTTCCTATTGATTGGTAGCTA

TCAATTGTGGAAACTTTATAAGAACAATAAAGTAC

CACCCAGATTTAAGAACTTTCCTACATTACCAAGT

AAAATCAACAGTCGACATCTAACGCATTTGACCAA

TGTTTGCTTTCAGTCCACGCTTATAATTTGTGAAC

TGGCCTTGGTATCCCAATCTAGCGATAGGGTTTAT

CCATTTATACTAAAGAAGGCTCTGTACTTGAATCT

CCTTTTCAATTTGGGTATTTCTCTCCCTACTCAAT

ACTTAGCTTATTTTAAAAGTACATTTTCAATGGGC

AACCAGCTTTTCTATTACATGTTTCAAATTCTTCT

ACAGCTCTTCTTGATATTGCAGAGGTACTATCATG

GTTCTAGTAACGAAAGGCTTACTGTTATTAGCGGA

CAAACTGCTATGATTTTAGAAGTGCTCCTTCTTTT

CAATTCTGTGGCAATTTTTATTTATGATCTATGCA

TTTTTGAGCCAATTAACGAATTATCTGAATACTAC

AAGAAAAATGGGTGGTATCCCCCCGTTCATGTACT

ATCCTATATTACATTTATCTGGATGAACAAACTGA

TTGTGGAAACTTACCGTAACAAGAAAATCAAAGAT

CCTAACCAGTTACCATTGCCGCCAGTAGATCTGAA

TATTAAGTCGATAAGTAAGGAATTTAAGGCTAACT

GGGAATTGGAAAAATGGTTGAATAGAAATTCTCTT

TGGAGGGCCATTTGGAAGTCATTTGGTAGGACTAT

TTCTGTGGCTATGCTGTATGAAACGACATCTGATT

TACTTTCTGTAGTACAGCCCCAGTTTCTACGGATA

TTCATAGATGGTTTGAACCCGGAAACATCTTCTAA

ATATCCTCCTTTAAATGGTGTATTTATTGCTCTAA

CCCTTTTCGTAATCAGCGTGGTTTCTGTGTTCCTC

ACCAATCAATTTTATATTGGAATTTTTGAGGCTGG

-continued

TTTGGGGATAAGAGGCTCTTTAGCTTCTTTAGTGT

ATCAGAAGTCCTTAAGATTGACGCTAGCAGAGCGT

AACGAAAAATCTACTGGTGACATCTTAAATTTGAT

GTCTGTGGATGTGTTAAGGATCCAGCGGTTTTTCG

AAAATGCCCAAACCATTATTGGCGCTCCTATTCAG

ATTATTGTTGTATTAACTTCCCTGTACTGGTTGCT

AGGAAAGGCTGTTATTGGAGGGTTGGTTACTATGG

CTATTATGATGCCTATCAATGCCTTCTTATCTAGA

AAGGTAAAAAAGCTATCAAAAACTCAAATGAAGTA

TAAGGACATGAGAATCAAGACTATTACAGAGCTTT

TGAATGCTATAAAATCTATTAAATTATACGCCTGG

GAGGAACCTATGATGGCAAGATTGAATCATGTTCG

TAATGATATGGAGTTGAAAAATTTTCGGAAAATTG

GTATAGTGAGCAATCTGATATATTTTGCGTGGAAT

TGTGTACCTTTAATGGTGACATGTTCCACATTTGG

CTTATTTTCTTTATTTAGTGATTCTCCGTTATCTC

CTGCCATTGTCTTCCCTTCATTATCTTTATTTAAT

ATTTTGAACAGTGCCATCTATTCCGTTCCATCCAT

GATAAATACCATTATAGAGACAAGCGTTTCTATGG

AAAGATTAAAGTCATTCCTACTTAGTGACGAAATT

GATGATTCGTTCATCGAACGTATTGATCCTTCAGC

GGATGAAAGAGCGTTACCTGCTATAGAGATGAATA

ATATTACATTTTTATGGAAATCAAAAGAAGTATTA

ACATCTAGCCAATCTGGAGATAATTTGAGGACAGA

TGAAGAGTCTATTATCGGATCTTCTCAAATTGCGT

TGAAGAATATCGATCATTTTGAAGCAAAAAGGGGT

GATTTAGTTTGTGTTGTTGGTCGGGTAGGAGCTGG

TAAATCAACATTTTTGAAGGCAATTCTTGGTCAAC

TTCCTTGCATGAGTGGTTCTAGGGACTCGATACCA

CCTAAACTGATCATTAGATCATCGTCTGTAGCCTA

CTGTTCACAAGAATCCTGGATAATGAACGCATCTG

TAAGAGAAAACATTCTATTTGGTCACAAGTTCGAC

CAAGATTATTATGACCTCACTATTAAAGCATGTCA

ATTGCTACCCGATTTGAAAATACTACCAGATGGTG

ATGAAACTTTGGTAGGTGAAAAGGGCATTTCCCTA

TCAGGCGGTCAGAAGGCCCGTCTTTCATTAGCCAG

AGCGGTGTACTCGAGAGCAGATATTTATTTGTTGG

ATGACATTTTATCTGCTGTTGATGCAGAAGTTAGT

AAAAATATTATTGAATATGTTTTGATCGGAAAGAC

GGCTTTATTAAAAAATAAAACAATTATTTTAACTA

CCAATACTGTATCAATTTTAAAACATTCGCAGATG

-continued

ATATATGCGCTAGAAAACGGTGAAATTGTTGAACA

AGGGAATTATGAGGATGTAATGAACCGTAAGAACA

ATACTTCAAAACTGAAAAAATTACTAGAGGAATTT

GATTCTCCGATTGATAATGGAAATGAAAGCGATGT

CCAAACTGAACACCGATCCGAAAGTGAAGTGGATG

AACCTCTGCAGCTTAAAGTAACTGAATCAGAAACT

GAGGATGAGGTTGTTACTGAGAGTGAATTAGAACT

AATCAAAGCCAATTCTAGAAGAGCTTCTCTAGCTA

CGCTAAGACCTAGACCCTTTGTGGGAGCACAATTG

GATTCCGTGAAGAAAACGGCGCAAAAGGCCGAGAA

GACAGAGGTGGGAAGAGTCAAAACAAAGATTTATC

TTGCGTATATTAAGGCTTGTGGAGTTTTAGGTGTT

GTTTTATTTTTCTTGTTTATGATATTAACAAGGGT

TTTCGACTTAGCAGAGAATTTTTGGTTAAAGTACT

GGTCAGAATCTAATGAAAAAAATGGTTCAAATGAA

AGGGTTTGGATGTTTGTTGGTGTGTATTCCTTAAT

CGGAGTAGCATCGGCCGCATTCAATAATTTACGGA

GTATTATGATGCTACTGTATTGTTCTATTAGGGGT

TCTAAGAAACTGCATGAAAGCATGGCCAAATCTGT

AATTAGAAGTCCTATGACTTTCTTTGAGACTACAC

CAGTTGGAAGGATCATAAACAGGTTCTCATCTGAT

ATGGATGCAGTGGACAGTAATCTACAGTACATTTT

CTCCTTTTTTTTCAAATCAATACTAACCTATTTGG

TTACTGTTATATTAGTCGGGTACAATATGCCATGG

TTTTTAGTGTTCAATATGTTTTTGGTGGTTATCTA

TATTTACTATCAAACATTTTACATTGTGCTATCTA

GGGAGCTAAAAAGATTGATCAGTATATCTTACTCT

CCGATTATGTCCTTAATGAGTGAGAGCTTGAACGG

TTATTCTATTATTGATGCATACGATCATTTTGAGA

GATTCATCTATCTAAATTATGAAAAAATCCAATAC

AACGTTGATTTTGTCTTCAACTTTAGATCAACGAA

TAGATGGTTATCCGTGAGATTGCAAACTATTGGTG

CTACAATTGTTTTGGCTACTGCAATCTTAGCACTA

GCAACAATGAATACTAAAAGGCAACTAAGTTCGGG

TATGGTTGGTCTACTAATGAGCTATTCATTAGAGG

TTACAGGTTCATTGACTTGGATTGTAAGGACAACT

GTGACGATTGAAACCAACATTGTATCAGTGGAGAG

AATTGTTGAGTACTGCGAATTACCACCTGAAGCAC

AGTCCATTAACCCTGAAAAGAGGCCAGATGAAAAT

TGGCCATCAAAGGGTGGTATTGAATTCAAAAACTA

-continued

TTCCACAAAATACAGAGAAAATTTGGATCCAGTGC
TGAATAATATTAACGTGAAGATTGAGCCATGTGAA
AAGGTTGGGATTGTTGGCAGAACAGGTGCAGGGAA
GTCTACACTGAGCCTGGCATTATTTAGAATACTAG
AACCTACCGAAGGTAAAATTATTATTGACGGCATT
GATATATCCGACATAGGTCTGTTCGATTTAAGAAG
CCATTTGGCAATTATTCCTCAGGATGCACAAGCTT
TTGAAGGTACAGTAAAGACCAATTTGGACCCTTTC
AATCGTTATTCAGAAGATGAACTTAAAAGGGCTGT
TGAGCAGGCACATTTAAAGCCTCATCTGGAAAAAA
TGCTGCACAGTAAACCAAGAGGTGATGATTCTAAT
GAAGAGGATGGCAATGTTAATGATATTCTGGATGT
CAAGATTAATGAGAACGGTAGTAACTTGTCAGTGG
GGCAAAGACAACTACTATGTTTGGCAAGAGCGCTG
CTAAACCGTTCCAAAATATTGGTCCTTGATGAAGC
AACGGCTTCTGTGGATATGGAAACCGATAAAATTA
TCCAAGACACTATAAGAAGAGAATTTAAGGACCGT
ACCATCTTAACAATTGCACATCGTATCGACACTGT
ATTGGACAGTGATAAGATAATTGTTCTTGACCAGG
GTAGTGTGAGGGAATTCGATTCACCCTCGAAATTG
TTATCCGATAAAACGTCTATTTTTTACAGTCTTTG
TGAGAAAGGTGGGTATTTGAAATAA.

As used herein, the term “T4_Fungal_4” refers to an ABC-transporter having the following amino acid sequence (SEQ ID NO: 6):

MSSLEVVDGCPYGYRPYPDSGTNALNPCFISVISA
WQAVFFLLIGSYQLWKLYKNNKVPPRFKNFPTLPS
KINSRHLTHLTNVCFQSTLIICELALVSQSSDRVY
PFILKKALYLNLLFNLGISLPTQYLAYFKSTFSMG
NQLFYYMFQILLQLFLILQRYYHGSSNERLTVISG
QTAMILEVLLLFNSVAIFIYDLCIFEPINELSEYY
KKNGWYPPVHVLSYITFIWMNKLIVETYRNKKIKD
PNQLPLPPVDLNIKSISKEFKANWELEKWLNRNSL
WRAIWKSFGRTISVAMLYETTSDLLSVVQPQFLRIF
IDGFNPETSSKYPPLNGVFIALTLFVISVVSVFLTN
QFYIGIFEAGLGIRGSLASLVYQKSLRLTLAERNE
KSTGDILNLMSVDVLRIQRFFENAQTIIGAPIQII
VVLTSLYWLLGKAVIGGLVTMAIMMPINAFLSRKV
KKLSKTQMKYKDMRIKTITELLNAIKSIKLYAWEE
PMMARLNHVRNDMELKNFRKIGIVSNLIYFAWNCV

-continued

PLMVTCSTFGLFSLFSDSPLSPAIVFPSLSLFNIL
NSAIYSVPSMINTIIETSVSMERLKSFLLSDEIDD
SFIERIDPSADERALPAIEMNNITFLWKSKEVLAS
SQSRDNLRTDEESIIGSSQIALKNIDHFEAKRGDL
VCVVGRVGAGKSTFLKAILGQLPCMSGSRDSIPPK
LIIRSSSVAYCSQESWIMNASVRENILFGHKFDQN
YYDLTIKACQLLPDLKILPDGDETLVGEKGISLSG
GQKARLSLARAVYSRADIYLLDDILSAVDAEVSKN
IIEYVLIGKTALLKNKTIILTTNTVSILKHSQMIY
ALENGEIVEQGNYEDVMNRKNNTSKLKKLLEEFDS
PIDNGNESDVQTEHRSESEVDEPLQLKVTESETED
EVVTESELELIKANSRRASLATLRPRPFVGAQLDS
VKKTAQEAEKTEVGRVKTKVYLAYIKACGVLGVVL
FFLFMILTRVFDLAENFWLKYWSESNEKNGSNERV
WMFVGVYSLIGVASAAFNNLRSIMMLLYCSIRGSK
KLHESMAKSVIRSPMTFFETTPVGRIINRFSSDMD
AVDSNLQYIFSFFFKSILTYLVTVILVGYNMPWFL
VFNMFLVVIYIYYQTFYIVLSRELKRLISISYSPI
MSLMSESLNGYSIIDAYDHFERFIYLNYEKIQYNV
DFVFNFRSTNRWLSVRLQTIGATIVLATAILALAT
MNTKRQLSSGMVGLLMSYSLEVTGSLTWIVRTTVM
IETNIVSVERIVEYCELPPEAQSINPEKRPDENWP
SKGGIEFKNYSTKYRENLDPVLNNINVKIEPCEKV
GIVGRTGAGKSTLSLALFRILEPTEGKIIIDGIDI
SDIGLFDLRSHLAIIPQDAQAFEGTVKTNLDPFNR
YSEDELKRAVEQAHLKPHLEKMLHSKPRGDDSNEE
DGNVNDILDVKINENGSNLSVGQRQLLCLARALLN
RSKILVLDEATASVDMETDKIIQDTIRREFKDRTI
LTIAHRIDTVLDSDKIIVLDQGSVREFDSPSKLLS
DKTSIFYSLCEKGGYLK*;

and encoded by the following nucleic acid sequence (SEQ ID NO: 25):

ATGTCTTCACTAGAAGTGGTAGATGGGTGCCCCTA
TGGATACCGACCATATCCAGATAGTGGCACAAATG
CATTAAATCCATGTTTTATATCAGTAATATCCGCC
TGGCAAGCCGTCTTTTTCCTATTGATTGGTAGCTA
TCAATTGTGGAAACTTTATAAGAACAATAAAGTAC
CACCCAGATTTAAGAACTTTCCTACATTACCAAGT
AAAATCAACAGTCGACATCTAACGCATTTGACCAA
TGTTTGCTTTCAGTCCACGCTTATAATTTGTGAAC
TGGCCTTGGTATCCCAATCTAGCGATAGGGTTTAT

-continued

CCATTTATACTAAAGAAGGCTCTGTACTTGAATCT
CCTTTTCAATTTGGGTATTTCTCTCCCTACTCAAT
ACTTAGCTTATTTTAAAAGTACATTTTCAATGGGC
AACCAGCTTTTCTATTACATGTTTCAAATTCTTCT
ACAGCTCTTCTTGATATTGCAGAGGTACTATCATG
GTTCTAGTAACGAAAGGCTTACTGTTATTAGCGGA
CAAACTGCTATGATTTTAGAAGTGCTCCTTCTTTT
CAATTCTGTGGCAATTTTTATTTATGATCTATGCA
TTTTTGAGCCAATTAACGAATTATCTGAATACTAC
AAGAAAAAATGGGTGGTATCCCCCCGTTCATGTACT
ATCCTATATTACATTTATCTGGATGAACAAACTGA
TTGTGGAAACTTACCGTAACAAGAAAATCAAAGAT
CCTAACCAGTTACCATTGCCGCCAGTAGATCTGAA
TATTAAGTCGATAAGTAAGGAATTTAAGGCTAACT
GGGAATTGGAAAAATGGTTGAATAGAAATTCTCTT
TGGAGGGCCATTTGGAAGTCATTTGGTAGGACTAT
TTCTGTGGCTATGCTGTATGAAACGACATCTGATT
TACTTTCTGTAGTACAGCCCCAGTTTCTACGGATA
TTCATAGATGGTTTGAACCCGGAAACATCTTCTAA
ATATCCTCCTTTAAATGGTGTATTTATTGCTCTAA
CCCTTTTCGTAATCAGCGTGGTTTCTGTGTTCCTC
ACCAATCAATTTTATATTGGAATTTTTGAGGCTGG
TTTGGGGATAAGAGGCTCTTTAGCTTCTTTAGTGT
ATCAGAAGTCCTTAAGATTGACGCTAGCAGAGCGT
AACGAAAAATCTACTGGTGACATCTTAAATTTGAT
GTCTGTGGATGTGTTAAGGATCCAGCGGTTTTTCG
AAAATGCCCAAACCATTATTGGCGCTCCTATTCAG
ATTATTGTTGTATTAACTTCCCTGTACTGGTTGCT
AGGAAAGGCTGTTATTGGAGGGTTGGTTACTATGG
CTATTATGATGCCTATCAATGCCTTCTTATCTAGA
AAGGTAAAAAAGCTATCAAAAACTCAAATGAAGTA
TAAGGACATGAGAATCAAGACTATTACAGAGCTTT
TGAATGCTATAAAATCTATTAAATTATACGCCTGG
GAGGAACCTATGATGGCAAGATTGAATCATGTTCG
TAATGATATGGAGTTGAAAAATTTTCGGAAAATTG
GTATAGTGAGCAATCTGATATATTTTGCGTGGAAT
TGTGTACCTTTAATGGTGACATGTTCCACATTTGG
CTTATTTTCTTTATTTAGTGATTCTCCGTTATCTC
CTGCCATTGTCTTCCCTTCATTATCTTTATTTAAT
ATTTTGAACAGTGCCATCTATTCCGTTCCATCCAT
GATAAATACCATTATAGAGACAAGCGTTTCTATGG

-continued

AAAGATTAAAGTCATTCCTACTTAGTGACGAAATT
GATGATTCGTTCATCGAACGTATTGATCCTTCAGC
GGATGAAAGAGCGTTACCTGCTATAGAGATGAATA
ATATTACATTTTTATGGAAATCAAAAGAAGTATTA
ACATCTAGCCAATCTGGAGATAATTTGAGGACAGA
TGAAGAGTCTATTATCGGATCTTCTCAAATTGCGT
TGAAGAATATCGATCATTTTGAAGCAAAAAGGGGT
GATTTAGTTTGTGTTGTTGGTCGGGTAGGAGCTGG
TAAATCAACATTTTTGAAGGCAATTCTTGGTCAAC
TTCCTTGCATGAGTGGTTCTAGGGACTCGATACCA
CCTAAACTGATCATTAGATCATCGTCTGTAGCCTA
CTGTTCACAAGAATCCTGGATAATGAACGCATCTG
TAAGAGAAAACATTCTATTTGGTCACAAGTTCGAC
CAAGATTATTATGACCTCACTATTAAAGCATGTCA
ATTGCTACCCGATTTGAAAATACTACCAGATGGTG
ATGAAACTTTGGTAGGTGAAAAGGGCATTTCCCTA
TCAGGCGGTCAGAAGGCCCGTCTTTCATTAGCCAG
AGCGGTGTACTCGAGAGCAGATATTTATTTGTTGG
ATGACATTTTATCTGCTGTTGATGCAGAAGTTAGT
AAAAATATTATTGAATATGTTTTGATCGGAAAGAC
GGCTTTATTAAAAAATAAAACAATTATTTTAACTA
CCAATACTGTATCAATTTTAAAACATTCGCAGATG
ATATATGCGCTAGAAAACGGTGAAATTGTTGAACA
AGGGAATTATGAGGATGTAATGAACCGTAAGAACA
ATACTTCAAAACTGAAAAAATTACTAGAGGAATTT
GATTCTCCGATTGATAATGGAAATGAAAGCGATGT
CCAAACTGAACACCGATCCGAAAGTGAAGTGGATG
AACCTCTGCAGCTTAAAGTAACTGAATCAGAAACT
GAGGATGAGGTTGTTACTGAGAGTGAATTAGAACT
AATCAAAGCCAATTCTAGAAGAGCTTCTCTAGCTA
CGCTAAGACCTAGACCCTTTGTGGGAGCACAATTG
GATTCCGTGAAGAAAACGGCGCAAAAGGCCGAGAA
GACAGAGGTGGGAAGAGTCAAAACAAAGATTTATC
TTGCGTATATTAAGGCTTGTGGAGTTTTAGGTGTT
GTTTTATTTTTCTTGTTTATGATATTAACAAGGGT
TTTCGACTTAGCAGAGAATTTTTGGTTAAAGTACT
GGTCAGAATCTAATGAAAAAAATGGTTCAAATGAA
AGGGTTTGGATGTTTGTTGGTGTGTATTCCTTAAT
CGGAGTAGCATCGGCCGCATTCAATAATTTACGGA
GTATTATGATGCTACTGTATTGTTCTATTAGGGGT

-continued

TCTAAGAAACTGCATGAAAGCATGGCCAAATCTGT
AATTAGAAGTCCTATGACTTTCTTTGAGACTACAC
CAGTTGGAAGGATCATAAACAGGTTCTCATCTGAT
ATGGATGCAGTGGACAGTAATCTACAGTACATTTT
CTCCTTTTTTTTCAAATCAATACTAACCTATTTGG
TTACTGTTATATTAGTCGGGTACAATATGCCATGG
TTTTTAGTGTTCAATATGTTTTTGGTGGTTATCTA
TATTTACTATCAAACATTTTACATTGTGCTATCTA
GGGAGCTAAAAAGATTGATCAGTATATCTTACTCT
CCGATTATGTCCTTAATGAGTGAGAGCTTGAACGG
TTATTCTATTATTGATGCATACGATCATTTTGAGA
GATTCATCTATCTAAATTATGAAAAAATCCAATAC
AACGTTGATTTTGTCTTCAACTTTAGATCAACGAA
TAGATGGTTATCCGTGAGATTGCAAACTATTGGTG
CTACAATTGTTTTGGCTACTGCAATCTTAGCACTA
GCAACAATGAATACTAAAAGGCAACTAAGTTCGGG
TATGGTTGGTCTACTAATGAGCTATTCATTAGAGG
TTACAGGTTCATTGACTTGGATTGTAAGGACAACT
GTGACGATTGAAACCAACATTGTATCAGTGGAGAG
AATTGTTGAGTACTGCGAATTACCACCTGAAGCAC
AGTCCATTAACCCTGAAAAGAGGCCAGATGAAAAT
TGGCCATCAAAGGGTGGTATTGAATTCAAAAACTA
TTCCACAAAATACAGAGAAAATTTGGATCCAGTGC
TGAATAATATTAACGTGAAGATTGAGCCATGTGAA
AAGGTTGGGATTGTTGGCAGAACAGGTGCAGGGAA
GTCTACACTGAGCCTGGCATTATTTAGAATACTAG
AACCTACCGAAGGTAAAATTATTATTGACGGCATT
GATATATCCGACATAGGTCTGTTCGATTTAAGAAG
CCATTTGGCAATTATTCCTCAGGATGCACAAGCTT
TTGAAGGTACAGTAAAGACCAATTTGGACCCTTTC
AATCGTTATTCAGAAGATGAACTTAAAAGGGCTGT
TGAGCAGGCACATTTAAAGCCTCATCTGGAAAAAA
TGCTGCACAGTAAACCAAGAGGTGATGATTCTAAT
GAAGAGGATGGCAATGTTAATGATATTCTGGATGT
CAAGATTAATGAGAACGGTAGTAACTTGTCAGTGG
GGCAAAGACAACTACTATGTTTGGCAAGAGCGCTG
CTAAACCGTTCCAAAATATTGGTCCTTGATGAAGC
AACGGCTTCTGTGGATATGGAAACCGATAAAATTA
TCCAAGACACTATAAGAAGAGAATTTAAGGACCGT
ACCATCTTAACAATTGCACATCGTATCGACACTGT
ATTGGACAGTGATAAGATAATTGTTCTTGACCAGG

-continued

GTAGTGTGAGGGAATTCGATTCACCCTCGAAATTG
TTATCCGATAAAACGTCTATTTTTTACAGTCTTTG
TGAGAAAGGTGGGTATTTGAAATAA.

As used herein, the term “T4_Fungal_5” refers to an ABC-transporter having the following amino acid sequence (SEQ ID NO: 7):

MTSPGSEKCTPRSDEDLERSEPQLQRRLLTPFLLS
KKVPPIPKEDERKPYPYLKTNPLSQILFWWLNPLL
RVGYKRTLDPNDFYYLEHSQDIETTYSNYEMHLAR
ILEKDRAKARAKDPTLTDEDLKNREYPKNAVIKAL
FLTFKWKYLWSIFLKLLSDIVLVLNPLLSKALINF
VDEKMYNPDMSVGRGVGYAIGVTFMLGTSGILINH
FLYLSLTVGAHCKAVLTTAIMNKSFRASAKSKHEY
PSGRVTSLMSTDLARIDLAIGFQPFAITVPVPIGV
AIALLIVNIGVSALAGIAVFLVCIVVISASSKSLL
KMRKGANQYTDARISYMREILQNMRIIKFYSWEDA
YEKSVVTERNSEMSIILKMQSIRNFLLALSLSLPA
IISMVAFLVLYGVSNDKNPGNIFSSISLFSVLAQQ
TMMLPMALATGADAKIGLERLRQYLQSGDIEKEYE
DHEKPGDRDVVLPDNVAVELNNASFIWEKFDDADD
NDGNSEKTKEVVVTSKSSLTDSSHIDKSTDSADGE
YIKSVFEGFNNINLTIKKGEFVIITGPIGSGKSSL
LVALAGFMKKTSGTLGVNGTMLLCGQPWVQNCTVR
DNILFGLEYDEARYDRVVEVCALGDDLKMFTAGDQ
TEIGERGITLSGGQKARINLARAVYANKDIILLDD
VLSAVDARVGKLIVDDCLTSFLGDKTRILATHQLS
LIEAADRVIYLNGDGTIHIGTVQELLESNEGFLKL
MEFSRKSESEDEEDVEAANEKDVSLQKAVSVVQEQ
DAHAGVLIGQEERAVNGIEWDIYKEYLHEGRGKLG
IFAIPTIIMLLVLDVFTSIFVNVWLSFWISHKFKA
RSDGFYIGLYVMFVILSVIWITAEFVVMGYFSSTA
ARRLNLKAMKRVLHTPMHFLDVTPMGRILNRFTKD
TDVLDNEIGEQARMFLHPAAYVIGVLILCIIYIPW
FAIAIPPLAILFTFITNFYIASSREVKRIEAIQRS
LVYNNFNEVLNGLQTLKAYNATSRFMEKNKRLLNR
MNEAYLLVIANQRWISVNLDLVSCCFVFLISMLSV
FRVFDINASSVGLVVTSVLQIGGLMSLIMRAYTTV
ENEMNSVERLCHYANKLEQEAPYIMNETKPRPTWP
EHGAIEFKHASMRYREGLPLVLKDLTISVKGGEKI
GICGRTGAGKSTIMNALYRLTELAEGSITIDGVEI

-continued

SQLGLYDLRSKLAIIPQDPVLFRGTIRKNLDPFGQ
NDDETLWDALRRSGLVEGSILNTIKSQSKDDPNFH
KFHLDQTVEDEGANFSLGERQLIALARALVRNSKI
LILDEATSSVDYETDSKIQKTISTEFSHCTILCIA
HRLKTILTYDRILVLEKGEVEEFDTPRVLYSKNGV
FRQMCERSEITSADFV*;

and encoded by the following nucleic acid sequence (SEQ ID NO: 26):

ATGTCTTCACTAGAAGTGGTAGATGGGTGCCCCTA
TGGATACCGACCATATCCAGATAGTGGCACAAATG
CATTAAATCCATGTTTTATATCAGTAATATCCGCC
TGGCAAGCCGTCTTTTTCCTATTGATTGGTAGCTA
TCAATTGTGGAAACTTTATAAGAACAATAAAGTAC
CACCCAGATTTAAGAACTTTCCTACATTACCAAGT
AAAATCAACAGTCGACATCTAACGCATTTGACCAA
TGTTTGCTTTCAGTCCACGCTTATAATTTGTGAAC
TGGCCTTGGTATCCCAATCTAGCGATAGGGTTTAT
CCATTTATACTAAAGAAGGCTCTGTACTTGAATCT
CCTTTTCAATTTGGGTATTTCTCTCCCTACTCAAT
ACTTAGCTTATTTTAAAAGTACATTTTCAATGGGC
AACCAGCTTTTCTATTACATGTTTCAAATTCTTCT
ACAGCTCTTCTTGATATTGCAGAGGTACTATCATG
GTTCTAGTAACGAAAGGCTTACTGTTATTAGCGGA
CAAACTGCTATGATTTTAGAAGTGCTCCTTCTTTT
CAATTCTGTGGCAATTTTTATTTATGATCTATGCA
TTTTTGAGCCAATTAACGAATTATCTGAATACTAC
AAGAAAAATGGGTGGTATCCCCCCGTTCATGTACT
ATCCTATATTACATTTATCTGGATGAACAAACTGA
TTGTGGAAACTTACCGTAACAAGAAAATCAAAGAT
CCTAACCAGTTACCATTGCCGCCAGTAGATCTGAA
TATTAAGTCGATAAGTAAGGAATTTAAGGCTAACT
GGGAATTGGAAAAATGGTTGAATAGAAATTCTCTT
TGGAGGGCCATTTGGAAGTCATTTGGTAGGACTAT
TTCTGTGGCTATGCTGTATGAAACGACATCTGATT
TACTTTCTGTAGTACAGCCCCAGTTTCTACGGATA
TTCATAGATGGTTTGAACCCGGAAACATCTTCTAA
ATATCCTCCTTTAAATGGTGTATTTATTGCTCTAA
CCCTTTTCGTAATCAGCGTGGTTTCTGTGTTCCTC
ACCAATCAATTTTATATTGGAATTTTTGAGGCTGG
TTTGGGGATAAGAGGCTCTTTAGCTTCTTTAGTGT
ATCAGAAGTCCTTAAGATTGACGCTAGCAGAGCGT

-continued

AACGAAAAATCTACTGGTGACATCTTAAATTTGAT
GTCTGTGGATGTGTTAAGGATCCAGCGGTTTTTCG
AAAATGCCCAAACCATTATTGGCGCTCCTATTCAG
ATTATTGTTGTATTAACTTCCCTGTACTGGTTGCT
AGGAAAGGCTGTTATTGGAGGGTTGGTTACTATGG
CTATTATGATGCCTATCAATGCCTTCTTATCTAGA
AAGGTAAAAAAGCTATCAAAAACTCAAATGAAGTA
TAAGGACATGAGAATCAAGACTATTACAGAGCTTT
TGAATGCTATAAAATCTATTAAATTATACGCCTGG
GAGGAACCTATGATGGCAAGATTGAATCATGTTCG
TAATGATATGGAGTTGAAAAATTTTCGGAAAATTG
GTATAGTGAGCAATCTGATATATTTTGCGTGGAAT
TGTGTACCTTTAATGGTGACATGTTCCACATTTGG
CTTATTTTCTTTATTTAGTGATTCTCCGTTATCTC
CTGCCATTGTCTTCCCTTCATTATCTTTATTTAAT
ATTTTGAACAGTGCCATCTATTCCGTTCCATCCAT
GATAAATACCATTATAGAGACAAGCGTTTCTATGG
AAAGATTAAAGTCATTCCTACTTAGTGACGAAATT
GATGATTCGTTCATCGAACGTATTGATCCTTCAGC
GGATGAAAGAGCGTTACCTGCTATAGAGATGAATA
ATATTACATTTTTATGGAAATCAAAAGAAGTATTA
ACATCTAGCCAATCTGGAGATAATTTGAGGACAGA
TGAAGAGTCTATTATCGGATCTTCTCAAATTGCGT
TGAAGAATATCGATCATTTTGAAGCAAAAAGGGGT
GATTTAGTTTGTGTTGTTGGTCGGGTAGGAGCTGG
TAAATCAACATTTTTGAAGGCAATTCTTGGTCAAC
TTCCTTGCATGAGTGGTTCTAGGGACTCGATACCA
CCTAAACTGATCATTAGATCATCGTCTGTAGCCTA
CTGTTCACAAGAATCCTGGATAATGAACGCATCTG
TAAGAGAAAACATTCTATTTGGTCACAAGTTCGAC
CAAGATTATTATGACCTCACTATTAAAGCATGTCA
ATTGCTACCCGATTTGAAAATACTACCAGATGGTG
ATGAAACTTTGGTAGGTGAAAAGGGCATTTCCCTA
TCAGGCGGTCAGAAGGCCCGTCTTTCATTAGCCAG
AGCGGTGTACTCGAGAGCAGATATTTATTTGTTGG
ATGACATTTTATCTGCTGTTGATGCAGAAGTTAGT
AAAAATATTATTGAATATGTTTTGATCGGAAAGAC
GGCTTTATTAAAAAATAAAACAATTATTTTAACTA
CCAATACTGTATCAATTTTAAAACATTCGCAGATG
ATATATGCGCTAGAAAACGGTGAAATTGTTGAACA

-continued

AGGGAATTATGAGGATGTAATGAACCGTAAGAACA

ATACTTCAAAACTGAAAAAATTACTAGAGGAATTT

GATTCTCCGATTGATAATGGAAATGAAAGCGATGT

CCAAACTGAACACCGATCCGAAAGTGAAGTGGATG

AACCTCTGCAGCTTAAAGTAACTGAATCAGAAACT

GAGGATGAGGTTGTTACTGAGAGTGAATTAGAACT

AATCAAAGCCAATTCTAGAAGAGCTTCTCTAGCTA

CGCTAAGACCTAGACCCTTTGTGGGAGCACAATTG

GATTCCGTGAAGAAAACGGCGCAAAAGGCCGAGAA

GACAGAGGTGGGAAGAGTCAAAACAAAGATTTATC

TTGCGTATATTAAGGCTTGTGGAGTTTTAGGTGTT

GTTTTATTTTTCTTGTTTATGATATTAACAAGGGT

TTTCGACTTAGCAGAGAATTTTTGGTTAAAGTACT

GGTCAGAATCTAATGAAAAAAATGGTTCAAATGAA

AGGGTTTGGATGTTTGTTGGTGTGTATTCCTTAAT

CGGAGTAGCATCGGCCGCATTCAATAATTTACGGA

GTATTATGATGCTACTGTATTGTTCTATTAGGGGT

TCTAAGAAACTGCATGAAAGCATGGCCAAATCTGT

AATTAGAAGTCCTATGACTTTCTTTGAGACTACAC

CAGTTGGAAGGATCATAAACAGGTTCTCATCTGAT

ATGGATGCAGTGGACAGTAATCTACAGTACATTTT

CTCCTTTTTTTTCAAATCAATACTAACCTATTTGG

TTACTGTTATATTAGTCGGGTACAATATGCCATGG

TTTTTAGTGTTCAATATGTTTTTGGTGGTTATCTA

TATTTACTATCAAACATTTTACATTGTGCTATCTA

GGGAGCTAAAAAGATTGATCAGTATATCTTACTCT

CCGATTATGTCCTTAATGAGTGAGAGCTTGAACGG

TTATTCTATTATTGATGCATACGATCATTTTGAGA

GATTCATCTATCTAAATTATGAAAAAATCCAATAC

AACGTTGATTTTGTCTTCAACTTTAGATCAACGAA

TAGATGGTTATCCGTGAGATTGCAAACTATTGGTG

CTACAATTGTTTTGGCTACTGCAATCTTAGCACTA

GCAACAATGAATACTAAAAGGCAACTAAGTTCGGG

TATGGTTGGTCTACTAATGAGCTATTCATTAGAGG

TTACAGGTTCATTGACTTGGATTGTAAGGACAACT

GTGACGATTGAAACCAACATTGTATCAGTGGAGAG

AATTGTTGAGTACTGCGAATTACCACCTGAAGCAC

AGTCCATTAACCCTGAAAAGAGGCCAGATGAAAAT

TGGCCATCAAAGGGTGGTATTGAATTCAAAAACTA

TTCCACAAAATACAGAGAAAATTTGGATCCAGTGC

TGAATAATATTAACGTGAAGATTGAGCCATGTGAA

-continued

AAGGTTGGGATTGTTGGCAGAACAGGTGCAGGGAA

GTCTACACTGAGCCTGGCATTATTTAGAATACTAG

AACCTACCGAAGGTAAAATTATTATTGACGGCATT

GATATATCCGACATAGGTCTGTTCGATTTAAGAAG

CCATTTGGCAATTATTCCTCAGGATGCACAAGCTT

TTGAAGGTACAGTAAAGACCAATTTGGACCCTTTC

AATCGTTATTCAGAAGATGAACTTAAAAGGGCTGT

TGAGCAGGCACATTTAAAGCCTCATCTGGAAAAAA

TGCTGCACAGTAAACCAAGAGGTGATGATTCTAAT

GAAGAGGATGGCAATGTTAATGATATTCTGGATGT

CAAGATTAATGAGAACGGTAGTAACTTGTCAGTGG

GGCAAAGACAACTACTATGTTTGGCAAGAGCGCTG

CTAAACCGTTCCAAAATATTGGTCCTTGATGAAGC

AACGGCTTCTGTGGATATGGAAACCGATAAAATTA

TCCAAGACACTATAAGAAGAGAATTTAAGGACCGT

ACCATCTTAACAATTGCACATCGTATCGACACTGT

ATTGGACAGTGATAAGATAATTGTTCTTGACCAGG

GTAGTGTGAGGGAATTCGATTCACCCTCGAAATTG

TTATCCGATAAAACGTCTATTTTTTACAGTCTTTG

TGAGAAAGGTGGGTATTTGAAATAA.

As used herein, the term "T4_Fungal_8" refers to an ABC-transporter having the following amino acid sequence (SEQ ID NO: 8):

MSGSNSNSNLDAISDSCPFWRYDDITECGRVQYIN

YYLPITLVGVSLLYLFKNAIQHYYRKPQEIKPSVA

SELLGSNLTDLPNENKPLLSESTQALYTNPDSNKT

GFSLKEEHFSINKVTLTEIHSNKHDAVKIVRRNWL

EKLRVFLEWVLCALQLCIYISVWSKYTNTQEDFPM

HASISGLMLWSLLLLVVSLRLANINQNISWINSGP

GNLWALSFACYLSLFCGSVLPLRSIYIGHITDEIA

STFYKLQFYLSLTLFLLLFTSQAGNRFAIIYKSTP

DITPSPEPIVSIASYITWAWVDKFLWKAHQNYIEM

KDVWGLMVEDYSILVIKRFNHFVQNKTKSRTFSFN

LIHFFMKFIAIQGAWATISSVISFVPTMLLRRILE

YVEDQSTAPLNLAWMYIFLMFLARILTAICAAQAL

FLGRRVCIRMKAIIISEIYSKALRRKISPNSTKEP

TDVVDPQELNDKQHVDGDEESATTANLGAIINLMA

VDAFKVSEICAYLHSFIEAIIMTIVALFLLYRLIG

WSALVGSAMIICFLPLNFKLASLLGTLQKKSLAIT

DKRIQKLNEAFQAIRIIKFFSWEENFEKDIQNTRD

-continued

EELNMLLKRSIVWALSSLVWFITPSIVTSASFAVY

IYVQGQTLTTPVAFTALSLFALLRNPLDMLSDMLS

FVIQSKVSLDRVQEFLNEEETKKYEQLTVSRNKLG

LQNATFTWDKNNQDFKLKNLTIDFKIGKLNVIVGP

TGSGKTSLLMGLLGEMELLNGKVFVPSLNPREELV

VEADGMTNSIAYCSQAAWLLNDTVRNNILFNAPYN

ENRYNAVISACGLKRDFEILSAGDQTEIGEKGITL

SGGQKQRVSLARSLYSSSR

HLLLDDCLSAVDSHTALWIYENCITGPLMEGRTCV

LVSHNVALTLKNADWVIIMENGRVKEQGEPVELLQ

KGSLGDDSMVKSSILSRTASSVNISETNSKISSGP

KAPAESDNANEESTTCGDRSKSSGKLIAEETKSNG

VVSLDVYKWYAVFFGGWKMISFLCFIFLFAQMISI

SQAWWLRAWASNNTLKVFSNLGLQTMRPFALSLQG

KEASPVTLSAVFPNGSLTTATEPNHSNAYYLSIYL

GIGVFQALCSSSKAIINFVAGIRASRKIFNLLLKN

VLYAKLRFFDSTPIGRIMNRFSKDIESIDQELTPY

MEGAFGSLIQCVSTIIVIAYITPQFLIVAAIVMLL

FYFVAYFYMSGARELKRLESMSRSPIHQHFSETLV

GITTIRAFSDERRFLVDNMKKIDDNNRPFFYLWVC

NRWLSYRIELIGALIVLAAGSFILLNIKSIDSGLA

GISLGFAIQFTDGALWVVRLYSNVEMNMNSVERLK

EYTTIEQEPSNVGALVPPCEWPQNGKIEVKDLSLR

YAAGLPKVIKNVTFTVDSKCKVGIVGRTGAGKSTI

ITALFRFLDPETGYIKIDDVDITTIGLKRLRQSIT

IIPQDPTLFTGTLKTNLDPYNEYSEAEIFEALKRV

NLVSSEELGNPSTSDSTSVHSANMNKFLDLENEVS

EGGSNLSQGQRQLICLARSLLRCPKVILLDEATAS

IDYNSDSKIQATIREEFSNSTILTIAHRLRSIIDY

DKILVMDAGEVKEYDHPYSLLLNRDSIFYHMCEDS

GELEVLIQLAKESFVKKLNAN;

and
encoded by the following nucleic acid sequence (SEQ ID NO: 27):

ATGTCAGGTTCAAATTCGAATTCAAATCTAGATGC

AATAAGTGATTCATGCCCATTTTGGCGCTATGATG

ATATTACAGAGTGTGGAAGAGTGCAGTATATCAAT

TACTACCTTCCAATAACATTGGTAGGCGTTTCTCT

CTTGTATTTATTCAAAAACGCGATCCAACATTATT

ACAGAAAGCCTCAAGAAATTAAGCCTAGTGTTGCT

TCCGAATTATTGGGCTCAAATCTCACAGACCTTCC

GAATGAAAACAAGCCTTTACTATCGGAGAGTACAC

-continued

AAGCATTATACACTAATCCGGATTCGAATAAGACA

GGATTCTCTCTAAAAGAGGAGCATTTCTCTATAAA

TAAAGTTACACTTACGGAAATTCATTCCAATAAGC

ATGACGCTGTGAAGATCGTAAGGAGAAACTGGCTT

GAAAAATTAAGAGTGTTCTTAGAATGGGTTCTATG

CGCCTTACAACTTTGCATCTACATTTCAGTCTGGT

CGAAATACACTAATACCCAAGAGGATTTCCCAATG

CACGCATCTATCTCAGGTCTAATGTTATGGTCTCT

ACTCTTGTTAGTAGTGTCATTGAGGTTGGCAAACA

TCAACCAGAATATAAGCTGGATCAATTCAGGACCG

GGAAACTTATGGGCCCTTTCATTTGCATGTTATCT

ATCACTATTCTGCGGATCCGTTTTGCCATTGAGAT

CTATCTATATCGGTCATATCACAGATGAAATTGCA

TCAACATTTTATAAGTTGCAATTTTACCTAAGTTT

GACACTATTCTTGTTACTTTTCACCTCTCAAGCGG

GAAATCGGTTTGCCATTATCTATAAAAGTACACCA

GATATAACACCGTCTCCTGAACCTATTGTGTCGAT

TGCAAGTTATATCACTTGGGCATGGGTAGATAAAT

TTCTTTGGAAAGCGCATCAAAATTATATCGAAATG

AAAGATGTTTGGGGTCTAATGGTGGAAGACTATTC

CATTCTCGTAATAAAGAGATTCAATCATTTTGTTC

AGAATAAAACCAAGTCTAGGACATTTTCATTTAAC

TTAATCCACTTTTTCATGAAATTTATCGCCATTCA

AGGTGCCTGGGCAACAATTTCGTCAGTTATTAGTT

TTGTTCCAACAATGTTGCTCAGACGTATTTTGGAG

TATGTTGAAGATCAATCAACTGCTCCATTAAATTT

GGCTTGGATGTATATTTTTCTTATGTTCCTTGCCA

GAATTTTAACTGCCATATGTGCTGCTCAGGCGCTA

TTTTTAGGGAGAAGGGTTTGTATCAGAATGAAGGC

TATCATAATTTCTGAAATCTACTCCAAGGCTTTGA

GAAGAAAAATTTCTCCAAATTCCACTAAGGAGCCA

ACTGATGTCGTTGATCCACAGGAATTAAATGACAA

ACAACACGTTGATGGAGATGAAGAATCAGCAACCA

CTGCAAATCTTGGTGCTATCATTAATTTGATGGCG

GTGGATGCTTTCAAAGTATCCGAAATATGTGCGTA

TTTGCACTCCTTTATAGAGGCGATCATCATGACCA

TTGTTGCATTATTCCTTTTATATCGGTTAATAGGC

TGGTCTGCTTTAGTTGGTAGTGCAATGATTATTTG

CTTCTTACCATTGAACTTCAAACTTGCCAGCTTGT

TAGGGACACTCCAAAAGAAATCCTTGGCAATCACA

GATAAAAGAATTCAGAAACTAAACGAAGCTTTCCA

-continued

GGCCATTCGTATTATCAAATTCTTCTCTTGGGAAG

AGAATTTTGAAAAGGACATACAAAACACAAGGGAT

GAAGAATTAAATATGCTTTTAAAAAGGTCTATCGT

TTGGGCTCTTTCTTCTCTTGTTTGGTTCATTACCC

CCTCTATTGTCACATCCGCTTCTTTTGCAGTCTAT

ATTTATGTGCAAGGCCAAACTTTAACTACTCCGGT

AGCATTTACTGCACTATCTCTATTTGCTCTACTAA

GAAATCCGTTAGACATGCTTTCTGATATGTTGTCT

TTTGTTATTCAATCCAAGGTCTCTTTGGATAGAGT

CCAAGAATTTTTAAATGAAGAGGAGACGAAAAAGT

ATGAGCAATTAACCGTATCAAGAAATAAACTTGGG

TTGCAAAACGCTACTTTTACATGGGATAAAAATAA

TCAAGATTTCAAGTTAAAAAACCTAACTATTGATT

TCAAAATTGGGAAATTAAACGTTATTGTAGGTCCA

ACTGGATCTGGTAAAACATCATTGTTAATGGGATT

ATTGGGTGAAATGGAGCTATTGAACGGAAAAGTTT

TCGTCCCTTCGCTCAATCCTAGGGAAGAGTTGGTT

GTAGAGGCCGATGGAATGACTAATTCAATCGCGTA

CTGCTCCCAAGCTGCCTGGTTGCTAAATGATACTG

TCAGGAACAATATTCTATTCAATGCGCCTTATAAT

GAGAATAGATATAATGCCGTCATCTCTGCGTGTGG

TTTGAAACGCGACTTCGAGATCTTAAGCGCTGGTG

ATCAGACAGAGATTGGCGAAAAGGGTATAACACTT

TCTGGTGGTCAAAAACAAAGAGTCTCGTTGGCCAG

ATCATTGTATTCTTCATCAAGACATTTGCTGTTAG

ATGATTGTTTGAGTGCCGTAGACTCGCACACGGCC

TTATGGATCTACGAAAATTGTATAACAGGCCCATT

AATGGAAGGAAGAACATGTGTATTGGTTTCTCACA

ATGTTGCATTAACTTTAAAAAATGCAGATTGGGTT

ATCATTATGGAAAATGGTAGAGTAAAAGAACAAGG

CGAACCAGTAGAATTGCTACAGAAGGGGTCCCTTG

GGGATGACTCCATGGTGAAATCATCAATTTTGTCC

CGTACGGCGTCCTCAGTTAATATTTCAGAAACTAA

CAGTAAGATTTCTAGTGGTCCGAAGGCTCCAGCGG

AATCGGATAATGCCAATGAGGAGTCCACCACCTGT

GGAGATCGTTCAAAGTCAAGCGGCAAGCTAATCGC

TGAAGAAACAAAATCAAACGGTGTTGTTTCCCTGG

ACGTCTATAAGTGGTATGCCGTGTTTTTCGGTGGA

TGGAAGATGATATCATTTTTGTGTTTCATTTTCTT

GTTTGCCCAAATGATCAGTATTTCACAGGCCTGGT

-continued

GGTTGCGTGCTTGGGCCTCCAACAACACTCTAAAA

GTTTTCTCCAACCTTGGATTGCAAACAATGAGGCC

ATTCGCTTTGTCCTTACAAGGAAAAGAAGCTTCTC

CTGTGACTCTTAGTGCTGTTTTCCCAAATGGCAGT

CTAACAACAGCCACGGAACCAAATCACTCGAACGC

GTATTATCTATCAATATATTTGGGTATTGGTGTAT

TCCAGGCTTTATGTTCATCTTCGAAAGCAATTATA

AACTTTGTGGCCGGTATTAGAGCTTCCAGGAAAAT

ATTCAATTTATTGTTGAAAAATGTGTTATACGCCA

AGCTGAGATTTTTTGATTCTACTCCAATAGGAAGA

ATAATGAACAGATTTTCTAAAGACATCGAATCAAT

AGATCAAGAATTGACTCCTTATATGGAAGGTGCAT

TTGGTTCCTTAATACAATGTGTTTCCACAATTATC

GTCATTGCATACATTACTCCCCAATTTTTGATTGT

CGCGGCGATTGTCATGTTATTGTTTTATTTTGTTG

CCTACTTTTACATGTCAGGAGCAAGAGAATTAAAG

CGTCTTGAATCGATGTCACGCTCTCCTATTCATCA

GCACTTCTCTGAGACTCTTGTGGGTATCACGACTA

TTCGAGCATTTTCTGACGAGCGGCGTTTTCTGGTT

GATAATATGAAGAAAATTGATGATAATAATAGGCC

TTTCTTTTACTTATGGGTCTGTAATAGATGGCTAT

CTTACAGAATCGAGCTGATAGGCGCCCTTATTGTT

TTGGCTGCAGGTAGTTTCATCTTATTGAACATAAA

ATCGATCGATTCTGGTTTGGCCGGTATTTCATTGG

GTTTCGCTATACAATTTACCGATGGTGCCCTTTGG

GTTGTTAGGTTATATTCCAACGTTGAAATGAATAT

GAATTCCGTCGAAAGGTTAAAAGAGTACACCACCA

TCGAGCAAGAACCTTCTAACGTTGGTGCCTTGGTA

CCTCCTTGCGAATGGCCACAAAATGGTAAAATCGA

AGTCAAGGATTTATCTTTACGCTATGCAGCTGGTC

TACCAAAGGTTATAAAAAATGTCACATTCACCGTC

GATTCAAAGTGTAAAGTAGGTATTGTTGGCAGGAC

TGGTGCTGGTAAATCTACTATTATCACAGCCCTTT

TCAGATTCTTAGACCCTGAAACTGGTTATATCAAA

ATCGATGACGTTGATATAACAACCATTGGTTTAAA

ACGTTTGCGCCAATCTATCACTATTATTCCACAGG

ACCCAACCCTTTTCACCGGTACTTTGAAAACCAAT

CTCGATCCATACAACGAATATTCGGAAGCTGAAAT

TTTCGAAGCTCTAAAACGTGTCAACCTTGTTTCCT

CAGAAGAACTTGGTAATCCTTCTACTTCGGATTCA

ACCTCGGTACATTCAGCAAATATGAATAAGTTTTT

-continued

```
GGATTTGGAAAATGAAGTCAGTGAAGGTGGTTCCA

ACCTCTCACAAGGACAACGTCAATTGATATGTTTG

GCCCGTTCATTATTGCGGTGTCCAAAGGTAATTCT

ACTTGATGAAGCCACAGCTTCAATCGATTATAACT

CAGACTCTAAAATCCAGGCTACTATAAGGGAAGAA

TTCAGTAATAGTACCATTCTCACGATTGCTCATCG

TTTACGATCAATTATTGATTATGATAAAATACTTG

TTATGGATGCTGGGGAGGTTAAAGAATATGATCAT

CCTTACTCCTTATTGTTGAATCGTGATAGTATATT

CTATCATATGTGTGAAGATAGTGGAGAATTAGAAG

TCTTGATACAATTAGCCAAAGAATCATTTGTCAAA

AAGCTCAATGCAAATTGA.
```

As used herein, the term "parent cell" refers to a cell that has an identical genetic background as a genetically modified host cell disclosed herein except that it does not comprise one or more particular genetic modifications engineered into the modified host cell, for example, one or more modifications selected from the group consisting of: heterologous expression of an enzyme of a steviol pathway, heterologous expression of an enzyme of a steviol glycoside pathway, heterologous expression of a geranylgeranyl diphosphate synthase, heterologous expression of a copalyl diphosphate synthase, heterologous expression of a kaurene synthase, heterologous expression of a kaurene oxidase (e.g., *Pisum sativum* kaurene oxidase), heterologous expression of a steviol synthase (kaurenoic acid hydroxylase), heterologous expression of a cytochrome P450 reductase, heterologous expression of a EUGT11, heterologous expression of a UGT74G1, heterologous expression of a UGT76G1, heterologous expression of a UGT85C2, heterologous expression of a UGT91D, and heterologous expression of a UGT40087 or its variant.

As used herein, the term "naturally occurring" refers to what is found in nature. For example, an ABC-transporter that is present in an organism that can be isolated from a source in nature and that has not been intentionally modified by a human in the laboratory is naturally occurring ABC-transporter. Conversely, as used herein, the term "non-naturally occurring" refers to what is not found in nature but is created by human intervention.

The term "medium" refers to a culture medium and/or fermentation medium.

The term "fermentation composition" refers to a composition which comprises genetically modified host cells and products or metabolites produced by the genetically modified host cells. An example of a fermentation composition is a whole cell broth, which can be the entire contents of a vessel (e.g., a flask, plate, or fermentor), including cells, aqueous phase, and compounds produced from the genetically modified host cells.

As used herein, the term "production" generally refers to an amount of steviol or steviol glycoside produced by a genetically modified host cell provided herein. In some embodiments, production is expressed as a yield of steviol or steviol glycoside by the host cell. In other embodiments, production is expressed as the productivity of the host cell in producing the steviol or steviol glycoside.

As used herein, the term "productivity" refers to production of a steviol or steviol glycoside by a host cell, expressed as the amount of steviol or steviol glycoside produced (by weight) per amount of fermentation broth in which the host cell is cultured (by volume) over time (per hour).

As used herein, the term "yield" refers to production of a steviol or steviol glycoside by a host cell, expressed as the amount of steviol or steviol glycoside produced per amount of carbon source consumed by the host cell, by weight.

As used herein, the term "an undetectable level" of a compound (e.g., Reb M, steviol glycosides, or other compounds) means a level of a compound that is too low to be measured and/or analyzed by a standard technique for measuring the compound. For instance, the term includes the level of a compound that is not detectable by the analytical methods known in the art.

The term "kaurene" refers to the compound kaurene, including any stereoisomer of kaurene. In particular embodiments, the term refers to the enantiomer known in the art as ent-kaurene. In particular embodiments, the term refers to the compound according to the following structure:

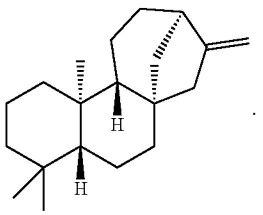

The term "kaurenol" refers to the compound kaurenol, including any stereoisomer of kaurenol. In particular embodiments, the term refers to the enantiomer known in the art as ent-kaurenol. In particular embodiments, the term refers to the compound according to the following structure.

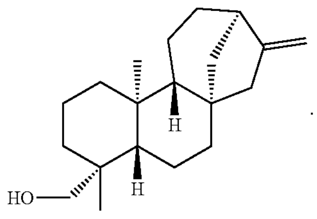

The term "kaurenal" refers to the compound kaurenal, including any stereoisomer of kaurenal. In particular embodiments, the term refers to the enantiomer known in the art as ent-kaurenal. In particular embodiments, the term refers to the compound according to the following structure.

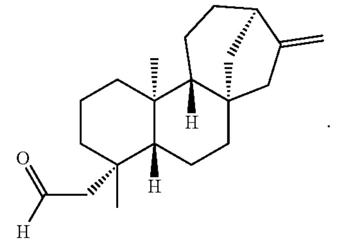

The term "kaurenoic acid" refers to the compound kaurenoic acid, including any stereoisomer of kaurenoic acid. In particular embodiments, the term refers to the enantiomer known in the art as ent-kaurenoic acid. In particular embodiments, the term refers to the compound according to the following structure.

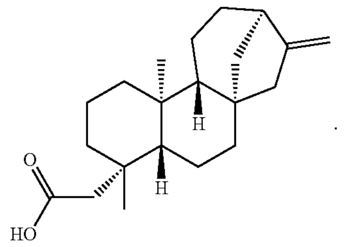

The term "steviol" refers to the compound steviol, including any stereoisomer of steviol. In particular embodiments, the term refers to the compound according to the following structure.

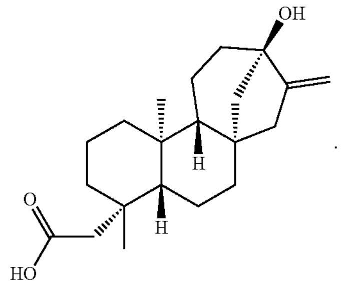

As used herein, the term "steviol glycoside(s)" refers to a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside D, rebaudioside N, rebaudioside O, synthetic steviol glycosides, e.g. enzymatically glucosylated steviol glycosides and combinations thereof.

As used herein, the term "Rebaudioside M" refers to the compound of the following structure.

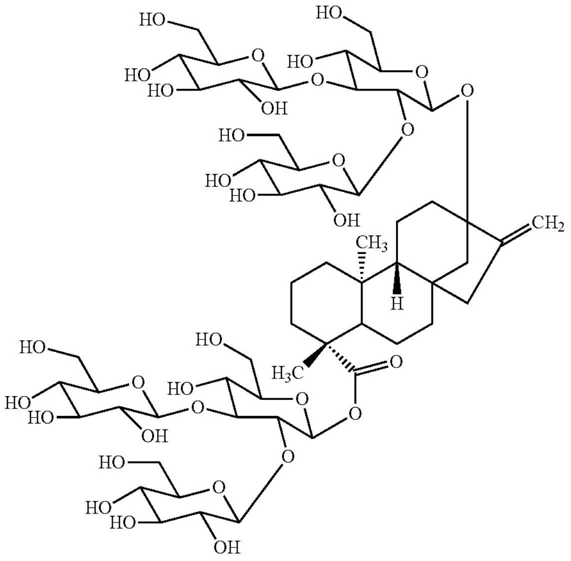

As used herein, the term "variant" refers to a polypeptide differing from a specifically recited "reference" polypeptide (e.g., a wild-type sequence) by amino acid insertions, deletions, mutations, and/or substitutions, but retains an activity that is substantially similar to the reference polypeptide. In some embodiments, the variant is created by recombinant DNA techniques or by mutagenesis. In some embodiments, a variant polypeptide differs from its reference polypeptide by the substitution of one basic residue for another (i.e. Arg for Lys), the substitution of one hydrophobic residue for another (i.e. Leu for Ile), or the substitution of one aromatic residue for another (i.e. Phe for Tyr), etc. In some embodiments, variants include analogs wherein conservative substitutions resulting in a substantial structural analogy of the reference sequence are obtained. Examples of such conservative substitutions, without limitation, include glutamic acid for aspartic acid and vice-versa; glutamine for asparagine and vice-versa; serine for threonine and vice-versa; lysine for arginine and vice-versa; or any of isoleucine, valine or leucine for each other.

As used herein, the term "sequence identity" or "percent identity," in the context or two or more nucleic acid or protein sequences, refers to two or more sequences or subsequences that are the same or have a specified percentage of amino acid residues or nucleotides that are the same. For example, the sequence can have a percent identity of at least 60%, at least 65%, at least 70%, at least 75%, at least 80%, at least 85%, at least 90%, at least 91% at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer programs and mathematical algorithms known in the art. Such algorithms that calculate percent sequence identity generally account for sequence gaps and mismatches over the comparison region. Programs that compare and align sequences, like Clustal W (Thompson et al., (1994) *Nucleic Acids Res.,* 22: 4673-4680), ALIGN (Myers et al., (1988) *CABIOS,* 4: 11-17), FASTA (Pearson et al., (1988) *PNAS,* 85:2444-2448; Pearson (1990), *Methods Enzymol.,* 183: 63-98) and gapped BLAST (Altschul et al., (1997) *Nucleic Acids Res.,* 25: 3389-3402) are useful for this purpose. The BLAST or BLAST 2.0 (Altschul et al., *J. Mol. Biol.* 215:403-10, 1990) is available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=2, Nucleic mismatch=−3, Expectation value=10.0, Word size=11, Max matches in a query range=0). For polypeptide sequence alignment and sequence identity calculations, BLASTP program is used with its default parameters (Alignment matrix=BLOSUM62; Gap costs: Existence=11, Extension=1; Compositional adjustments=Conditional compositional score, matrix adjustment; Expectation value=10.0; Word size=6; Max matches in a query range=0). Alternatively, the following program and parameters can be used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix. In the embodiments described herein, the sequence identity is calculated using BLASTN or BLASTP programs using their default parameters. In the embodiments described herein, the sequence alignment of two or more sequences are performed using Clustal W using the suggested default parameters (Dealign input sequences: no; Mbed-like clustering guide-tree: yes; Mbed-like clustering iteration: yes; number of combined iterations: default(0); Max guide tree iterations: default; Max HMM iterations: default; Order: input).

6.2 ABC-transporter, Nucleic Acids, Expression Cassettes, and Host Cells

In one aspect, provided herein are recombinant nucleic acids which express ABC-transporters. ABC-transporters of the invention can be identified by sequence-based searches against the sequences of known ABC-transporters. An exemplary sequence database of known ABC-transporters is provided by (Kovalchuk and Driessen, Phylogenetic Analysis of Fungal ABC Transporters, BMC Genomics, 2010, 11:177). ABC-transporter BLAST databases may also be generated from additional organisms. In preferred embodiments, fungal sequence databases from (1) *Hansenula polymorpha* DL-1 (NRRL-Y-7560), (2) *Yarrowia lipolytica* ATCC 18945, (3) *Arxula adeninivorans* ATCC 76597, (4) *S. cerevisiae* CAT-1, (5) *Lipomyces starkeyi* ATCC 58690, (6)*Kluyveromyces marxianus*, (7) *Kluyveromyces marxianus* DMKU3-1042, (8) *Komagataella phaffii* NRRL Y-11430, (9) *S. cerevisiae* MBG3370, (10) *S. cerevisiae* MBG3373, (11) *K. lactis* ATCC 8585, (12) *Candida utilis* ATCC 22023, (13) *Pichia pastoris* ATCC 28485, and (14) *Aspergillus oryzae* NRRL5590 serve as sources of ABC-transporters of the invention.

Nucleotide ORF sequences generated from de novo genomic sequencing, assembly, and annotation of various organisms are analyzed by the tblastn algorithm using Biopython or any other suitable sequence analysis software. The tblastn algorithm provides alignments of protein sequences of known ABC-transporters with translated DNA of the nucleotide ORF sequences for each organism in all 6 possible reading frames using BLAST. Exemplary BLAST parameters are standard with evalue=1e-25 (Tables 4 and 5). Hits can be subsequently filtered to ensure a global alignment of at least 2000 nucleotides.

In other embodiments of the invention, the entire proteome of an organism can be pulled from Uniprot using the Uniprot API in order to create a database for a BLAST search. The blastp algorithm can be applied to the Uniprot derived database. In one embodiment, BLAST parameters can be standard, with evalue=0.001. In particular embodiments, filtering can be performed based on a percent identity cutoff of ≥40%, and a percent aligned length cutoff of ≥60%. In preferred embodiments, hits have to match at least one of the 610 seed sequences from the reference.

Once nucleotide sequences are identified, primers can be designed to amplify each complete ORF amplified via PCR. Each PCR primer should ideally have flanking homology to the promoter and terminator DNA sequences of a promoter and terminator used in a heterologous nucleotide expression cassette added to the ends to facilitate homologous recombination of the amplified gene into a landing pad target site to produce the specific ABC-transporter expression cassette. Each ABC-transporter gene can be transformed individually as a single copy into the parental Reb M yeast strain described herein and screened for the ability to increase product titers when overexpressed in vivo.

In certain embodiments the recombinant nucleic acids encode a polypeptide that has the amino acid sequence provided in any of SEQ ID NOS: 1-8. In certain embodiments, the recombinant nucleic acid contains the nucleotide sequence provided in any of SEQ ID NOS: 20-27.

Also provided herein are host cells comprising one or more of the ABC-transporter polypeptides or nucleic acids provided herein that are capable of producing steviol glycosides. In certain embodiments, the host cells can produce steviol glycosides from a carbon source in a culture medium. In particular embodiments, the host cells can produce steviol from a carbon source in a culture medium and can further produce Reb A or Reb D from the steviol. In particular embodiments, the host cells can further produce Reb M from the Reb D. In particular embodiments, the Reb D and/or Reb M is transported to the lumen of one or more organelles. In particular embodiments, the Reb D and/or Reb M is transported to the extracellular space (i.e., supernatant).

In certain embodiments, host cells expressing ABC-transporters according to the above embodiments produce at least 20%, at least 30%, at least 40%, at least 50%, at least 60%, at least 70%, at least 80%, at least 90%, or at least 100% more total steviol glycoside (TSG) compared to the parent host cell lacking the ABC-transporter expression cassette.

In certain embodiments, host cells expressing ABC-transporters according to the above embodiments produce at least 20%, at least 30%, at least 40%, at least 50%, at least 60%, at least 70%, or at least 75% more TSG in the supernatant compared to the parent host cell lacking the ABC-transporter expression cassette. In a particular embodiment, host cells expressing ABC-transporters according to the above embodiments produce at least 2-fold, at least 3-fold, at least 4-fold, or at least 5-fold more TSG in the supernatant compared to the parent host cell lacking the ABC-transporter expression cassette.

In advantageous embodiments, the host cell can comprise one or more enzymatic pathways capable of making kaurenoic acid, said pathways taken individually or together. As described herein, the host cells comprise a *Stevia rebaudiana* kaurenoic acid hydroxylase provided herein, capable of converting kaurenoic acid to steviol. In certain embodiments, the host cell further comprises one or more enzymes capable of converting farnesyl diphosphate to geranylgeranyl diphosphate. In certain embodiments, the host cell further comprises one or more enzymes capable of converting geranylgeranyl diphosphate to copalyl diphosphate. In certain embodiments, the host cell further comprises one or more enzymes capable of converting copalyl diphosphate to kaurene. In certain embodiments, the host cell further comprises one or more enzymes capable of converting kaurene to kaurenoic acid. In certain embodiments, the host cell further comprises one or more enzymes capable of converting steviol to one or more steviol glycosides. In certain embodiments, the host cell further comprises one, two, three, four, or more enzymes together capable of converting steviol to Reb A. In certain embodiments, the host cell further comprises one or more enzymes capable of converting Reb A to Reb D. In certain embodiments, the host cell further comprises one or more enzymes capable of converting Reb D to Reb M. Useful enzymes and nucleic acids encoding the enzymes are known to those of skill. Particularly useful enzymes and nucleic acids are described in the sections below and further described, for example, in US 2014/0329281 A1, US 2014/0357588 A1, US 2015/0159188, WO 2016/038095 A2, and US 2016/0198748 A1.

In further embodiments, the host cells further comprise one or more enzymes capable of making geranylgeranyl diphosphate from a carbon source. These include enzymes of the DXP pathway and enzymes of the MEV pathway. Useful enzymes and nucleic acids encoding the enzymes are known to those of skill in the art. Exemplary enzymes of each pathway are described below and further described, for example, in US 2016/0177341 A1 which is incorporated herein by reference in its entirety.

In some embodiments, the host cells comprise one or more or all of the isoprenoid pathway enzymes selected from the group consisting of: (a) an enzyme that condenses two molecules of acetyl-coenzyme A to form acetoacetyl-CoA (e.g., an acetyl-coA thiolase); (b) an enzyme that condenses acetoacetyl-CoA with another molecule of acetyl-CoA to form 3-hydroxy-3-methylglutaryl-CoA (HMG-CoA) (e.g., an HMG-CoA synthase); (c) an enzyme that converts HMG-CoA into mevalonate (e.g., an HMG-CoA reductase); (d) an enzyme that converts mevalonate into mevalonate 5-phosphate (e.g., a mevalonate kinase); (e) an enzyme that converts mevalonate 5-phosphate into mevalonate 5-pyrophosphate (e.g., a phosphomevalonate kinase); (0 an enzyme that converts mevalonate 5-pyrophosphate into isopentenyl diphosphate (IPP) (e.g., a mevalonate pyrophosphate decarboxylase); (g) an enzyme that converts IPP into dimethylallyl pyrophosphate (DMAPP) (e.g., an IPP isomerase); (h) a polyprenyl synthase that can condense IPP and/or DMAPP molecules to form polyprenyl compounds containing more than five carbons; (i) an enzyme that condenses IPP with DMAPP to form geranyl pyrophosphate (GPP) (e.g., a GPP synthase); (j) an enzyme that condenses two molecules of IPP with one molecule of DMAPP (e.g., an FPP synthase); (k) an enzyme that condenses IPP with GPP to form farnesyl pyrophosphate (FPP) (e.g., an FPP synthase); (1) an enzyme that condenses IPP and DMAPP to form geranylgeranyl pyrophosphate (GGPP); and (m) an enzyme that condenses IPP and FPP to form GGPP.

In certain embodiments, the additional enzymes are native. In advantageous embodiments, the additional enzymes are heterologous. In certain embodiments, two or more enzymes can be combined in one polypeptide.

6.3 Cell Strains

Host cells useful compositions and methods provided herein include archae, prokaryotic, or eukaryotic cells.

Suitable prokaryotic hosts include, but are not limited, to any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella jlexneri, Shigella sonnei*, and *Staphylococcus aureus*. In a particular embodiment, the host cell is an *Escherichia coli* cell.

Suitable archae hosts include, but are not limited to, cells belonging to the genera: *Aeropyrum, Archaeglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella,*

*Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), Kluveromyces *marxianus, Arxula adeninivorans*, or *Hansenula polymorpha* (now known as *Pichia angusta*). In some embodiments, the host microbe is a strain of the genus *Candida*, such as *Candida lipolytica, Candida guilliermondii, Candida krusei, Candida pseudotropicalis*, or *Candida utilis*.

In a particular embodiment, the host microbe is *Saccharomyces cerevisiae*. In some embodiments, the host is a strain of *Saccharomyces cerevisiae* selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the host microbe is a strain of *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host microbe is a microbe that is suitable for industrial fermentation. In particular embodiments, the microbe is conditioned to subsist under high solvent concentration, high temperature, expanded substrate utilization, nutrient limitation, osmotic stress due to sugar and salts, acidity, sulfite and bacterial contamination, or combinations thereof, which are recognized stress conditions of the industrial fermentation environment.

6.4 The Steviol and Steviol Glycoside Biosynthesis Pathways

Figure 1:
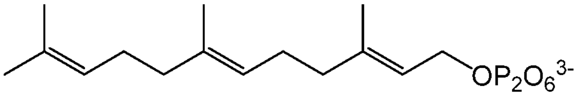
FIG. 1 is a schematic showing an enzymatic pathway from the native yeast metabolite farnesyl pyrophosphate (FPP) to steviol.
Figure 1:
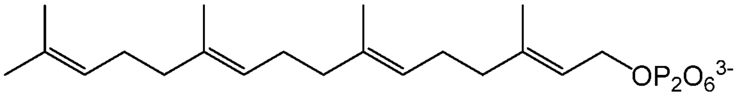
Figure 1:
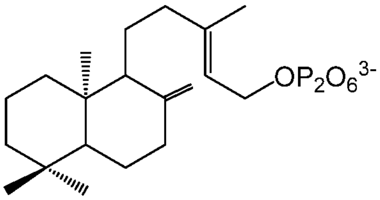
Figure 1:
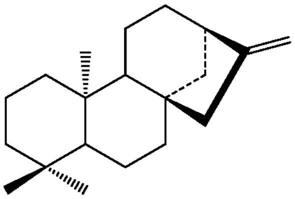
Figure 1:
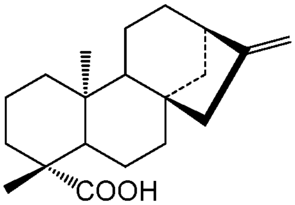
Figure 1:
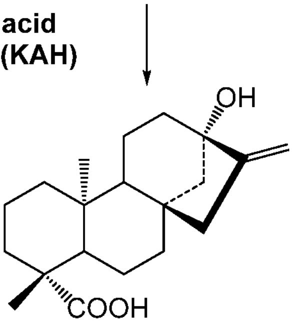

In some embodiments, a steviol biosynthesis pathway and/or a steviol glycoside biosynthesis pathway is activated in the genetically modified host cells provided herein by engineering the cells to express polynucleotides and/or polypeptides encoding one or more enzymes of the pathway. FIG. 1 illustrates an exemplary steviol biosynthesis pathway.

Thus, in some embodiments, the genetically modified host cells provided herein comprise a heterologous polynucleotide encoding a polypeptide having geranylgeranyl diphosphate synthase (GGPPS) activity. In some embodiments, the genetically modified host cells provided herein comprise a heterologous polynucleotide encoding a polypeptide having copalyl diphosphate synthase or ent-copalyl pyrophosphate synthase (CDPS; also referred to as ent-copalyl pyrophosphate synthase or CPS) activity. In some embodiments, the genetically modified host cells provided herein comprise a heterologous polynucleotide encoding a polypeptide having kaurene synthase (KS; also referred to as ent-kaurene synthase) activity. In particular embodiments, the genetically modified host cells provided herein comprise a heterologous polynucleotide encoding a polypeptide having kaurene oxidase activity (KO; also referred to as ent-kaurene 19-oxidase) as described herein. In particular embodiments, the genetically modified host cells provided herein comprise a heterologous polynucleotide encoding a polypeptide having kaurenoic acid hydroxylase polypeptide activity (KAH; also referred to as steviol synthase) according to the embodiments provided herein. In some embodiments, the genetically modified host cells provided herein comprise a heterologous polynucleotide encoding a polypeptide having cytochrome P450 reductase (CPR) activity.

In some embodiments, the genetically modified host cells provided herein comprise a heterologous polynucleotide encoding a polypeptide having UGT74G1 activity. In some embodiments, the genetically modified host cells provided herein comprise a heterologous polynucleotide encoding a polypeptide having UGT76G1 activity. In some embodiments, the genetically modified host cells provided herein comprise a heterologous polynucleotide encoding a polypeptide having UGT85C2 activity. In some embodiments, the genetically modified host cells provided herein comprise a heterologous polynucleotide encoding a polypeptide having UGT91D activity. In some embodiments, the genetically modified host cells provided herein comprise a heterologous polynucleotide encoding a polypeptide having $UGT_{AD}$ activity. As described below, $UGT_{AD}$ refers to a uridine diphosphate-dependent glycosyl transferase capable of transferring a glucose moiety to the C-2' position of the 19-O-glucose of Reb A to produce Reb D.

In certain embodiments, the host cell comprises a variant enzyme. In certain embodiments, the variant can comprise up to 15, 10, 9, 8, 7, 6, 5, 4, 3, 2, or 1 amino acid substitutions relative to the relevant polypeptide. In certain embodiments, the variant can comprise up to 15, 10, 9, 8, 7, 6, 5, 4, 3, 2, or 1 conservative amino acid substitutions relative to the reference polypeptide. In certain embodiments, any of the nucleic acids described herein can be optimized for the host cell, for instance codon optimized.

Exemplary nucleic acids and enzymes of a steviol biosynthesis pathway and/or a steviol glycoside biosynthesis pathway are described below.

6.4.1 Geranylgeranyl Diphosphate Synthase (GGPPS)

Geranylgeranyl diphosphate synthases (EC 2.5.1.29) catalyze the conversion of farnesyl pyrophosphate into geranylgeranyl diphosphate. Illustrative examples of enzymes include those of *Stevia rebaudiana* (accession no. ABD92926), *Gibberella fujikuroi* (accession no. CAA75568), *Mus musculus* (accession no. AAH69913), *Thalassiosira pseudonana* (accession no. XP_002288339), *Streptomyces clavuligerus* (accession no. ZP_05004570), *Sulfulobus acidocaldarius* (accession no. BAA43200), Synechococcus sp. (accession no. ABC98596), *Arabidopsis thaliana* (accession no. NP_195399), and *Blakeslea trispora* (accession no. AFC92798.1), and those described in US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these GGPPS nucleic acids. In certain embodiments, provided herein are cells and methods using a nucleic acid that encodes a polypeptide having at least 80%, 85%, 90%, 95% sequence identity to at least one of these GGPPS enzymes.

6.4.2 Copalyl Diphosphate Synthase (CDPS)

Copalyl diphosphate synthases (EC 5.5.1.13) catalyze the conversion of geranylgeranyl diphosphate into copalyl diphosphate. Illustrative examples of enzymes include those of *Stevia rebaudiana* (accession no. AAB87091), *Streptomyces clavuligerus* (accession no. EDY51667), *Bradyrhizobium japonicum* (accession no. AAC28895.1), *Zea mays* (accession no. AY562490), *Arabidopsis thaliana* (accession no. NM_116512), and *Oryza sativa* (accession no. Q5MQ85.1), and those described in US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these CDPS nucleic acids. In certain embodiments, provided herein are cells and methods using a nucleic acid that encodes a polypeptide having at least 80%, 95%, 90%, or 95% sequence identity to at least one of these CDPS enzymes.

6.4.3 Kaurene Synthase (KS)

Kaurene synthases (EC 4.2.3.19) catalyze the conversion of copalyl diphosphate into kaurene and diphosphate. Illustrative examples of enzymes include those of *Bradyrhizobium japonicum* (accession no. AAC28895.1), *Phaeosphaeria* sp. (accession no. 013284), *Arabidopsis thaliana* (accession no. Q9SAK2), and *Picea glauca* (accession no. ADB55711.1), and those described in US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these KS nucleic acids. In certain embodiments, provided herein are cells and methods using a nucleic acid that encodes a polypeptide having at least 80%, 85%, 85%, 90%, or 95% sequence identity to at least one of these KS enzymes.

6.4.4 Bifunctional Copalyl Diphosphate Synthase (CDPS) and Kaurene Synthase (KS)

CDPS-KS bifunctional enzymes (EC 5.5.1.13 and EC 4.2.3.19) also can be used. Illustrative examples of enzymes include those of *Phomopsis amygdali* (accession no. BAG30962), *Physcomitrella patens* (accession no. BAF61135), and *Gibberella fujikuroi* (accession no. Q9UVY5.1), and those described in US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these CDPS-KS nucleic acids. In certain embodiments, provided herein are cells and methods using a nucleic acid that encodes a polypeptide having at least 80%, 85%, 90%, or 95% sequence identity to at least one of these CDPS-KS enzymes.

6.4.5 Ent-Kaurene Oxidase (KO)

Ent-kaurene oxidases (EC 1.14.13.78; also referred to as kaurene oxidases herein) catalyze the conversion of kaurene into kaurenoic acid. Illustrative examples of enzymes include those of *Oryza sativa* (accession no. Q5Z5R4), *Gibberella fujikuroi* (accession no. 094142), *Arabidopsis thaliana* (accession no. Q93ZB2), *Stevia rebaudiana* (accession no. AAQ63464.1), and *Pisum sativum* (Uniprot no. Q6XAF4), and those described in US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these KO nucleic acids. In certain embodiments, provided herein are cells and methods using a nucleic acid that encodes a polypeptide having at least 80%, 85%, 90%, or 95% sequence identity to at least one of these KO enzymes.

6.4.6 Steviol Synthase (KAH)

Steviol synthases, or kaurenoic acid hydroxylases (KAH), (EC 1.14.13) catalyze the conversion of kaurenoic acid into steviol. Illustrative examples of enzymes include those of *Stevia rebaudiana* (accession no. ACD93722), *Stevia rebaudiana* (SEQ ID NO:10) *Arabidopsis thaliana* (accession no. NP_197872), *Vitis vinifera* (accession no. XP_002282091), and *Medicago trunculata* (accession no. ABC59076), and those described in US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these KAH nucleic acids. In certain embodiments, provided herein are cells and methods using a nucleic acid that encodes a polypeptide having at least 80%, 85%, 90%, or 95% sequence identity to at least one of these KAH enzymes.

6.4.7 Cytochrome P450 Reductase (CPR)

Cytochrome P450 reductases (EC 1.6.2.4) are necessary for the activity of KO and/or KAH above. Illustrative examples of enzymes include those of *Stevia rebaudiana* (accession no. ABB88839) *Arabidopsis thaliana* (accession no. NP_194183), *Gibberella fujikuroi* (accession no. CAE09055), and *Artemisia annua* (accession no. ABC47946.1), and those described in US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these CPR nucleic acids. In certain embodiments, provided herein are cells and methods using a nucleic acid that encodes a polypeptide having at least 80%, 85%, 90%, or 95% sequence identity to at least one of these CPR enzymes.

6.4.8 UDP Glycosyltransferase 74G1 (UGT74G1)

A UGT74G1 is capable of functioning as a uridine 5'-diphospho glucosyl: steviol 19-COOH transferase and as a uridine 5'-diphospho glucosyl: steviol-13-O-glucoside 19-COOH transferase. As shown in FIG. 1, a UGT74G1 is capable of converting steviol to 19-glycoside. A UGT74G1 is also capable of converting steviolmonoside to rubusoside. A UGT74G1 may be also capable of converting steviolbioside to stevioside. Illustrative examples of enzymes include those of *Stevia rebaudiana* (e.g., those of Richman et al., 2005, Plant J. 41: 56-67 and US 2014/0329281 and WO 2016/038095 A2 and accession no. AAR06920.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT74G1 nucleic acids. In certain embodiments, provided herein are cells and methods using a nucleic acid that encodes a polypeptide having at least 80%, 85%, 90%, or 95% sequence identity to at least one of these UGT74G1 enzymes.

6.4.9 UDP Glycosyltransferase 76G1 (UGT76G1)

A UGT76G1 is capable of transferring a glucose moiety to the C-3' of the C-13-0-glucose of the acceptor molecule, a steviol 1,2 glycoside. Thus, a UGT76G1 is capable of functioning as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. UGT76G1 is capable of converting steviolbioside to Reb B. A UGT76G1 is also capable of converting stevioside to Reb A. A UGT76G1 is also capable of converting Reb D to Reb M. Illustrative examples of enzymes include those of *Stevia rebaudiana* (e.g., those of Richman et al., 2005*, Plant J.* 41: 56-67 and US 2014/0329281 A1 and WO 2016/038095 A2 and accession no. AAR06912.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT76G1 nucleic acids. In certain embodiments, provided herein are cells and methods using a nucleic acid that encodes a polypeptide having at least 80%, 85%, 90%, or 95% sequence identity to at least one of these UGT76G1 enzymes.

6.4.10 UDP Glycosyltransferase 85C2 (UGT85C2)

A UGT85C2 is capable of functioning as a uridine 5'-diphospho glucosyl:steviol 13-OH transferase, and a uridine 5'-diphospho glucosyl:steviol-19-O-glucoside 13-OH transferase. A UGT85C2 is capable of converting steviol to steviolmonoside, and is also capable of converting 19-glycoside to rubusoside. Illustrative examples of enzymes include those of *Stevia rebaudiana* (e.g., those of Richman et al., 2005, Plant J. 41: 56-67 and US 2014/0329281 A1 and WO 2016/038095 A2 and accession no. AAR06916.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT85C2 nucleic acids. In certain embodiments, provided herein are cells and methods using a nucleic acid that encodes a polypeptide having at least 80%, 85%, 90%, or 95% sequence identity to at least one of these UGT85C2 enzymes.

6.4.11 UDP-Glycosyltransferase 91D (UGT91D)

A UGT91D is capable of functioning as a uridine 5'-diphosphoglucosyl:steviol-13-O-glucoside transferase, transferring a glucose moiety to the C-2' of the 13-O-glucose of the acceptor molecule, steviol-13-O-glucoside (steviolmonoside) to produce steviolbioside. A UGT91D is also capable of functioning as a uridine 5'-diphosphoglucosyl: rubusoside transferase, transferring a glucose moiety to the C-2' of the 13-O-glucose of the acceptor molecule, rubusoside, to provide stevioside. A UGT91D is also referred to as UGT91D2, UGT91D2e, or UGT91D-like3. Illustrative examples of UGT91D enzymes include those of *Stevia rebaudiana* (e.g., those of UGT sequence with accession no. ACE87855.1, US 2014/0329281 A1, WO 2016/038095 A2, and SEQ ID NO:7). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT91D nucleic acids. In certain embodiments, provided herein are cells and methods using a nucleic acid that encodes a polypeptide having at least 80%, 85%, 90%, or 95% sequence identity to at least one of these UGT91D enzymes.

6.4.12 Uridine Diphosphate-Dependent Glycosyl Transferase Capable of Converting Reb a to Reb D ($UGT_{AD}$)

A uridine diphosphate-dependent glycosyl transferase ($UGT_{AD}$) is capable of transferring a glucose moiety to the C-2' position of the 19-O-glucose of Reb A to produce Reb D. A $UGT_{AD}$ is also capable of transferring a glucose moiety to the C-2' position of the 19-O-glucose of stevioside to produce Reb E. Useful examples of UGTs include Os_UGT_91C1 from *Oryza sativa* (also referred to as EUGT11 in Houghton-Larsen et al., WO 2013/022989 A2; XP_015629141.1) and Sl_UGT_101249881 from *Solanum lycopersicum* (also referred to as UGTSL2 in Markosyan et al., WO2014/193888 A1; XP_004250485.1). Further useful UGTs include UGT40087 (XP_004982059.1; as described in WO 2018/031955), sr. UGT_9252778, Bd UGT10840 (XP_003560669.1), Hv_UGT_V1 (BAJ94055.1), Bd UGT10850 (XP_010230871.1), and Ob_UGT91B1_like (XP_006650455.1). Any UGT or UGT variant can be used in the compositions and methods described herein. Nucleic acids encoding these enzymes are useful in the cells and methods provided herein. In certain embodiments, provided herein are cells and methods using a nucleic acid having at least 80%, 85%, 90%, or 95% sequence identity to at least one of the UGTs. In certain embodiments, provided herein are cells and methods using a nucleic acid that encodes a polypeptide having at least 80%, 85%, 90%, or 95% sequence identity to at least one of these UGTs. In certain embodiments, provided herein are a nucleic acid that encodes a UGT variant described herein.

6.5 MEV Pathway FPP and/or GGPP Production

In some embodiments, a genetically modified host cell provided herein comprises one or more heterologous enzymes of the MEV pathway, useful for the formation of FPP and/or GGPP. In some embodiments, the one or more enzymes of the MEV pathway comprise an enzyme that condenses acetyl-CoA with malonyl-CoA to form acetoacetyl-CoA. In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate. In some embodiments, the one or more enzymes of the MEV pathway comprise an enzyme that converts isopentenyl pyrophosphate to dimethylallyl diphosphate.

In some embodiments, the one or more enzymes of the MEV pathway are selected from the group consisting of acetyl-CoA thiolase, acetoacetyl-CoA synthetase, HMG-CoA synthase, HMG-CoA reductase, mevalonate kinase, phosphomevalonate kinase, mevalonate pyrophosphate decarboxylase, and isopentyl diphosphate:dimethylallyl diphosphate isomerase (IDI or IPP isomerase). In some embodiments, with regard to the enzyme of the MEV pathway capable of catalyzing the formation of acetoacetyl-CoA, the genetically modified host cell comprises either an enzyme that condenses two molecules of acetyl-CoA to form acetoacetyl-CoA, e.g., acetyl-CoA thiolase; or an enzyme that condenses acetyl-CoA with malonyl-CoA to form acetoacetyl-CoA, e.g., acetoacetyl-CoA synthase. In some embodiments, the genetically modified host cell comprises both an enzyme that condenses two molecules of acetyl-CoA to form acetoacetyl-CoA, e.g., acetyl-CoA thiolase; and an enzyme that condenses acetyl-CoA with malonyl-CoA to form acetoacetyl-CoA, e.g., acetoacetyl-CoA synthase.

In some embodiments, the host cell comprises one or more heterologous nucleotide sequences encoding more than one enzyme of the MEV pathway. In some embodiments, the host cell comprises one or more heterologous nucleotide sequences encoding two enzymes of the MEV pathway. In some embodiments, the host cell comprises one or more heterologous nucleotide sequences encoding an enzyme that can convert HMG-CoA into mevalonate and an enzyme that can convert mevalonate into mevalonate 5-phosphate. In some embodiments, the host cell comprises one or more heterologous nucleotide sequences encoding three enzymes of the MEV pathway. In some embodiments, the host cell comprises one or more heterologous nucleotide sequences encoding four enzymes of the MEV pathway. In some embodiments, the host cell comprises one or more heterologous nucleotide sequences encoding five enzymes of the MEV pathway. In some embodiments, the host cell comprises one or more heterologous nucleotide sequences encoding six enzymes of the MEV pathway. In some embodiments, the host cell comprises one or more heterologous nucleotide sequences encoding seven enzymes of the MEV pathway. In some embodiments, the host cell comprises a plurality of heterologous nucleic acids encoding all of the enzymes of the MEV pathway.

In some embodiments, the genetically modified host cell further comprises a heterologous nucleic acid encoding an enzyme that can convert isopentenyl pyrophosphate (IPP) into dimethylallyl pyrophosphate (DMAPP). In some embodiments, the genetically modified host cell further comprises a heterologous nucleic acid encoding an enzyme that can condense IPP and/or DMAPP molecules to form a polyprenyl compound. In some embodiments, the genetically modified host cell further comprise a heterologous nucleic acid encoding an enzyme that can modify IPP or a polyprenyl to form an isoprenoid compound such as FPP.

6.5.1 Conversion of Acetyl-CoA to Acetoacetyl-CoA

In some embodiments, the genetically modified host cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denarificans*), and (L20428; *Saccharomyces cerevisiae*).

Acetyl-CoA thiolase catalyzes the reversible condensation of two molecules of acetyl-CoA to yield acetoacetyl-CoA, but this reaction is thermodynamically unfavorable; acetoacetyl-CoA thiolysis is favored over acetoacetyl-CoA synthesis. Acetoacetyl-CoA synthase (AACS) (alternately referred to as acetyl-CoA:malonyl-CoA acyltransferase; EC 2.3.1.194) condenses acetyl-CoA with malonyl-CoA to form acetoacetyl-CoA. In contrast to acetyl-CoA thiolase, AACS-catalyzed acetoacetyl-CoA synthesis is essentially an energy-favored reaction, due to the associated decarboxylation of malonyl-CoA. In addition, AACS exhibits no thiolysis activity against acetoacetyl-CoA, and thus the reaction is irreversible.

In host cells comprising acetyl-CoA thiolase and a heterologous ADA and/or phosphotransacetylase (PTA), the reversible reaction catalyzed by acetyl-CoA thiolase, which favors acetoacetyl-CoA thiolysis, may result in a large acetyl-CoA pool. In view of the reversible activity of ADA, this acetyl-CoA pool may in turn drive ADA towards the reverse reaction of converting acetyl-CoA to acetaldehyde, thereby diminishing the benefits provided by ADA towards acetyl-CoA production. Similarly, the activity of PTA is reversible, and thus, a large acetyl-CoA pool may drive PTA towards the reverse reaction of converting acetyl-CoA to acetyl phosphate. Therefore, in some embodiments, in order to provide a strong pull on acetyl-CoA to drive the forward reaction of ADA and PTA, the MEV pathway of the genetically modified host cell provided herein utilizes an acetoacetyl-CoA synthase to form acetoacetyl-CoA from acetyl-CoA and malonyl-CoA.

In some embodiments, the AACS is from *Streptomyces* sp. strain CL190 (Okamura et al., *Proc Natl Acad Sci USA* 107(25):11265-70 (2010). Representative AACS nucleotide sequences of *Streptomyces* sp. strain CL190 include accession number AB540131.1. Representative AACS protein sequences of *Streptomyces* sp. strain CL190 include accession numbers D7URV0, BAJ10048. Other acetoacetyl-CoA synthases useful for the compositions and methods provided herein include, but are not limited to, *Streptomyces* sp. (AB183750; KO-3988 BAD86806); *S. anulatus* strain 9663 (FN178498; CAX48662); *Streptomyces* sp. KO-3988 (AB212624; BAE78983); *Actinoplanes* sp. A40644 (AB113568; BAD07381); *Streptomyces* sp. C (NZ_ACEW010000640; ZP_05511702); *Nocardiopsis dassonvillei* DSM 43111 (NZ_ABUI01000023; ZP_04335288); *Mycobacterium ulcerans* Agy99 (NC_008611; YP 907152); *Mycobacterium marinum* M (NC_010612; YP_001851502); *Streptomyces* sp. Mg1 (NZ_DS570501; ZP_05002626); *Streptomyces* sp. AA4 (NZ_ACEV01000037; ZP_05478992); *S. roseosporus* NRRL 15998 (NZ ABYB01000295; ZP_04696763); *Streptomyces* sp. ACTE (NZ ADFD01000030; ZP_06275834); *S. viridochromogenes* DSM 40736 (NZ_ACEZ01000031; ZP_05529691); *Frankia* sp. CcI3 (NC_007777; YP_480101); *Nocardia brasiliensis* (NC_018681; YP_006812440.1); and *Austwickia chelonae* (NZ_BAGZ01000005; ZP_10950493.1). Additional suitable acetoacetyl-CoA synthases include those described in U.S. Patent Application Publication Nos. 2010/0285549 and 2011/0281315, the contents of which are incorporated by reference in their entireties.

Acetoacetyl-CoA synthases also useful in the compositions and methods provided herein include those molecules which are said to be "derivatives" of any of the acetoacetyl-CoA synthases described herein. Such a "derivative" has the following characteristics: (1) it shares substantial homology with any of the acetoacetyl-CoA synthases described herein; and (2) is capable of catalyzing the irreversible condensation of acetyl-CoA with malonyl-CoA to form acetoacetyl-CoA. A derivative of an acetoacetyl-CoA synthase is said to share "substantial homology" with acetoacetyl-CoA synthase if the amino acid sequences of the derivative is at least 80%, and more preferably at least 90%, and most preferably at least 95%, the same as that of acetoacetyl-CoA synthase.

6.5.2 Conversion of Acetoacetyl-CoA to HMG-CoA

In some embodiments, the host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

6.5.3 Conversion of HMG-CoA to Mevalonate

In some embodiments, the host cell comprises a heterologous nucleotide sequence encoding an enzyme that can convert HMG-CoA into mevalonate, e.g., a HMG-CoA reductase. In some embodiments, HMG-CoA reductase is an NADH-using hydroxymethylglutaryl-CoA reductase-CoA reductase. HMG-CoA reductases (EC 1.1.1.34; EC 1.1.1.88) catalyze the reductive deacylation of (S)-HMG-CoA to (R)-mevalonate, and can be categorized into two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH. See, e.g., Hedl et al., *Journal of Bacteriology* 186 (7): 1927-1932 (2004). Co-factor specificities for select class II HMG-CoA reductases are provided below.

Co-factor specificities for select class II HMG-CoA reductases

| Source | Coenzyme specificity | $K_m^{NADPH}$ (μm) | $K_m^{NADH}$ (μm) |
|---|---|---|---|
| *P. mevalonii* | NADH | | 80 |
| *A. fulgidus* | NAD(P)H | 500 | 160 |
| *S. aureus* | NAD(P)H | 70 | 100 |
| *E. faecalis* | NADPH | 30 | |

Useful HMG-CoA reductases for the compositions and methods provided herein include HMG-CoA reductases that are capable of utilizing NADH as a cofactor, e.g., HMG-CoA reductase from *P. mevalonii, A. fulgidus* or *S. aureus*. In particular embodiments, the HMG-CoA reductase is capable of only utilizing NADH as a cofactor, e.g., HMG-CoA reductase from *P. mevalonii, S. pomeroyi* or *D. acidovorans*.

In some embodiments, the NADH-using HMG-CoA reductase is from *Pseudomonas mevalonii*. The sequence of the wild-type mvaA gene of *Pseudomonas mevalonii*, which encodes HMG-CoA reductase (EC 1.1.1.88), has been previously described. See Beach and Rodwell, *J. Bacteriol.* 171:2994-3001 (1989). Representative mvaA nucleotide sequences of *Pseudomonas mevalonii* include accession number M24015. Representative HMG-CoA reductase protein sequences of *Pseudomonas mevalonii* include accession numbers AAA25837, P13702, MVAA_PSEMV.

In some embodiments, the NADH-using HMG-CoA reductase is from *Silicibacter pomeroyi*. Representative HMG-CoA reductase nucleotide sequences of *Silicibacter pomeroyi* include accession number NC_006569.1. Representative HMG-CoA reductase protein sequences of *Silicibacter pomeroyi* include accession number YP_164994.

In some embodiments, the NADH-using HMG-CoA reductase is from *Delftia acidovorans*. A representative HMG-CoA reductase nucleotide sequences of *Delftia acidovorans* includes NC_010002 REGION: complement (319980 . . . 321269). Representative HMG-CoA reductase protein sequences of *Delftia acidovorans* include accession number YP_001561318.

In some embodiments, the NADH-using HMG-CoA reductases is from *Solanum tuberosum* (Crane et al., *J. Plant Physiol.* 159:1301-1307 (2002)).

NADH-using HMG-CoA reductases also useful in the compositions and methods provided herein include those molecules which are said to be "derivatives" of any of the NADH-using HMG-CoA reductases described herein, e.g., from *P. mevalonii, S. pomeroyi* and *D. acidovorans*. Such a "derivative" has the following characteristics: (1) it shares substantial homology with any of the NADH-using HMG-CoA reductases described herein; and (2) is capable of catalyzing the reductive deacylation of (S)-HMG-CoA to (R)-mevalonate while preferentially using NADH as a cofactor. A derivative of an NADH-using HMG-CoA reductase is said to share "substantial homology" with NADH-using HMG-CoA reductase if the amino acid sequences of the derivative is at least 80%, and more preferably at least 90%, and most preferably at least 95%, the same as that of NADH-using HMG-CoA reductase.

As used herein, the phrase "NADH-using" means that the NADH-using HMG-CoA reductase is selective for NADH over NADPH as a cofactor, for example, by demonstrating a higher specific activity for NADH than for NADPH. In some embodiments, selectivity for NADH as a cofactor is expressed as a $k_{cat}^{(NADH)}/k_{cat}^{(NADPH)}$) ratio. In some embodiments, the NADH-using HMG-CoA reductase has a $k_{cat}^{(NADH)}/k_{cat}^{(NADPH)}$ ratio of at least 5, 10, 15, 20, 25 or greater than 25. In some embodiments, the NADH-using HMG-CoA reductase uses NADH exclusively. For example, an NADH-using HMG-CoA reductase that uses NADH exclusively displays some activity with NADH supplied as the sole cofactor in vitro, and displays no detectable activity when NADPH is supplied as the sole cofactor. Any method for determining cofactor specificity known in the art can be utilized to identify HMG-CoA reductases having a preference for NADH as cofactor, including those described by Kim et al., *Protein Science* 9:1226-1234 (2000); and Wilding et al., *J. Bacteria* 182(18):5147-52 (2000), the contents of which are hereby incorporated in their entireties.

In some embodiments, the NADH-using HMG-CoA reductase is engineered to be selective for NADH over NAPDH, for example, through site-directed mutagenesis of the cofactor-binding pocket. Methods for engineering NADH-selectivity are described in Watanabe et al., *Micro-*

*biology* 153:3044-3054 (2007), and methods for determining the cofactor specificity of HMG-CoA reductases are described in Kim et al., *Protein Sci.* 9:1226-1234 (2000), the contents of which are hereby incorporated by reference in their entireties.

In some embodiments, the NADH-using HMG-CoA reductase is derived from a host species that natively comprises a mevalonate degradative pathway, for example, a host species that catabolizes mevalonate as its sole carbon source. Within these embodiments, the NADH-using HMG-CoA reductase, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: Anderson et al., *J. Bacteriol,* 171(12):6468-6472 (1989); Beach et al., *J. Bacteriol.* 171: 2994-3001 (1989); Bensch et al., *J. Biol. Chem.* 245:3755-3762; Fimongnari et al., *Biochemistry* 4:2086-2090 (1965); Siddiqi et al., *Biochem. Biophys. Res. Commun.* 8:110-113 (1962); Siddiqi et al., *J. Bacteria* 93:207-214 (1967); and Takatsuji et al., *Biochem. Biophys. Res. Commun.* 110:187-193 (1983), the contents of which are hereby incorporated by reference in their entireties.

In some embodiments of the compositions and methods provided herein, the host cell comprises both a NADH-using HMGr and an NADPH-using HMG-CoA reductase. Illustrative examples of nucleotide sequences encoding an NADPH-using HMG-CoA reductase include, but are not limited to: (NM_206548; *Drosophila melanogaster*), (NC_002758, Locus tag SAV2545, GeneID 1122570; *Staphylococcus aureus*), (AB015627; *Streptomyces* sp. KO 3988), (AX128213, providing the sequence encoding a truncated HMG-CoA reductase; *Saccharomyces cerevisiae*), and (NC_001145: complement (115734.118898; *Saccharomyces cerevisiae*).

6.5.4 Conversion of Mevalonate to Mevalonate-5-Phosphate

In some embodiments, the host cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

6.5.5 Conversion of Mevalonate-5-Phosphate to Mevalonate-5-Pyrophosphate

In some embodiments, the host cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; Hevea *brasiliensis*), (NM_006556; *Homo sapiens*), and (NC_001145. complement 712315.713670; *Saccharomyces cerevisiae*).

6.5.6 Conversion of Mevalonate-5-Pyrophosphate to IPP

In some embodiments, the host cell comprises a heterologous nucleotide sequence encoding an enzyme that can convert mevalonate 5-pyrophosphate into isopentenyl diphosphate (IPP), e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

6.5.7 Conversion of IPP to DMAPP

In some embodiments, the host cell further comprises a heterologous nucleotide sequence encoding an enzyme that can convert IPP generated via the MEV pathway into dimethylallyl pyrophosphate (DMAPP), e.g., an IPP isomerase. Illustrative examples of nucleotide sequences encoding such an enzyme include, but are not limited to: (NC_000913, 3031087.3031635; *Escherichia coli*), and (AF082326*; Haematococcus pluvialis*).

6.5.8 Polyprenyl Synthases

In some embodiments, the host cell further comprises a heterologous nucleotide sequence encoding a polyprenyl synthase that can condense IPP and/or DMAPP molecules to form polyprenyl compounds containing more than five carbons.

In some embodiments, the host cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745*; Clarkia breweri*), (AY953508*; Ips pini*), (DQ286930; *Lycopersicon esculentum*), (AF182828*; Mentha* x *piperita*), (AF182827*; Mentha* x *piperita*), (MPI249453*; Mentha* x *piperita*), (PZE431697, Locus CAD24425; *Paracoccus zeaxanthinifaciens*), (AY866498*; Picrorhiza kurrooa*), (AY351862; *Vitis vinifera*), and (AF203881, Locus AAF12843; *Zymomonas mobilis*).

In some embodiments, the host cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar *Copenhageni* str. *Fiocruz* L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP_779706; *Xylella fastidiosa* Temecula1).

In some embodiments, the host cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar *israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; Hevea *brasiliensis*), (AB017971; *Homo sapiens*), (MCI276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus aciditrophicus* SB), (NC_006840, Locus YP_204095; *Vibrio fischeri* ES114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

While examples of the enzymes of the mevalonate pathway are described above, in certain embodiments, enzymes of the DXP pathway can be used as an alternative or additional pathway to produce DMAPP and IPP in the host cells, compositions and methods described herein. Enzymes and nucleic acids encoding the enzymes of the DXP pathway are well-known and characterized in the art, e.g., WO 2012/135591 A2.

6.6 Methods of Producing Steviol Glycosides

In another aspect, provided herein is a method for the production of a steviol glycoside, the method comprising the steps of: (a) culturing a population of any of the genetically modified host cells described herein that are capable of producing a steviol glycoside in a medium with a carbon source under conditions suitable for making the steviol glycoside compound; and (b) recovering said steviol glycoside compound from the medium.

In some embodiments, the genetically modified host cell produces an increased amount of the steviol glycoside compared to a parent cell not comprising the one or more modifications, or a parent cell comprising only a subset of the one or more modifications of the genetically modified host cell, but is otherwise genetically identical. In some embodiments, the increased amount is at least 1%, 5%, 10%, 15%, 20%, 25%, 30%, 35%, 40%, 45%, 50%, 55%, 60%, 65%, 70%, 75%, 80%, 85%, 90%, 95%, 100% or greater than 100%, as measured, for example, in yield, production, and/or productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the host cell produces an elevated level of a steviol glycoside that is greater than about 1 grams per liter of fermentation medium. In some embodiments, the host cell produces an elevated level of a steviol glycoside that is greater than about 5 grams per liter of fermentation medium. In some embodiments, the host cell produces an elevated level of a steviol glycoside that is greater than about 10 grams per liter of fermentation medium. In some embodiments, the steviol glycoside is produced in an amount from about 10 to about 50 grams, from about 10 to about 15 grams, more than about 15 grams, more than about 20 grams, more than about 25 grams, or more than about 30 grams per liter of cell culture.

In some embodiments, the host cell produces an elevated level of a steviol glycoside that is greater than about 50 milligrams per gram of dry cell weight. In some such embodiments, the steviol glycoside is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by a parent cell, on a per unit volume of cell culture basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit dry cell weight basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit volume of cell culture per unit time basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit dry cell weight per unit time basis.

In most embodiments, the production of the elevated level of steviol glycoside by the host cell is inducible by the presence of an inducing compound. Such a host cell can be manipulated with ease in the absence of the inducing compound. The inducing compound is then added to induce the production of the elevated level of steviol glycoside by the host cell. In other embodiments, production of the elevated level of steviol glycoside by the host cell is inducible by changing culture conditions, such as, for example, the growth temperature, media constituents, and the like.

6.7 Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing steviol glycosides provided herein may be performed in a suitable culture medium (e.g., with or without pantothenate supplementation) in a suitable container, including but not limited to a cell culture plate, a microtiter plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium is any culture medium in which a genetically modified microorganism capable of producing an steviol glycoside can subsist, i.e., maintain growth and viability. In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, xylose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium is sufficient to promote cell growth, but is not so high as to repress growth of the microorganism used. Typically, cultures are run with a carbon source, such as glucose, being added at levels to achieve the desired level of growth and biomass. In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or steviol glycoside production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of steviol glycoside. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

In some embodiments, the carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. The carbon source concentration is typically maintained below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

Other suitable fermentation medium and methods are described in, e.g., WO 2016/196321.

6.8 Fermentation Compositions

In another aspect, provided herein are fermentation compositions comprising a genetically modified host cell described herein and steviol glycosides produced from genetically modified host cell. The fermentation compositions may further comprise a medium. In certain embodiments, the fermentation compositions comprise a genetically modified host cell, and further comprise Reb A, Reb D, and Reb M. In certain embodiments, the fermentation compositions provided herein comprise Reb M as a major component of the steviol glycosides produced from the genetically modified host cell. In certain embodiments, the fermentation compositions comprise Reb A, Reb D, and Reb M at a ratio of at least 1:7:50. In certain embodiments, the fermentation compositions comprise Reb A, Reb D, and Reb Mat a ratio of at least 1:7:50 to 1:100:1000. In certain embodiments, the fermentation compositions comprise a ratio of at least 1:7:50 to 1:200:2000. In certain embodiments, the ratio of Reb A, Reb D, and Reb M are based on the total content of steviol glycosides that are associated with the genetically modified host cell and the medium. In certain embodiments, the ratio of Reb A, Reb D, and Reb M are based on the total content of steviol glycosides in the medium. In certain embodiments, the ratio of Reb A, Reb D, and Reb M are based on the total content of steviol glycosides that are associated with the genetically modified host cell.

In certain embodiments, the fermentation compositions provided herein contain Reb M2 at an undetectable level. In certain embodiments, the fermentation compositions provided herein contain non-naturally occurring steviol glycosides at an undetectable level.

6.9 Recovery of Steviol Glycosides

Once the steviol glycoside is produced by the host cell, it may be recovered or isolated for subsequent use using any suitable separation and purification methods known in the art. In some embodiments, a clarified aqueous phase comprising the steviol glycoside is separated from the fermentation by centrifugation. In other embodiments, a clarified aqueous phase comprising the steviol glycoside is separated from the fermentation by adding a demulsifier into the fermentation reaction. Illustrative examples of demulsifiers include flocculants and coagulants.

The steviol glycoside produced in these cells may be present in the culture supernatant and/or associated with the host cells. In embodiments where some of the steviol glycoside is associated with the host cell, the recovery of the steviol glycoside may comprise a method of improving the release of the steviol glycosides from the cells. In some embodiments, this could take the form of washing the cells with hot water or buffer treatment, with or without a surfactant, and with or without added buffers or salts. In some embodiments, the temperature is any temperature deemed suitable for releasing the steviol glycosides. In some embodiments, the temperature is in a range from 40 to 95° C.; or from 60 to 90° C.; or from 75 to 85° C. In some embodiments, the temperature is 40, 45, 50, 55, 65, 70, 75, 80, 85, 90, or 95° C. In some embodiments physical or chemical cell disruption is used to enhance the release of steviol glycosides from the host cell. Alternatively and/or subsequently, the steviol glycoside in the culture medium can be recovered using an isolation unit operations including, but not limited to solvent extraction, membrane clarification, membrane concentration, adsorption, chromatography, evaporation, chemical derivatization, crystallization, and drying.

6.10 Methods of Making Genetically Modified Cells

Also provided herein are methods for producing a host cell that is genetically engineered to comprise one or more of the modifications described above, e.g., one or more nucleic heterologous nucleic acids encoding *Stevia rebaudiana* kaurenoic acid hydroxylase, and/or biosynthetic pathway enzymes, e.g., for a steviol glycoside compound. Expression of a heterologous enzyme in a host cell can be accomplished by introducing into the host cells a nucleic acid comprising a nucleotide sequence encoding the enzyme under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell. In other embodiments, the nucleic acid is a linear piece of double stranded DNA that can integrate via homology the nucleotide sequence into the chromosome of the host cell.

Nucleic acids encoding these proteins can be introduced into the host cell by any method known to one of skill in the art without limitation (see, for example, Hinnen et al. (1978) *Proc. Natl. Acad. Sci. USA* 75:1292-3; Cregg et al. (1985) *Mol. Cell. Biol.* 5:3376-3385; Goeddel et al. eds, 1990, Methods in Enzymology, vol. 185, Academic Press, Inc; CA; Krieger, 1990, Gene Transfer and Expression—A Laboratory Manual, Stockton Press, NY; Sambrook et al., 1989, Molecular Cloning—*A Laboratory Manual*, Cold Spring Harbor Laboratory, NY; and Ausubel et al., eds., Current Edition, Current Protocols in Molecular Biology, Greene Publishing Associates and Wiley Interscience, NY). Exemplary techniques include, but are not limited to, spheroplasting, electroporation, PEG 1000 mediated transformation, and lithium acetate or lithium chloride mediated transformation.

The amount of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, KAN®, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the KAN® gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

Described herein are specific genes and proteins useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias." Codon optimization for other host cells can be readily determined using codon usage tables or can be performed using commercially available software, such as CodonOp (www.idtdna.com/CodonOptfrom) from Integrated DNA Technologies.

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, Methods in Mol Biol 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum, Kluyveromyces* spp., including *K. thermotolerans, K. lactis*, and *K. marxianus, Pichia* spp., *Hansenula* spp., including *H polymorpha, Candida* spp., *Trichosporon* spp., *Yamadazyma* spp., including *Y.* spp. stipitis, *Torulaspora pretoriensis, Issatchenkia orientalis,*

*Schizosaccharomyces* spp., including *S. pombe, Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia. coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous UDP glycosyltransferases, KAH, or any biosynthetic pathway genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., Branched-Chain Amino Acids Methods Enzymology, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above-mentioned databases in accordance with the teachings herein.

7. EXAMPLES

Example 1. Yeast Transformation Methods

Each DNA construct was integrated into *Saccharomyces cerevisiae* (CEN.PK2) using standard molecular biology techniques for an optimized lithium acetate transformation. Briefly, cells were grown overnight in yeast extract peptone dextrose (YPD) media at 30° C. with shaking (200 rpm), diluted to an OD600 of 0.1 in 100 mL YPD, and grown to an OD600 of 0.6-0.8. For each transformation, 5 mL of culture was harvested by centrifugation, washed in 5 mL of sterile water, spun down again, resuspended in 1 mL of 100 mM lithium acetate, and transferred to a microcentrifuge tube. Cells were spun down (13,000× g) for 30 seconds, the supernatant was removed, and the cells were resuspended in a transformation mix consisting of 240 μL 50% PEG, 36 μL 1 M lithium acetate, 10 μL boiled salmon sperm DNA, and 74 μL of donor DNA. The donor DNA included a plasmid carrying the F-CphI endonuclease gene expressed under the yeast TDH3 promoter for expression (see Example 4). Following a heat shock at 42° C. for 40 minutes, cells were recovered overnight in YPD media containing the appropriate antibiotic to select for cells that have taken up the F-CphI plasmid. After recovery over night, the cells are briefly spun down by centrifugation and plated on YPD media containing the appropriate antibiotic to select for cells that have taken up the F-CphI plasmid. DNA integration was confirmed by colony PCR with primers specific to the integrations.

Example 2: Generation of a Base Yeast Strain Capable of High Flux to Farnesylpyrophosphate (FPP) and the Isoprenoid Farnesene A farnesene production strain was created from a wild-type *Saccharomyces cerevisiae* strain (CEN.PK2) by expressing the genes of the mevalonate pathway under the control of GAL1 or GAL10 promoters. This strain comprised the following chromosomally integrated mevalonate pathway genes from *S. cerevisiae*: acetyl-CoA thiolase, HMG-CoA synthase, HMG-CoA reductase, mevalonate kinase, phosphomevalonate kinase, mevalonate pyrophosphate decarboxylase, and IPP:DMAPP isomerase. In addition, the strain contained multiple copies of farnesene synthase from *Artemisia annua*, also under the control of either GAL1 or GAL10 promoters. All heterologous genes described herein were codon optimized using publicly available or other suitable algorithms. The strain also contained a deletion of the GAL80 gene, and the ERGS gene encoding squalene synthase was downregulated by replacing the native promoter with promoter of the yeast gene MET3 (Westfall et al., *Proc. Natl. Acad. Sci. USA* 109(3), 2012, pp. E111-E118). Examples of how to create *S. cerevisiae* strains with high flux to isoprenoids are described in the U.S. Pat. Nos. 8,415,136 and 8,236,512 which are incorporated herein in their entireties.

Example 3. Generation of a Base Yeast Strain Capable of High Flux to Reb M

Figure 2:
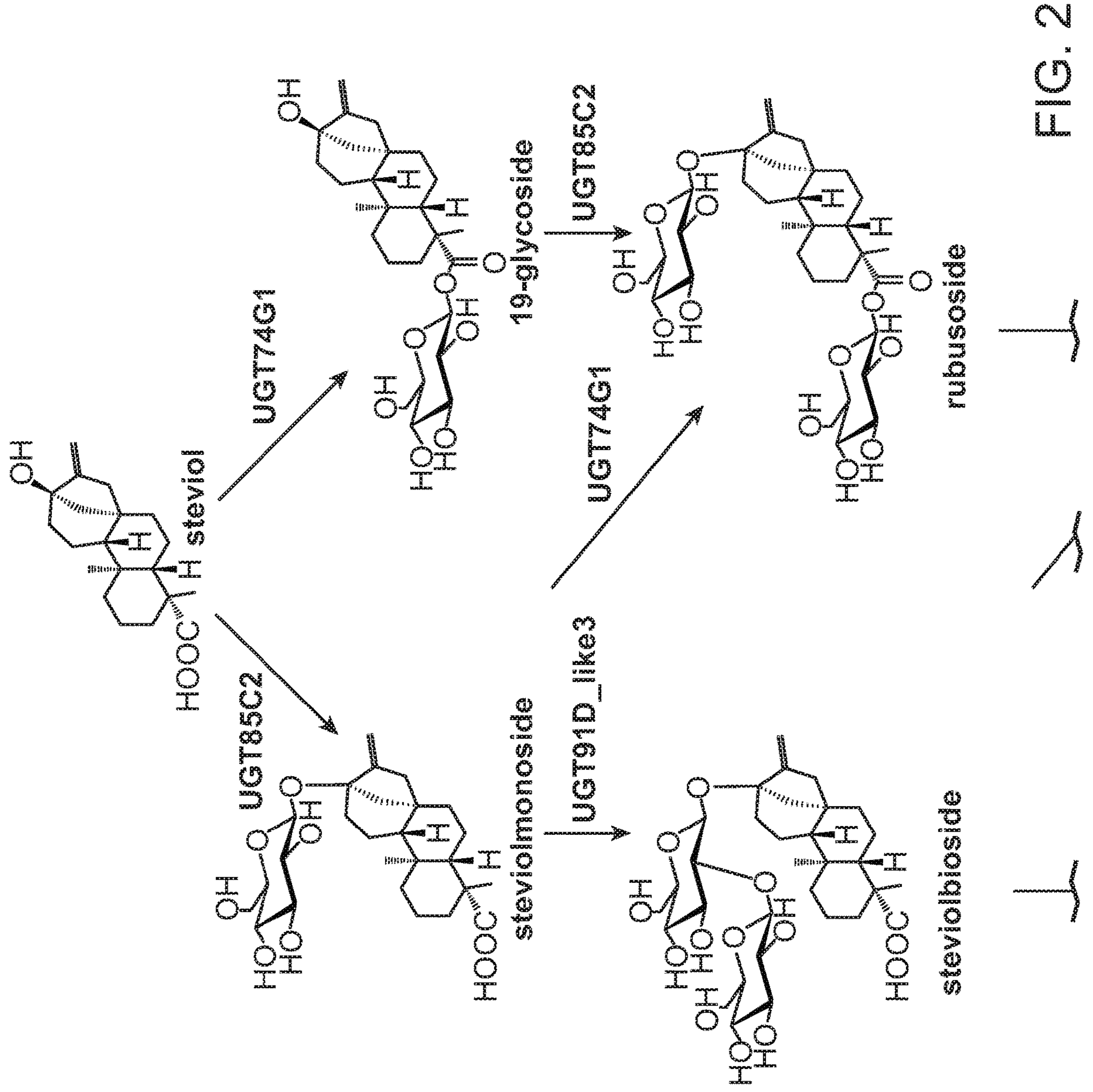
FIG. 2 is a schematic showing an enzymatic pathway from steviol to Rebaudioside M.
Figure 2:
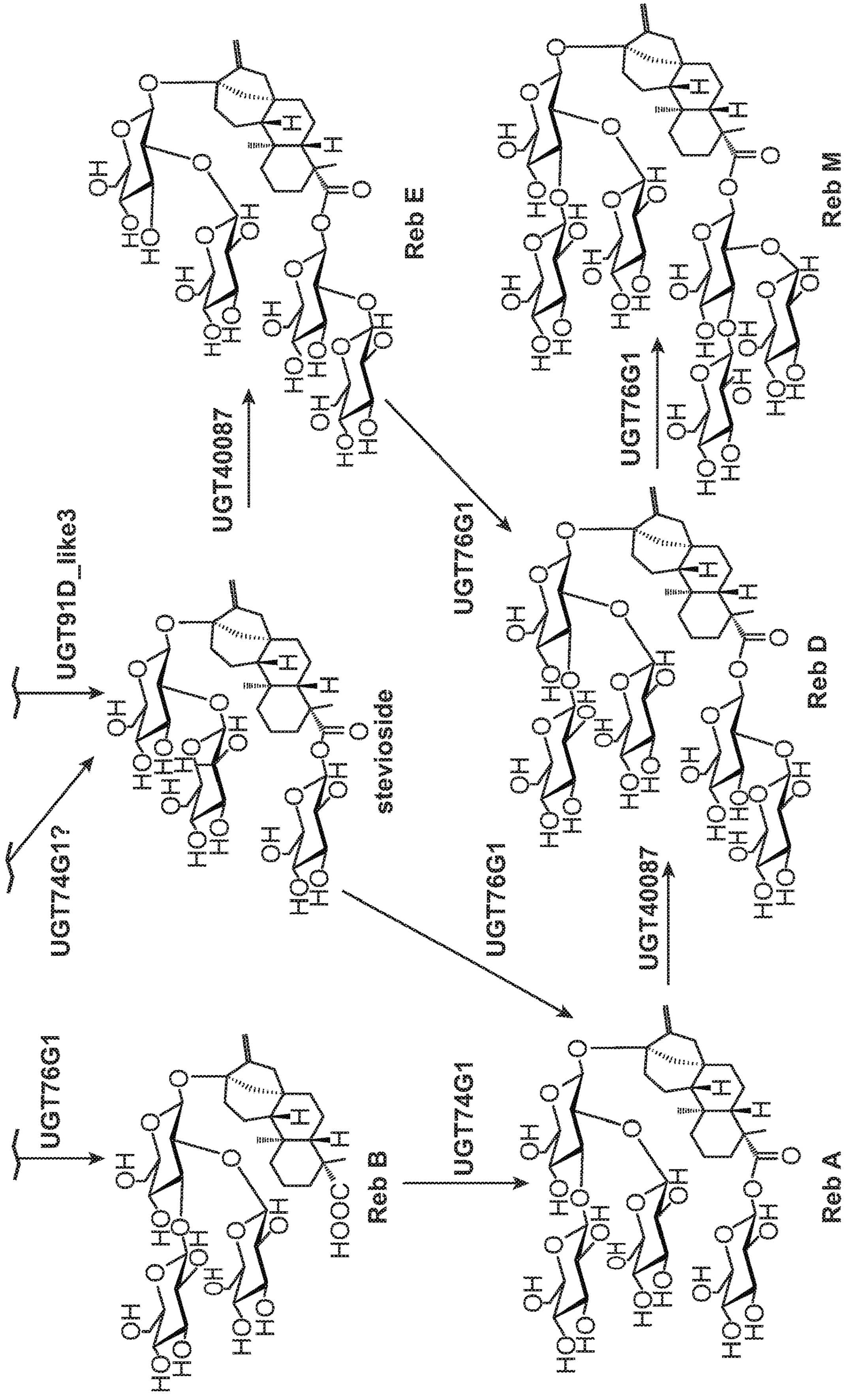

FIG. 1 shows an exemplary biosynthetic pathway from FPP to steviol. FIG. 2 shows an exemplary biosynthetic pathway from steviol to the glycoside Reb M. To convert the farnesene base strain described above to have high flux to the C20 isoprenoid kaurene, four copies of a geranylgeranylpyrophosphate synthase (GGPPS) were integrated into the genome, followed by two copies of a copalyldiphosphate synthase and a single copy of a kaurene synthase. At this point all copies of farnesene synthase were removed from the strain. Once the new strain was confirmed to make ent-kaurene, the remaining genes for converting ent-kaurene to Reb M were inserted into the genome. Table 1 lists all genes and promoters used to convert FPP to Reb M. Each gene after kaurene synthase was integrated as a single copy, except for the Sr.KAH enzyme for which two gene copies were integrated. The strain containing all genes described in Table 1 primarily produced Reb M.

TABLE 1

Genes, promoters, and amino acid sequences of the enzymes used to convert FPP to Reb M.

| Enzyme name | SEQ ID | Promoter |
|---|---|---|
| Bt.GGPPS | SEQ ID NO: 9 | PGAL1 |
| ent-Os, CDPS | SEQ ID NO: 10[1] | PGAL1 |
| ent-Pg.Ks | SEQ ID NO: 11 | PGAL1 |
| Ps.KO | SEQ ID NO: 12 | PGAL1 |
| Sr.KAH | SEQ ID NO: 13 | PGAL1 |
| At.CPR | SEQ ID NO: 14 | PGAL3 |
| UGT85C2 | SEQ ID NO: 15 | PGAL10 |
| UGT74G1 | SEQ ID NO: 16 | PGAL1 |

TABLE 1-continued

| Genes, promoters, and amino acid sequences of the enzymes used to convert FPP to Reb M. | | |
|---|---|---|
| Enzyme name | SEQ ID | Promoter |
| UGT91D_like3 | SEQ ID NO: 17 | PGAL1 |
| UGT76G1 | SEQ ID NO: 18 | PGAL10 |
| UGT40087 | SEQ ID NO: 19 | PGAL1 |

[1]First 65 amino acids removed and replaced with methionine

Example 4. Generation of a Strain to Screen for Steviol Glycoside Transporters

To rapidly screen for steviol glycoside transporters in vivo in a strain producing Reb M, a landing pad was inserted into the strain described above. The landing pad consisted of 500 bp of locus-targeting DNA sequences on either end of the construct to the genomic region downstream of the SFM1 open reading frame (see FIG. 3). Internally, the landing pad contained a GAL1 promoter and a yeast terminator flanking an endonuclease recognition site (F-CphI).

Example 5: Yeast Culturing Conditions

Yeast colonies with an overexpressed transporter protein were picked into 96-well microtiter plates containing Bird Seed Media (BSM, originally described by van Hoek et al., *Biotechnology and Bioengineering* 68(5), 2000, pp. 517-523) with 20 g/L sucrose, 3.75 g/L ammonium sulfate, and 1 g/L lysine. Cells were cultured at 28° C. in a high capacity microtiter plate incubator shaking at 1000 rpm and 80% humidity for 3 days until the cultures reached carbon exhaustion. The growth-saturated cultures were subcultured into fresh plates containing BSM with 40 g/L sucrose and 3.75 g/L ammonium sulfate by taking 14.4 μL from the saturated cultures and diluting into 360 μL of fresh media. Cells in the production media were cultured at 30° C. in a high capacity microtiter plate shaker at 1000 rpm and 80% humidity for an additional 3 days prior to extraction and analysis.

Example 6: Whole Cell Broth Sample Prep Conditions for Analysis of Steviol Glycosides To analyze the amount of all steviol glycosides produced in the culture, upon culturing completion the whole cell broth was diluted with 628 μL of 100% ethanol, sealed with a foil seal, and shaken at 1250 rpm for 30 seconds to extract the steviol glycosides. 314 μL of water was added to each well directly to dilute the extraction. The plate was briefly centrifuged to pellet solids. An internal standard, 208 μL of 50:50 ethanol:water mixture containing 0.48 mg/L rebaudioside N, was transferred to a new 250 μL assay plate and 2 μL of the culture/ethanol mixture was added to the assay plate. A foil seal was applied to the plate prior to analysis.

Example 7: Culture Supernatant Sample Prep Conditions for Analysis of Steviol Glycosides To analyze the amount of all steviol glycosides produced and excreted into the culture media, upon culturing completion the whole-cell broth was centrifuged for 5 minutes at 2000× g to pellet the cells. A 240 μL aliquot of the resulting supernatant was transferred to an empty 96-well microtiter plate. The supernatant samples were diluted with 480 μL of 100% ethanol, sealed with a foil seal, and shaken at 1250 rpm for 30 seconds to extract the steviol glycosides. To dilute the extraction 240 μL of water was added to each well. The plate was briefly centrifuged to pellet any solids. An internal standard, 208 μL of 50:50 ethanol:water mixture containing 0.48 mg/L rebaudioside N, was transferred to a new 250 μL assay plate and 2 μL of the culture/ethanol mixture was added to the assay plate. A foil seal was applied to the plate prior to analysis.

Example 8: Analytical Methods

Samples for steviol glycoside measurements were analyzed by mass spectrometer (Agilent 6470-QQQ) with a RapidFire 365 system autosampler with C8 cartridge using the configurations shown in Tables 2 and 3.

TABLE 2

| RapidFire 365 system configuration | |
|---|---|
| Pump 1, Line A: 2 mM ammonium formate in water | 100% A, 1.5 mL/min |
| Pump 2, Line A: 35% acetonitrile in water | 100% A, 1.5 mL/min |
| Pump 3, Line A: 80% acetonitrile in water | 100% A, 0.8 mL/min |
| State 1: Aspirate | 600 ms |
| State 2: Load/Wash | 3000 ms |
| State 3: Extra wash | 1500 ms |
| State 4: Elute | 5000 ms |
| State 5: Re-equilibrate | 1000 ms |

TABLE 3

| 6470-QQQ MS method configurations | |
|---|---|
| Ion Source | AJS ESI |
| Time Filtering peak width | 0.02 min |
| Stop Time | No limit/as pump |
| Scan Type | MRM |
| Diverter Valve | To MS |
| Delta EMV | (+)0/(−)300 |
| Ion Mode (polarity) | Negative |
| Gas Temp | 250° C. |
| Gas Flow | 11 L/min |
| Nebulizer | 30 psi |
| Sheath Gas Temp | 350° C. |
| Sheath Gas Flow | 11 L/min |
| Negative Capillary V | 2500 V |

The peak areas from a chromatogram from a mass spectrometer were used to generate the calibration curve. The molar ratios of relevant compounds were determined by quantifying the amount in moles of each compound through external calibration using an authentic standard, and then taking the appropriate ratios.

Example 9. Screening for Transporters Capable of Increasing Titers of Steviol Glycosides In Vivo In the Reb M-producing strain without additional transporters expressed, approximately 80% of the higher molecular weight steviol glycosides Reb D and Reb M were found to be associated with the biomass (see FIG. 4). This biomass association is likely attributed to Reb D and Reb M not being efficiently transported out of the cell and retained in the cytoplasm. The accumulation of Reb D and Reb M could result in product inhibition which would decrease the carbon flux through the steviol glycoside metabolic pathway. Therefore, expression of one or more transporters that will transport steviol glycosides (especially Reb D and Reb M) out of the cytoplasm and into the media (supernatant) is expected to relieve product inhibition and thereby increase carbon flux through the pathway, resulting in higher steviol glycoside titers. To identify transporters capable of exporting higher molecular weight steviol glycosides out of the cell and thus relieving product inhibition, we screened a number of transporters identified from a variety of fungi for the ability to increase total steviol glycoside titers, particularly the titers of higher molecular weight glycosides (i.e. Reb D and Reb M).

All proteins annotated to be a transporter from the *S. cerevisiae* genome were amplified via PCR, using CEN.PK2 as the genomic DNA source. Each PCR primer had 40 bp of flanking homology to the PGAL1 and yeast terminator DNA sequences in the landing pad (see FIG. 3) added to the ends to facilitate homologous recombination of the amplified gene into the landing pad. In addition to screening all the endogenous *S. cerevisiae* transport proteins found in CEN.PK2, an extended bioinformatics search was performed for ABC-transporter proteins from a small number of fungi and additional *S. cerevisiae* strains.

To make a library of fungal ABC-transporters, we first obtained amino acid sequences from the publication "Phylogenetic Analysis of Fungal ABC Transporters" by Kovalchuk and Driessen (Kovalchuk and Driessen, *BMC Genomics,* 11, 2010, pp. 177-197) in which a phylogenetic analysis of ABC transporters was performed for 27 fungal species. From this literature source, a total of 610 amino acid sequences were chosen, which included all transporters designated as belonging to the ABC-C, ABC-D, and ABC-G subfamilies. Next, we developed in-house BLAST databases for the following fungi: (1) *Hansenula polymorpha* DL-1 (NRRL-Y-7560), (2) *Yarrowia lipolytica* ATCC 18945, (3) *Arxula adeninivorans* ATCC 76597, (4) *S. cerevisiae* CAT-1, (5) *Lipomyces starkeyi* ATCC 58690, (6) *Kluyveromyces marxianus*, (7) *Kluyveromyces marxianus* DMKU3-1042, (8) *Komagataella phaffii* NRRL Y-11430, (9) *S. cerevisiae* MBG3370, (10) *S. cerevisiae* MBG3373, (11) *Kluyveromyces lactis* ATCC 8585, (12) *Candida utilis* ATCC 22023, (13) *Pichia pastoris* ATCC 28485, and (14) *Aspergillus oryzae* NRRL5590.

For organisms in which we already had in-house nucleotide ORF sequences from a de novo genomic sequencing, assembling, and annotation effort, we applied tBLASTn using Biopython. The tBLASTn algorithm allowed for rapid alignments of protein sequences (in this case the 610 seed sequences from Kovalchuk and Driessen (*BMC Genomics,* 11, 2010, pp. 177-197)) with translated DNA of the nucleotide ORF sequences for each organism in all six possible reading frames using BLAST. tBLASTn parameters were standard with evalue=1 $e^{-25}$ (see Table 4). All computations were executed via the biopython API (v 1.70 downloaded from PyPI) using Python 2.7.12 and Ubuntu 16.04.5 LTS (GNU/Linux 4.4.0-138-generic x86_64). Hits were subsequently filtered to ensure a global alignment of at least 2000 nucleotides. All matches meeting these criteria were taken to the next step of the workflow.

TABLE 4 tBLASTn default parameters

| tBLASTn (2.2.31 BLAST + release) option | Setting used |
|---|---|
| word_size | 3 |
| gapopen | 11 |
| gapextend | 1 |
| matrix | BLOSUM62 |
| threshold | 13 |
| seg | 12 2.2 2.5 |
| soft_masking | FALSE |
| lcase_masking | N/A |
| db_soft_mask | None |
| db_hard_mask | None |
| xdrop_gap_final | 25 |
| window_size | 40 |
| db_gen_code | 1 |
| max_intron_length | 0 |
| comp_based_stats | 2 |

For the remainder of the organisms for which there was not in-house genomic sequence, the entire proteome of the organism was obtained from Uniprot using the Uniprot API in order to create a database for a BLASTp search. In most cases Uniprot had an exact entry for a species for which we had in-house genomic DNA, but in other cases there was a close but not exact match to the fungal strains in-house. In the latter cases we relied on the high probability that the gene sequences would be similar enough that primers designed against the Uniprot reference would still amplify the in-house genomic DNA. We then applied BLASTp using Biopython to the Uniprot derived database. BLAST parameters were standard, with evalue=0.001 (see Table 5). A subsequent filtering was performed based on a percent identity cutoff of ≥40%, and a percent aligned length cutoff of ≥60%. All computations were executed via the biopython API (v 1.70 downloaded from PyPI) using Python 2.7.12 and Ubuntu 16.04.5 LTS (GNU/Linux 4.4.0-138-generic x86_64). Hits had to match at least one of the 610 seed sequences from the reference. Hits were then converted to nucleotide sequence using the Uniprot ID mapping service to EMBL identifiers. The European Molecular Biology Laboratory allows for extraction of nucleotide sequences from a Uniprot entry. We took any hits fitting these criteria to the next step of the workflow.

TABLE 5

BLASTp default parameters

| BLASTp (2.2.31 BLAST + release) option | Setting used |
|---|---|
| word_size | 3 |
| word_size | 2 |
| word size | 6 |
| gapopen | 11 |
| gapextend | 1 |
| gapopen | 9 |
| gapextend | 1 |
| matrix | BLOSUM62 |
| matrix | PAM30 |
| threshold | 11 |
| threshold | 16 |
| Threshold | 21 |
| comp_based_stats | 2 |
| comp_based_stats | 0 |
| seg | No |
| soft_masking | FALSE |
| lcase_masking | N/A |
| db_soft_mask | None |
| db_hard_mask | None |

TABLE 5-continued

| BLASTp default parameters | |
|---|---|
| BLASTp (2.2.31 BLAST + release) option | Setting used |
| xdrop_gap_final | 25 |
| window_size | 40 |
| window_size | 15 |
| use_sw_tback | N/A |

Once all nucleotide sequences had been identified, primers were designed to amplify each complete ORF via PCR. Each PCR primer had 40 bp of flanking homology to the PGAL1 and yeast terminator DNA sequences in the landing pad (FIG. 3) added to the ends to facilitate homologous recombination of the amplified gene into the landing pad. Each transporter gene was transformed individually as a single copy into the Reb M-producing yeast strain described above and screened for the ability to increase product titers when overexpressed in vivo.

Example 11: Overexpression of Transporters that Lead to an Increase in Steviol Glycoside Production In Vivo The in vivo *S. cerevisiae* transporter screen found eight transporters that statistically increased total steviol glycoside (TSG) production when overexpressed, compared to the parent Reb M strain that contained no overexpressed transporter (see FIG. 5). TSG was calculated as the sum in micromoles of all steviol glycosides produced by the cell (as measured by whole cell broth extraction). All of the identified transporters fall into the class of transporters known as ABC-transporters. Overexpression of these transporters increased TSG from 20% to two-fold over parent. Increases in TSG by transporter overexpression could be due to increased transport of all steviol glycosides, or just a subset of steviol glycosides. Therefore, the data was also analyzed to determine the effect transporter overexpression had on just the higher molecular weight steviol glycosides Reb D and Reb M. Of the eight transporters that increased TSG, seven of them also increased overall production of Reb D and Reb M, as shown in FIG. 6. Increases of Reb D and Reb M with overexpression of transporters ranged from 30% increase to two-fold increase.

Example 12: Extracellular and Intracellular Transport of Steviol Glycosides

Seven out of eight Reb M strains harboring overexpressed transporters that resulted in more total steviol glycosides in the whole cell broth also increased the total steviol glycoside content in the supernatant (FIG. 7). While four of the transporters increased the total steviol glycosides in the whole cell broth by nearly two-fold (FIG. 5), the typical increase of TSG in the supernatant was less and ranged from 35 to 70% (FIG. 7). However, transporter T4_Fungal_5 increased the TSG in the supernatant approximately five-fold (FIG. 7). The data shown in FIGS. 5 and 7 demonstrates that strains with certain overexpressed transporters are making more TSG, but the increase in TSG is not always reflected with a linear increase in TSG in the supernatant.

Looking explicitly at the fraction of total steviol glycosides produced that is located in the supernatant (FIG. 8) shows that the majority of the transporters (six out of eight) showed a lower proportion of TSG in the supernatant relative to parent. This suggests that the transporters were removing the steviol glycosides from the cytosol, thereby relieving product inhibition and allowing for greater product formation, but they were not transporting the steviol glycosides into the media. Instead, these transporters are most likely transporting the steviol glycosides into the vacuole or some other cellular compartment. In contrast, transporter T4_Fungal_5 resulted in nearly 100% of the TSG produced being located in the supernatant (FIG. 8). This indicates that T4_Fungal_5 is likely a plasma membrane transporter that is capable of removing steviol glycosides from the cell's cytoplasm and transporting it out of the cell and into the media. In addition, the data in FIG. 4 shows that transporter T4_Fungal_5 exports the higher molecular weight steviol glycosides Reb D and Reb M out of the cell and into the media; indeed, nearly 100% of both Reb D and Reb M were located in the supernatant fraction.

One of the hits from the transporter screen was the endogenous *S. cerevisiae* ABC-transporter BPT1. This protein is annotated in the *Saccharomyces* Genome Database to be localized to the vacuole. Transporters T4_Fungal_2 and T4_Fungal_4 have protein sequences that are 99% identical to CEN.PK2 BPT1 and are derived from *S. cerevisiae* strains CAT-1 and MBG3373, respectively; they are alleles of BPT1. All other transporters are 30-43% identical in protein sequence to BPT1 and represent novel ABC-transporters that can transport steviol glycosides across membranes (see Table 6). Of the remaining non-BPT1 transporters that export out steviol glycosides, no protein sequence is higher than 53% identical to any other protein, showing that the remaining five proteins are unique sequences.

TABLE 6

Percent identity of all transporters that increase steviol glycoside titers.

| | T4_Fungal_8 | T4_Fungal_1 | T4_Fungal_3 | T4_Fungal_5 | T4_Fungal_10 | CENPK_BPT1 | T4_Fungal_2 | T4_Fungal_4 |
|---|---|---|---|---|---|---|---|---|
| T4_Fungal_8 | 100 | 47.56 | 52.95 | 30.27 | 31.50 | 30.50 | 30.57 | 30.64 |
| T4_Fungal_1 | | 100 | 53.12 | 30.05 | 31.29 | 30.41 | 30.34 | 30.41 |
| T4_Fungal_3 | | | 100 | 31.53 | 33.43 | 32.36 | 32.43 | 32.50 |
| T4_Fungal_5 | | | | 100 | 31.74 | 31.05 | 30.89 | 30.89 |
| T4_Fungal_10 | | | | | 100 | 43.47 | 43.40 | 43.40 |
| CENPK_BPT1 | | | | | | 100 | 99.49 | 99.55 |
| T4_Fungal_2 | | | | | | | 100 | 99.81 |
| T4_Fungal_4 | | | | | | | | 100 |

Example 13: BPT1 and T4_Fungal_5 Cellular Localization

To determine the cellular localization of overexpressed BPT1 and T4_Fungal_5 protein in the Reb M-producing strains, we created GFP-transporter fusion proteins. Each transporter (BPT1 or T4_Fungal_5) protein had a GFP protein fused to the C-terminal of the transporter; the GFP-transporter fusion proteins were expressed via a GAL1 promoter and contained a yeast terminator. Strains were constructed as outlined in Example 4, with the only difference being that a transporter-GFP fusion protein was used in place of the transporter-only protein. Cells with properly integrated transporter-GFP constructs were confirmed via colony PCR, cultured as in Example 5, and confirmed to have activity equivalent to the strains containing transporter without a C-terminal GFP tag (FIG. 9).

To visualize protein localization via GFP, cells were propagated as in Example 5 but were harvested after 2 days in production media for observation. Cells were washed twice with equal volumes of PBS and then resuspended to an $OD_{600}$ of 1.0 in PBS. Cells were fixed using 1% agarose pads mounted on a glass slide and visualized at 100× magnification with an oil immersion using a standard fluorescence microscope at a 488 nm excitation or under bright field. Cells expressing BPT1 C-terminally tagged with GFP showed fluorescence patterns consistent with the fusion protein being localized to the vacuole (FIG. 10). This was the expected result, since it has been reported that BPT1 is normally localized to the vacuole in yeast (Sharma et al., *Eukaryot. Cell* 1(3), 2002, pp. 391-400). The C-terminally tagged T4_Fungal_5 protein showed a different GFP localization, consistent with the protein being localized to the plasma membrane (FIG. 11).

Example 14: Directed Evolution of T4_Fungal_5 Protein Using Error-Prone PCR and Growth Selection The transporter T4_Fungal_5 actively removes both Reb D and Reb M from the cytoplasm (see FIG. 4). Reb D is the immediate substrate for Reb M (FIG. 2), thus removing Reb D from the cytosol reduces the overall amount of Reb M produced by the yeast. T4_Fungal_5 was therefore subjected to enzyme evolution to increase both its overall activity and its specificity for Reb M. The DNA coding sequence (CDS) of T4_Fungal_5 was subjected to mutagenesis via error-prone PCR using GeneMorph II Random Mutagenesis Kit (Agilent Technologies, Inc) and the resulting DNA library was transformed into a Reb M yeast strain similar to the one used in the transporter screen mentioned in Example 11 but having two additional copies of UGT76G1 both expressed under GAL1 promoters. An additional transformation using the wild type T4_Fungal_5 transporter was performed as a control. The transformations were performed as described in Example 1. After the overnight recovery, the cultures were transferred into production medium supplemented with the selective antibiotic for continued growth. The $OD_{600}$ of the cultures were monitored and serial dilutions of the cultures with fresh antibiotic-containing production medium were performed to avoid carbon starvation. The culture was sampled daily for both glycerol stock archives and plated for individual colony formation on antibiotic containing YPD agar plates. The TSG and Reb M titers of 88 colonies from each daily sample were assessed and compared using methods described in Examples 6, 7, and 8. From this data, the time point which had highest percent of colonies producing TSG titers equal to or greater than that of the control strain (expressing wild type T4_Fungal_5) was identified. Additional colonies from this time point were plated from the glycerol stock and 900 colonies were picked and screened. The screen identified eight isolates that increased Reb M titers by 26% to 47% and increased the Reb M/TSG ratio by 10% over the control (FIGS. 12 and 13). Data in FIGS. 12 and 13 show that the mutations identified in the T4_Fungal_5 transporter increased both overall activity on steviol glycosides and specificity for Reb M.

Sanger sequencing of the T4_Fungal_5 gene revealed that all eight isolates harbored the same nucleic acid substitutions, resulting in four amino acid substitutions: V666A, Y942N, L956P, and E1320V. This mutant allele was named "Fungal_5_muA". To verify the causality of Fungal_5_muA on the improved titer and specificity, the mutant allele was amplified from one of the isolates and re-introduced into the parent strain. The resulting strain recapitulated the phenotypes and demonstrated the application of Fungal_5_muA in improvement of steviol glycoside production and specificity. When T4_Fungal_5 and Fungal_5_muA were expressed under the weaker GAL3 promoter, 30% more Reb M in whole cell broth and 40% more extracellular Reb M were produced by the strain with Fungal_5_muA than by the strain with the wild type T4_Fungal_5 (FIG. 14), consistent with earlier data.

Example 15: Further Improvement of Fungal_5_muA

To further improve Fungal_5_muA by removing potentially detrimental mutations, we created additional T4 Fungal_5 mutant variants with either one, two, or three amino acid substitutions identified in Fungal_5_muA and introduced them into the yeast strain used for screening the mutagenesis library of T4_Fungal_5 in Example 14. Although single reversion of V666A in Fungal_5_muA had negligible impacts on either TSG or Reb M production, reversion of E1320V was beneficial and the V666A Y942N L956P triple mutant produced 14% more TSG and 12% more Reb M than the Fungal_5_muA strain (FIGS. 15 and 16). Further reversion of L956P in the triple mutant (V666A Y942N), however, led to 10% decrease in Reb M and 19% decrease in TSG produced as compared to the V666A Y942N L956P triple mutant. Compared to the Fungal_5_muA strain, the single Y942N mutant strain produced 21% more TSG but 10% lower amounts of Reb M. These data demonstrate that the Y942N mutation benefitted overall activity of T4_Fungal_5 in exporting steviol glycosides but had negative effect on its specificity for Reb M.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

```
SEQUENCE LISTING;
Bt.GGPPS
                                        SEQ ID NO: 9
MLTSSKSIESFPKNVQPYGKHYQNGLEPVGKSQED

ILLEPFHYLCSNPGKDVRTKMIEAFNAWLKVPKDD

LIVITRVIEMLHSASLLIDDVEDDSVLRRGVPAAH

HIYGTPQTINCANYVYFLALKEIAKLNKPNMITIY

TDELINLHRGQGMELFWRDTLTCPTEKEFLDMVND
```

-continued

KTGGLLRLAVKLMQEASQSGTDYTGLVSKIGIHFQ

VRDDYMNLQSKNYADNKGFCEDLTEGKFSFPIIHS

IRSDPSNRQLLNILKQRSSSIELKQFALQLLENTN

TFQYCRDFLRVLEKEAREEIKLLGGNIMLEKIMDV

LSVNE;

Ent-Os.CDPS

SEQ ID NO: 10

MEHARPPQGGDDDVAASTSELPYMIESIKSKLRAA

RNSLGETTVSAYDTAWIALVNRLDGGGERSPQFPE

AIDWIARNQLPDGSWGDAGMFIVQDRLINTLGCVV

ALATWGVHEEQRARGLAYIQDNLWRLGEDDEEWMM

VGFEITFPVLLEKAKNLGLDINYDDPALQDIYAKR

QLKLAKIPREALHARPTTLLHSLEGMENLDWERLL

QFKCPAGSLHSSPAASAYALSETGDKELLEYLETA

INNFDGGAPCTYPVDNFDRLWSVDRLRRLGISRYF

TSEIEEYLEYAYRHLSPDGMSYGGLCPVKDIDDTA

MAFRLLRLHGYNVSSSVFNHFEKDGEYFCFAGQSS

QSLTAMYNSYRASQIVFPGDDDGLEQLRAYCRAFL

EERRATGNLRDKWVIANGLPSEVEYALDFPWKASL

PRVETRVYLEQYGASEDAWIGKGLYRMTLVNNDLY

LEAAKADFTNFQRLSRLEWLSLKRWYIRNNLQAHG

VTEQSVLRAYFLAAANIFEPNRAAERLGWARTAIL

AEAIASHLRQYSANGAADGMTERLISGLASHDWDW

RESNDSAARSLLYALDELIDLHAFGNASDSLREAW

KQWLMSWTNESQGSTGGDTALLLVRTIEICSGRHG

SAEQSLKNSEDYARLEQIASSMCSKLATKILAQNG

GSMDNVEGIDQEVDVEMKELIQRVYGSSSNDVSSV

TRQTFLDVVKSFCYVAHCSPETIDGHISKVLFEDV

N;

Ent-Pg.KS

SEQ ID NO: 11

MKREQYTILNEKESMAEELILRIKRMFSEIENTQT

SASAYDTAWVAMVPSLDSSQQPQFPQCLSWIIDNQ

LLDGSWGIPYLIIKDRLCHTLACVIALRKWNAGNQ

NVETGLRFLRENIEGIVHEDEYTPIGFQIIFPAML

EEARGLGLELPYDLTPIKLMLTHREKIMKGKAIDH

MHEYDSSLIYTVEGIHKIVDWNKVLKHQNKDGSLF

NSPSATACALMHTRKSNCLEYLSSMLQKLGNGVPS

VYPINLYARISMIDRLQRLGLARHFRNEIIHALDD

IYRYWMQRETSREGKSLTPDIVSTSIAFMLLRLHG

YDVPADVFCCYDLHSIEQSGEAVTAMLSLYRASQI

MFPGETILEEIKTVSRKYLDKRKENGGIYDHNIVM

-continued

KDLRGEVEYALSVPWYASLERIENRRYIDQYGVND

TWIAKTSYKIPCISNDLFLALAKQDYNICQAIQQK

ELRELERWFADNKFSHLNFARQKLIYCYFSAAATL

FSPELSAARVVWAKNGVITTVVDDFFDVGGSSEEI

HSFVEAVRVWDEAATDGLSENVQILFSALYNTVDE

IVQQAFVFQGRDISIHLREIWYRLVNSMMTEAQWA

RTHCLPSMHEYMENAEPSIALEPIVLSSLYFVGPK

LSEEIICHPEYYNLMHLLNICGRLLNDIQGCKREA

HQGKLNSVTLYMEENSGTTMEDAIVYLRKTIDESR

QLLLKEVLRPSIVPRECKQLHWNMMRILQLFYLKN

DGFTSPTEMLGYVNAVIVDPIL;

Ps.KO

SEQ ID NO: 12

MDTLTLSLGFLSLFLFLFLLKRSTHKHSKLSHVPV

VPGLPVIGNLLQLKEKKPHKTFTKMAQKYGPIFSI

KAGSSKIIVLNTAHLAKEAMVTRYSSISKRKLSTA

LTILTSDKCMVAMSDYNDFHKMVKKHILASVLGAN

AQKRLRFHREVMMENMSSKFNEHVKTLSDSAVDFR

KIFVSELFGLALKQALGSDIESIYVEGLTATLSRE

DLYNTLVVDFMEGAIEVDWRDFFPYLKWIPNKSFE

KKIRRVDRQRKIIMKALINEQKKRLTSGKELDCYY

DYLVSEAKEVTEEQMIMLLWEPIIETSDTTLVTTE

WAMYELAKDKNRQDRLYEELLNVCGHEKVTDEELS

KLPYLGAVFHETLRKHSPVPIVPLRYVDEDTELGG

YHIPAGSEIAINIYGCNMDSNLWENPDQWIPERFL

DEKYAQADLYKTMAFGGGKRVCAGSLQAMLIACTA

IGRLVQEFEWELGHGEEENVDTMGLTTHRLHPLQV

KLKPRNRIY;

Sr.KAH

SEQ ID NO: 13

MEASYLYISILLLLASYLFTTQLRRKSANLPPTVF

PSIPIIGHLYLLKKPLYRTLAKIAAKYGPILQLQL

GYRRVLVISSPSAAEECFTNNDVIFANRPKTLFGK

IVGGTSLGSLSYGDQWRNLRRVASIEILSVHRLNE

FHDIRVDENRLLIRKLRSSSSPVTLITVFYALTLN

VIMRMISGKRYFDSGDRELEEEGKRFREILDETLL

LAGASNVGDYLPILNWLGVKSLEKKLIALQKKRDD

FFQGLIEQVRKSRGAKVGKGRKTMIELLLSLQESE

PEYYTDAMIRSFVLGLLAAGSDTSAGTMEWAMSLL

VNHPHVLKKAQAEIDRVIGNNRLIDESDIGNIPYI

GCIINETLRLYPAGPLLFPHESSADCVISGYNIPR

-continued

GTMLIVNQWAIHHDPKVWDDPETFKPERFQGLEGT
RDGFKLMPFGSGRRGCPGEGLAIRLLGMTLGSVIQ
CFDWERVGDEMVDMTEGLGVTLPKAVPLVAKCKPR
SEMTNLLSEL;

At.CPR

SEQ ID NO: 14

MSSSSSSSTSMIDLMAAIIKGEPVIVSDPANASAY
ESVAAELSSMLIENRQFAMIVTTSIAVLIGCIVML
VWRRSGSGNSKRVEPLKPLVIKPREEEIDDGRKKV
TIFFGTQTGTAEGFAKALGEEAKARYEKTRFKIVD
LDDYAADDDEYEEKLKKEDVAFFFLATYGDGEPTD
NAARFYKWFTEGNDRGEWLKNLKYGVFGLGNRQYE
HFNKVAKVVDDILVEQGAQRLVQVGLGDDDQCIED
DFTAWREALWPELDTILREEGDTAVATPYTAAVLE
YRVSIHDSEDAKFNDINMANGNGYTVFDAQHPYKA
NVAVKRELHTPESDRSCIHLEFDIAGSGLTYETGD
HVGVLCDNLSETVDEALRLLDMSPDTYFSLHAEKE
DGTPISSSLPPPFPPCNLRTALTRYACLLSSPKKS
ALVALAAHASDPTEAERLKHLASPAGKDEYSKWVV
ESQRSLLEVMAEFPSAKPPLGVFFAGVAPRLQPRF
YSISSSPKIAETRIHVTCALVYEKMPTGRIHKGVC
STWMKNAVPYEKSENCSSAPIFVRQSNFKLPSDSK
VPIIMIGPGTGLAPFRGFLQERLALVESGVELGPS
VLFFGCRNRRMDFIYEEELQRFVESGALAELSVAF
SREGPTKEYVQHKMMDKASDIWNMISQGAYLYVCG
DAKGMARDVHRSLHTIAQEQGSMDSTKAEGFVKNL
QTSGRYLRDVW;

UGT85C2

SEQ ID NO: 15

MDAMATTEKKPHVIFIPFPAQSHIKAMLKLAQLLH
HKGLQITFVNTDFIHNQFLESSGPHCLDGAPGFRF
ETIPDGVSHSPEASIPIRESLLRSIETNFLDRFID
LVTKLPDPPTCIISDGFLSVFTIDAAKKLGIPVMM
YWTLAACGFMGFYHIHSLIEKGFAPLKDASYLTNG
YLDTVIDWVPGMEGIRLKDFPLDWSTDLNDKVLMF
TTEAPQRSHKVSHHIFHTFDELEPSIIKTLSLRYN
HIYTIGPLQLLLDQIPEEKKQTGITSLHGYSLVKE
EPECFQWLQSKEPNSVVYVNFGSTTVMSLEDMTEF
GWGLANSNHYFLWIIRSNLVIGENAVLPPELEEHI
KKRGFIASWCSQEKVLKHPSVGGFLTHCGWGSTIE
SLSAGVPMICWPYSWDQLTNCRYICKEWEVGLEMG
TKVKRDEVKRLVQELMGEGGHKMRNKAKDWKEKAR

-continued

IAIAPNGSSSLNIDKMVKEITVLARN;

UGT74G1

SEQ ID NO: 16

MAEQQKIKKSPHVLLIPFPLQGHINPFIQFGKRLI
SKGVKTTLVTTIHTLNSTLNHSNTTTTSIEIQAIS
DGCDEGGFMSAGESYLETFKQVGSKSLADLIKKLQ
SEGTTIDAIIYDSMTEWVLDVAIEFGIDGGSFFTQ
ACVVNSLYYHVHKGLISLPLGETVSVPGFPVLQRW
ETPLILQNHEQIQSPWSQMLFGQFANIDQARWVFT
NSFYKLEEEVIEWTRKIWNLKVIGPTLPSMYLDKR
LDDDKDNGFNLYKANHHECMNWLDDKPKESVVYVA
FGSLVKHGPEQVEEITRALIDSDVNFLWVIKHKEE
GKLPENLSEVIKTGKGLIVAWCKQLDVLAHESVGC
FVTHCGFNSTLEAISLGVPVVAMPQFSDQTTNAKL
LDEILGVGVRVKADENGIVRRGNLASCIKMIMEEE
RGVIIRKNAVKWKDLAKVAVHEGGSSDNDIVEFVS
ELIKA;

UGT91D_like3

SEQ ID NO: 17

MYNVTYHQNSKAMATSDSIVDDRKQLHVATFPWLA
FGHILPYLQLSKLIAEKGHKVSFLSTTRNIQRLSS
HISPLINVVQLTLPRVQELPEDAEATTDVHPEDIP
YLKKASDGLQPEVTRFLEQHSPDWIIYDYTHYWLP
SIAASLGISRAHFSVTTPWAIAYMGPSADAMINGS
DGRTTVEDLTTPPKWFPFPTKVCWRKHDLARLVPY
KAPGISDGYRMGLVLKGSDCLLSKCYHEFGTQWLP
LLETLHQVPVVPVGLLPPEIPGDEKDETWVSIKKW
LDGKQKGSVVYVALGSEVLVSQTEVVELALGLELS
GLPFVWAYRKPKGPAKSDSVELPDGFVERTRDRGL
VWTSWAPQLRILSHESVCGFLTHCGSGSIVEGLMF
GHPLIMLPIFGDQPLNARLLEDKQVGIEIPRNEED
GCLTKESVARSLRSVVVEKEGEIYKANARELSKIY
NDTKVEKEYVSQFVDYLEKNARAVAIDHES;

UGT76G1

SEQ ID NO: 18

MENKTETTVRRRRRIILFPVPFQGHINPILQLANV
LYSKGFSITIFHTNFNKPKTSNYPHFTFRFILDND
PQDERISNLPTHGPLAGMRIPIINEHGADELRREL
ELLMLASEEDEEVSCLITDALWYFAQSVADSLNLR
RLVLMTSSLFNFHAHVSLPQFDELGYLDPDDKTRL
EEQASGFPMLKVKDIKSAYSNWQILKEILGKMIKQ
TKASSGVIWNSFKELEESELETVIREIPAPSFLIP
LPKHLTASSSSLLDHDRTVFQWLDQQPPSSVLYVS
FGSTSEVDEKDFLEIARGLVDSKQSFLWVVRPGFV

-continued

KGSTWVEPLPDGFLGERGRIVKWVPQQEVLAHGAI
GAFWTHSGWNSTLESVCEGVPMIFSDFGLDQPLNA
RYMSDVLKVGVYLENGWERGEIANAIRRVMVDEEG
EYIRQNARVLKQKADVSLMKGGSSYESLESLVSYI
SSL;

UGT40087

SEQ ID NO: 19

MDASDSSPLHIVIFPWLAFGHMLASLELAERLAAR
GHRVSFVSTPRNISRLRPVPPALAPLIDFVALPLP
RVDGLPDGAEATSDIPPGKTELHLKALDGLAAPFA
AFLDAACADGSTNKVDWLFLDNFQYWAAAAAADHK
IPCALNLTFAASTSAEYGVPRVEPPVDGSTASILQ
RFVLTLEKCQFVIQRACFELEPEPLPLLSDIFGKP
VIPYGLVPPCPPAEGHKREHGNAALSWLDKQQPES
VLFIALGSEPPVTVEQLHEIALGLELAGTTFLWAL
KKPNGLLLEADGDILPPGFEERTRDRGLVAMGWVP
QPIILAHSSVGAFLTHGGWASTIEGVMSGHPMLFL
TFLDEQRINAQLIERKKAGLRVPRREKDGSYDRQG
IAGAIRAVMCEEESKSVFAANAKKMQEIVSDRNCQ
EKYIDELIQRLGSFEK;

Funga1_5_muA

SEQ ID NO: 28

MTSPGSEKCTPRSDEDLERSEPQLQRRLLTPFLLS
KKVPPIPKEDERKPYPYLKTNPLSQILFWWLNPLL
RVGYKRTLDPNDFYYLEHSQDIETTYSNYEMHLAR
ILEKDRAKARAKDPTLTDEDLKNREYPKNAVIKAL
FLTFKWKYLWSIFLKLLSDIVLVLNPLLSKALINF
VDEKMYNPDMSVGRGVGYAIGVTFMLGTSGILINH
FLYLSLTVGAHCKAVLTTAIMNKSFRASAKSKHEY
PSGRVTSLMSTDLARIDLAIGFQPFAITVPVPIGV
AIALLIVNIGVSALAGIAVFLVCIVVISASSKSLL
KMRKGANQYTDARISYMREILQNMRIIKFYSWEDA
YEKSVVTERNSEMSIILKMQSIRNFLLALSLSLPA
IISMVAFLVLYGVSNDKNPGNIFSSISLFSVLAQQ
TMMLPMALATGADAKIGLERLRQYLQSGDIEKEYE
DHEKPGDRDVVLPDNVAVELNNASFIWEKFDDADD
NDGNSEKTKEVVVTSKSSLTDSSHIDKSTDSADGE
YIKSVFEGFNNINLTIKKGEFVIITGPIGSGKSSL
LVALAGFMKKTSGTLGVNGTMLLCGQPWVQNCTVR
DNILFGLEYDEARYDRVVEVCALGDDLKMFTAGDQ
TEIGERGITLSGGQKARINLARAVYANKDIILLDD
ALSAVDARVGKLIVDDCLTSFLGDKTRILATHQLS

-continued

LIEAADRVIYLNGDGTIHIGTVQELLESNEGFLKL
MEFSRKSESEDEEDVEAANEKDVSLQKAVSVVQEQ
DAHAGVLIGQEERAVNGIEWDIYKEYLHEGRGKLG
IFAIPTIIMLLVLDVFTSIFVNVWLSFWISHKFKA
RSDGFYIGLYVMFVILSVIWITAEFVVMGNFSSTA
ARRLNLKAMKRVLHTPMHFLDVTPMGRILNRFTKD
TDVLDNEIGEQARMFLHPAAYVIGVLILCIINIPW
FAIAIPPLAIPFTFITNFYIASSREVKRIEAIQRS
LVYNNFNEVLNGLQTLKAYNATSRFMEKNKRLLNR
MNEAYLLVIANQRWISVNLDLVSCCFVFLISMLSV
FRVFDINASSVGLVVTSVLQIGGLMSLIMRAYTTV
ENEMNSVERLCHYANKLEQEAPYIMNETKPRPTWP
EHGAIEFKHASMRYREGLPLVLKDLTISVKGGEKI
GICGRTGAGKSTIMNALYRLTELAEGSITIDGVEI
SQLGLYDLRSKLAIIPQDPVLFRGTIRKNLDPFGQ
NDDETLWDALRRSGLVEGSILNTIKSQSKDDPNFH
KFHLDQTVEDEGANFSLGERQLIALARALVRNSKI
LILDEATSSVDYETDSKIQKTISTVFSHCTILCIA
HRLKTILTYDRILVLEKGEVEEFDTPRVLYSKNGV
FRQMCERSEITSADFV,

Funga1_5_muA2

SEQ ID NO: 29

MTSPGSEKCTPRSDEDLERSEPQLQRRLLTPFLLS
KKVPPIPKEDERKPYPYLKTNPLSQILFWWLNPLL
RVGYKRTLDPNDFYYLEHSQDIETTYSNYEMHLAR
ILEKDRAKARAKDPTLTDEDLKNREYPKNAVIKAL
FLTFKWKYLWSIFLKLLSDIVLVLNPLLSKALINF
VDEKMYNPDMSVGRGVGYAIGVTFMLGTSGILINH
FLYLSLTVGAHCKAVLTTAIMNKSFRASAKSKHEY
PSGRVTSLMSTDLARIDLAIGFQPFAITVPVPIGV
AIALLIVNIGVSALAGIAVFLVCIVVISASSKSLL
KMRKGANQYTDARISYMREILQNMRIIKFYSWEDA
YEKSVVTERNSEMSIILKMQSIRNFLLALSLSLPA
IISMVAFLVLYGVSNDKNPGNIFSSISLFSVLAQQ
TMMLPMALATGADAKIGLERLRQYLQSGDIEKEYE
DHEKPGDRDVVLPDNVAVELNNASFIWEKFDDADD
NDGNSEKTKEVVVTSKSSLTDSSHIDKSTDSADGE
YIKSVFEGFNNINLTIKKGEFVIITGPIGSGKSSL
LVALAGFMKKTSGTLGVNGTMLLCGQPWVQNCTVR
DNILFGLEYDEARYDRVVEVCALGDDLKMFTAGDQ
TEIGERGITLSGGQKARINLARAVYANKDIILLDD
ALSAVDARVGKLIVDDCLTSFLGDKTRILATHQLS

-continued

LIEAADRVIYLNGDGTIHIGTVQELLESNEGFLKL

MEFSRKSESEDEEDVEAANEKDVSLQKAVSVVQEQ

DAHAGVLIGQEERAVNGIEWDIYKEYLHEGRGKLG

IFAIPTIIMLLVLDVFTSIFVNVWLSFWISHKFKA

RSDGFYIGLYVMFVILSVIWITAEFVVMGNFSSTA

ARRLNLKAMKRVLHTPMHFLDVTPMGRILNRFTKD

TDVLDNEIGEQARMFLHPAAYVIGVLILCIINIPW

FAIAIPPLAIPFTFITNFYIASSREVKRIEAIQRS

LVYNNFNEVLNGLQTLKAYNATSRFMEKNKRLLNR

MNEAYLLVIANQRWISVNLDLVSCCFVFLISMLSV

FRVFDINASSVGLVVTSVLQIGGLMSLIMRAYTTV

ENEMNSVERLCHYANKLEQEAPYIMNETKPRPTWP

EHGAIEFKHASMRYREGLPLVLKDLTISVKGGEKI

GICGRTGAGKSTIMNALYRLTELAEGSITIDGVEI

SQLGLYDLRSKLAIIPQDPVLFRGTIRKNLDPFGQ

NDDETLWDALRRSGLVEGSILNTIKSQSKDDPNFH

KFHLDQTVEDEGANFSLGERQLIALARALVRNSKI

LILDEATSSVDYETDSKIQKTISTEFSHCTILCIA

HRLKTILTYDRILVLEKGEVEEFDTPRVLYSKNGV

FRQMCERSEITSADFV,

Funga1_5_muA3

SEQ ID NO: 30

MTSPGSEKCTPRSDEDLERSEPQLQRRLLTPFLLS

KKVPPIPKEDERKPYPYLKTNPLSQILFWWLNPLL

RVGYKRTLDPNDFYYLEHSQDIETTYSNYEMHLAR

ILEKDRAKARAKDPTLTDEDLKNREYPKNAVIKAL

FLTFKWKYLWSIFLKLLSDIVLVLNPLLSKALINF

VDEKMYNPDMSVGRGVGYAIGVTFMLGTSGILINH

FLYLSLTVGAHCKAVLTTAIMNKSFRASAKSKHEY

PSGRVTSLMSTDLARIDLAIGFQPFAITVPVPIGV

AIALLIVNIGVSALAGIAVFLVCIVVISASSKSLL

-continued

KMRKGANQYTDARISYMREILQNMRIIKFYSWEDA

YEKSVVTERNSEMSIILKMQSIRNFLLALSLSLPA

IISMVAFLVLYGVSNDKNPGNIFSSISLFSVLAQQ

TMMLPMALATGADAKIGLERLRQYLQSGDIEKEYE

DHEKPGDRDVVLPDNVAVELNNASFIWEKFDDADD

NDGNSEKTKEVVVTSKSSLTDSSHIDKSTDSADGE

YIKSVFEGFNNINLTIKKGEFVIITGPIGSGKSSL

LVALAGFMKKTSGTLGVNGTMLLCGQPWVQNCTVR

DNILFGLEYDEARYDRVVEVCALGDDLKMFTAGDQ

TEIGERGITLSGGQKARINLARAVYANKDIILLDD

ALSAVDARVGKLIVDDCLTSFLGDKTRILATHQLS

LIEAADRVIYLNGDGTIHIGTVQELLESNEGFLKL

MEFSRKSESEDEEDVEAANEKDVSLQKAVSVVQEQ

DAHAGVLIGQEERAVNGIEWDIYKEYLHEGRGKLG

IFAIPTIIMLLVLDVFTSIFVNVWLSFWISHKFKA

RSDGFYIGLYVMFVILSVIWITAEFVVMGNFSSTA

ARRLNLKAMKRVLHTPMHFLDVTPMGRILNRFTKD

TDVLDNEIGEQARMFLHPAAYVIGVLILCIINIPW

FAIAIPPLAILFTFITNFYIASSREVKRIEAIQRS

LVYNNFNEVLNGLQTLKAYNATSRFMEKNKRLLNR

MNEAYLLVIANQRWISVNLDLVSCCFVFLISNLSV

FRVFDINASSVGLVVTSVLQIGGLMSLIMRAYTTV

ENEMNSVERLCHYANKLEQEAPYIMNETKPRPTWP

EHGAIEFKHASMRYREGLPLVLKDLTISVKGGEKI

GICGRTGAGKSTIMNALYRLTELAEGSITIDGVEI

SQLGLYDLRSKLAIIPQDPVLFRGTIRKNLDPFGQ

NDDETLWDALRRSGLVEGSILNTIKSQSKDDPNEH

KEHLDQTVEDEGANFSLGERQLIALARALVRNSKI

LILDEATSSVDYETDSKIQKTISTEFSHCTILCIA

HRLKTILTYDRILVLEKGEVEEFDTPRVLYSKNGV

ERQMCERSEITSADFV,

What is claimed is:

1. A genetically modified host cell capable of producing one or more steviol glycosides comprising a heterologous nucleic acid encoding an ABC-transporter having transporter activity and comprising an amino acid sequence having at least 90% sequence identity to an amino acid sequence selected from the group consisting of SEQ ID NO: 2, SEQ ID NO: 3, SEQ ID NO: 5, SEQ ID NO: 7, SEQ ID NO: 8, SEQ ID NO: 28, SEQ ID NO: 29, and SEQ ID NO: 30.

2. The genetically modified host cell of claim 1, further comprising a nucleic acid encoding geranylgeranyl pyrophosphate synthase (GGPPS), ent-copalyl pyrophosphate synthase (CPS), ent-kaurene synthase (KS), ent-kaurene 19-oxidase (KO), ent-kaurenoic acid 13-hydroxylase (KAH), cytochrome p450 reductase (CPR), and one or more UDP-glucosyltransferases (UGT).

3. The genetically modified host cell of claim 2, wherein the one or more UDP-glucosyltransferases (UGT) are selected from the group consisting of UGT85C2, UGT74G1, UGT91D_like3, UGT76G1, EUGT11, and UGT40087.

4. The genetically modified host cell of claim 3, wherein the geranylgeranyl pyrophosphate synthase (GGPPS) has GGPPS activity and comprises an amino acid sequence having at least 90% sequence identity to SEQ ID NO: 9, the ent-copalyl pyrophosphate synthase (CPS) has CPS activity and comprises an amino acid sequence having at least 90% sequence identity to SEQ ID NO: 10, the ent-kaurene synthase (KS) has KS activity and comprises an amino acid sequence having at least 90% sequence identity to SEQ ID NO: 11, the ent-kaurene 19-oxidase (KO) has KO activity and comprises an amino acid sequence having at least 90% sequence identity to SEQ ID NO: 12, the ent-kaurenoic acid 13-hydroxylase (KAH) has KAH activity and comprises an amino acid sequence having at least 90% sequence identity to SEQ ID NO: 13, the cytochrome p450 reductase (CPR) has CPR activity and comprises an amino acid sequence having at least 90% sequence identity to SEQ ID NO: 14, and the one or more UDP-glucosyltransferases (UGT) have UGT activity and comprise an amino acid sequence having at least 90% sequence identity to an amino acid sequence-selected from the group consisting of SEQ ID NO: 15, SEQ ID NO: 16, SEQ ID NO: 17, SEQ ID NO:18, and SEQ ID NO: 19.

5. The genetically modified host cell of claim 1, wherein the ABC-transporter comprises an amino acid sequence having:

(i) at least 90% sequence identity to an amino acid sequence selected from the group consisting of SEQ ID NO: 2, SEQ ID NO: 7, SEQ ID NO: 29, and SEQ ID NO: 30; and (ii) one or more amino acid substitutions selected from V666A, Y942N, L956P, and E1320V.

6. The genetically modified host cell of claim 5, wherein the ABC-transporter comprises an amino acid sequence selected from the group consisting of SEQ ID NO: 7, SEQ ID NO: 29, and SEQ ID NO: 30 having one or more amino acid substitutions selected from V666A, Y942N, L956P, and E1320V.

7. The genetically modified host cell of claim 6, further comprising a nucleic acid encoding geranylgeranyl pyrophosphate synthase (GGPPS) comprising an amino acid sequence of SEQ ID NO: 9.

8. The genetically modified host cell of claim 1, further comprising an UDP-glucosyltransferase (UGT) having UGT activity and an amino acid sequence having at least 90% sequence identity to the amino acid sequence of SEQ ID NO: 18.

9. The genetically modified host cell of claim 2, wherein the geranylgeranyl pyrophosphate synthase (GGPPS) comprises an amino acid sequence of SEQ ID NO: 9.

10. The genetically modified host cell of claim 3, wherein the geranylgeranyl pyrophosphate synthase (GGPPS) comprises an amino acid sequence of SEQ ID NO: 9.

11. The genetically modified host cell of claim 10, wherein the ent-copalyl pyrophosphate synthase (CPS) comprises an amino acid sequence of SEQ ID NO: 10, the ent-kaurene synthase (KS) comprises an amino acid sequence of SEQ ID NO: 11, the ent-kaurene 19-oxidase (KO) comprises an amino acid sequence of SEQ ID NO: 12, the ent-kaurenoic acid 13-hydroxylase (KAH) comprises an amino acid sequence of SEQ ID NO: 13, the cytochrome p450 reductase (CPR) comprises an amino acid sequence of SEQ ID NO: 14, and the one or more UDP-glucosyltransferases (UGT) comprise an amino acid sequence selected from the group consisting of SEQ ID NO: 15, SEQ ID NO: 16, SEQ ID NO: 17, SEQ ID NO:18, and SEQ ID NO: 19.

12. The genetically modified host cell of claim 1, wherein the host cell is selected from the group consisting of a bacterial cell, a fungal cell, an algal cell, an insect cell, and a plant cell.

13. The genetically modified host cell of claim 12, wherein the host cell is a *Saccharomyces cerevisiae* cell.

14. The genetically modified host cell of claim 1, wherein at least 50% of the one or more steviol glycosides accumulate within a lumen of an organelle.

15. The genetically modified host cell of claim 1, wherein at least 50% of the one or more steviol glycosides accumulate extracellularly.

16. The genetically modified host cell of claim 1, wherein the one or more steviol glycosides is selected from the group consisting of Reb A, Reb B, Reb D, Reb E, and Reb M.

17. A genetically modified host cell capable of producing one or more steviol glycosides, comprising:

a heterologous nucleic acid encoding an ABC-transporter comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 28, SEQ ID NO: 29, SEQ ID NO: 30, and SEQ ID NO: 7 having one or more amino acid substitutions selected from V666A, Y942N, L956P, and E1320V; and a nucleic acid encoding geranylgeranyl pyrophosphate synthase (GGPPS) comprising an amino acid sequence of SEQ ID NO: 9, ent-copalyl pyrophosphate synthase (CPS) comprising an amino acid sequence of SEQ ID NO: 10, ent-kaurene synthase (KS) comprising an amino acid sequence of SEQ ID NO: 11, ent-kaurene 19-oxidase (KO) comprising an amino acid sequence of SEQ ID NO: 12, ent-kaurenoic acid 13-hydroxylase (KAH) comprising an amino acid sequence of SEQ ID NO: 13, cytochrome p450 reductase (CPR) comprising an amino acid sequence of SEQ ID NO: 14, and one or more UDP-glucosyltransferases (UGT) selected from the group consisting of UGT85C2, UGT74G1, UGT91D-like3, UGT76G1, EUGT11, and UGT40087.

18. A method for producing steviol or one or more steviol glycosides comprising the steps:

a. culturing a population of the host cells of claim 1 in a medium with a carbon source under conditions suitable for making steviol or one or more steviol glycosides to yield a culture broth; and b. recovering said steviol or one or more steviol glycosides from the culture broth.

19. A method for producing Reb D comprising the steps:

a. culturing a population of the host cells of claim 1 in a medium with a carbon source under conditions suitable for making Reb D to yield a culture broth; and b. recovering said Reb D compound from the culture broth.

20. A method for producing Reb M comprising the steps:

a. culturing a population of the host cells of claim 1 in a medium with a carbon source under conditions suitable for making Reb M to yield a culture broth; and b. recovering said Reb M compound from the culture broth.

* * * * *

SEQUENCE LISTING

<160> NUMBER OF SEQ ID NOS: 30

<210> SEQ ID NO 1
<211> LENGTH: 1559
<212> TYPE: PRT
<213> ORGANISM: Artificial Sequence
<220> FEATURE:
<223> OTHER INFORMATION: Synthetic: CEN.PK.BPT1 ABC-transporter

<400> SEQUENCE: 1

Met Ser Ser Leu Glu Val Val Asp Gly Cys Pro Tyr Gly Tyr Arg Pro
1 5 10 15

-continued

```
Tyr Pro Asp Ser Gly Thr Asn Ala Leu Asn Pro Cys Phe Ile Ser Val
            20                  25                  30

Ile Ser Ala Trp Gln Ala Val Phe Phe Leu Leu Ile Gly Ser Tyr Gln
        35                  40                  45

Leu Trp Lys Leu Tyr Lys Asn Asn Lys Val Pro Pro Arg Phe Lys Asn
    50                  55                  60

Phe Pro Thr Leu Pro Ser Lys Ile Asn Ser Arg His Leu Thr His Leu
65                  70                  75                  80

Thr Asn Val Cys Phe Gln Ser Thr Leu Ile Ile Cys Glu Leu Ala Leu
                85                  90                  95

Val Ser Gln Ser Ser Asp Arg Val Tyr Pro Phe Ile Leu Lys Lys Ala
            100                 105                 110

Leu Tyr Leu Asn Leu Leu Phe Asn Leu Gly Ile Ser Leu Pro Thr Gln
        115                 120                 125

Tyr Leu Ala Tyr Phe Lys Ser Thr Phe Ser Met Gly Asn Gln Leu Phe
    130                 135                 140

Tyr Tyr Met Phe Gln Ile Leu Leu Gln Leu Phe Leu Ile Leu Gln Arg
145                 150                 155                 160

Tyr Tyr His Gly Ser Ser Asn Glu Arg Leu Thr Val Ile Ser Gly Gln
                165                 170                 175

Thr Ala Met Ile Leu Glu Val Leu Leu Leu Phe Asn Ser Val Ala Ile
            180                 185                 190

Phe Ile Tyr Asp Leu Cys Ile Phe Glu Pro Ile Asn Glu Leu Ser Glu
        195                 200                 205

Tyr Tyr Lys Lys Asn Gly Trp Tyr Pro Pro Val His Val Leu Ser Tyr
    210                 215                 220

Ile Thr Phe Ile Trp Met Asn Lys Leu Ile Val Glu Thr Tyr Arg Asn
225                 230                 235                 240

Lys Lys Ile Lys Asp Pro Asn Gln Leu Pro Leu Pro Pro Val Asp Leu
                245                 250                 255

Asn Ile Lys Ser Ile Ser Lys Glu Phe Lys Ala Asn Trp Glu Leu Glu
            260                 265                 270

Lys Trp Leu Asn Arg Asn Ser Leu Trp Arg Ala Ile Trp Lys Ser Phe
        275                 280                 285

Gly Arg Thr Ile Ser Val Ala Met Leu Tyr Glu Thr Thr Ser Asp Leu
    290                 295                 300

Leu Ser Val Val Gln Pro Gln Phe Leu Arg Ile Phe Ile Asp Gly Leu
305                 310                 315                 320

Asn Pro Glu Thr Ser Ser Lys Tyr Pro Pro Leu Asn Gly Val Phe Ile
                325                 330                 335

Ala Leu Thr Leu Phe Val Ile Ser Val Val Ser Val Phe Leu Thr Asn
            340                 345                 350

Gln Phe Tyr Ile Gly Ile Phe Glu Ala Gly Leu Gly Ile Arg Gly Ser
        355                 360                 365

Leu Ala Ser Leu Val Tyr Gln Lys Ser Leu Arg Leu Thr Leu Ala Glu
    370                 375                 380

Arg Asn Glu Lys Ser Thr Gly Asp Ile Leu Asn Leu Met Ser Val Asp
385                 390                 395                 400

Val Leu Arg Ile Gln Arg Phe Phe Glu Asn Ala Gln Thr Ile Ile Gly
                405                 410                 415

Ala Pro Ile Gln Ile Ile Val Val Leu Thr Ser Leu Tyr Trp Leu Leu
            420                 425                 430
```

```
Gly Lys Ala Val Ile Gly Gly Leu Val Thr Met Ala Ile Met Met Pro
        435                 440                 445

Ile Asn Ala Phe Leu Ser Arg Lys Val Lys Lys Leu Ser Lys Thr Gln
    450                 455                 460

Met Lys Tyr Lys Asp Met Arg Ile Lys Thr Ile Thr Glu Leu Leu Asn
465                 470                 475                 480

Ala Ile Lys Ser Ile Lys Leu Tyr Ala Trp Glu Glu Pro Met Met Ala
                485                 490                 495

Arg Leu Asn His Val Arg Asn Asp Met Glu Leu Lys Asn Phe Arg Lys
            500                 505                 510

Ile Gly Ile Val Ser Asn Leu Ile Tyr Phe Ala Trp Asn Cys Val Pro
        515                 520                 525

Leu Met Val Thr Cys Ser Thr Phe Gly Leu Phe Ser Leu Phe Ser Asp
    530                 535                 540

Ser Pro Leu Ser Pro Ala Ile Val Phe Pro Ser Leu Ser Leu Phe Asn
545                 550                 555                 560

Ile Leu Asn Ser Ala Ile Tyr Ser Val Pro Ser Met Ile Asn Thr Ile
                565                 570                 575

Ile Glu Thr Ser Val Ser Met Glu Arg Leu Lys Ser Phe Leu Leu Ser
            580                 585                 590

Asp Glu Ile Asp Asp Ser Phe Ile Glu Arg Ile Asp Pro Ser Ala Asp
        595                 600                 605

Glu Arg Ala Leu Pro Ala Ile Glu Met Asn Asn Ile Thr Phe Leu Trp
    610                 615                 620

Lys Ser Lys Glu Val Leu Thr Ser Ser Gln Ser Gly Asp Asn Leu Arg
625                 630                 635                 640

Thr Asp Glu Glu Ser Ile Ile Gly Ser Ser Gln Ile Ala Leu Lys Asn
                645                 650                 655

Ile Asp His Phe Glu Ala Lys Arg Gly Asp Leu Val Cys Val Val Gly
            660                 665                 670

Arg Val Gly Ala Gly Lys Ser Thr Phe Leu Lys Ala Ile Leu Gly Gln
        675                 680                 685

Leu Pro Cys Met Ser Gly Ser Arg Asp Ser Ile Pro Pro Lys Leu Ile
    690                 695                 700

Ile Arg Ser Ser Ser Val Ala Tyr Cys Ser Gln Glu Ser Trp Ile Met
705                 710                 715                 720

Asn Ala Ser Val Arg Glu Asn Ile Leu Phe Gly His Lys Phe Asp Gln
                725                 730                 735

Asp Tyr Tyr Asp Leu Thr Ile Lys Ala Cys Gln Leu Leu Pro Asp Leu
            740                 745                 750

Lys Ile Leu Pro Asp Gly Asp Glu Thr Leu Val Gly Glu Lys Gly Ile
        755                 760                 765

Ser Leu Ser Gly Gly Gln Lys Ala Arg Leu Ser Leu Ala Arg Ala Val
    770                 775                 780

Tyr Ser Arg Ala Asp Ile Tyr Leu Leu Asp Asp Ile Leu Ser Ala Val
785                 790                 795                 800

Asp Ala Glu Val Ser Lys Asn Ile Ile Glu Tyr Val Leu Ile Gly Lys
                805                 810                 815

Thr Ala Leu Leu Lys Asn Lys Thr Ile Ile Leu Thr Thr Asn Thr Val
            820                 825                 830

Ser Ile Leu Lys His Ser Gln Met Ile Tyr Ala Leu Glu Asn Gly Glu
        835                 840                 845

Ile Val Glu Gln Gly Asn Tyr Glu Asp Val Met Asn Arg Lys Asn Asn
```

-continued

```
    850                 855                 860

Thr Ser Lys Leu Lys Lys Leu Leu Glu Glu Phe Asp Ser Pro Ile Asp
865                 870                 875                 880

Asn Gly Asn Glu Ser Asp Val Gln Thr Glu His Arg Ser Glu Ser Glu
                885                 890                 895

Val Asp Glu Pro Leu Gln Leu Lys Val Thr Glu Ser Glu Thr Glu Asp
            900                 905                 910

Glu Val Val Thr Glu Ser Glu Leu Glu Leu Ile Lys Ala Asn Ser Arg
        915                 920                 925

Arg Ala Ser Leu Ala Thr Leu Arg Pro Arg Pro Phe Val Gly Ala Gln
    930                 935                 940

Leu Asp Ser Val Lys Lys Thr Ala Gln Lys Ala Glu Lys Thr Glu Val
945                 950                 955                 960

Gly Arg Val Lys Thr Lys Ile Tyr Leu Ala Tyr Ile Lys Ala Cys Gly
                965                 970                 975

Val Leu Gly Val Val Leu Phe Phe Leu Phe Met Ile Leu Thr Arg Val
            980                 985                 990

Phe Asp Leu Ala Glu Asn Phe Trp  Leu Lys Tyr Trp Ser  Glu Ser Asn
        995                 1000                1005

Glu Lys  Asn Gly Ser Asn Glu  Arg Val Trp Met Phe  Val Gly Val
    1010                 1015                 1020

Tyr Ser  Leu Ile Gly Val Ala  Ser Ala Ala Phe Asn  Asn Leu Arg
    1025                 1030                 1035

Ser Ile  Met Met Leu Leu Tyr  Cys Ser Ile Arg Gly  Ser Lys Lys
    1040                 1045                 1050

Leu His  Glu Ser Met Ala Lys  Ser Val Ile Arg Ser  Pro Met Thr
    1055                 1060                 1065

Phe Phe  Glu Thr Thr Pro Val  Gly Arg Ile Ile Asn  Arg Phe Ser
    1070                 1075                 1080

Ser Asp  Met Asp Ala Val Asp  Ser Asn Leu Gln Tyr  Ile Phe Ser
    1085                 1090                 1095

Phe Phe  Phe Lys Ser Ile Leu  Thr Tyr Leu Val Thr  Val Ile Leu
    1100                 1105                 1110

Val Gly  Tyr Asn Met Pro Trp  Phe Leu Val Phe Asn  Met Phe Leu
    1115                 1120                 1125

Val Val  Ile Tyr Ile Tyr Tyr  Gln Thr Phe Tyr Ile  Val Leu Ser
    1130                 1135                 1140

Arg Glu  Leu Lys Arg Leu Ile  Ser Ile Ser Tyr Ser  Pro Ile Met
    1145                 1150                 1155

Ser Leu  Met Ser Glu Ser Leu  Asn Gly Tyr Ser Ile  Ile Asp Ala
    1160                 1165                 1170

Tyr Asp  His Phe Glu Arg Phe  Ile Tyr Leu Asn Tyr  Glu Lys Ile
    1175                 1180                 1185

Gln Tyr  Asn Val Asp Phe Val  Phe Asn Phe Arg Ser  Thr Asn Arg
    1190                 1195                 1200

Trp Leu  Ser Val Arg Leu Gln  Thr Ile Gly Ala Thr  Ile Val Leu
    1205                 1210                 1215

Ala Thr  Ala Ile Leu Ala Leu  Ala Thr Met Asn Thr  Lys Arg Gln
    1220                 1225                 1230

Leu Ser  Ser Gly Met Val Gly  Leu Leu Met Ser Tyr  Ser Leu Glu
    1235                 1240                 1245

Val Thr  Gly Ser Leu Thr Trp  Ile Val Arg Thr Thr  Val Thr Ile
    1250                 1255                 1260
```

Glu Thr Asn Ile Val Ser Val Glu Arg Ile Val Glu Tyr Cys Glu
1265 1270 1275

Leu Pro Pro Glu Ala Gln Ser Ile Asn Pro Glu Lys Arg Pro Asp
1280 1285 1290

Glu Asn Trp Pro Ser Lys Gly Gly Ile Glu Phe Lys Asn Tyr Ser
1295 1300 1305

Thr Lys Tyr Arg Glu Asn Leu Asp Pro Val Leu Asn Asn Ile Asn
1310 1315 1320

Val Lys Ile Glu Pro Cys Glu Lys Val Gly Ile Val Gly Arg Thr
1325 1330 1335

Gly Ala Gly Lys Ser Thr Leu Ser Leu Ala Leu Phe Arg Ile Leu
1340 1345 1350

Glu Pro Thr Glu Gly Lys Ile Ile Ile Asp Gly Ile Asp Ile Ser
1355 1360 1365

Asp Ile Gly Leu Phe Asp Leu Arg Ser His Leu Ala Ile Ile Pro
1370 1375 1380

Gln Asp Ala Gln Ala Phe Glu Gly Thr Val Lys Thr Asn Leu Asp
1385 1390 1395

Pro Phe Asn Arg Tyr Ser Glu Asp Glu Leu Lys Arg Ala Val Glu
1400 1405 1410

Gln Ala His Leu Lys Pro His Leu Glu Lys Met Leu His Ser Lys
1415 1420 1425

Pro Arg Gly Asp Asp Ser Asn Glu Glu Asp Gly Asn Val Asn Asp
1430 1435 1440

Ile Leu Asp Val Lys Ile Asn Glu Asn Gly Ser Asn Leu Ser Val
1445 1450 1455

Gly Gln Arg Gln Leu Leu Cys Leu Ala Arg Ala Leu Leu Asn Arg
1460 1465 1470

Ser Lys Ile Leu Val Leu Asp Glu Ala Thr Ala Ser Val Asp Met
1475 1480 1485

Glu Thr Asp Lys Ile Ile Gln Asp Thr Ile Arg Arg Glu Phe Lys
1490 1495 1500

Asp Arg Thr Ile Leu Thr Ile Ala His Arg Ile Asp Thr Val Leu
1505 1510 1515

Asp Ser Asp Lys Ile Ile Val Leu Asp Gln Gly Ser Val Arg Glu
1520 1525 1530

Phe Asp Ser Pro Ser Lys Leu Leu Ser Asp Lys Thr Ser Ile Phe
1535 1540 1545

Tyr Ser Leu Cys Glu Lys Gly Gly Tyr Leu Lys
1550 1555

<210> SEQ ID NO 2
<211> LENGTH: 1620
<212> TYPE: PRT
<213> ORGANISM: Artificial Sequence
<220> FEATURE:
<223> OTHER INFORMATION: Synthetic: T4_Fungal_1 ABC-transporter

<400> SEQUENCE: 2

Met Ser Leu Glu Leu Ser Asn Ser Thr Leu Cys Asp Ser Tyr Trp Ala
1 5 10 15

Val Asp Asp Phe Thr Ala Cys Gly Arg Gln Leu Val Glu Ser Trp Val
20 25 30

Ser Val Pro Leu Val Leu Ser Ala Leu Val Val Ala Phe Asn Leu Leu
35 40 45

Arg Asn Ser Leu Ala Ser Glu Lys Thr Asp Pro Tyr Ser Lys Leu Asp
50 55 60

Ala Glu Gln Gln Pro Leu Leu Gln Asn Gly His Ala Leu Tyr Thr Ser
65 70 75 80

Ser Ile Glu Ser Asp Asn Thr Asp Ile Phe Gln Arg His Phe Asp Ile
85 90 95

Ala Leu Leu Lys Pro Val Lys Asp Asp Gly Lys Pro Ile Gly Val Val
100 105 110

Arg Ile Val Tyr Arg Asp Thr Ala Glu Lys Leu Lys Val Ala Leu Glu
115 120 125

Glu Ile Leu Leu Ile Ser Gln Thr Val Leu Ala Phe Leu Ala Leu Ser
130 135 140

Arg Leu Glu Asp Ile Ser Glu Ser Arg Phe Leu Leu Val Lys Tyr Ile
145 150 155 160

Asn Phe Ser Leu Trp Leu Tyr Leu Thr Val Ile Thr Ser Ala Arg Leu
165 170 175

Leu Asn Val Thr Lys Gly Phe Ser Ala Asn Arg Val Asp Leu Trp Tyr
180 185 190

His Cys Ala Ile Leu Tyr Asn Leu Gln Trp Phe Asn Ser Val Met Leu
195 200 205

Phe Arg Ser Ala Leu Leu His His Val Ser Gly Thr Tyr Gly Tyr Trp
210 215 220

Phe Tyr Val Thr Gln Phe Val Ile Asn Thr Leu Leu Cys Leu Thr Asn
225 230 235 240

Gly Leu Glu Lys Leu Ser Asp Lys Pro Ala Ile Val Tyr Glu Glu Glu
245 250 255

Gly Val Ile Pro Ser Pro Glu Thr Thr Ser Ser Leu Ile Asp Ile Met
260 265 270

Thr Tyr Gly Tyr Leu Asp Lys Met Val Phe Ser Ser Tyr Trp Lys Pro
275 280 285

Ile Thr Met Glu Glu Val Trp Gly Leu Arg Tyr Asp Asp Tyr Ser His
290 295 300

Asp Val Leu Ile Arg Phe His Lys Leu Lys Ser Ser Ile Arg Phe Thr
305 310 315 320

Leu Arg Leu Phe Leu Gln Phe Lys Lys Glu Leu Ala Leu Gln Thr Leu
325 330 335

Cys Thr Cys Ile Glu Ala Leu Leu Ile Phe Val Pro Pro Leu Cys Leu
340 345 350

Lys Lys Ile Leu Glu Tyr Ile Glu Ser Pro His Thr Lys Ser Arg Ser
355 360 365

Met Ala Trp Phe Tyr Val Leu Ile Met Phe Gly Ser Gly Val Ile Ala
370 375 380

Cys Ser Phe Ser Gly Arg Gly Leu Phe Leu Gly Arg Arg Ile Cys Thr
385 390 395 400

Arg Met Arg Ser Ile Leu Ile Gly Glu Ile Tyr Ser Lys Ala Leu Arg
405 410 415

Arg Arg Leu Gly Ser Thr Asp Lys Glu Lys Thr Thr Glu Glu Glu Asp
420 425 430

Asp Lys Ser Ala Lys Ser Lys Lys Glu Asp Glu Pro Ser Asn Lys Glu
435 440 445

Leu Gly Gly Ile Ile Asn Leu Met Ala Val Asp Ala Phe Lys Val Ser
450 455 460

-continued

```
Glu Ile Gly Gly Tyr Leu His Tyr Phe Pro Asn Ser Phe Val Met Ala
465                 470                 475                 480

Ala Val Ala Ile Tyr Met Leu Tyr Lys Leu Leu Gly Trp Ser Ser Leu
                485                 490                 495

Ile Gly Thr Ala Thr Leu Ile Ala Ile Leu Pro Ile Asn Tyr Met Leu
            500                 505                 510

Val Glu Lys Leu Ser Lys Tyr Gln Lys Gln Met Leu Leu Val Thr Asp
        515                 520                 525

Lys Arg Ile Gln Lys Thr Asn Glu Ala Phe Gln Asn Ile Arg Ile Ile
    530                 535                 540

Lys Tyr Phe Ala Trp Glu Asp Lys Phe Ala Asp Thr Ile Met Lys Ile
545                 550                 555                 560

Arg Glu Glu Glu Leu Gly Tyr Leu Val Gly Arg Cys Val Val Trp Ala
                565                 570                 575

Leu Leu Ile Phe Leu Trp Leu Val Val Pro Thr Ile Val Thr Leu Ile
            580                 585                 590

Thr Phe Tyr Ala Tyr Thr Val Ile Gln Gly Asn Pro Leu Thr Ser Pro
        595                 600                 605

Ile Ala Phe Thr Ala Leu Ser Leu Phe Thr Leu Leu Arg Gly Pro Leu
    610                 615                 620

Asp Ala Leu Ala Asp Met Leu Ser Met Val Met Gln Cys Lys Val Ser
625                 630                 635                 640

Leu Asp Arg Val Glu Asp Phe Leu Asn Glu Pro Glu Thr Thr Lys Tyr
                645                 650                 655

Gln Gln Leu Ser Ala Pro Arg Gly Pro Asn Ser Pro Leu Ile Gly Phe
            660                 665                 670

Glu Asn Ala Thr Phe Tyr Trp Ser Lys Asn Ser Lys Ala Glu Phe Ala
        675                 680                 685

Leu Lys Asp Leu Asn Ile Asp Phe Lys Val Gly Lys Leu Asn Val Val
    690                 695                 700

Ile Gly Pro Thr Gly Ser Gly Lys Ser Ser Leu Leu Leu Ala Leu Leu
705                 710                 715                 720

Gly Glu Met Asp Leu Asp Lys Gly Asn Val Phe Leu Pro Gly Ala Ile
                725                 730                 735

Pro Arg Asp Asp Leu Thr Pro Asn Pro Val Thr Gly Leu Met Glu Ser
            740                 745                 750

Val Ala Tyr Cys Ser Gln Thr Ala Trp Leu Leu Asn Ala Thr Val Lys
        755                 760                 765

Asp Asn Ile Ile Phe Ala Ser Pro Phe Asn Gln Glu Arg Tyr Asp Ala
    770                 775                 780

Val Ile His Ala Cys Gly Leu Thr Arg Asp Leu Ser Ile Leu Glu Ala
785                 790                 795                 800

Gly Asp Glu Thr Glu Ile Gly Glu Lys Gly Ile Thr Leu Ser Gly Gly
                805                 810                 815

Gln Lys Gln Arg Val Ser Leu Ala Arg Ala Leu Tyr Ser Ser Ala Ser
            820                 825                 830

Tyr Leu Leu Leu Asp Asp Cys Leu Ser Ala Val Asp Ser His Thr Ala
        835                 840                 845

Val His Ile Tyr Asp Tyr Cys Ile Asn Gly Glu Leu Met Lys Gly Arg
    850                 855                 860

Thr Cys Ile Leu Val Ser His Asn Val Ser Leu Thr Val Lys Glu Ala
865                 870                 875                 880

Asp Phe Val Val Met Met Asp Asn Gly Arg Ile Lys Ala Gln Gly Ser
```

-continued

```
            885                 890                 895

Val Asp Glu Leu Met Gln Glu Gly Leu Leu Asn Glu Glu Val Val Lys
        900                 905                 910

Ser Val Met Gln Ser Arg Ser Ala Ser Thr Ala Asn Leu Ala Ala Leu
    915                 920                 925

Asp Asp Asn Ser Pro Ile Ser Ser Glu Ala Ile Ala Glu Gly Leu Ala
930                 935                 940

Lys Lys Thr Gln Lys Pro Glu Gln Ser Lys Lys Ser Lys Leu Ile Glu
945                 950                 955                 960

Asp Glu Thr Lys Ser Asp Gly Ser Val Lys Pro Glu Ile Tyr Tyr Ala
            965                 970                 975

Tyr Phe Arg Tyr Phe Gly Asn Pro Ala Leu Trp Ile Met Ile Ala Phe
        980                 985                 990

Leu Phe Ile Gly Ser Gln Ser Val  Asn Val Tyr Gln Ser  Tyr Trp Leu
    995                 1000                1005

Arg Arg  Trp Ser Ala Ile Glu  Asp Lys Arg Asp Leu  Ser Ala Phe
    1010                1015                1020

Ser Asn  Ser Asn Asp Met Thr  Leu Phe Leu Phe Pro  Thr Phe His
    1025                1030                1035

Ser Ile  Asn Trp His Arg Pro  Leu Val Asn Tyr Ala  Leu Gln Pro
    1040                1045                1050

Phe Gly  Leu Ala Val Glu Glu  Arg Ser Thr Met Tyr  Tyr Ile Thr
    1055                1060                1065

Ile Tyr  Thr Leu Ile Gly Leu  Ala Phe Ala Thr Leu  Gly Ser Ser
    1070                1075                1080

Arg Val  Ile Leu Thr Phe Ile  Gly Gly Leu Asn Val  Ser Arg Lys
    1085                1090                1095

Ile Phe  Lys Asp Leu Leu Asp  Lys Leu Leu His Ala  Lys Leu Arg
    1100                1105                1110

Phe Phe  Asp Gln Thr Pro Ile  Gly Arg Ile Met Asn  Arg Phe Ser
    1115                1120                1125

Lys Asp  Ile Glu Ala Ile Asp  Gln Glu Leu Ala Leu  Tyr Ala Glu
    1130                1135                1140

Glu Phe  Val Thr Tyr Leu Ile  Ser Cys Leu Ser Thr  Leu Val Val
    1145                1150                1155

Val Cys  Ala Val Thr Pro Ala  Phe Leu Val Ala Gly  Val Leu Ile
    1160                1165                1170

Leu Leu  Val Tyr Tyr Gly Val  Gly Val Leu Tyr Leu  Glu Leu Ser
    1175                1180                1185

Arg Asp  Leu Lys Arg Phe Glu  Ser Ile Thr Lys Ser  Pro Ile His
    1190                1195                1200

Gln His  Phe Ser Glu Thr Leu  Val Gly Met Thr Thr  Ile Arg Ala
    1205                1210                1215

Tyr Gly  Asp Glu Arg Arg Phe  Leu Lys Gln Asn Phe  Glu Lys Ile
    1220                1225                1230

Asp Val  Asn Asn Arg Pro Phe  Trp Tyr Val Trp Val  Asn Asn Arg
    1235                1240                1245

Trp Leu  Ala Tyr Arg Ser Asp  Met Ile Gly Ala Phe  Ile Ile Phe
    1250                1255                1260

Phe Ala  Ala Ala Phe Ala Val  Ala Tyr Ser Asp Lys  Ile Asp Ala
    1265                1270                1275

Gly Leu  Ala Gly Ile Ser Leu  Ser Phe Ser Val Ser  Phe Arg Tyr
    1280                1285                1290
```

Thr Ala Val Trp Val Val Arg Met Tyr Ala Tyr Val Glu Met Ser
1295 1300 1305

Met Asn Ser Val Glu Arg Val Gln Glu Tyr Ile Glu Gln Thr Pro
1310 1315 1320

Gln Glu Pro Pro Lys Tyr Leu Pro Gln Asp Pro Val Asn Ser Trp
1325 1330 1335

Pro Ser Asn Gly Val Ile Asp Val Gln Asn Ile Cys Ile Arg Tyr
1340 1345 1350

Ser Pro Glu Leu Pro Arg Val Ile Asp Asn Val Ser Phe His Val
1355 1360 1365

Asn Ala Gly Glu Lys Ile Gly Val Val Gly Arg Thr Gly Ala Gly
1370 1375 1380

Lys Ser Thr Ile Ile Thr Ser Phe Phe Arg Phe Val Asp Leu Glu
1385 1390 1395

Ser Gly Ser Ile Lys Ile Asp Gly Leu Asp Ile Ser Lys Ile Gly
1400 1405 1410

Leu Lys Pro Leu Arg Lys Gly Leu Thr Ile Ile Pro Gln Asp Pro
1415 1420 1425

Thr Leu Phe Ser Gly Thr Ile Arg Ser Asn Leu Asp Ile Phe Gly
1430 1435 1440

Glu Tyr Gly Asp Leu Gln Met Phe Glu Ala Leu Arg Arg Val Asn
1445 1450 1455

Leu Ile Ser Val Asp Asp Tyr Gln Arg Ile Val Asp Gly Asn Gly
1460 1465 1470

Ala Ala Val Ala Asp Glu Thr Ala Gln Ala Arg Gly Asp Asn Val
1475 1480 1485

Asn Lys Phe Leu Asp Leu Asp Ser Thr Val Ser Glu Gly Gly Gly
1490 1495 1500

Asn Leu Ser Gln Gly Glu Arg Gln Leu Leu Cys Leu Ala Arg Ser
1505 1510 1515

Ile Leu Lys Met Pro Lys Ile Leu Met Leu Asp Glu Ala Thr Ala
1520 1525 1530

Ser Ile Asp Tyr Glu Ser Asp Ala Lys Ile Gln Ala Thr Ile Arg
1535 1540 1545

Glu Glu Phe Ser Ser Ser Thr Val Leu Thr Ile Ala His Arg Leu
1550 1555 1560

Lys Thr Ile Ile Asp Tyr Asp Lys Ile Leu Leu Leu Asp His Gly
1565 1570 1575

Lys Val Lys Glu Tyr Asp His Pro Tyr Lys Leu Ile Thr Asn Lys
1580 1585 1590

Lys Ser Asp Phe Arg Lys Met Cys Gln Asp Thr Gly Glu Phe Asp
1595 1600 1605

Asp Leu Val Asn Leu Ala Lys Gln Ala Tyr Arg Lys
1610 1615 1620

<210> SEQ ID NO 3
<211> LENGTH: 1515
<212> TYPE: PRT
<213> ORGANISM: Artificial Sequence
<220> FEATURE:
<223> OTHER INFORMATION: Synthetic: T4_Fungal_10 ABC-transporter

<400> SEQUENCE: 3

Met Gly Gln Ser Glu Arg Ala Ala Leu Ile Ala Phe Ala Ser Arg Asn
1 5 10 15

-continued

```
Thr Thr Glu Cys Trp Leu Cys Arg Asp Lys Glu Gly Phe Gly Pro Ile
            20                  25                  30

Ser Tyr Tyr Gly Asp Phe Thr Val Cys Phe Ile Asp Gly Val Leu Leu
        35                  40                  45

Asn Phe Ala Ala Leu Phe Met Leu Ile Phe Gly Thr Tyr Gln Val Val
    50                  55                  60

Lys Leu Ser Lys Lys Glu His Pro Gly Ile Lys Tyr Arg Arg Asp Trp
65                  70                  75                  80

Leu Leu Phe Ser Arg Ile Thr Leu Val Gly Cys Phe Leu Leu Phe Thr
                85                  90                  95

Ser Met Ala Ala Tyr Tyr Ser Ser Glu Lys His Glu Ser Ile Ala Leu
            100                 105                 110

Thr Ser Gln Tyr Thr Leu Thr Leu Met Ser Ile Phe Val Ala Leu Met
        115                 120                 125

Leu His Trp Val Glu Tyr His Arg Ser Arg Ile Ser Asn Gly Ile Val
    130                 135                 140

Leu Phe Tyr Trp Leu Phe Glu Thr Leu Phe Gln Gly Ser Lys Trp Val
145                 150                 155                 160

Asn Phe Ser Ile Arg His Ala Tyr Asn Leu Asn His Glu Trp Pro Val
                165                 170                 175

Ser Tyr Ser Val Tyr Ile Leu Thr Ile Phe Gln Thr Ile Ser Ala Phe
            180                 185                 190

Met Ile Leu Ile Leu Glu Ala Gly Phe Glu Lys Pro Leu Pro Ser Tyr
        195                 200                 205

Gln Arg Val Ile Glu Ser Tyr Ser Lys Gln Lys Arg Asn Pro Val Asp
    210                 215                 220

Asn Ser His Ile Phe Gln Arg Leu Ser Phe Ser Trp Met Thr Glu Leu
225                 230                 235                 240

Met Lys Thr Gly Tyr Lys Lys Tyr Leu Thr Glu Gln Asp Leu Tyr Lys
                245                 250                 255

Leu Pro Lys Ser Phe Gly Ala Lys Glu Ile Ser His Lys Phe Ser Glu
            260                 265                 270

Arg Trp Gln Tyr Gln Leu Lys His Lys Ala Asn Pro Ser Leu Ala Trp
        275                 280                 285

Ala Leu Leu Ser Thr Phe Gly Gly Lys Ile Leu Leu Gly Gly Ile Phe
    290                 295                 300

Lys Val Ala Tyr Asp Ile Leu Gln Phe Thr Gln Pro Gln Leu Leu Arg
305                 310                 315                 320

Ile Leu Ile Lys Phe Val Ser Asp Tyr Thr Ser Thr Pro Glu Pro Gln
                325                 330                 335

Leu Pro Leu Val Arg Gly Val Met Leu Ser Ile Ala Met Phe Val Val
            340                 345                 350

Ser Val Val Gln Thr Ser Ile Leu His Gln Tyr Phe Leu Asn Ala Phe
        355                 360                 365

Asp Thr Gly Met His Ile Lys Ser Gly Met Thr Ser Val Ile Tyr Gln
    370                 375                 380

Lys Ala Leu Val Leu Ser Ser Glu Ala Ser Ala Ser Ser Ser Thr Gly
385                 390                 395                 400

Asp Ile Val Asn Leu Met Ser Val Asp Val Gln Arg Leu Gln Asp Leu
                405                 410                 415

Thr Gln Trp Gly Gln Ile Ile Trp Ser Gly Pro Phe Gln Ile Ile Leu
            420                 425                 430
```

```
Cys Leu Val Ser Leu Tyr Lys Leu Leu Gly Pro Cys Met Trp Val Gly
        435                 440                 445

Val Ile Ile Met Ile Ile Met Ile Pro Ile Asn Ser Val Ile Val Arg
    450                 455                 460

Ile Gln Lys Lys Leu Gln Lys Ile Gln Met Lys Asn Lys Asp Glu Arg
465                 470                 475                 480

Thr Arg Val Thr Ser Glu Ile Leu Asn Asn Ile Lys Ser Leu Lys Val
                485                 490                 495

Tyr Gly Trp Glu Ile Pro Tyr Lys Ala Lys Leu Asp His Val Arg Asn
            500                 505                 510

Asp Lys Glu Leu Lys Asn Leu Lys Lys Met Gly Cys Thr Leu Ala Leu
        515                 520                 525

Ala Ser Phe Gln Phe Asn Ile Val Pro Phe Leu Val Ser Cys Ser Thr
    530                 535                 540

Phe Ala Val Phe Val Phe Thr Glu Asp Arg Pro Leu Ser Thr Asp Leu
545                 550                 555                 560

Val Phe Pro Ala Leu Thr Leu Phe Asn Leu Leu Ser Phe Pro Leu Ala
                565                 570                 575

Val Val Pro Asn Ala Ile Ser Ser Phe Ile Glu Ala Ser Val Ser Val
            580                 585                 590

Asn Arg Leu Tyr Ala Phe Leu Thr Asn Glu Glu Leu Gln Thr Asp Ala
        595                 600                 605

Val His Arg Glu Pro Lys Val Asn Asn Ile Gly Asp Glu Gly Val Lys
    610                 615                 620

Val Ser Asp Ala Thr Phe Leu Trp Gln Arg Lys Pro Glu Tyr Lys Val
625                 630                 635                 640

Ala Leu Lys Asn Ile Asn Phe Ser Ala Lys Lys Gly Glu Leu Thr Cys
                645                 650                 655

Ile Val Gly Lys Val Gly Ser Gly Lys Ser Ala Leu Ile Gln Ser Leu
            660                 665                 670

Leu Gly Asp Leu Ile Arg Val Lys Gly Tyr Ala Ala Val His Gly Ser
        675                 680                 685

Val Ala Tyr Val Ser Gln Val Ala Trp Ile Met Asn Gly Thr Val Lys
    690                 695                 700

Asp Asn Ile Ile Phe Gly His Lys Tyr Asp Pro Glu Phe Tyr Glu Leu
705                 710                 715                 720

Thr Ile Lys Ala Cys Ala Leu Ala Ile Asp Leu Ser Met Leu Pro Asp
                725                 730                 735

Gly Asp Gln Thr Leu Val Gly Glu Lys Gly Ile Ser Leu Ser Gly Gly
            740                 745                 750

Gln Lys Ala Arg Leu Ser Leu Ala Arg Ala Val Tyr Ala Arg Ala Asp
        755                 760                 765

Thr Tyr Leu Leu Asp Asp Pro Leu Ala Ala Val Asp Glu His Val Ala
    770                 775                 780

Lys His Leu Ile Glu His Val Leu Gly Pro His Gly Leu Leu His Ser
785                 790                 795                 800

Lys Thr Lys Val Leu Ala Thr Asn Lys Ile Ser Val Leu Ser Ile Ala
                805                 810                 815

Asp Ser Ile Thr Leu Met Glu Asn Gly Glu Ile Ile Gln Gln Gly Thr
            820                 825                 830

Tyr Glu Glu Thr Asn Asn Thr Thr Asp Ser Pro Leu Ser Lys Leu Ile
        835                 840                 845

Ser Glu Phe Gly Lys Lys Gly Lys Ala Thr Pro Ser Gln Ser Thr Thr
```

```
    850                 855                 860

Ser Leu Thr Lys Leu Ala Thr Ser Asp Leu Gly Ser Ser Ser Asp Ser
865                 870                 875                 880

Lys Val Ser Asp Val Ser Ile Asp Val Ser Gln Leu Asp Thr Glu Asn
                885                 890                 895

Leu Thr Glu Ala Glu Glu Leu Lys Ser Leu Arg Arg Ala Ser Met Ala
            900                 905                 910

Thr Leu Gly Ser Ile Gly Phe Asp Asp Asp Glu Asn Ile Ala Arg Arg
        915                 920                 925

Glu His Arg Glu Gln Gly Lys Val Lys Trp Asp Ile Tyr Met Glu Tyr
    930                 935                 940

Ala Arg Ala Cys Asn Pro Arg Ser Val Cys Val Phe Leu Phe Phe Ile
945                 950                 955                 960

Val Leu Ser Met Leu Leu Ser Val Leu Gly Asn Phe Trp Leu Lys His
                965                 970                 975

Trp Ser Glu Val Asn Thr Gly Glu Gly Tyr Asn Pro His Ala Ala Arg
            980                 985                 990

Tyr Leu Leu Ile Tyr Phe Ala Leu  Gly Val Gly Ser Ala  Leu Ala Thr
        995                 1000                1005

Leu Ile  Gln Thr Ile Val Leu  Trp Val Phe Cys Thr  Ile His Gly
    1010                1015                1020

Ser Arg  Tyr Leu His Asp Ala  Met Ala Thr Ser Val  Leu Lys Ala
    1025                1030                1035

Pro Met  Ser Phe Phe Glu Thr  Thr Pro Ile Gly Arg  Ile Leu Asn
    1040                1045                1050

Arg Phe  Ser Asn Asp Ile Tyr  Lys Val Asp Glu Val  Leu Gly Arg
    1055                1060                1065

Thr Phe  Ser Gln Phe Phe Ala  Asn Val Val Lys Val  Ser Phe Thr
    1070                1075                1080

Ile Ile  Val Ile Cys Met Ala  Thr Trp Gln Phe Ile  Phe Ile Ile
    1085                1090                1095

Leu Pro  Leu Ser Val Leu Tyr  Ile Tyr Tyr Gln Gln  Tyr Tyr Leu
    1100                1105                1110

Arg Thr  Ser Arg Glu Leu Arg  Arg Leu Asp Ser Val  Thr Arg Ser
    1115                1120                1125

Pro Ile  Tyr Ala His Phe Gln  Glu Thr Leu Gly Gly  Leu Thr Thr
    1130                1135                1140

Ile Arg  Gly Tyr Ser Gln Gln  Thr Arg Phe Val His  Ile Asn Gln
    1145                1150                1155

Thr Arg  Val Asp Asn Asn Met  Ser Ala Phe Tyr Pro  Ser Val Asn
    1160                1165                1170

Ala Asn  Arg Trp Leu Ala Phe  Arg Leu Glu Phe Ile  Gly Ser Ile
    1175                1180                1185

Ile Ile  Leu Gly Ser Ser Met  Leu Ala Val Ile Arg  Leu Gly Asn
    1190                1195                1200

Gly Thr  Leu Thr Ala Gly Met  Ile Gly Leu Ser Leu  Ser Phe Ala
    1205                1210                1215

Leu Gln  Ile Thr Gln Ser Leu  Asn Trp Ile Val Arg  Met Thr Val
    1220                1225                1230

Glu Val  Glu Thr Asn Ile Val  Ser Val Glu Arg Ile  Lys Glu Tyr
    1235                1240                1245

Ala Glu  Leu Lys Ser Glu Ala  Pro Tyr Ile Ile Glu  Asp His Arg
    1250                1255                1260
```

Pro Pro Ala Ser Trp Pro Glu Lys Gly Asp Val Lys Phe Val Asn
1265 1270 1275

Tyr Ser Thr Arg Tyr Arg Pro Glu Leu Glu Leu Ile Leu Lys Asp
1280 1285 1290

Ile Asn Leu His Ile Leu Pro Lys Glu Lys Ile Gly Ile Val Gly
1295 1300 1305

Arg Thr Gly Ala Gly Lys Ser Ser Leu Thr Leu Ala Leu Phe Arg
1310 1315 1320

Ile Ile Glu Ala Ala Ser Gly His Ile Ile Ile Asp Gly Ile Pro
1325 1330 1335

Ile Asp Ser Ile Gly Leu Ala Asp Leu Arg His Arg Leu Ser Ile
1340 1345 1350

Ile Pro Gln Asp Ser Gln Ile Phe Glu Gly Thr Ile Arg Glu Asn
1355 1360 1365

Ile Asp Pro Ser Lys Gln Tyr Thr Asp Glu Gln Ile Trp Asp Ala
1370 1375 1380

Leu Glu Leu Ser His Leu Lys Asn His Val Lys Asn Met Gly Pro
1385 1390 1395

Asp Gly Leu Glu Thr Met Leu Ser Glu Gly Gly Gly Asn Leu Ser
1400 1405 1410

Val Gly Gln Arg Gln Leu Met Cys Leu Ala Arg Ala Leu Leu Ile
1415 1420 1425

Ser Ser Lys Ile Leu Val Leu Asp Glu Ala Thr Ala Ala Val Asp
1430 1435 1440

Val Glu Thr Asp Gln Leu Ile Gln Lys Thr Ile Arg Glu Ala Phe
1445 1450 1455

Lys Glu Arg Thr Ile Leu Thr Ile Ala His Arg Ile Asn Thr Ile
1460 1465 1470

Met Asp Ser Asp Arg Ile Ile Val Leu Asp Lys Gly Arg Val Thr
1475 1480 1485

Glu Phe Asp Thr Pro Ala Asn Leu Leu Asn Lys Lys Asp Ser Ile
1490 1495 1500

Phe Tyr Ser Leu Cys Val Glu Ala Gly Leu Ala Glu
1505 1510 1515

<210> SEQ ID NO 4
<211> LENGTH: 1559
<212> TYPE: PRT
<213> ORGANISM: Artificial Sequence
<220> FEATURE:
<223> OTHER INFORMATION: Synthetic: T4_Fungal_2 ABC-transporter

<400> SEQUENCE: 4

Met Ser Ser Leu Glu Val Val Asp Gly Cys Pro Tyr Gly Tyr Arg Pro
1 5 10 15

Tyr Pro Asp Ser Gly Thr Asn Ala Leu Asn Pro Cys Phe Ile Ser Val
20 25 30

Ile Ser Ala Trp Gln Ala Val Phe Phe Leu Leu Ile Gly Ser Tyr Gln
35 40 45

Leu Trp Lys Leu Tyr Lys Asn Asn Lys Val Pro Pro Arg Phe Lys Asn
50 55 60

Phe Pro Thr Leu Pro Ser Lys Ile Asn Ser Arg His Leu Thr His Leu
65 70 75 80

Thr Asn Val Cys Phe Gln Ser Thr Leu Ile Ile Cys Glu Leu Ala Leu
85 90 95

-continued

```
Val Ser Gln Ser Ser Asp Arg Val Tyr Pro Phe Ile Leu Lys Lys Ala
            100                 105                 110

Leu Tyr Leu Asn Leu Leu Phe Asn Leu Gly Ile Ser Leu Pro Thr Gln
        115                 120                 125

Tyr Leu Ala Tyr Phe Lys Ser Thr Phe Ser Met Gly Asn Gln Leu Phe
    130                 135                 140

Tyr Tyr Met Phe Gln Ile Leu Leu Gln Leu Phe Leu Ile Leu Gln Arg
145                 150                 155                 160

Tyr Tyr His Gly Ser Ser Asn Glu Arg Leu Thr Val Ile Ser Gly Gln
                165                 170                 175

Thr Ala Met Ile Leu Glu Val Leu Leu Leu Phe Asn Ser Val Ala Ile
            180                 185                 190

Phe Ile Tyr Asp Leu Cys Ile Phe Glu Pro Ile Asn Glu Leu Ser Glu
        195                 200                 205

Tyr Tyr Lys Lys Asn Gly Trp Tyr Pro Pro Val His Val Leu Ser Tyr
    210                 215                 220

Ile Thr Phe Ile Trp Met Asn Lys Leu Ile Val Glu Thr Tyr Arg Asn
225                 230                 235                 240

Lys Lys Ile Lys Asp Pro Asn Gln Leu Pro Leu Pro Pro Val Asp Leu
                245                 250                 255

Asn Ile Lys Ser Ile Ser Lys Glu Phe Lys Ala Asn Trp Glu Leu Glu
            260                 265                 270

Lys Trp Leu Asn Arg Asn Ser Leu Trp Arg Ala Ile Trp Lys Ser Phe
        275                 280                 285

Gly Arg Thr Ile Ser Val Ala Met Leu Tyr Glu Thr Thr Ser Asp Leu
    290                 295                 300

Leu Ser Val Val Gln Pro Gln Phe Leu Arg Ile Phe Ile Asp Gly Phe
305                 310                 315                 320

Asn Pro Glu Thr Ser Ser Lys Tyr Pro Pro Leu Asn Gly Val Phe Ile
                325                 330                 335

Ala Leu Thr Leu Phe Val Ile Ser Val Val Ser Val Phe Leu Thr Asn
            340                 345                 350

Gln Phe Tyr Ile Gly Ile Phe Glu Ala Gly Leu Gly Ile Arg Gly Ser
        355                 360                 365

Leu Ala Ser Leu Val Tyr Gln Lys Ser Leu Arg Leu Thr Leu Ala Glu
    370                 375                 380

Arg Asn Glu Lys Ser Thr Gly Asp Ile Leu Asn Leu Met Ser Val Asp
385                 390                 395                 400

Val Leu Arg Ile Gln Arg Phe Phe Glu Asn Ala Gln Thr Ile Ile Gly
                405                 410                 415

Ala Pro Ile Gln Ile Ile Val Val Leu Thr Ser Leu Tyr Trp Leu Leu
            420                 425                 430

Gly Lys Ala Val Val Gly Gly Leu Val Thr Met Ala Ile Met Met Pro
        435                 440                 445

Ile Asn Ala Phe Leu Ser Arg Lys Val Lys Lys Leu Ser Lys Thr Gln
    450                 455                 460

Met Lys Tyr Lys Asp Met Arg Ile Lys Thr Ile Thr Glu Leu Leu Asn
465                 470                 475                 480

Ala Ile Lys Ser Ile Lys Leu Tyr Ala Trp Glu Glu Pro Met Met Ala
                485                 490                 495

Arg Leu Asn His Val Arg Asn Asp Met Glu Leu Lys Asn Phe Arg Lys
            500                 505                 510
```

-continued

```
Ile Gly Ile Val Ser Asn Leu Ile Tyr Phe Ala Trp Asn Cys Val Pro
        515                 520                 525

Leu Met Val Thr Cys Ser Thr Phe Gly Leu Phe Ser Leu Phe Ser Asp
    530                 535                 540

Ser Pro Leu Ser Pro Ala Ile Val Phe Pro Ser Leu Ser Leu Phe Asn
545                 550                 555                 560

Ile Leu Asn Ser Ala Ile Tyr Ser Val Pro Ser Met Ile Asn Thr Ile
                565                 570                 575

Ile Glu Thr Ser Val Ser Met Glu Arg Leu Lys Ser Phe Leu Leu Ser
            580                 585                 590

Asp Glu Ile Asp Asp Ser Phe Ile Glu Arg Ile Asp Pro Ser Ala Asp
        595                 600                 605

Glu Arg Ala Leu Pro Ala Ile Glu Met Asn Asn Ile Thr Phe Leu Trp
    610                 615                 620

Lys Ser Lys Glu Val Leu Ala Ser Ser Gln Ser Gly Asp Asn Leu Arg
625                 630                 635                 640

Thr Asp Glu Glu Ser Ile Ile Gly Ser Ser Gln Ile Ala Leu Lys Asn
                645                 650                 655

Ile Asp His Phe Glu Ala Lys Arg Gly Asp Leu Val Cys Val Val Gly
            660                 665                 670

Arg Val Gly Ala Gly Lys Ser Thr Phe Leu Lys Ala Ile Leu Gly Gln
        675                 680                 685

Leu Pro Cys Met Ser Gly Ser Arg Asp Ser Ile Pro Pro Lys Leu Ile
    690                 695                 700

Ile Arg Ser Ser Ser Val Ala Tyr Cys Ser Gln Glu Ser Trp Ile Met
705                 710                 715                 720

Asn Ala Ser Val Arg Glu Asn Ile Leu Phe Gly His Lys Phe Asp Gln
                725                 730                 735

Asn Tyr Tyr Asp Leu Thr Ile Lys Ala Cys Gln Leu Leu Pro Asp Leu
            740                 745                 750

Lys Ile Leu Pro Asp Gly Asp Glu Thr Leu Val Gly Glu Lys Gly Ile
        755                 760                 765

Ser Leu Ser Gly Gly Gln Lys Ala Arg Leu Ser Leu Ala Arg Ala Val
    770                 775                 780

Tyr Ser Arg Ala Asp Ile Tyr Leu Leu Asp Asp Ile Leu Ser Ala Val
785                 790                 795                 800

Asp Ala Glu Val Ser Lys Asn Ile Ile Glu Tyr Val Leu Ile Gly Lys
                805                 810                 815

Thr Ala Leu Leu Lys Asn Lys Thr Ile Ile Leu Thr Thr Asn Thr Val
            820                 825                 830

Ser Ile Leu Lys His Ser Gln Met Ile Tyr Ala Leu Glu Asn Gly Glu
        835                 840                 845

Ile Val Glu Gln Gly Asn Tyr Glu Asp Val Met Asn Arg Lys Asn Asn
    850                 855                 860

Thr Ser Lys Leu Lys Lys Leu Leu Glu Glu Phe Asp Ser Pro Ile Asp
865                 870                 875                 880

Asn Gly Asn Glu Ser Asp Val Gln Thr Glu His Arg Ser Glu Ser Glu
                885                 890                 895

Val Asp Glu Pro Leu Gln Leu Lys Val Thr Glu Ser Glu Thr Glu Asp
            900                 905                 910

Glu Val Val Thr Glu Ser Glu Leu Glu Leu Ile Lys Ala Asn Ser Arg
        915                 920                 925

Arg Ala Ser Leu Ala Thr Leu Arg Pro Arg Pro Phe Val Gly Ala Gln
```

-continued

```
    930                 935                 940

Leu Asp Ser Val Lys Lys Thr Ala Gln Glu Ala Glu Lys Thr Glu Val
945                 950                 955                 960

Gly Arg Val Lys Thr Lys Val Tyr Leu Ala Tyr Ile Lys Ala Cys Gly
                965                 970                 975

Val Leu Gly Val Val Leu Phe Phe Leu Phe Met Ile Leu Thr Arg Val
            980                 985                 990

Phe Asp Leu Ala Glu Asn Phe Trp  Leu Lys Tyr Trp Ser  Glu Ser Asn
        995                 1000                 1005

Glu Lys  Asn Gly Ser Asn Glu  Arg Val Trp Met Phe  Val Gly Val
    1010                 1015                 1020

Tyr Ser  Leu Ile Gly Val Ala  Ser Ala Ala Phe Asn  Asn Leu Arg
    1025                 1030                 1035

Ser Ile  Met Met Leu Leu Tyr  Cys Ser Ile Arg Gly  Ser Lys Lys
    1040                 1045                 1050

Leu His  Glu Ser Met Ala Lys  Ser Val Ile Arg Ser  Pro Met Thr
    1055                 1060                 1065

Phe Phe  Glu Thr Thr Pro Val  Gly Arg Ile Ile Asn  Arg Phe Ser
    1070                 1075                 1080

Ser Asp  Met Asp Ala Val Asp  Ser Asn Leu Gln Tyr  Ile Phe Ser
    1085                 1090                 1095

Phe Phe  Phe Lys Ser Ile Leu  Thr Tyr Leu Val Thr  Val Ile Leu
    1100                 1105                 1110

Val Gly  Tyr Asn Met Pro Trp  Phe Leu Val Phe Asn  Met Phe Leu
    1115                 1120                 1125

Val Val  Ile Tyr Ile Tyr Tyr  Gln Thr Phe Tyr Ile  Val Leu Ser
    1130                 1135                 1140

Arg Glu  Leu Lys Arg Leu Ile  Ser Ile Ser Tyr Ser  Pro Ile Met
    1145                 1150                 1155

Ser Leu  Met Ser Glu Ser Leu  Asn Gly Tyr Ser Ile  Ile Asp Ala
    1160                 1165                 1170

Tyr Asp  His Phe Glu Arg Phe  Ile Tyr Leu Asn Tyr  Glu Lys Ile
    1175                 1180                 1185

Gln Tyr  Asn Val Asp Phe Val  Phe Asn Phe Arg Ser  Thr Asn Arg
    1190                 1195                 1200

Trp Leu  Ser Val Arg Leu Gln  Thr Ile Gly Ala Thr  Ile Val Leu
    1205                 1210                 1215

Ala Thr  Ala Ile Leu Ala Leu  Ala Thr Met Asn Thr  Lys Arg Gln
    1220                 1225                 1230

Leu Ser  Ser Gly Met Val Gly  Leu Leu Met Ser Tyr  Ser Leu Glu
    1235                 1240                 1245

Val Thr  Gly Ser Leu Thr Trp  Ile Val Arg Thr Thr  Val Met Ile
    1250                 1255                 1260

Glu Thr  Asn Ile Val Ser Val  Glu Arg Ile Val Glu  Tyr Cys Glu
    1265                 1270                 1275

Leu Pro  Pro Glu Ala Gln Ser  Ile Asn Pro Glu Lys  Arg Pro Asp
    1280                 1285                 1290

Glu Asn  Trp Pro Ser Lys Gly  Gly Ile Glu Phe Lys  Asn Tyr Ser
    1295                 1300                 1305

Thr Lys  Tyr Arg Glu Asn Leu  Asp Pro Val Leu Asn  Asn Ile Asn
    1310                 1315                 1320

Val Lys  Ile Glu Pro Cys Glu  Lys Val Gly Ile Val  Gly Arg Thr
    1325                 1330                 1335
```

Gly Ala Gly Lys Ser Thr Leu Ser Leu Ala Leu Phe Arg Ile Leu
1340 1345 1350

Glu Pro Thr Glu Gly Lys Ile Ile Ile Asp Gly Ile Gly Ile Ser
1355 1360 1365

Asp Ile Gly Leu Phe Asp Leu Arg Ser His Leu Ala Ile Ile Pro
1370 1375 1380

Gln Asp Ala Gln Ala Phe Glu Gly Thr Val Lys Thr Asn Leu Asp
1385 1390 1395

Pro Phe Asn Arg Tyr Ser Glu Asp Glu Leu Lys Arg Ala Val Glu
1400 1405 1410

Gln Ala His Leu Lys Pro His Leu Glu Lys Met Leu His Ser Lys
1415 1420 1425

Pro Arg Gly Asp Asp Ser Asn Glu Glu Asp Gly Asn Val Asn Asp
1430 1435 1440

Ile Leu Asp Val Lys Ile Asn Glu Asn Gly Ser Asn Leu Ser Val
1445 1450 1455

Gly Gln Arg Gln Leu Leu Cys Leu Ala Arg Ala Leu Leu Asn Arg
1460 1465 1470

Ser Lys Ile Leu Val Leu Asp Glu Ala Thr Ala Ser Val Asp Met
1475 1480 1485

Glu Thr Asp Lys Ile Ile Gln Asp Thr Ile Arg Arg Glu Phe Lys
1490 1495 1500

Asp Arg Thr Ile Leu Thr Ile Ala His Arg Ile Asp Thr Val Leu
1505 1510 1515

Asp Ser Asp Lys Ile Ile Val Leu Asp Gln Gly Ser Val Arg Glu
1520 1525 1530

Phe Asp Ser Pro Ser Lys Leu Leu Ser Asp Lys Thr Ser Ile Phe
1535 1540 1545

Tyr Ser Leu Cys Glu Lys Gly Gly Tyr Leu Lys
1550 1555

<210> SEQ ID NO 5
<211> LENGTH: 1638
<212> TYPE: PRT
<213> ORGANISM: Artificial Sequence
<220> FEATURE:
<223> OTHER INFORMATION: Synthetic: T4_Fungal_3 ABC-transporter

<400> SEQUENCE: 5

Met Asn Ser Tyr Asn Glu Ser Ala Pro Thr Gly Cys Ser Phe Trp Asp
1 5 10 15

Asn Asp Asp Ile Ser Pro Cys Ile Arg Lys Ser Leu Leu Asp Ser Tyr
20 25 30

Leu Pro Ala Ala Ile Val Val Gly Ser Leu Leu Tyr Leu Leu Leu Ile
35 40 45

Gly Ala Gln Gln Ile Lys Thr His Arg Lys Leu Tyr Ala Lys Asp Glu
50 55 60

Thr Gln Pro Leu Leu Glu Pro Ala Asn Gly Ser Pro Thr Asp Tyr Ser
65 70 75 80

Asn Thr Tyr Gly Thr Ile Asp Tyr Glu Glu Glu Gln Ser Thr Ala Glu
85 90 95

Leu Thr Thr Ser Gln Lys His Phe Asp Ile Ser Arg Leu Glu Pro Leu
100 105 110

Lys Asp Asp Gly Thr Pro Leu Gly Leu Val Lys Tyr Val Gln Arg Asp
115 120 125

-continued

```
Gly Trp Glu Lys Val Lys Leu Ile Leu Glu Phe Val Ile Leu Ile Phe
    130                 135                 140

Gln Leu Val Ile Ala Val Val Ala Leu Phe Val Pro Ser Leu Asn Gln
145                 150                 155                 160

Glu Trp Glu Gly Tyr Lys Leu Thr Pro Ile Val Arg Val Phe Val Trp
                165                 170                 175

Ile Phe Leu Phe Ala Leu Gly Ser Ile Arg Ala Leu Asn Lys Ser Gly
            180                 185                 190

Pro Phe Pro Leu Ala Asn Ile Ser Leu Leu Tyr Tyr Ile Val Asn Ile
        195                 200                 205

Val Pro Ser Ala Leu Ser Phe Arg Ser Val Leu Ile His Pro Gln Asn
    210                 215                 220

Ser Gln Leu Val Asn Tyr Tyr Tyr Ser Phe Gln Phe Ile Asn Asn Thr
225                 230                 235                 240

Leu Leu Phe Leu Leu Leu Gly Ser Ala Arg Val Phe Asp His Pro Ser
                245                 250                 255

Val Leu Phe Asp Thr Asp Asp Gly Val Lys Pro Ser Pro Glu Asn Asn
            260                 265                 270

Ser Asn Phe Phe Glu Ile Val Thr Tyr Ser Trp Ile Asp Pro Leu Ile
        275                 280                 285

Phe Lys Ala Tyr Lys Thr Pro Leu Gln Phe Asn Asp Ile Trp Gly Leu
    290                 295                 300

Arg Ile Asp Asp Tyr Ala Tyr Phe Leu Leu Arg Arg Phe Lys Asp Leu
305                 310                 315                 320

Gly Phe Thr Arg Thr Phe Thr Tyr Lys Ile Phe Tyr Phe Ser Lys Gly
                325                 330                 335

Asp Leu Ala Ala Gln Ala Leu Trp Ala Ser Ile Asp Ser Met Leu Ile
            340                 345                 350

Phe Gly Pro Ser Leu Leu Leu Lys Arg Ile Leu Glu Tyr Val Asp Asn
        355                 360                 365

Pro Gly Met Thr Ser Arg Asn Met Ala Trp Leu Tyr Val Leu Thr Met
    370                 375                 380

Phe Phe Ile Gln Ile Ser Asp Ser Leu Val Ser Gly Arg Ser Leu Tyr
385                 390                 395                 400

Leu Gly Arg Arg Val Cys Ile Arg Met Lys Ala Leu Ile Ile Gly Glu
                405                 410                 415

Val Tyr Ala Lys Ala Leu Arg Arg Arg Met Thr Ser Pro Glu Glu Leu
            420                 425                 430

Ile Glu Glu Val Asp Pro Lys Asp Gly Lys Ala Pro Ile Ala Asp Gln
        435                 440                 445

Thr Ser Lys Glu Glu Ser Lys Ser Thr Glu Leu Gly Gly Ile Ile Asn
    450                 455                 460

Leu Met Ala Val Asp Ala Ser Lys Val Ser Glu Leu Cys Ser Tyr Leu
465                 470                 475                 480

His Phe Phe Val Asn Ser Phe Phe Met Ile Ile Val Ala Val Thr Leu
                485                 490                 495

Leu Tyr Arg Leu Leu Gly Trp Ser Ala Leu Ala Gly Ser Ser Ser Ile
            500                 505                 510

Leu Ile Leu Leu Pro Leu Asn Tyr Lys Leu Ala Ser Lys Ile Gly Glu
        515                 520                 525

Phe Gln Lys Glu Met Leu Gly Ile Thr Asp Asn Arg Ile Gln Lys Leu
    530                 535                 540
```

-continued

```
Asn Glu Ala Phe Gln Ser Ile Arg Ile Ile Lys Phe Phe Ala Trp Glu
545                 550                 555                 560

Glu Asn Phe Ala Lys Glu Ile Met Lys Val Arg Asn Glu Glu Ile Arg
                565                 570                 575

Tyr Leu Arg Tyr Arg Val Ile Val Trp Thr Cys Ser Ala Phe Val Trp
            580                 585                 590

Phe Ile Thr Pro Thr Leu Val Thr Leu Ile Ser Phe Tyr Phe Tyr Val
        595                 600                 605

Val Phe Gln Gly Lys Ile Leu Thr Thr Pro Val Ala Phe Thr Ala Leu
    610                 615                 620

Ser Leu Phe Asn Leu Leu Arg Ser Pro Leu Asp Gln Leu Ser Asp Met
625                 630                 635                 640

Leu Ser Phe Met Val Gln Ser Lys Val Ser Leu Asp Arg Val Gln Lys
                645                 650                 655

Phe Leu Glu Glu Gln Glu Ser Asp Lys Tyr Glu Gln Leu Thr His Thr
            660                 665                 670

Arg Gly Ala Asn Ser Pro Glu Val Gly Phe Glu Asn Ala Thr Leu Ser
        675                 680                 685

Trp Asn Lys Gly Ser Lys Asn Asp Phe Gln Leu Lys Asp Ile Asp Ile
    690                 695                 700

Ala Phe Lys Val Gly Lys Leu Asn Val Ile Ile Gly Pro Thr Gly Ser
705                 710                 715                 720

Gly Lys Thr Ser Leu Leu Leu Gly Leu Leu Gly Glu Met Gln Leu Thr
                725                 730                 735

Asn Gly Lys Ile Phe Leu Pro Gly Ser Thr Pro Arg Asp Glu Leu Ile
            740                 745                 750

Pro Asn Pro Glu Thr Gly Met Thr Glu Ala Val Ala Tyr Cys Ser Gln
        755                 760                 765

Ile Ala Trp Leu Leu Asn Asp Thr Val Lys Asn Asn Ile Val Phe Ala
    770                 775                 780

Ala Pro Phe Asn Gln Gln Arg Tyr Asp Ala Val Ile Asp Ala Cys Gly
785                 790                 795                 800

Leu Thr Arg Asp Leu Lys Val Leu Asp Ala Gly Asp Ala Thr Glu Ile
                805                 810                 815

Gly Glu Lys Gly Ile Thr Leu Ser Gly Gly Gln Lys Gln Arg Val Ser
            820                 825                 830

Leu Ala Arg Ala Leu Tyr Ser Asn Ala Arg His Val Leu Leu Asp Asp
        835                 840                 845

Cys Leu Ser Ala Val Asp Ser His Thr Ala Ala Trp Ile Tyr Glu Asn
    850                 855                 860

Cys Ile Thr Gly Pro Leu Met Lys Asp Arg Thr Cys Ile Leu Val Ser
865                 870                 875                 880

His Asn Val Ala Leu Thr Val Arg Asp Ala Ala Trp Ile Val Ala Met
                885                 890                 895

Asp Asn Gly Arg Val Leu Glu Gln Gly Thr Cys Glu Asp Leu Leu Ser
            900                 905                 910

Ser Gly Ser Leu Gly His Asp Asp Leu Val Ser Thr Val Ile Ser Ser
        915                 920                 925

Arg Ser Gln Ser Ser Val Asn Leu Lys Gln Leu Asn Val Ser Asp Thr
    930                 935                 940

Ser Glu Ile His Gln Lys Leu Lys Lys Ile Ala Glu Ser Asp Lys Ala
945                 950                 955                 960

Asp Gln Leu Asp Glu Glu Arg Leu Ser Pro Arg Gly Lys Leu Ile Glu
```

-continued

```
                965                 970                 975

Asp Glu Thr Lys Ser Ser Gly Ala Val Ser Trp Glu Val Tyr Lys Phe
            980                 985                 990

Tyr Gly Arg Ala Phe Gly Gly Val  Phe Ile Trp Phe Val  Phe Val Ala
        995                 1000                 1005

Ala Phe  Ala Ala Ser Gln Gly  Ser Asn Ile Met Gln  Ser Val Trp
    1010                 1015                 1020

Leu Lys  Ile Trp Ala Ala Ala  Asn Asp Lys Leu Val  Ser Pro Ala
    1025                 1030                 1035

Phe Thr  Met Ser Ile Asp Arg  Ser Leu Asn Ala Leu  Lys Glu Gly
    1040                 1045                 1050

Phe Arg  Ala Ser Val Ala Ser  Val Glu Trp Ser Arg  Pro Leu Gly
    1055                 1060                 1065

Gly Glu  Met Phe Arg Val Tyr  Gly Glu Glu Ser Ser  His Ser Ser
    1070                 1075                 1080

Gly Tyr  Tyr Ile Thr Ile Tyr  Ala Leu Ile Gly Leu  Ser Tyr Ala
    1085                 1090                 1095

Leu Ile  Ser Ala Phe Arg Val  Tyr Val Val Phe Met  Gly Gly Ile
    1100                 1105                 1110

Val Ala  Ser Asn Lys Ile Phe  Glu Asp Met Leu Thr  Lys Ile Phe
    1115                 1120                 1125

Asn Ala  Lys Leu Arg Phe Phe  Asp Ser Thr Pro Ile  Gly Arg Ile
    1130                 1135                 1140

Met Asn  Arg Phe Ser Lys Asp  Thr Glu Ser Ile Asp  Gln Glu Leu
    1145                 1150                 1155

Ala Pro  Tyr Ala Glu Gly Phe  Ile Val Ser Val Leu  Gln Cys Gly
    1160                 1165                 1170

Ala Thr  Ile Leu Leu Ile Cys  Ile Ile Thr Pro Gly  Phe Ile Val
    1175                 1180                 1185

Phe Ala  Ala Phe Ile Val Ile  Ile Tyr Tyr Tyr Ile  Gly Ala Leu
    1190                 1195                 1200

Tyr Leu  Ala Ser Ser Arg Glu  Leu Lys Arg Tyr Asp  Ser Ile Thr
    1205                 1210                 1215

Val Ser  Pro Ile His Gln His  Phe Ser Glu Thr Leu  Val Gly Val
    1220                 1225                 1230

Thr Thr  Ile Arg Ala Tyr Gly  Asp Glu Arg Arg Phe  Met Arg Gln
    1235                 1240                 1245

Asn Leu  Glu Lys Ile Asp Asn  Asn Asn Arg Ser Phe  Phe Tyr Leu
    1250                 1255                 1260

Trp Val  Ala Asn Arg Trp Leu  Ala Leu Arg Val Asp  Phe Val Gly
    1265                 1270                 1275

Ala Leu  Val Ser Leu Leu Ser  Ala Ala Phe Val Met  Leu Ser Ile
    1280                 1285                 1290

Gly His  Ile Asp Ala Gly Met  Ala Gly Leu Ser Leu  Ser Tyr Ala
    1295                 1300                 1305

Ile Ala  Phe Thr Gln Ser Ala  Leu Trp Val Val Arg  Leu Tyr Ser
    1310                 1315                 1320

Val Val  Glu Met Asn Met Asn  Ser Val Glu Arg Leu  Glu Glu Tyr
    1325                 1330                 1335

Leu Asn  Ile Asp Gln Glu Pro  Asp Arg Glu Ile Pro  Asp Asn Lys
    1340                 1345                 1350

Pro Pro  Ser Ser Trp Pro Glu  Thr Gly Glu Ile Glu  Val Asp Asp
    1355                 1360                 1365
```

Val Ser Leu Arg Tyr Ala Pro Ser Leu Pro Lys Val Ile Lys Asn
1370 1375 1380

Val Ser Phe Lys Val Glu Pro Arg Ser Lys Ile Gly Ile Val Gly
1385 1390 1395

Arg Thr Gly Ala Gly Lys Ser Thr Ile Ile Thr Ala Phe Phe Arg
1400 1405 1410

Phe Val Asp Pro Glu Ser Gly Ser Ile Lys Ile Asp Gly Ile Asp
1415 1420 1425

Ile Thr Ser Ile Gly Leu Lys Asp Leu Arg Asn Ala Val Thr Ile
1430 1435 1440

Ile Pro Gln Asp Pro Thr Leu Phe Thr Gly Thr Ile Arg Ser Asn
1445 1450 1455

Leu Asp Pro Phe Asn Gln Tyr Ser Asp Ala Glu Ile Phe Glu Ser
1460 1465 1470

Leu Lys Arg Val Asn Leu Val Ser Thr Asp Glu Pro Thr Ser Gly
1475 1480 1485

Ser Ser Ser Asp Asn Ile Glu Asp Ser Asn Glu Asn Val Asn Lys
1490 1495 1500

Phe Leu Asn Leu Asn Asn Thr Val Ser Glu Gly Gly Ser Asn Leu
1505 1510 1515

Ser Gln Gly Gln Arg Gln Leu Thr Cys Leu Ala Arg Ser Leu Leu
1520 1525 1530

Lys Ser Pro Lys Ile Ile Leu Leu Asp Glu Ala Thr Ala Ser Ile
1535 1540 1545

Asp Tyr Asn Thr Asp Ser Lys Ile Gln Thr Thr Ile Arg Glu Glu
1550 1555 1560

Phe Ser Asp Ser Thr Ile Leu Thr Ile Ala His Arg Leu Arg Ser
1565 1570 1575

Ile Ile Asp Tyr Asp Lys Ile Leu Val Met Asp Ala Gly Arg Val
1580 1585 1590

Val Glu Tyr Asp Asp Pro Tyr Lys Leu Ile Ser Asp Gln Asn Ser
1595 1600 1605

Leu Phe Tyr Ser Met Cys Ser Asn Ser Gly Glu Leu Asp Thr Leu
1610 1615 1620

Val Lys Leu Ala Lys Glu Ala Phe Ile Ala Lys Arg Asn Lys Lys
1625 1630 1635

<210> SEQ ID NO 6
<211> LENGTH: 1559
<212> TYPE: PRT
<213> ORGANISM: Artificial Sequence
<220> FEATURE:
<223> OTHER INFORMATION: Synthetic: T4_Fungal_4 ABC-transporter

<400> SEQUENCE: 6

Met Ser Ser Leu Glu Val Val Asp Gly Cys Pro Tyr Gly Tyr Arg Pro
1 5 10 15

Tyr Pro Asp Ser Gly Thr Asn Ala Leu Asn Pro Cys Phe Ile Ser Val
20 25 30

Ile Ser Ala Trp Gln Ala Val Phe Phe Leu Leu Ile Gly Ser Tyr Gln
35 40 45

Leu Trp Lys Leu Tyr Lys Asn Asn Lys Val Pro Pro Arg Phe Lys Asn
50 55 60

Phe Pro Thr Leu Pro Ser Lys Ile Asn Ser Arg His Leu Thr His Leu
65 70 75 80

-continued

```
Thr Asn Val Cys Phe Gln Ser Thr Leu Ile Ile Cys Glu Leu Ala Leu
                85                  90                  95

Val Ser Gln Ser Ser Asp Arg Val Tyr Pro Phe Ile Leu Lys Lys Ala
            100                 105                 110

Leu Tyr Leu Asn Leu Leu Phe Asn Leu Gly Ile Ser Leu Pro Thr Gln
        115                 120                 125

Tyr Leu Ala Tyr Phe Lys Ser Thr Phe Ser Met Gly Asn Gln Leu Phe
    130                 135                 140

Tyr Tyr Met Phe Gln Ile Leu Leu Gln Leu Phe Leu Ile Leu Gln Arg
145                 150                 155                 160

Tyr Tyr His Gly Ser Ser Asn Glu Arg Leu Thr Val Ile Ser Gly Gln
                165                 170                 175

Thr Ala Met Ile Leu Glu Val Leu Leu Leu Phe Asn Ser Val Ala Ile
            180                 185                 190

Phe Ile Tyr Asp Leu Cys Ile Phe Glu Pro Ile Asn Glu Leu Ser Glu
        195                 200                 205

Tyr Tyr Lys Lys Asn Gly Trp Tyr Pro Pro Val His Val Leu Ser Tyr
    210                 215                 220

Ile Thr Phe Ile Trp Met Asn Lys Leu Ile Val Glu Thr Tyr Arg Asn
225                 230                 235                 240

Lys Lys Ile Lys Asp Pro Asn Gln Leu Pro Leu Pro Pro Val Asp Leu
                245                 250                 255

Asn Ile Lys Ser Ile Ser Lys Glu Phe Lys Ala Asn Trp Glu Leu Glu
            260                 265                 270

Lys Trp Leu Asn Arg Asn Ser Leu Trp Arg Ala Ile Trp Lys Ser Phe
        275                 280                 285

Gly Arg Thr Ile Ser Val Ala Met Leu Tyr Glu Thr Thr Ser Asp Leu
    290                 295                 300

Leu Ser Val Val Gln Pro Gln Phe Leu Arg Ile Phe Ile Asp Gly Phe
305                 310                 315                 320

Asn Pro Glu Thr Ser Ser Lys Tyr Pro Pro Leu Asn Gly Val Phe Ile
                325                 330                 335

Ala Leu Thr Leu Phe Val Ile Ser Val Val Ser Val Phe Leu Thr Asn
            340                 345                 350

Gln Phe Tyr Ile Gly Ile Phe Glu Ala Gly Leu Gly Ile Arg Gly Ser
        355                 360                 365

Leu Ala Ser Leu Val Tyr Gln Lys Ser Leu Arg Leu Thr Leu Ala Glu
    370                 375                 380

Arg Asn Glu Lys Ser Thr Gly Asp Ile Leu Asn Leu Met Ser Val Asp
385                 390                 395                 400

Val Leu Arg Ile Gln Arg Phe Phe Glu Asn Ala Gln Thr Ile Ile Gly
                405                 410                 415

Ala Pro Ile Gln Ile Ile Val Val Leu Thr Ser Leu Tyr Trp Leu Leu
            420                 425                 430

Gly Lys Ala Val Ile Gly Gly Leu Val Thr Met Ala Ile Met Met Pro
        435                 440                 445

Ile Asn Ala Phe Leu Ser Arg Lys Val Lys Lys Leu Ser Lys Thr Gln
    450                 455                 460

Met Lys Tyr Lys Asp Met Arg Ile Lys Thr Ile Thr Glu Leu Leu Asn
465                 470                 475                 480

Ala Ile Lys Ser Ile Lys Leu Tyr Ala Trp Glu Glu Pro Met Met Ala
                485                 490                 495
```

-continued

```
Arg Leu Asn His Val Arg Asn Asp Met Glu Leu Lys Asn Phe Arg Lys
            500                 505                 510

Ile Gly Ile Val Ser Asn Leu Ile Tyr Phe Ala Trp Asn Cys Val Pro
        515                 520                 525

Leu Met Val Thr Cys Ser Thr Phe Gly Leu Phe Ser Leu Phe Ser Asp
    530                 535                 540

Ser Pro Leu Ser Pro Ala Ile Val Phe Pro Ser Leu Ser Leu Phe Asn
545                 550                 555                 560

Ile Leu Asn Ser Ala Ile Tyr Ser Val Pro Ser Met Ile Asn Thr Ile
                565                 570                 575

Ile Glu Thr Ser Val Ser Met Glu Arg Leu Lys Ser Phe Leu Leu Ser
            580                 585                 590

Asp Glu Ile Asp Asp Ser Phe Ile Glu Arg Ile Asp Pro Ser Ala Asp
        595                 600                 605

Glu Arg Ala Leu Pro Ala Ile Glu Met Asn Asn Ile Thr Phe Leu Trp
    610                 615                 620

Lys Ser Lys Glu Val Leu Ala Ser Ser Gln Ser Arg Asp Asn Leu Arg
625                 630                 635                 640

Thr Asp Glu Glu Ser Ile Ile Gly Ser Ser Gln Ile Ala Leu Lys Asn
                645                 650                 655

Ile Asp His Phe Glu Ala Lys Arg Gly Asp Leu Val Cys Val Val Gly
            660                 665                 670

Arg Val Gly Ala Gly Lys Ser Thr Phe Leu Lys Ala Ile Leu Gly Gln
        675                 680                 685

Leu Pro Cys Met Ser Gly Ser Arg Asp Ser Ile Pro Pro Lys Leu Ile
    690                 695                 700

Ile Arg Ser Ser Ser Val Ala Tyr Cys Ser Gln Glu Ser Trp Ile Met
705                 710                 715                 720

Asn Ala Ser Val Arg Glu Asn Ile Leu Phe Gly His Lys Phe Asp Gln
                725                 730                 735

Asn Tyr Tyr Asp Leu Thr Ile Lys Ala Cys Gln Leu Leu Pro Asp Leu
            740                 745                 750

Lys Ile Leu Pro Asp Gly Asp Glu Thr Leu Val Gly Glu Lys Gly Ile
        755                 760                 765

Ser Leu Ser Gly Gly Gln Lys Ala Arg Leu Ser Leu Ala Arg Ala Val
    770                 775                 780

Tyr Ser Arg Ala Asp Ile Tyr Leu Leu Asp Asp Ile Leu Ser Ala Val
785                 790                 795                 800

Asp Ala Glu Val Ser Lys Asn Ile Ile Glu Tyr Val Leu Ile Gly Lys
                805                 810                 815

Thr Ala Leu Leu Lys Asn Lys Thr Ile Ile Leu Thr Thr Asn Thr Val
            820                 825                 830

Ser Ile Leu Lys His Ser Gln Met Ile Tyr Ala Leu Glu Asn Gly Glu
        835                 840                 845

Ile Val Glu Gln Gly Asn Tyr Glu Asp Val Met Asn Arg Lys Asn Asn
    850                 855                 860

Thr Ser Lys Leu Lys Lys Leu Leu Glu Glu Phe Asp Ser Pro Ile Asp
865                 870                 875                 880

Asn Gly Asn Glu Ser Asp Val Gln Thr Glu His Arg Ser Glu Ser Glu
                885                 890                 895

Val Asp Glu Pro Leu Gln Leu Lys Val Thr Glu Ser Glu Thr Glu Asp
            900                 905                 910

Glu Val Val Thr Glu Ser Glu Leu Glu Leu Ile Lys Ala Asn Ser Arg
```

```
        915                 920                 925

Arg Ala Ser Leu Ala Thr Leu Arg Pro Arg Pro Phe Val Gly Ala Gln
    930                 935                 940

Leu Asp Ser Val Lys Lys Thr Ala Gln Glu Ala Glu Lys Thr Glu Val
945                 950                 955                 960

Gly Arg Val Lys Thr Lys Val Tyr Leu Ala Tyr Ile Lys Ala Cys Gly
                965                 970                 975

Val Leu Gly Val Val Leu Phe Phe Leu Phe Met Ile Leu Thr Arg Val
            980                 985                 990

Phe Asp Leu Ala Glu Asn Phe Trp  Leu Lys Tyr Trp Ser  Glu Ser Asn
        995                 1000                 1005

Glu Lys  Asn Gly Ser Asn Glu  Arg Val Trp Met Phe  Val Gly Val
    1010                 1015                 1020

Tyr Ser  Leu Ile Gly Val Ala  Ser Ala Ala Phe Asn  Asn Leu Arg
    1025                 1030                 1035

Ser Ile  Met Met Leu Leu Tyr  Cys Ser Ile Arg Gly  Ser Lys Lys
    1040                 1045                 1050

Leu His  Glu Ser Met Ala Lys  Ser Val Ile Arg Ser  Pro Met Thr
    1055                 1060                 1065

Phe Phe  Glu Thr Thr Pro Val  Gly Arg Ile Ile Asn  Arg Phe Ser
    1070                 1075                 1080

Ser Asp  Met Asp Ala Val Asp  Ser Asn Leu Gln Tyr  Ile Phe Ser
    1085                 1090                 1095

Phe Phe  Phe Lys Ser Ile Leu  Thr Tyr Leu Val Thr  Val Ile Leu
    1100                 1105                 1110

Val Gly  Tyr Asn Met Pro Trp  Phe Leu Val Phe Asn  Met Phe Leu
    1115                 1120                 1125

Val Val  Ile Tyr Ile Tyr Tyr  Gln Thr Phe Tyr Ile  Val Leu Ser
    1130                 1135                 1140

Arg Glu  Leu Lys Arg Leu Ile  Ser Ile Ser Tyr Ser  Pro Ile Met
    1145                 1150                 1155

Ser Leu  Met Ser Glu Ser Leu  Asn Gly Tyr Ser Ile  Ile Asp Ala
    1160                 1165                 1170

Tyr Asp  His Phe Glu Arg Phe  Ile Tyr Leu Asn Tyr  Glu Lys Ile
    1175                 1180                 1185

Gln Tyr  Asn Val Asp Phe Val  Phe Asn Phe Arg Ser  Thr Asn Arg
    1190                 1195                 1200

Trp Leu  Ser Val Arg Leu Gln  Thr Ile Gly Ala Thr  Ile Val Leu
    1205                 1210                 1215

Ala Thr  Ala Ile Leu Ala Leu  Ala Thr Met Asn Thr  Lys Arg Gln
    1220                 1225                 1230

Leu Ser  Ser Gly Met Val Gly  Leu Leu Met Ser Tyr  Ser Leu Glu
    1235                 1240                 1245

Val Thr  Gly Ser Leu Thr Trp  Ile Val Arg Thr Thr  Val Met Ile
    1250                 1255                 1260

Glu Thr  Asn Ile Val Ser Val  Glu Arg Ile Val Glu  Tyr Cys Glu
    1265                 1270                 1275

Leu Pro  Pro Glu Ala Gln Ser  Ile Asn Pro Glu Lys  Arg Pro Asp
    1280                 1285                 1290

Glu Asn  Trp Pro Ser Lys Gly  Gly Ile Glu Phe Lys  Asn Tyr Ser
    1295                 1300                 1305

Thr Lys  Tyr Arg Glu Asn Leu  Asp Pro Val Leu Asn  Asn Ile Asn
    1310                 1315                 1320
```

Val Lys Ile Glu Pro Cys Glu Lys Val Gly Ile Val Gly Arg Thr
1325 1330 1335

Gly Ala Gly Lys Ser Thr Leu Ser Leu Ala Leu Phe Arg Ile Leu
1340 1345 1350

Glu Pro Thr Glu Gly Lys Ile Ile Ile Asp Gly Ile Asp Ile Ser
1355 1360 1365

Asp Ile Gly Leu Phe Asp Leu Arg Ser His Leu Ala Ile Ile Pro
1370 1375 1380

Gln Asp Ala Gln Ala Phe Glu Gly Thr Val Lys Thr Asn Leu Asp
1385 1390 1395

Pro Phe Asn Arg Tyr Ser Glu Asp Glu Leu Lys Arg Ala Val Glu
1400 1405 1410

Gln Ala His Leu Lys Pro His Leu Glu Lys Met Leu His Ser Lys
1415 1420 1425

Pro Arg Gly Asp Asp Ser Asn Glu Glu Asp Gly Asn Val Asn Asp
1430 1435 1440

Ile Leu Asp Val Lys Ile Asn Glu Asn Gly Ser Asn Leu Ser Val
1445 1450 1455

Gly Gln Arg Gln Leu Leu Cys Leu Ala Arg Ala Leu Leu Asn Arg
1460 1465 1470

Ser Lys Ile Leu Val Leu Asp Glu Ala Thr Ala Ser Val Asp Met
1475 1480 1485

Glu Thr Asp Lys Ile Ile Gln Asp Thr Ile Arg Arg Glu Phe Lys
1490 1495 1500

Asp Arg Thr Ile Leu Thr Ile Ala His Arg Ile Asp Thr Val Leu
1505 1510 1515

Asp Ser Asp Lys Ile Ile Val Leu Asp Gln Gly Ser Val Arg Glu
1520 1525 1530

Phe Asp Ser Pro Ser Lys Leu Leu Ser Asp Lys Thr Ser Ile Phe
1535 1540 1545

Tyr Ser Leu Cys Glu Lys Gly Gly Tyr Leu Lys
1550 1555

<210> SEQ ID NO 7
<211> LENGTH: 1381
<212> TYPE: PRT
<213> ORGANISM: Artificial Sequence
<220> FEATURE:
<223> OTHER INFORMATION: Synthetic: T4_Fungal_5 ABC-transporter

<400> SEQUENCE: 7

Met Thr Ser Pro Gly Ser Glu Lys Cys Thr Pro Arg Ser Asp Glu Asp
1 5 10 15

Leu Glu Arg Ser Glu Pro Gln Leu Gln Arg Arg Leu Leu Thr Pro Phe
20 25 30

Leu Leu Ser Lys Lys Val Pro Pro Ile Pro Lys Glu Asp Glu Arg Lys
35 40 45

Pro Tyr Pro Tyr Leu Lys Thr Asn Pro Leu Ser Gln Ile Leu Phe Trp
50 55 60

Trp Leu Asn Pro Leu Leu Arg Val Gly Tyr Lys Arg Thr Leu Asp Pro
65 70 75 80

Asn Asp Phe Tyr Tyr Leu Glu His Ser Gln Asp Ile Glu Thr Thr Tyr
85 90 95

Ser Asn Tyr Glu Met His Leu Ala Arg Ile Leu Glu Lys Asp Arg Ala
100 105 110

```
Lys Ala Arg Ala Lys Asp Pro Thr Leu Thr Asp Glu Asp Leu Lys Asn
        115                 120                 125

Arg Glu Tyr Pro Lys Asn Ala Val Ile Lys Ala Leu Phe Leu Thr Phe
    130                 135                 140

Lys Trp Lys Tyr Leu Trp Ser Ile Phe Leu Lys Leu Leu Ser Asp Ile
145                 150                 155                 160

Val Leu Val Leu Asn Pro Leu Leu Ser Lys Ala Leu Ile Asn Phe Val
                165                 170                 175

Asp Glu Lys Met Tyr Asn Pro Asp Met Ser Val Gly Arg Gly Val Gly
            180                 185                 190

Tyr Ala Ile Gly Val Thr Phe Met Leu Gly Thr Ser Gly Ile Leu Ile
        195                 200                 205

Asn His Phe Leu Tyr Leu Ser Leu Thr Val Gly Ala His Cys Lys Ala
    210                 215                 220

Val Leu Thr Thr Ala Ile Met Asn Lys Ser Phe Arg Ala Ser Ala Lys
225                 230                 235                 240

Ser Lys His Glu Tyr Pro Ser Gly Arg Val Thr Ser Leu Met Ser Thr
                245                 250                 255

Asp Leu Ala Arg Ile Asp Leu Ala Ile Gly Phe Gln Pro Phe Ala Ile
            260                 265                 270

Thr Val Pro Val Pro Ile Gly Val Ala Ile Ala Leu Leu Ile Val Asn
        275                 280                 285

Ile Gly Val Ser Ala Leu Ala Gly Ile Ala Val Phe Leu Val Cys Ile
    290                 295                 300

Val Val Ile Ser Ala Ser Ser Lys Ser Leu Leu Lys Met Arg Lys Gly
305                 310                 315                 320

Ala Asn Gln Tyr Thr Asp Ala Arg Ile Ser Tyr Met Arg Glu Ile Leu
                325                 330                 335

Gln Asn Met Arg Ile Ile Lys Phe Tyr Ser Trp Glu Asp Ala Tyr Glu
            340                 345                 350

Lys Ser Val Val Thr Glu Arg Asn Ser Glu Met Ser Ile Ile Leu Lys
        355                 360                 365

Met Gln Ser Ile Arg Asn Phe Leu Leu Ala Leu Ser Leu Ser Leu Pro
    370                 375                 380

Ala Ile Ile Ser Met Val Ala Phe Leu Val Leu Tyr Gly Val Ser Asn
385                 390                 395                 400

Asp Lys Asn Pro Gly Asn Ile Phe Ser Ser Ile Ser Leu Phe Ser Val
                405                 410                 415

Leu Ala Gln Gln Thr Met Met Leu Pro Met Ala Leu Ala Thr Gly Ala
            420                 425                 430

Asp Ala Lys Ile Gly Leu Glu Arg Leu Arg Gln Tyr Leu Gln Ser Gly
        435                 440                 445

Asp Ile Glu Lys Glu Tyr Glu Asp His Glu Lys Pro Gly Asp Arg Asp
    450                 455                 460

Val Val Leu Pro Asp Asn Val Ala Val Glu Leu Asn Asn Ala Ser Phe
465                 470                 475                 480

Ile Trp Glu Lys Phe Asp Asp Ala Asp Asp Asn Asp Gly Asn Ser Glu
                485                 490                 495

Lys Thr Lys Glu Val Val Val Thr Ser Lys Ser Ser Leu Thr Asp Ser
            500                 505                 510

Ser His Ile Asp Lys Ser Thr Asp Ser Ala Asp Gly Glu Tyr Ile Lys
        515                 520                 525
```

-continued

```
Ser Val Phe Glu Gly Phe Asn Asn Ile Asn Leu Thr Ile Lys Lys Gly
    530                 535                 540

Glu Phe Val Ile Ile Thr Gly Pro Ile Gly Ser Gly Lys Ser Ser Leu
545                 550                 555                 560

Leu Val Ala Leu Ala Gly Phe Met Lys Lys Thr Ser Gly Thr Leu Gly
                565                 570                 575

Val Asn Gly Thr Met Leu Leu Cys Gly Gln Pro Trp Val Gln Asn Cys
            580                 585                 590

Thr Val Arg Asp Asn Ile Leu Phe Gly Leu Glu Tyr Asp Glu Ala Arg
        595                 600                 605

Tyr Asp Arg Val Val Glu Val Cys Ala Leu Gly Asp Asp Leu Lys Met
    610                 615                 620

Phe Thr Ala Gly Asp Gln Thr Glu Ile Gly Glu Arg Gly Ile Thr Leu
625                 630                 635                 640

Ser Gly Gly Gln Lys Ala Arg Ile Asn Leu Ala Arg Ala Val Tyr Ala
                645                 650                 655

Asn Lys Asp Ile Ile Leu Leu Asp Asp Val Leu Ser Ala Val Asp Ala
            660                 665                 670

Arg Val Gly Lys Leu Ile Val Asp Asp Cys Leu Thr Ser Phe Leu Gly
        675                 680                 685

Asp Lys Thr Arg Ile Leu Ala Thr His Gln Leu Ser Leu Ile Glu Ala
    690                 695                 700

Ala Asp Arg Val Ile Tyr Leu Asn Gly Asp Gly Thr Ile His Ile Gly
705                 710                 715                 720

Thr Val Gln Glu Leu Leu Glu Ser Asn Glu Gly Phe Leu Lys Leu Met
                725                 730                 735

Glu Phe Ser Arg Lys Ser Glu Ser Glu Asp Glu Glu Asp Val Glu Ala
            740                 745                 750

Ala Asn Glu Lys Asp Val Ser Leu Gln Lys Ala Val Ser Val Val Gln
        755                 760                 765

Glu Gln Asp Ala His Ala Gly Val Leu Ile Gly Gln Glu Glu Arg Ala
    770                 775                 780

Val Asn Gly Ile Glu Trp Asp Ile Tyr Lys Glu Tyr Leu His Glu Gly
785                 790                 795                 800

Arg Gly Lys Leu Gly Ile Phe Ala Ile Pro Thr Ile Ile Met Leu Leu
                805                 810                 815

Val Leu Asp Val Phe Thr Ser Ile Phe Val Asn Val Trp Leu Ser Phe
            820                 825                 830

Trp Ile Ser His Lys Phe Lys Ala Arg Ser Asp Gly Phe Tyr Ile Gly
        835                 840                 845

Leu Tyr Val Met Phe Val Ile Leu Ser Val Ile Trp Ile Thr Ala Glu
    850                 855                 860

Phe Val Val Met Gly Tyr Phe Ser Ser Thr Ala Ala Arg Arg Leu Asn
865                 870                 875                 880

Leu Lys Ala Met Lys Arg Val Leu His Thr Pro Met His Phe Leu Asp
                885                 890                 895

Val Thr Pro Met Gly Arg Ile Leu Asn Arg Phe Thr Lys Asp Thr Asp
            900                 905                 910

Val Leu Asp Asn Glu Ile Gly Glu Gln Ala Arg Met Phe Leu His Pro
        915                 920                 925

Ala Ala Tyr Val Ile Gly Val Leu Ile Leu Cys Ile Ile Tyr Ile Pro
    930                 935                 940

Trp Phe Ala Ile Ala Ile Pro Pro Leu Ala Ile Leu Phe Thr Phe Ile
```

-continued

```
945                 950                 955                 960

Thr Asn Phe Tyr Ile Ala Ser Ser Arg Glu Val Lys Arg Ile Glu Ala
                965                 970                 975

Ile Gln Arg Ser Leu Val Tyr Asn Asn Phe Asn Glu Val Leu Asn Gly
            980                 985                 990

Leu Gln Thr Leu Lys Ala Tyr Asn  Ala Thr Ser Arg Phe  Met Glu Lys
        995                 1000                1005

Asn Lys  Arg Leu Leu Asn Arg  Met Asn Glu Ala Tyr  Leu Leu Val
    1010                 1015                 1020

Ile Ala  Asn Gln Arg Trp Ile  Ser Val Asn Leu Asp  Leu Val Ser
    1025                 1030                 1035

Cys Cys  Phe Val Phe Leu Ile  Ser Met Leu Ser Val  Phe Arg Val
    1040                 1045                 1050

Phe Asp  Ile Asn Ala Ser Ser  Val Gly Leu Val Val  Thr Ser Val
    1055                 1060                 1065

Leu Gln  Ile Gly Gly Leu Met  Ser Leu Ile Met Arg  Ala Tyr Thr
    1070                 1075                 1080

Thr Val  Glu Asn Glu Met Asn  Ser Val Glu Arg Leu  Cys His Tyr
    1085                 1090                 1095

Ala Asn  Lys Leu Glu Gln Glu  Ala Pro Tyr Ile Met  Asn Glu Thr
    1100                 1105                 1110

Lys Pro  Arg Pro Thr Trp Pro  Glu His Gly Ala Ile  Glu Phe Lys
    1115                 1120                 1125

His Ala  Ser Met Arg Tyr Arg  Glu Gly Leu Pro Leu  Val Leu Lys
    1130                 1135                 1140

Asp Leu  Thr Ile Ser Val Lys  Gly Gly Glu Lys Ile  Gly Ile Cys
    1145                 1150                 1155

Gly Arg  Thr Gly Ala Gly Lys  Ser Thr Ile Met Asn  Ala Leu Tyr
    1160                 1165                 1170

Arg Leu  Thr Glu Leu Ala Glu  Gly Ser Ile Thr Ile  Asp Gly Val
    1175                 1180                 1185

Glu Ile  Ser Gln Leu Gly Leu  Tyr Asp Leu Arg Ser  Lys Leu Ala
    1190                 1195                 1200

Ile Ile  Pro Gln Asp Pro Val  Leu Phe Arg Gly Thr  Ile Arg Lys
    1205                 1210                 1215

Asn Leu  Asp Pro Phe Gly Gln  Asn Asp Asp Glu Thr  Leu Trp Asp
    1220                 1225                 1230

Ala Leu  Arg Arg Ser Gly Leu  Val Glu Gly Ser Ile  Leu Asn Thr
    1235                 1240                 1245

Ile Lys  Ser Gln Ser Lys Asp  Asp Pro Asn Phe His  Lys Phe His
    1250                 1255                 1260

Leu Asp  Gln Thr Val Glu Asp  Glu Gly Ala Asn Phe  Ser Leu Gly
    1265                 1270                 1275

Glu Arg  Gln Leu Ile Ala Leu  Ala Arg Ala Leu Val  Arg Asn Ser
    1280                 1285                 1290

Lys Ile  Leu Ile Leu Asp Glu  Ala Thr Ser Ser Val  Asp Tyr Glu
    1295                 1300                 1305

Thr Asp  Ser Lys Ile Gln Lys  Thr Ile Ser Thr Glu  Phe Ser His
    1310                 1315                 1320

Cys Thr  Ile Leu Cys Ile Ala  His Arg Leu Lys Thr  Ile Leu Thr
    1325                 1330                 1335

Tyr Asp  Arg Ile Leu Val Leu  Glu Lys Gly Glu Val  Glu Glu Phe
    1340                 1345                 1350
```

```
Asp Thr Pro Arg Val Leu Tyr Ser Lys Asn Gly Val Phe Arg Gln
    1355                1360                1365

Met Cys Glu Arg Ser Glu Ile Thr Ser Ala Asp Phe Val
    1370                1375                1380
```

<210> SEQ ID NO 8
<211> LENGTH: 1650
<212> TYPE: PRT
<213> ORGANISM: Artificial Sequence
<220> FEATURE:
<223> OTHER INFORMATION: Synthetic: T4_Fungal_8 ABC-transporter

<400> SEQUENCE: 8

```
Met Ser Gly Ser Asn Ser Asn Ser Asn Leu Asp Ala Ile Ser Asp Ser
1               5                   10                  15

Cys Pro Phe Trp Arg Tyr Asp Asp Ile Thr Glu Cys Gly Arg Val Gln
            20                  25                  30

Tyr Ile Asn Tyr Tyr Leu Pro Ile Thr Leu Val Gly Val Ser Leu Leu
        35                  40                  45

Tyr Leu Phe Lys Asn Ala Ile Gln His Tyr Tyr Arg Lys Pro Gln Glu
    50                  55                  60

Ile Lys Pro Ser Val Ala Ser Glu Leu Leu Gly Ser Asn Leu Thr Asp
65                  70                  75                  80

Leu Pro Asn Glu Asn Lys Pro Leu Leu Ser Glu Ser Thr Gln Ala Leu
                85                  90                  95

Tyr Thr Asn Pro Asp Ser Asn Lys Thr Gly Phe Ser Leu Lys Glu Glu
            100                 105                 110

His Phe Ser Ile Asn Lys Val Thr Leu Thr Glu Ile His Ser Asn Lys
        115                 120                 125

His Asp Ala Val Lys Ile Val Arg Arg Asn Trp Leu Glu Lys Leu Arg
    130                 135                 140

Val Phe Leu Glu Trp Val Leu Cys Ala Leu Gln Leu Cys Ile Tyr Ile
145                 150                 155                 160

Ser Val Trp Ser Lys Tyr Thr Asn Thr Gln Glu Asp Phe Pro Met His
                165                 170                 175

Ala Ser Ile Ser Gly Leu Met Leu Trp Ser Leu Leu Leu Leu Val Val
            180                 185                 190

Ser Leu Arg Leu Ala Asn Ile Asn Gln Asn Ile Ser Trp Ile Asn Ser
        195                 200                 205

Gly Pro Gly Asn Leu Trp Ala Leu Ser Phe Ala Cys Tyr Leu Ser Leu
    210                 215                 220

Phe Cys Gly Ser Val Leu Pro Leu Arg Ser Ile Tyr Ile Gly His Ile
225                 230                 235                 240

Thr Asp Glu Ile Ala Ser Thr Phe Tyr Lys Leu Gln Phe Tyr Leu Ser
                245                 250                 255

Leu Thr Leu Phe Leu Leu Leu Phe Thr Ser Gln Ala Gly Asn Arg Phe
            260                 265                 270

Ala Ile Ile Tyr Lys Ser Thr Pro Asp Ile Thr Pro Ser Pro Glu Pro
        275                 280                 285

Ile Val Ser Ile Ala Ser Tyr Ile Thr Trp Ala Trp Val Asp Lys Phe
    290                 295                 300

Leu Trp Lys Ala His Gln Asn Tyr Ile Glu Met Lys Asp Val Trp Gly
305                 310                 315                 320

Leu Met Val Glu Asp Tyr Ser Ile Leu Val Ile Lys Arg Phe Asn His
                325                 330                 335
```

```
Phe Val Gln Asn Lys Thr Lys Ser Arg Thr Phe Ser Phe Asn Leu Ile
            340                 345                 350

His Phe Phe Met Lys Phe Ile Ala Ile Gln Gly Ala Trp Ala Thr Ile
        355                 360                 365

Ser Ser Val Ile Ser Phe Val Pro Thr Met Leu Leu Arg Arg Ile Leu
    370                 375                 380

Glu Tyr Val Glu Asp Gln Ser Thr Ala Pro Leu Asn Leu Ala Trp Met
385                 390                 395                 400

Tyr Ile Phe Leu Met Phe Leu Ala Arg Ile Leu Thr Ala Ile Cys Ala
                405                 410                 415

Ala Gln Ala Leu Phe Leu Gly Arg Arg Val Cys Ile Arg Met Lys Ala
            420                 425                 430

Ile Ile Ile Ser Glu Ile Tyr Ser Lys Ala Leu Arg Arg Lys Ile Ser
        435                 440                 445

Pro Asn Ser Thr Lys Glu Pro Thr Asp Val Val Asp Pro Gln Glu Leu
    450                 455                 460

Asn Asp Lys Gln His Val Asp Gly Asp Glu Glu Ser Ala Thr Thr Ala
465                 470                 475                 480

Asn Leu Gly Ala Ile Ile Asn Leu Met Ala Val Asp Ala Phe Lys Val
                485                 490                 495

Ser Glu Ile Cys Ala Tyr Leu His Ser Phe Ile Glu Ala Ile Ile Met
            500                 505                 510

Thr Ile Val Ala Leu Phe Leu Leu Tyr Arg Leu Ile Gly Trp Ser Ala
        515                 520                 525

Leu Val Gly Ser Ala Met Ile Ile Cys Phe Leu Pro Leu Asn Phe Lys
    530                 535                 540

Leu Ala Ser Leu Leu Gly Thr Leu Gln Lys Lys Ser Leu Ala Ile Thr
545                 550                 555                 560

Asp Lys Arg Ile Gln Lys Leu Asn Glu Ala Phe Gln Ala Ile Arg Ile
                565                 570                 575

Ile Lys Phe Phe Ser Trp Glu Glu Asn Phe Glu Lys Asp Ile Gln Asn
            580                 585                 590

Thr Arg Asp Glu Glu Leu Asn Met Leu Leu Lys Arg Ser Ile Val Trp
        595                 600                 605

Ala Leu Ser Ser Leu Val Trp Phe Ile Thr Pro Ser Ile Val Thr Ser
    610                 615                 620

Ala Ser Phe Ala Val Tyr Ile Tyr Val Gln Gly Gln Thr Leu Thr Thr
625                 630                 635                 640

Pro Val Ala Phe Thr Ala Leu Ser Leu Phe Ala Leu Leu Arg Asn Pro
                645                 650                 655

Leu Asp Met Leu Ser Asp Met Leu Ser Phe Val Ile Gln Ser Lys Val
            660                 665                 670

Ser Leu Asp Arg Val Gln Glu Phe Leu Asn Glu Glu Glu Thr Lys Lys
        675                 680                 685

Tyr Glu Gln Leu Thr Val Ser Arg Asn Lys Leu Gly Leu Gln Asn Ala
    690                 695                 700

Thr Phe Thr Trp Asp Lys Asn Asn Gln Asp Phe Lys Leu Lys Asn Leu
705                 710                 715                 720

Thr Ile Asp Phe Lys Ile Gly Lys Leu Asn Val Ile Val Gly Pro Thr
                725                 730                 735

Gly Ser Gly Lys Thr Ser Leu Leu Met Gly Leu Leu Gly Glu Met Glu
            740                 745                 750
```

```
Leu Leu Asn Gly Lys Val Phe Val Pro Ser Leu Asn Pro Arg Glu Glu
        755                 760                 765

Leu Val Val Glu Ala Asp Gly Met Thr Asn Ser Ile Ala Tyr Cys Ser
    770                 775                 780

Gln Ala Ala Trp Leu Leu Asn Asp Thr Val Arg Asn Asn Ile Leu Phe
785                 790                 795                 800

Asn Ala Pro Tyr Asn Glu Asn Arg Tyr Asn Ala Val Ile Ser Ala Cys
                805                 810                 815

Gly Leu Lys Arg Asp Phe Glu Ile Leu Ser Ala Gly Asp Gln Thr Glu
            820                 825                 830

Ile Gly Glu Lys Gly Ile Thr Leu Ser Gly Gly Gln Lys Gln Arg Val
        835                 840                 845

Ser Leu Ala Arg Ser Leu Tyr Ser Ser Ser Arg His Leu Leu Leu Asp
    850                 855                 860

Asp Cys Leu Ser Ala Val Asp Ser His Thr Ala Leu Trp Ile Tyr Glu
865                 870                 875                 880

Asn Cys Ile Thr Gly Pro Leu Met Glu Gly Arg Thr Cys Val Leu Val
                885                 890                 895

Ser His Asn Val Ala Leu Thr Leu Lys Asn Ala Asp Trp Val Ile Ile
            900                 905                 910

Met Glu Asn Gly Arg Val Lys Glu Gln Gly Glu Pro Val Glu Leu Leu
        915                 920                 925

Gln Lys Gly Ser Leu Gly Asp Asp Ser Met Val Lys Ser Ser Ile Leu
    930                 935                 940

Ser Arg Thr Ala Ser Ser Val Asn Ile Ser Glu Thr Asn Ser Lys Ile
945                 950                 955                 960

Ser Ser Gly Pro Lys Ala Pro Ala Glu Ser Asp Asn Ala Asn Glu Glu
                965                 970                 975

Ser Thr Thr Cys Gly Asp Arg Ser Lys Ser Ser Gly Lys Leu Ile Ala
            980                 985                 990

Glu Glu Thr Lys Ser Asn Gly Val  Val Ser Leu Asp Val  Tyr Lys Trp
        995                 1000                1005

Tyr Ala  Val Phe Phe Gly Gly  Trp Lys Met Ile Ser  Phe Leu Cys
    1010                1015                1020

Phe Ile  Phe Leu Phe Ala Gln  Met Ile Ser Ile Ser  Gln Ala Trp
    1025                1030                1035

Trp Leu  Arg Ala Trp Ala Ser  Asn Asn Thr Leu Lys  Val Phe Ser
    1040                1045                1050

Asn Leu  Gly Leu Gln Thr Met  Arg Pro Phe Ala Leu  Ser Leu Gln
    1055                1060                1065

Gly Lys  Glu Ala Ser Pro Val  Thr Leu Ser Ala Val  Phe Pro Asn
    1070                1075                1080

Gly Ser  Leu Thr Thr Ala Thr  Glu Pro Asn His Ser  Asn Ala Tyr
    1085                1090                1095

Tyr Leu  Ser Ile Tyr Leu Gly  Ile Gly Val Phe Gln  Ala Leu Cys
    1100                1105                1110

Ser Ser  Ser Lys Ala Ile Ile  Asn Phe Val Ala Gly  Ile Arg Ala
    1115                1120                1125

Ser Arg  Lys Ile Phe Asn Leu  Leu Leu Lys Asn Val  Leu Tyr Ala
    1130                1135                1140

Lys Leu  Arg Phe Phe Asp Ser  Thr Pro Ile Gly Arg  Ile Met Asn
    1145                1150                1155

Arg Phe  Ser Lys Asp Ile Glu  Ser Ile Asp Gln Glu  Leu Thr Pro
```

```
    1160                1165                1170

Tyr Met  Glu Gly Ala Phe Gly  Ser Leu Ile Gln Cys  Val Ser Thr
    1175                1180                1185

Ile Ile  Val Ile Ala Tyr Ile  Thr Pro Gln Phe Leu  Ile Val Ala
    1190                1195                1200

Ala Ile  Val Met Leu Leu Phe  Tyr Phe Val Ala Tyr  Phe Tyr Met
    1205                1210                1215

Ser Gly  Ala Arg Glu Leu Lys  Arg Leu Glu Ser Met  Ser Arg Ser
    1220                1225                1230

Pro Ile  His Gln His Phe Ser  Glu Thr Leu Val Gly  Ile Thr Thr
    1235                1240                1245

Ile Arg  Ala Phe Ser Asp Glu  Arg Arg Phe Leu Val  Asp Asn Met
    1250                1255                1260

Lys Lys  Ile Asp Asp Asn Asn  Arg Pro Phe Phe Tyr  Leu Trp Val
    1265                1270                1275

Cys Asn  Arg Trp Leu Ser Tyr  Arg Ile Glu Leu Ile  Gly Ala Leu
    1280                1285                1290

Ile Val  Leu Ala Ala Gly Ser  Phe Ile Leu Leu Asn  Ile Lys Ser
    1295                1300                1305

Ile Asp  Ser Gly Leu Ala Gly  Ile Ser Leu Gly Phe  Ala Ile Gln
    1310                1315                1320

Phe Thr  Asp Gly Ala Leu Trp  Val Val Arg Leu Tyr  Ser Asn Val
    1325                1330                1335

Glu Met  Asn Met Asn Ser Val  Glu Arg Leu Lys Glu  Tyr Thr Thr
    1340                1345                1350

Ile Glu  Gln Glu Pro Ser Asn  Val Gly Ala Leu Val  Pro Pro Cys
    1355                1360                1365

Glu Trp  Pro Gln Asn Gly Lys  Ile Glu Val Lys Asp  Leu Ser Leu
    1370                1375                1380

Arg Tyr  Ala Ala Gly Leu Pro  Lys Val Ile Lys Asn  Val Thr Phe
    1385                1390                1395

Thr Val  Asp Ser Lys Cys Lys  Val Gly Ile Val Gly  Arg Thr Gly
    1400                1405                1410

Ala Gly  Lys Ser Thr Ile Ile  Thr Ala Leu Phe Arg  Phe Leu Asp
    1415                1420                1425

Pro Glu  Thr Gly Tyr Ile Lys  Ile Asp Asp Val Asp  Ile Thr Thr
    1430                1435                1440

Ile Gly  Leu Lys Arg Leu Arg  Gln Ser Ile Thr Ile  Ile Pro Gln
    1445                1450                1455

Asp Pro  Thr Leu Phe Thr Gly  Thr Leu Lys Thr Asn  Leu Asp Pro
    1460                1465                1470

Tyr Asn  Glu Tyr Ser Glu Ala  Glu Ile Phe Glu Ala  Leu Lys Arg
    1475                1480                1485

Val Asn  Leu Val Ser Ser Glu  Glu Leu Gly Asn Pro  Ser Thr Ser
    1490                1495                1500

Asp Ser  Thr Ser Val His Ser  Ala Asn Met Asn Lys  Phe Leu Asp
    1505                1510                1515

Leu Glu  Asn Glu Val Ser Glu  Gly Gly Ser Asn Leu  Ser Gln Gly
    1520                1525                1530

Gln Arg  Gln Leu Ile Cys Leu  Ala Arg Ser Leu Leu  Arg Cys Pro
    1535                1540                1545

Lys Val  Ile Leu Leu Asp Glu  Ala Thr Ala Ser Ile  Asp Tyr Asn
    1550                1555                1560
```

```
Ser Asp  Ser Lys Ile Gln Ala  Thr Ile Arg Glu Glu  Phe Ser Asn
    1565                 1570                 1575

Ser Thr  Ile Leu Thr Ile Ala  His Arg Leu Arg Ser  Ile Ile Asp
    1580                 1585                 1590

Tyr Asp  Lys Ile Leu Val Met  Asp Ala Gly Glu Val  Lys Glu Tyr
    1595                 1600                 1605

Asp His  Pro Tyr Ser Leu Leu  Leu Asn Arg Asp Ser  Ile Phe Tyr
    1610                 1615                 1620

His Met  Cys Glu Asp Ser Gly  Glu Leu Glu Val Leu  Ile Gln Leu
    1625                 1630                 1635

Ala Lys  Glu Ser Phe Val Lys  Lys Leu Asn Ala Asn
    1640                 1645                 1650
```

```
<210> SEQ ID NO 9
<211> LENGTH: 320
<212> TYPE: PRT
<213> ORGANISM: Artificial Sequence
<220> FEATURE:
<223> OTHER INFORMATION: Synthetic: Bt.GGPPS

<400> SEQUENCE: 9

Met Leu Thr Ser Ser Lys Ser Ile Glu Ser Phe Pro Lys Asn Val Gln
1               5                   10                  15

Pro Tyr Gly Lys His Tyr Gln Asn Gly Leu Glu Pro Val Gly Lys Ser
            20                  25                  30

Gln Glu Asp Ile Leu Leu Glu Pro Phe His Tyr Leu Cys Ser Asn Pro
        35                  40                  45

Gly Lys Asp Val Arg Thr Lys Met Ile Glu Ala Phe Asn Ala Trp Leu
    50                  55                  60

Lys Val Pro Lys Asp Asp Leu Ile Val Ile Thr Arg Val Ile Glu Met
65                  70                  75                  80

Leu His Ser Ala Ser Leu Leu Ile Asp Asp Val Glu Asp Asp Ser Val
                85                  90                  95

Leu Arg Arg Gly Val Pro Ala Ala His His Ile Tyr Gly Thr Pro Gln
            100                 105                 110

Thr Ile Asn Cys Ala Asn Tyr Val Tyr Phe Leu Ala Leu Lys Glu Ile
        115                 120                 125

Ala Lys Leu Asn Lys Pro Asn Met Ile Thr Ile Tyr Thr Asp Glu Leu
    130                 135                 140

Ile Asn Leu His Arg Gly Gln Gly Met Glu Leu Phe Trp Arg Asp Thr
145                 150                 155                 160

Leu Thr Cys Pro Thr Glu Lys Glu Phe Leu Asp Met Val Asn Asp Lys
                165                 170                 175

Thr Gly Gly Leu Leu Arg Leu Ala Val Lys Leu Met Gln Glu Ala Ser
            180                 185                 190

Gln Ser Gly Thr Asp Tyr Thr Gly Leu Val Ser Lys Ile Gly Ile His
        195                 200                 205

Phe Gln Val Arg Asp Asp Tyr Met Asn Leu Gln Ser Lys Asn Tyr Ala
    210                 215                 220

Asp Asn Lys Gly Phe Cys Glu Asp Leu Thr Glu Gly Lys Phe Ser Phe
225                 230                 235                 240

Pro Ile Ile His Ser Ile Arg Ser Asp Pro Ser Asn Arg Gln Leu Leu
                245                 250                 255

Asn Ile Leu Lys Gln Arg Ser Ser Ser Ile Glu Leu Lys Gln Phe Ala
            260                 265                 270
```

Leu Gln Leu Leu Glu Asn Thr Asn Thr Phe Gln Tyr Cys Arg Asp Phe
275 280 285

Leu Arg Val Leu Glu Lys Glu Ala Arg Glu Glu Ile Lys Leu Leu Gly
290 295 300

Gly Asn Ile Met Leu Glu Lys Ile Met Asp Val Leu Ser Val Asn Glu
305 310 315 320

<210> SEQ ID NO 10
<211> LENGTH: 736
<212> TYPE: PRT
<213> ORGANISM: Artificial Sequence
<220> FEATURE:
<223> OTHER INFORMATION: Synthetic: Ent-Os.CDPS

<400> SEQUENCE: 10

Met Glu His Ala Arg Pro Pro Gln Gly Gly Asp Asp Asp Val Ala Ala
1 5 10 15

Ser Thr Ser Glu Leu Pro Tyr Met Ile Glu Ser Ile Lys Ser Lys Leu
20 25 30

Arg Ala Ala Arg Asn Ser Leu Gly Glu Thr Thr Val Ser Ala Tyr Asp
35 40 45

Thr Ala Trp Ile Ala Leu Val Asn Arg Leu Asp Gly Gly Gly Glu Arg
50 55 60

Ser Pro Gln Phe Pro Glu Ala Ile Asp Trp Ile Ala Arg Asn Gln Leu
65 70 75 80

Pro Asp Gly Ser Trp Gly Asp Ala Gly Met Phe Ile Val Gln Asp Arg
85 90 95

Leu Ile Asn Thr Leu Gly Cys Val Val Ala Leu Ala Thr Trp Gly Val
100 105 110

His Glu Glu Gln Arg Ala Arg Gly Leu Ala Tyr Ile Gln Asp Asn Leu
115 120 125

Trp Arg Leu Gly Glu Asp Asp Glu Glu Trp Met Met Val Gly Phe Glu
130 135 140

Ile Thr Phe Pro Val Leu Leu Glu Lys Ala Lys Asn Leu Gly Leu Asp
145 150 155 160

Ile Asn Tyr Asp Asp Pro Ala Leu Gln Asp Ile Tyr Ala Lys Arg Gln
165 170 175

Leu Lys Leu Ala Lys Ile Pro Arg Glu Ala Leu His Ala Arg Pro Thr
180 185 190

Thr Leu Leu His Ser Leu Glu Gly Met Glu Asn Leu Asp Trp Glu Arg
195 200 205

Leu Leu Gln Phe Lys Cys Pro Ala Gly Ser Leu His Ser Ser Pro Ala
210 215 220

Ala Ser Ala Tyr Ala Leu Ser Glu Thr Gly Asp Lys Glu Leu Leu Glu
225 230 235 240

Tyr Leu Glu Thr Ala Ile Asn Asn Phe Asp Gly Gly Ala Pro Cys Thr
245 250 255

Tyr Pro Val Asp Asn Phe Asp Arg Leu Trp Ser Val Asp Arg Leu Arg
260 265 270

Arg Leu Gly Ile Ser Arg Tyr Phe Thr Ser Glu Ile Glu Glu Tyr Leu
275 280 285

Glu Tyr Ala Tyr Arg His Leu Ser Pro Asp Gly Met Ser Tyr Gly Gly
290 295 300

Leu Cys Pro Val Lys Asp Ile Asp Asp Thr Ala Met Ala Phe Arg Leu
305 310 315 320

-continued

```
Leu Arg Leu His Gly Tyr Asn Val Ser Ser Ser Val Phe Asn His Phe
                325                 330                 335

Glu Lys Asp Gly Glu Tyr Phe Cys Phe Ala Gly Gln Ser Ser Gln Ser
            340                 345                 350

Leu Thr Ala Met Tyr Asn Ser Tyr Arg Ala Ser Gln Ile Val Phe Pro
        355                 360                 365

Gly Asp Asp Asp Gly Leu Glu Gln Leu Arg Ala Tyr Cys Arg Ala Phe
    370                 375                 380

Leu Glu Glu Arg Arg Ala Thr Gly Asn Leu Arg Asp Lys Trp Val Ile
385                 390                 395                 400

Ala Asn Gly Leu Pro Ser Glu Val Glu Tyr Ala Leu Asp Phe Pro Trp
                405                 410                 415

Lys Ala Ser Leu Pro Arg Val Glu Thr Arg Val Tyr Leu Glu Gln Tyr
            420                 425                 430

Gly Ala Ser Glu Asp Ala Trp Ile Gly Lys Gly Leu Tyr Arg Met Thr
        435                 440                 445

Leu Val Asn Asn Asp Leu Tyr Leu Glu Ala Ala Lys Ala Asp Phe Thr
    450                 455                 460

Asn Phe Gln Arg Leu Ser Arg Leu Glu Trp Leu Ser Leu Lys Arg Trp
465                 470                 475                 480

Tyr Ile Arg Asn Asn Leu Gln Ala His Gly Val Thr Glu Gln Ser Val
                485                 490                 495

Leu Arg Ala Tyr Phe Leu Ala Ala Ala Asn Ile Phe Glu Pro Asn Arg
            500                 505                 510

Ala Ala Glu Arg Leu Gly Trp Ala Arg Thr Ala Ile Leu Ala Glu Ala
        515                 520                 525

Ile Ala Ser His Leu Arg Gln Tyr Ser Ala Asn Gly Ala Ala Asp Gly
    530                 535                 540

Met Thr Glu Arg Leu Ile Ser Gly Leu Ala Ser His Asp Trp Asp Trp
545                 550                 555                 560

Arg Glu Ser Asn Asp Ser Ala Ala Arg Ser Leu Leu Tyr Ala Leu Asp
                565                 570                 575

Glu Leu Ile Asp Leu His Ala Phe Gly Asn Ala Ser Asp Ser Leu Arg
            580                 585                 590

Glu Ala Trp Lys Gln Trp Leu Met Ser Trp Thr Asn Glu Ser Gln Gly
        595                 600                 605

Ser Thr Gly Gly Asp Thr Ala Leu Leu Leu Val Arg Thr Ile Glu Ile
    610                 615                 620

Cys Ser Gly Arg His Gly Ser Ala Glu Gln Ser Leu Lys Asn Ser Glu
625                 630                 635                 640

Asp Tyr Ala Arg Leu Glu Gln Ile Ala Ser Ser Met Cys Ser Lys Leu
                645                 650                 655

Ala Thr Lys Ile Leu Ala Gln Asn Gly Gly Ser Met Asp Asn Val Glu
            660                 665                 670

Gly Ile Asp Gln Glu Val Asp Val Glu Met Lys Glu Leu Ile Gln Arg
        675                 680                 685

Val Tyr Gly Ser Ser Ser Asn Asp Val Ser Ser Val Thr Arg Gln Thr
    690                 695                 700

Phe Leu Asp Val Val Lys Ser Phe Cys Tyr Val Ala His Cys Ser Pro
705                 710                 715                 720

Glu Thr Ile Asp Gly His Ile Ser Lys Val Leu Phe Glu Asp Val Asn
                725                 730                 735
```

<210> SEQ ID NO 11
<211> LENGTH: 757
<212> TYPE: PRT
<213> ORGANISM: Artificial Sequence
<220> FEATURE:
<223> OTHER INFORMATION: Synthetic: Ent-Pg.KS

<400> SEQUENCE: 11

```
Met Lys Arg Glu Gln Tyr Thr Ile Leu Asn Glu Lys Glu Ser Met Ala
1               5                   10                  15

Glu Glu Leu Ile Leu Arg Ile Lys Arg Met Phe Ser Glu Ile Glu Asn
            20                  25                  30

Thr Gln Thr Ser Ala Ser Ala Tyr Asp Thr Ala Trp Val Ala Met Val
        35                  40                  45

Pro Ser Leu Asp Ser Ser Gln Gln Pro Gln Phe Pro Gln Cys Leu Ser
    50                  55                  60

Trp Ile Ile Asp Asn Gln Leu Leu Asp Gly Ser Trp Gly Ile Pro Tyr
65                  70                  75                  80

Leu Ile Ile Lys Asp Arg Leu Cys His Thr Leu Ala Cys Val Ile Ala
                85                  90                  95

Leu Arg Lys Trp Asn Ala Gly Asn Gln Asn Val Glu Thr Gly Leu Arg
            100                 105                 110

Phe Leu Arg Glu Asn Ile Glu Gly Ile Val His Glu Asp Glu Tyr Thr
        115                 120                 125

Pro Ile Gly Phe Gln Ile Ile Phe Pro Ala Met Leu Glu Glu Ala Arg
    130                 135                 140

Gly Leu Gly Leu Glu Leu Pro Tyr Asp Leu Thr Pro Ile Lys Leu Met
145                 150                 155                 160

Leu Thr His Arg Glu Lys Ile Met Lys Gly Lys Ala Ile Asp His Met
                165                 170                 175

His Glu Tyr Asp Ser Ser Leu Ile Tyr Thr Val Glu Gly Ile His Lys
            180                 185                 190

Ile Val Asp Trp Asn Lys Val Leu Lys His Gln Asn Lys Asp Gly Ser
        195                 200                 205

Leu Phe Asn Ser Pro Ser Ala Thr Ala Cys Ala Leu Met His Thr Arg
    210                 215                 220

Lys Ser Asn Cys Leu Glu Tyr Leu Ser Ser Met Leu Gln Lys Leu Gly
225                 230                 235                 240

Asn Gly Val Pro Ser Val Tyr Pro Ile Asn Leu Tyr Ala Arg Ile Ser
                245                 250                 255

Met Ile Asp Arg Leu Gln Arg Leu Gly Leu Ala Arg His Phe Arg Asn
            260                 265                 270

Glu Ile Ile His Ala Leu Asp Asp Ile Tyr Arg Tyr Trp Met Gln Arg
        275                 280                 285

Glu Thr Ser Arg Glu Gly Lys Ser Leu Thr Pro Asp Ile Val Ser Thr
    290                 295                 300

Ser Ile Ala Phe Met Leu Leu Arg Leu His Gly Tyr Asp Val Pro Ala
305                 310                 315                 320

Asp Val Phe Cys Cys Tyr Asp Leu His Ser Ile Glu Gln Ser Gly Glu
                325                 330                 335

Ala Val Thr Ala Met Leu Ser Leu Tyr Arg Ala Ser Gln Ile Met Phe
            340                 345                 350

Pro Gly Glu Thr Ile Leu Glu Glu Ile Lys Thr Val Ser Arg Lys Tyr
        355                 360                 365
```

-continued

```
Leu Asp Lys Arg Lys Glu Asn Gly Gly Ile Tyr Asp His Asn Ile Val
    370                 375                 380

Met Lys Asp Leu Arg Gly Glu Val Glu Tyr Ala Leu Ser Val Pro Trp
385                 390                 395                 400

Tyr Ala Ser Leu Glu Arg Ile Glu Asn Arg Arg Tyr Ile Asp Gln Tyr
                405                 410                 415

Gly Val Asn Asp Thr Trp Ile Ala Lys Thr Ser Tyr Lys Ile Pro Cys
            420                 425                 430

Ile Ser Asn Asp Leu Phe Leu Ala Leu Ala Lys Gln Asp Tyr Asn Ile
        435                 440                 445

Cys Gln Ala Ile Gln Gln Lys Glu Leu Arg Glu Leu Glu Arg Trp Phe
    450                 455                 460

Ala Asp Asn Lys Phe Ser His Leu Asn Phe Ala Arg Gln Lys Leu Ile
465                 470                 475                 480

Tyr Cys Tyr Phe Ser Ala Ala Ala Thr Leu Phe Ser Pro Glu Leu Ser
                485                 490                 495

Ala Ala Arg Val Val Trp Ala Lys Asn Gly Val Ile Thr Thr Val Val
            500                 505                 510

Asp Asp Phe Phe Asp Val Gly Gly Ser Ser Glu Glu Ile His Ser Phe
        515                 520                 525

Val Glu Ala Val Arg Val Trp Asp Glu Ala Ala Thr Asp Gly Leu Ser
    530                 535                 540

Glu Asn Val Gln Ile Leu Phe Ser Ala Leu Tyr Asn Thr Val Asp Glu
545                 550                 555                 560

Ile Val Gln Gln Ala Phe Val Phe Gln Gly Arg Asp Ile Ser Ile His
                565                 570                 575

Leu Arg Glu Ile Trp Tyr Arg Leu Val Asn Ser Met Met Thr Glu Ala
            580                 585                 590

Gln Trp Ala Arg Thr His Cys Leu Pro Ser Met His Glu Tyr Met Glu
        595                 600                 605

Asn Ala Glu Pro Ser Ile Ala Leu Glu Pro Ile Val Leu Ser Ser Leu
    610                 615                 620

Tyr Phe Val Gly Pro Lys Leu Ser Glu Glu Ile Ile Cys His Pro Glu
625                 630                 635                 640

Tyr Tyr Asn Leu Met His Leu Leu Asn Ile Cys Gly Arg Leu Leu Asn
                645                 650                 655

Asp Ile Gln Gly Cys Lys Arg Glu Ala His Gln Gly Lys Leu Asn Ser
            660                 665                 670

Val Thr Leu Tyr Met Glu Glu Asn Ser Gly Thr Thr Met Glu Asp Ala
        675                 680                 685

Ile Val Tyr Leu Arg Lys Thr Ile Asp Glu Ser Arg Gln Leu Leu Leu
    690                 695                 700

Lys Glu Val Leu Arg Pro Ser Ile Val Pro Arg Glu Cys Lys Gln Leu
705                 710                 715                 720

His Trp Asn Met Met Arg Ile Leu Gln Leu Phe Tyr Leu Lys Asn Asp
                725                 730                 735

Gly Phe Thr Ser Pro Thr Glu Met Leu Gly Tyr Val Asn Ala Val Ile
            740                 745                 750

Val Asp Pro Ile Leu
        755
```

<210> SEQ ID NO 12
<211> LENGTH: 499
<212> TYPE: PRT

<213> ORGANISM: Artificial Sequence
<220> FEATURE:
<223> OTHER INFORMATION: Synthetic: Ps.KO

<400> SEQUENCE: 12

```
Met Asp Thr Leu Thr Leu Ser Leu Gly Phe Leu Ser Leu Phe Leu Phe
1               5                   10                  15

Leu Phe Leu Leu Lys Arg Ser Thr His Lys His Ser Lys Leu Ser His
            20                  25                  30

Val Pro Val Val Pro Gly Leu Pro Val Ile Gly Asn Leu Leu Gln Leu
        35                  40                  45

Lys Glu Lys Lys Pro His Lys Thr Phe Thr Lys Met Ala Gln Lys Tyr
    50                  55                  60

Gly Pro Ile Phe Ser Ile Lys Ala Gly Ser Ser Lys Ile Ile Val Leu
65                  70                  75                  80

Asn Thr Ala His Leu Ala Lys Glu Ala Met Val Thr Arg Tyr Ser Ser
                85                  90                  95

Ile Ser Lys Arg Lys Leu Ser Thr Ala Leu Thr Ile Leu Thr Ser Asp
            100                 105                 110

Lys Cys Met Val Ala Met Ser Asp Tyr Asn Asp Phe His Lys Met Val
        115                 120                 125

Lys Lys His Ile Leu Ala Ser Val Leu Gly Ala Asn Ala Gln Lys Arg
    130                 135                 140

Leu Arg Phe His Arg Glu Val Met Met Glu Asn Met Ser Ser Lys Phe
145                 150                 155                 160

Asn Glu His Val Lys Thr Leu Ser Asp Ser Ala Val Asp Phe Arg Lys
                165                 170                 175

Ile Phe Val Ser Glu Leu Phe Gly Leu Ala Leu Lys Gln Ala Leu Gly
            180                 185                 190

Ser Asp Ile Glu Ser Ile Tyr Val Glu Gly Leu Thr Ala Thr Leu Ser
        195                 200                 205

Arg Glu Asp Leu Tyr Asn Thr Leu Val Val Asp Phe Met Glu Gly Ala
    210                 215                 220

Ile Glu Val Asp Trp Arg Asp Phe Phe Pro Tyr Leu Lys Trp Ile Pro
225                 230                 235                 240

Asn Lys Ser Phe Glu Lys Lys Ile Arg Arg Val Asp Arg Gln Arg Lys
                245                 250                 255

Ile Ile Met Lys Ala Leu Ile Asn Glu Gln Lys Lys Arg Leu Thr Ser
            260                 265                 270

Gly Lys Glu Leu Asp Cys Tyr Tyr Asp Tyr Leu Val Ser Glu Ala Lys
        275                 280                 285

Glu Val Thr Glu Glu Gln Met Ile Met Leu Leu Trp Glu Pro Ile Ile
    290                 295                 300

Glu Thr Ser Asp Thr Thr Leu Val Thr Thr Glu Trp Ala Met Tyr Glu
305                 310                 315                 320

Leu Ala Lys Asp Lys Asn Arg Gln Asp Arg Leu Tyr Glu Glu Leu Leu
                325                 330                 335

Asn Val Cys Gly His Glu Lys Val Thr Asp Glu Glu Leu Ser Lys Leu
            340                 345                 350

Pro Tyr Leu Gly Ala Val Phe His Glu Thr Leu Arg Lys His Ser Pro
        355                 360                 365

Val Pro Ile Val Pro Leu Arg Tyr Val Asp Glu Asp Thr Glu Leu Gly
    370                 375                 380

Gly Tyr His Ile Pro Ala Gly Ser Glu Ile Ala Ile Asn Ile Tyr Gly
```

385 390 395 400

Cys Asn Met Asp Ser Asn Leu Trp Glu Asn Pro Asp Gln Trp Ile Pro
405 410 415

Glu Arg Phe Leu Asp Glu Lys Tyr Ala Gln Ala Asp Leu Tyr Lys Thr
420 425 430

Met Ala Phe Gly Gly Gly Lys Arg Val Cys Ala Gly Ser Leu Gln Ala
435 440 445

Met Leu Ile Ala Cys Thr Ala Ile Gly Arg Leu Val Gln Glu Phe Glu
450 455 460

Trp Glu Leu Gly His Gly Glu Glu Glu Asn Val Asp Thr Met Gly Leu
465 470 475 480

Thr Thr His Arg Leu His Pro Leu Gln Val Lys Leu Lys Pro Arg Asn
485 490 495

Arg Ile Tyr

<210> SEQ ID NO 13
<211> LENGTH: 500
<212> TYPE: PRT
<213> ORGANISM: Artificial Sequence
<220> FEATURE:
<223> OTHER INFORMATION: Synthetic: Sr.KAH

<400> SEQUENCE: 13

Met Glu Ala Ser Tyr Leu Tyr Ile Ser Ile Leu Leu Leu Leu Ala Ser
1 5 10 15

Tyr Leu Phe Thr Thr Gln Leu Arg Arg Lys Ser Ala Asn Leu Pro Pro
20 25 30

Thr Val Phe Pro Ser Ile Pro Ile Ile Gly His Leu Tyr Leu Leu Lys
35 40 45

Lys Pro Leu Tyr Arg Thr Leu Ala Lys Ile Ala Ala Lys Tyr Gly Pro
50 55 60

Ile Leu Gln Leu Gln Leu Gly Tyr Arg Arg Val Leu Val Ile Ser Ser
65 70 75 80

Pro Ser Ala Ala Glu Glu Cys Phe Thr Asn Asn Asp Val Ile Phe Ala
85 90 95

Asn Arg Pro Lys Thr Leu Phe Gly Lys Ile Val Gly Gly Thr Ser Leu
100 105 110

Gly Ser Leu Ser Tyr Gly Asp Gln Trp Arg Asn Leu Arg Arg Val Ala
115 120 125

Ser Ile Glu Ile Leu Ser Val His Arg Leu Asn Glu Phe His Asp Ile
130 135 140

Arg Val Asp Glu Asn Arg Leu Leu Ile Arg Lys Leu Arg Ser Ser Ser
145 150 155 160

Ser Pro Val Thr Leu Ile Thr Val Phe Tyr Ala Leu Thr Leu Asn Val
165 170 175

Ile Met Arg Met Ile Ser Gly Lys Arg Tyr Phe Asp Ser Gly Asp Arg
180 185 190

Glu Leu Glu Glu Glu Gly Lys Arg Phe Arg Glu Ile Leu Asp Glu Thr
195 200 205

Leu Leu Leu Ala Gly Ala Ser Asn Val Gly Asp Tyr Leu Pro Ile Leu
210 215 220

Asn Trp Leu Gly Val Lys Ser Leu Glu Lys Lys Leu Ile Ala Leu Gln
225 230 235 240

Lys Lys Arg Asp Asp Phe Phe Gln Gly Leu Ile Glu Gln Val Arg Lys
245 250 255

Ser Arg Gly Ala Lys Val Gly Lys Gly Arg Lys Thr Met Ile Glu Leu
260 265 270

Leu Leu Ser Leu Gln Glu Ser Glu Pro Glu Tyr Tyr Thr Asp Ala Met
275 280 285

Ile Arg Ser Phe Val Leu Gly Leu Leu Ala Ala Gly Ser Asp Thr Ser
290 295 300

Ala Gly Thr Met Glu Trp Ala Met Ser Leu Leu Val Asn His Pro His
305 310 315 320

Val Leu Lys Lys Ala Gln Ala Glu Ile Asp Arg Val Ile Gly Asn Asn
325 330 335

Arg Leu Ile Asp Glu Ser Asp Ile Gly Asn Ile Pro Tyr Ile Gly Cys
340 345 350

Ile Ile Asn Glu Thr Leu Arg Leu Tyr Pro Ala Gly Pro Leu Leu Phe
355 360 365

Pro His Glu Ser Ser Ala Asp Cys Val Ile Ser Gly Tyr Asn Ile Pro
370 375 380

Arg Gly Thr Met Leu Ile Val Asn Gln Trp Ala Ile His His Asp Pro
385 390 395 400

Lys Val Trp Asp Asp Pro Glu Thr Phe Lys Pro Glu Arg Phe Gln Gly
405 410 415

Leu Glu Gly Thr Arg Asp Gly Phe Lys Leu Met Pro Phe Gly Ser Gly
420 425 430

Arg Arg Gly Cys Pro Gly Glu Gly Leu Ala Ile Arg Leu Leu Gly Met
435 440 445

Thr Leu Gly Ser Val Ile Gln Cys Phe Asp Trp Glu Arg Val Gly Asp
450 455 460

Glu Met Val Asp Met Thr Glu Gly Leu Gly Val Thr Leu Pro Lys Ala
465 470 475 480

Val Pro Leu Val Ala Lys Cys Lys Pro Arg Ser Glu Met Thr Asn Leu
485 490 495

Leu Ser Glu Leu
500

<210> SEQ ID NO 14
<211> LENGTH: 711
<212> TYPE: PRT
<213> ORGANISM: Artificial Sequence
<220> FEATURE:
<223> OTHER INFORMATION: Synthetic: At.CPR

<400> SEQUENCE: 14

Met Ser Ser Ser Ser Ser Ser Ser Thr Ser Met Ile Asp Leu Met Ala
1 5 10 15

Ala Ile Ile Lys Gly Glu Pro Val Ile Val Ser Asp Pro Ala Asn Ala
20 25 30

Ser Ala Tyr Glu Ser Val Ala Ala Glu Leu Ser Ser Met Leu Ile Glu
35 40 45

Asn Arg Gln Phe Ala Met Ile Val Thr Thr Ser Ile Ala Val Leu Ile
50 55 60

Gly Cys Ile Val Met Leu Val Trp Arg Arg Ser Gly Ser Gly Asn Ser
65 70 75 80

Lys Arg Val Glu Pro Leu Lys Pro Leu Val Ile Lys Pro Arg Glu Glu
85 90 95

Glu Ile Asp Asp Gly Arg Lys Lys Val Thr Ile Phe Phe Gly Thr Gln
100 105 110

-continued

```
Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Asn Met Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Tyr Glu Thr Gly Asp His Val
            340                 345                 350

Gly Val Leu Cys Asp Asn Leu Ser Glu Thr Val Asp Glu Ala Leu Arg
        355                 360                 365

Leu Leu Asp Met Ser Pro Asp Thr Tyr Phe Ser Leu His Ala Glu Lys
    370                 375                 380

Glu Asp Gly Thr Pro Ile Ser Ser Ser Leu Pro Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430

Thr Glu Ala Glu Arg Leu Lys His Leu Ala Ser Pro Ala Gly Lys Asp
        435                 440                 445

Glu Tyr Ser Lys Trp Val Val Glu Ser Gln Arg Ser Leu Leu Glu Val
    450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
            500                 505                 510

Glu Lys Met Pro Thr Gly Arg Ile His Lys Gly Val Cys Ser Thr Trp
        515                 520                 525
```

-continued

```
Met Lys Asn Ala Val Pro Tyr Glu Lys Ser Glu Asn Cys Ser Ser Ala
    530                 535                 540

Pro Ile Phe Val Arg Gln Ser Asn Phe Lys Leu Pro Ser Asp Ser Lys
545                 550                 555                 560

Val Pro Ile Ile Met Ile Gly Pro Gly Thr Gly Leu Ala Pro Phe Arg
                565                 570                 575

Gly Phe Leu Gln Glu Arg Leu Ala Leu Val Glu Ser Gly Val Glu Leu
            580                 585                 590

Gly Pro Ser Val Leu Phe Phe Gly Cys Arg Asn Arg Arg Met Asp Phe
        595                 600                 605

Ile Tyr Glu Glu Glu Leu Gln Arg Phe Val Glu Ser Gly Ala Leu Ala
    610                 615                 620

Glu Leu Ser Val Ala Phe Ser Arg Glu Gly Pro Thr Lys Glu Tyr Val
625                 630                 635                 640

Gln His Lys Met Met Asp Lys Ala Ser Asp Ile Trp Asn Met Ile Ser
                645                 650                 655

Gln Gly Ala Tyr Leu Tyr Val Cys Gly Asp Ala Lys Gly Met Ala Arg
            660                 665                 670

Asp Val His Arg Ser Leu His Thr Ile Ala Gln Glu Gln Gly Ser Met
        675                 680                 685

Asp Ser Thr Lys Ala Glu Gly Phe Val Lys Asn Leu Gln Thr Ser Gly
    690                 695                 700

Arg Tyr Leu Arg Asp Val Trp
705                 710
```

<210> SEQ ID NO 15
<211> LENGTH: 481
<212> TYPE: PRT
<213> ORGANISM: Artificial Sequence
<220> FEATURE:
<223> OTHER INFORMATION: Synthetic: UGT85C2

<400> SEQUENCE: 15

```
Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175
```

```
Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn


<210> SEQ ID NO 16
<211> LENGTH: 460
<212> TYPE: PRT
<213> ORGANISM: Artificial Sequence
<220> FEATURE:
<223> OTHER INFORMATION: Synthetic: UGT74G1

<400> SEQUENCE: 16

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
```

```
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
    370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
    450                 455                 460
```

<210> SEQ ID NO 17

<211> LENGTH: 485
<212> TYPE: PRT
<213> ORGANISM: Artificial Sequence
<220> FEATURE:
<223> OTHER INFORMATION: Synthetic: UGT91D_like3

<400> SEQUENCE: 17

```
Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Tyr Leu Gln Leu Ser Lys Leu
        35                  40                  45

Ile Ala Glu Lys Gly His Lys Val Ser Phe Leu Ser Thr Thr Arg Asn
    50                  55                  60

Ile Gln Arg Leu Ser Ser His Ile Ser Pro Leu Ile Asn Val Val Gln
65                  70                  75                  80

Leu Thr Leu Pro Arg Val Gln Glu Leu Pro Glu Asp Ala Glu Ala Thr
                85                  90                  95

Thr Asp Val His Pro Glu Asp Ile Pro Tyr Leu Lys Lys Ala Ser Asp
            100                 105                 110

Gly Leu Gln Pro Glu Val Thr Arg Phe Leu Glu Gln His Ser Pro Asp
        115                 120                 125

Trp Ile Ile Tyr Asp Tyr Thr His Tyr Trp Leu Pro Ser Ile Ala Ala
    130                 135                 140

Ser Leu Gly Ile Ser Arg Ala His Phe Ser Val Thr Thr Pro Trp Ala
145                 150                 155                 160

Ile Ala Tyr Met Gly Pro Ser Ala Asp Ala Met Ile Asn Gly Ser Asp
                165                 170                 175

Gly Arg Thr Thr Val Glu Asp Leu Thr Thr Pro Pro Lys Trp Phe Pro
            180                 185                 190

Phe Pro Thr Lys Val Cys Trp Arg Lys His Asp Leu Ala Arg Leu Val
        195                 200                 205

Pro Tyr Lys Ala Pro Gly Ile Ser Asp Gly Tyr Arg Met Gly Leu Val
    210                 215                 220

Leu Lys Gly Ser Asp Cys Leu Leu Ser Lys Cys Tyr His Glu Phe Gly
225                 230                 235                 240

Thr Gln Trp Leu Pro Leu Leu Glu Thr Leu His Gln Val Pro Val Val
                245                 250                 255

Pro Val Gly Leu Leu Pro Pro Glu Ile Pro Gly Asp Glu Lys Asp Glu
            260                 265                 270

Thr Trp Val Ser Ile Lys Lys Trp Leu Asp Gly Lys Gln Lys Gly Ser
        275                 280                 285

Val Val Tyr Val Ala Leu Gly Ser Glu Val Leu Val Ser Gln Thr Glu
    290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
                325                 330                 335

Leu Pro Asp Gly Phe Val Glu Arg Thr Arg Asp Arg Gly Leu Val Trp
            340                 345                 350

Thr Ser Trp Ala Pro Gln Leu Arg Ile Leu Ser His Glu Ser Val Cys
        355                 360                 365

Gly Phe Leu Thr His Cys Gly Ser Gly Ser Ile Val Glu Gly Leu Met
    370                 375                 380
```

-continued

Phe Gly His Pro Leu Ile Met Leu Pro Ile Phe Gly Asp Gln Pro Leu
385 390 395 400

Asn Ala Arg Leu Leu Glu Asp Lys Gln Val Gly Ile Glu Ile Pro Arg
405 410 415

Asn Glu Glu Asp Gly Cys Leu Thr Lys Glu Ser Val Ala Arg Ser Leu
420 425 430

Arg Ser Val Val Val Glu Lys Glu Gly Glu Ile Tyr Lys Ala Asn Ala
435 440 445

Arg Glu Leu Ser Lys Ile Tyr Asn Asp Thr Lys Val Glu Lys Glu Tyr
450 455 460

Val Ser Gln Phe Val Asp Tyr Leu Glu Lys Asn Ala Arg Ala Val Ala
465 470 475 480

Ile Asp His Glu Ser
485

<210> SEQ ID NO 18
<211> LENGTH: 458
<212> TYPE: PRT
<213> ORGANISM: Artificial Sequence
<220> FEATURE:
<223> OTHER INFORMATION: Synthetic: UGT76G1

<400> SEQUENCE: 18

Met Glu Asn Lys Thr Glu Thr Thr Val Arg Arg Arg Arg Arg Ile Ile
1 5 10 15

Leu Phe Pro Val Pro Phe Gln Gly His Ile Asn Pro Ile Leu Gln Leu
20 25 30

Ala Asn Val Leu Tyr Ser Lys Gly Phe Ser Ile Thr Ile Phe His Thr
35 40 45

Asn Phe Asn Lys Pro Lys Thr Ser Asn Tyr Pro His Phe Thr Phe Arg
50 55 60

Phe Ile Leu Asp Asn Asp Pro Gln Asp Glu Arg Ile Ser Asn Leu Pro
65 70 75 80

Thr His Gly Pro Leu Ala Gly Met Arg Ile Pro Ile Ile Asn Glu His
85 90 95

Gly Ala Asp Glu Leu Arg Arg Glu Leu Glu Leu Leu Met Leu Ala Ser
100 105 110

Glu Glu Asp Glu Glu Val Ser Cys Leu Ile Thr Asp Ala Leu Trp Tyr
115 120 125

Phe Ala Gln Ser Val Ala Asp Ser Leu Asn Leu Arg Arg Leu Val Leu
130 135 140

Met Thr Ser Ser Leu Phe Asn Phe His Ala His Val Ser Leu Pro Gln
145 150 155 160

Phe Asp Glu Leu Gly Tyr Leu Asp Pro Asp Asp Lys Thr Arg Leu Glu
165 170 175

Glu Gln Ala Ser Gly Phe Pro Met Leu Lys Val Lys Asp Ile Lys Ser
180 185 190

Ala Tyr Ser Asn Trp Gln Ile Leu Lys Glu Ile Leu Gly Lys Met Ile
195 200 205

Lys Gln Thr Lys Ala Ser Ser Gly Val Ile Trp Asn Ser Phe Lys Glu
210 215 220

Leu Glu Glu Ser Glu Leu Glu Thr Val Ile Arg Glu Ile Pro Ala Pro
225 230 235 240

Ser Phe Leu Ile Pro Leu Pro Lys His Leu Thr Ala Ser Ser Ser Ser
245 250 255

```
Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455


<210> SEQ ID NO 19
<211> LENGTH: 436
<212> TYPE: PRT
<213> ORGANISM: Artificial Sequence
<220> FEATURE:
<223> OTHER INFORMATION: Synthetic: UGT40087

<400> SEQUENCE: 19

Met Asp Ala Ser Asp Ser Ser Pro Leu His Ile Val Ile Phe Pro Trp
1               5                   10                  15

Leu Ala Phe Gly His Met Leu Ala Ser Leu Glu Leu Ala Glu Arg Leu
            20                  25                  30

Ala Ala Arg Gly His Arg Val Ser Phe Val Ser Thr Pro Arg Asn Ile
        35                  40                  45

Ser Arg Leu Arg Pro Val Pro Pro Ala Leu Ala Pro Leu Ile Asp Phe
    50                  55                  60

Val Ala Leu Pro Leu Pro Arg Val Asp Gly Leu Pro Asp Gly Ala Glu
65                  70                  75                  80

Ala Thr Ser Asp Ile Pro Pro Gly Lys Thr Glu Leu His Leu Lys Ala
                85                  90                  95

Leu Asp Gly Leu Ala Ala Pro Phe Ala Ala Phe Leu Asp Ala Ala Cys
            100                 105                 110

Ala Asp Gly Ser Thr Asn Lys Val Asp Trp Leu Phe Leu Asp Asn Phe
        115                 120                 125

Gln Tyr Trp Ala Ala Ala Ala Ala Ala Asp His Lys Ile Pro Cys Ala
    130                 135                 140

Leu Asn Leu Thr Phe Ala Ala Ser Thr Ser Ala Glu Tyr Gly Val Pro
145                 150                 155                 160
```

Arg Val Glu Pro Pro Val Asp Gly Ser Thr Ala Ser Ile Leu Gln Arg
165 170 175

Phe Val Leu Thr Leu Glu Lys Cys Gln Phe Val Ile Gln Arg Ala Cys
180 185 190

Phe Glu Leu Glu Pro Glu Pro Leu Pro Leu Leu Ser Asp Ile Phe Gly
195 200 205

Lys Pro Val Ile Pro Tyr Gly Leu Val Pro Pro Cys Pro Pro Ala Glu
210 215 220

Gly His Lys Arg Glu His Gly Asn Ala Ala Leu Ser Trp Leu Asp Lys
225 230 235 240

Gln Gln Pro Glu Ser Val Leu Phe Ile Ala Leu Gly Ser Glu Pro Pro
245 250 255

Val Thr Val Glu Gln Leu His Glu Ile Ala Leu Gly Leu Glu Leu Ala
260 265 270

Gly Thr Thr Phe Leu Trp Ala Leu Lys Lys Pro Asn Gly Leu Leu Leu
275 280 285

Glu Ala Asp Gly Asp Ile Leu Pro Pro Gly Phe Glu Glu Arg Thr Arg
290 295 300

Asp Arg Gly Leu Val Ala Met Gly Trp Val Pro Gln Pro Ile Ile Leu
305 310 315 320

Ala His Ser Ser Val Gly Ala Phe Leu Thr His Gly Gly Trp Ala Ser
325 330 335

Thr Ile Glu Gly Val Met Ser Gly His Pro Met Leu Phe Leu Thr Phe
340 345 350

Leu Asp Glu Gln Arg Ile Asn Ala Gln Leu Ile Glu Arg Lys Lys Ala
355 360 365

Gly Leu Arg Val Pro Arg Arg Glu Lys Asp Gly Ser Tyr Asp Arg Gln
370 375 380

Gly Ile Ala Gly Ala Ile Arg Ala Val Met Cys Glu Glu Glu Ser Lys
385 390 395 400

Ser Val Phe Ala Ala Asn Ala Lys Lys Met Gln Glu Ile Val Ser Asp
405 410 415

Arg Asn Cys Gln Glu Lys Tyr Ile Asp Glu Leu Ile Gln Arg Leu Gly
420 425 430

Ser Phe Glu Lys
435

<210> SEQ ID NO 20
<211> LENGTH: 4680
<212> TYPE: DNA
<213> ORGANISM: Artificial Sequence
<220> FEATURE:
<223> OTHER INFORMATION: Synthetic: nucleic acid sequence

<400> SEQUENCE: 20
atgtcttcac tagaagtggt agatgggtgc ccctatggat accgaccata tccagatagt 60
ggcacaaatg cattaaatcc atgttttata tcagtaatat ccgcctggca agccgtcttt 120
ttcctattga ttggtagcta tcaattgtgg aaactttata agaacaataa agtaccaccc 180
agatttaaga actttcctac attaccaagt aaaatcaaca gtcgacatct aacgcatttg 240
accaatgttt gctttcagtc cacgcttata atttgtgaac tggccttggt atcccaatct 300
agcgataggg tttatccatt tatactaaag aaggctctgt acttgaatct ccttttcaat 360
ttgggtattt ctctccctac tcaatactta gcttatttta aaagtacatt ttcaatgggc 420

-continued

```
aaccagcttt tctattacat gtttcaaatt cttctacagc tcttcttgat attgcagagg    480
tactatcatg gttctagtaa cgaaaggctt actgttatta gcggacaaac tgctatgatt    540
ttagaagtgc tccttctttt caattctgtg gcaattttta tttatgatct atgcattttt    600
gagccaatta acgaattatc tgaatactac aagaaaaatg ggtggtatcc ccccgttcat    660
gtactatcct atattacatt tatctggatg aacaaactga ttgtggaaac ttaccgtaac    720
aagaaaatca aagatcctaa ccagttacca ttgccgccag tagatctgaa tattaagtcg    780
ataagtaagg aatttaaggc taactgggaa ttggaaaaat ggttgaatag aaattctctt    840
tggagggcca tttggaagtc atttggtagg actatttctg tggctatgct gtatgaaacg    900
acatctgatt tactttctgt agtacagccc cagtttctac ggatattcat agatggtttg    960
aacccggaaa catcttctaa atatcctcct ttaaatggtg tatttattgc tctaaccctt   1020
ttcgtaatca gcgtggtttc tgtgttcctc accaatcaat tttatattgg aatttttgag   1080
gctggtttgg ggataagagg ctctttagct tctttagtgt atcagaagtc cttaagattg   1140
acgctagcag agcgtaacga aaaatctact ggtgacatct taaatttgat gtctgtggat   1200
gtgttaagga tccagcggtt tttcgaaaat gcccaaacca ttattggcgc tcctattcag   1260
attattgttg tattaacttc cctgtactgg ttgctaggaa aggctgttat tggagggttg   1320
gttactatgg ctattatgat gcctatcaat gccttcttat ctagaaaggt aaaaaagcta   1380
tcaaaaactc aaatgaagta taaggacatg agaatcaaga ctattacaga gcttttgaat   1440
gctataaaat ctattaaatt atacgcctgg gaggaaccta tgatggcaag attgaatcat   1500
gttcgtaatg atatggagtt gaaaaatttt cggaaaattg gtatagtgag caatctgata   1560
tattttgcgt ggaattgtgt acctttaatg gtgacatgtt ccacatttgg cttattttct   1620
ttatttagtg attctccgtt atctcctgcc attgtcttcc cttcattatc tttatttaat   1680
attttgaaca gtgccatcta ttccgttcca tccatgataa ataccattat agagacaagc   1740
gtttctatgg aaagattaaa gtcattccta cttagtgacg aaattgatga ttcgttcatc   1800
gaacgtattg atccttcagc ggatgaaaga gcgttacctg ctatagagat gaataatatt   1860
acatttttat ggaaatcaaa agaagtatta acatctagcc aatctggaga taatttgagg   1920
acagatgaag agtctattat cggatcttct caaattgcgt tgaagaatat cgatcatttt   1980
gaagcaaaaa ggggtgattt agtttgtgtt gttggtcggg taggagctgg taaatcaaca   2040
tttttgaagg caattcttgg tcaacttcct tgcatgagtg gttctaggga ctcgatacca   2100
cctaaactga tcattagatc atcgtctgta gcctactgtt cacaagaatc ctggataatg   2160
aacgcatctg taagagaaaa cattctattt ggtcacaagt tcgaccaaga ttattatgac   2220
ctcactatta aagcatgtca attgctaccc gatttgaaaa tactaccaga tggtgatgaa   2280
actttggtag gtgaaaaggg catttcccta tcaggcggtc agaaggcccg tctttcatta   2340
gccagagcgg tgtactcgag agcagatatt tatttgttgg atgacatttt atctgctgtt   2400
gatgcagaag ttagtaaaaa tattattgaa tatgttttga tcggaaagac ggctttatta   2460
aaaaataaaa caattatttt aactaccaat actgtatcaa ttttaaaaca ttcgcagatg   2520
atatatgcgc tagaaaacgg tgaaattgtt gaacaaggga attatgagga tgtaatgaac   2580
cgtaagaaca atacttcaaa actgaaaaaa ttactagagg aatttgattc tccgattgat   2640
aatggaaatg aaagcgatgt ccaaactgaa caccgatccg aaagtgaagt ggatgaacct   2700
ctgcagctta aagtaactga atcagaaact gaggatgagg ttgttactga gagtgaatta   2760
gaactaatca aagccaattc tagaagagct tctctagcta cgctaagacc tagacccttt   2820
```

gtgggagcac aattggattc cgtgaagaaa acggcgcaaa aggccgagaa gacagaggtg 2880
ggaagagtca aaacaaagat ttatcttgcg tatattaagg cttgtggagt tttaggtgtt 2940
gttttatttt tcttgtttat gatattaaca agggttttcg acttagcaga gaatttttgg 3000
ttaaagtact ggtcagaatc taatgaaaaa aatggttcaa atgaaagggt ttggatgttt 3060
gttggtgtgt attccttaat cggagtagca tcggccgcat tcaataattt acggagtatt 3120
atgatgctac tgtattgttc tattaggggt tctaagaaac tgcatgaaag catggccaaa 3180
tctgtaatta gaagtcctat gactttcttt gagactacac cagttggaag gatcataaac 3240
aggttctcat ctgatatgga tgcagtggac agtaatctac agtacatttt ctcctttttt 3300
ttcaaatcaa tactaaccta tttggttact gttatattag tcgggtacaa tatgccatgg 3360
tttttagtgt tcaatatgtt tttggtggtt atctatattt actatcaaac attttacatt 3420
gtgctatcta gggagctaaa aagattgatc agtatatctt actctccgat tatgtcctta 3480
atgagtgaga gcttgaacgg ttattctatt attgatgcat acgatcattt tgagagattc 3540
atctatctaa attatgaaaa aatccaatac aacgttgatt ttgtcttcaa ctttagatca 3600
acgaatagat ggttatccgt gagattgcaa actattggtg ctacaattgt tttggctact 3660
gcaatcttag cactagcaac aatgaatact aaaaggcaac taagttcggg tatggttggt 3720
ctactaatga gctattcatt agaggttaca ggttcattga cttggattgt aaggacaact 3780
gtgacgattg aaaccaacat tgtatcagtg gagagaattg ttgagtactg cgaattacca 3840
cctgaagcac agtccattaa ccctgaaaag aggccagatg aaaattggcc atcaaagggt 3900
ggtattgaat tcaaaaacta ttccacaaaa tacagagaaa atttggatcc agtgctgaat 3960
aatattaacg tgaagattga gccatgtgaa aaggttggga ttgttggcag aacaggtgca 4020
gggaagtcta cactgagcct ggcattattt agaatactag aacctaccga aggtaaaatt 4080
attattgacg gcattgatat atccgacata ggtctgttcg atttaagaag ccatttggca 4140
attattcctc aggatgcaca agcttttgaa ggtacagtaa agaccaattt ggaccctttc 4200
aatcgttatt cagaagatga acttaaaagg gctgttgagc aggcacattt aaagcctcat 4260
ctggaaaaaa tgctgcacag taaaccaaga ggtgatgatt ctaatgaaga ggatggcaat 4320
gttaatgata ttctggatgt caagattaat gagaacggta gtaacttgtc agtggggcaa 4380
agacaactac tatgtttggc aagagcgctg ctaaaccgtt ccaaaatatt ggtccttgat 4440
gaagcaacgg cttctgtgga tatggaaacc gataaaatta tccaagacac tataagaaga 4500
gaatttaagg accgtaccat cttaacaatt gcacatcgta tcgacactgt attggacagt 4560
gataagataa ttgttcttga ccagggtagt gtgagggaat tcgattcacc ctcgaaattg 4620
ttatccgata aaacgtctat tttttacagt ctttgtgaga aaggtgggta tttgaaataa 4680

<210> SEQ ID NO 21
<211> LENGTH: 4680
<212> TYPE: DNA
<213> ORGANISM: Artificial Sequence
<220> FEATURE:
<223> OTHER INFORMATION: Synthetic: nucleic acid sequence

<400> SEQUENCE: 21
atgtcttcac tagaagtggt agatgggtgc ccctatggat accgaccata tccagatagt 60
ggcacaaatg cattaaatcc atgttttata tcagtaatat ccgcctggca agccgtcttt 120
ttcctattga ttggtagcta tcaattgtgg aaactttata agaacaataa agtaccaccc 180

-continued

```
agatttaaga actttcctac attaccaagt aaaatcaaca gtcgacatct aacgcatttg    240
accaatgttt gctttcagtc cacgcttata atttgtgaac tggccttggt atcccaatct    300
agcgataggg tttatccatt tatactaaag aaggctctgt acttgaatct ccttttcaat    360
ttgggtattt ctctccctac tcaatactta gcttatttta aaagtacatt ttcaatgggc    420
aaccagcttt tctattacat gtttcaaatt cttctacagc tcttcttgat attgcagagg    480
tactatcatg gttctagtaa cgaaaggctt actgttatta gcggacaaac tgctatgatt    540
ttagaagtgc tccttctttt caattctgtg gcaattttta tttatgatct atgcattttt    600
gagccaatta acgaattatc tgaatactac aagaaaaatg ggtggtatcc ccccgttcat    660
gtactatcct atattacatt tatctggatg aacaaactga ttgtggaaac ttaccgtaac    720
aagaaaatca aagatcctaa ccagttacca ttgccgccag tagatctgaa tattaagtcg    780
ataagtaagg aatttaaggc taactgggaa ttggaaaaat ggttgaatag aaattctctt    840
tggagggcca tttggaagtc atttggtagg actatttctg tggctatgct gtatgaaacg    900
acatctgatt tactttctgt agtacagccc cagtttctac ggatattcat agatggtttg    960
aacccggaaa catcttctaa atatcctcct ttaaatggtg tatttattgc tctaaccctt   1020
ttcgtaatca gcgtggtttc tgtgttcctc accaatcaat tttatattgg aatttttgag   1080
gctggtttgg ggataagagg ctctttagct tctttagtgt atcagaagtc cttaagattg   1140
acgctagcag agcgtaacga aaaatctact ggtgacatct taaatttgat gtctgtggat   1200
gtgttaagga tccagcggtt tttcgaaaat gcccaaacca ttattggcgc tcctattcag   1260
attattgttg tattaacttc cctgtactgg ttgctaggaa aggctgttat tggagggttg   1320
gttactatgg ctattatgat gcctatcaat gccttcttat ctagaaaggt aaaaaagcta   1380
tcaaaaactc aaatgaagta taaggacatg agaatcaaga ctattacaga gcttttgaat   1440
gctataaaat ctattaaatt atacgcctgg gaggaaccta tgatggcaag attgaatcat   1500
gttcgtaatg atatggagtt gaaaaatttt cggaaaattg gtatagtgag caatctgata   1560
tattttgcgt ggaattgtgt acctttaatg gtgacatgtt ccacatttgg cttattttct   1620
ttatttagtg attctccgtt atctcctgcc attgtcttcc cttcattatc tttatttaat   1680
attttgaaca gtgccatcta ttccgttcca tccatgataa ataccattat agagacaagc   1740
gtttctatgg aaagattaaa gtcattccta cttagtgacg aaattgatga ttcgttcatc   1800
gaacgtattg atccttcagc ggatgaaaga gcgttacctg ctatagagat gaataatatt   1860
acatttttat ggaaatcaaa agaagtatta acatctagcc aatctggaga taatttgagg   1920
acagatgaag agtctattat cggatcttct caaattgcgt tgaagaatat cgatcatttt   1980
gaagcaaaaa ggggtgattt agtttgtgtt gttggtcggg taggagctgg taaatcaaca   2040
tttttgaagg caattcttgg tcaacttcct tgcatgagtg gttctaggga ctcgatacca   2100
cctaaactga tcattagatc atcgtctgta gcctactgtt cacaagaatc ctggataatg   2160
aacgcatctg taagagaaaa cattctattt ggtcacaagt tcgaccaaga ttattatgac   2220
ctcactatta aagcatgtca attgctaccc gatttgaaaa tactaccaga tggtgatgaa   2280
actttggtag gtgaaaaggg catttcccta tcaggcggtc agaaggcccg tctttcatta   2340
gccagagcgg tgtactcgag agcagatatt tatttgttgg atgacatttt atctgctgtt   2400
gatgcagaag ttagtaaaaa tattattgaa tatgttttga tcggaaagac ggctttatta   2460
aaaaataaaa caattatttt aactaccaat actgtatcaa ttttaaaaca ttcgcagatg   2520
atatatgcgc tagaaaacgg tgaaattgtt gaacaaggga attatgagga tgtaatgaac   2580
```

cgtaagaaca atacttcaaa actgaaaaaa ttactagagg aatttgattc tccgattgat 2640
aatggaaatg aaagcgatgt ccaaactgaa caccgatccg aaagtgaagt ggatgaacct 2700
ctgcagctta aagtaactga atcagaaact gaggatgagg ttgttactga gagtgaatta 2760
gaactaatca aagccaattc tagaagagct tctctagcta cgctaagacc tagacccttt 2820
gtgggagcac aattggattc cgtgaagaaa acggcgcaaa aggccgagaa gacagaggtg 2880
ggaagagtca aaacaaagat ttatcttgcg tatattaagg cttgtggagt tttaggtgtt 2940
gttttatttt tcttgtttat gatattaaca agggttttcg acttagcaga gaatttttgg 3000
ttaaagtact ggtcagaatc taatgaaaaa aatggttcaa atgaaagggt ttggatgttt 3060
gttggtgtgt attccttaat cggagtagca tcggccgcat tcaataattt acggagtatt 3120
atgatgctac tgtattgttc tattaggggt tctaagaaac tgcatgaaag catggccaaa 3180
tctgtaatta gaagtcctat gactttcttt gagactacac cagttggaag gatcataaac 3240
aggttctcat ctgatatgga tgcagtggac agtaatctac agtacatttt ctcctttttt 3300
ttcaaatcaa tactaaccta tttggttact gttatattag tcgggtacaa tatgccatgg 3360
tttttagtgt tcaatatgtt tttggtggtt atctatattt actatcaaac attttacatt 3420
gtgctatcta gggagctaaa aagattgatc agtatatctt actctccgat tatgtcctta 3480
atgagtgaga gcttgaacgg ttattctatt attgatgcat acgatcattt tgagagattc 3540
atctatctaa attatgaaaa aatccaatac aacgttgatt ttgtcttcaa ctttagatca 3600
acgaatagat ggttatccgt gagattgcaa actattggtg ctacaattgt tttggctact 3660
gcaatcttag cactagcaac aatgaatact aaaaggcaac taagttcggg tatggttggt 3720
ctactaatga gctattcatt agaggttaca ggttcattga cttggattgt aaggacaact 3780
gtgacgattg aaaccaacat tgtatcagtg gagagaattg ttgagtactg cgaattacca 3840
cctgaagcac agtccattaa ccctgaaaag aggccagatg aaaattggcc atcaaagggt 3900
ggtattgaat tcaaaaacta ttccacaaaa tacagagaaa atttggatcc agtgctgaat 3960
aatattaacg tgaagattga gccatgtgaa aaggttggga ttgttggcag aacaggtgca 4020
gggaagtcta cactgagcct ggcattattt agaatactag aacctaccga aggtaaaatt 4080
attattgacg gcattgatat atccgacata ggtctgttcg atttaagaag ccatttggca 4140
attattcctc aggatgcaca agcttttgaa ggtacagtaa agaccaattt ggaccctttc 4200
aatcgttatt cagaagatga acttaaaagg gctgttgagc aggcacattt aaagcctcat 4260
ctggaaaaaa tgctgcacag taaaccaaga ggtgatgatt ctaatgaaga ggatggcaat 4320
gttaatgata ttctggatgt caagattaat gagaacggta gtaacttgtc agtggggcaa 4380
agacaactac tatgtttggc aagagcgctg ctaaaccgtt ccaaaatatt ggtccttgat 4440
gaagcaacgg cttctgtgga tatggaaacc gataaaatta tccaagacac tataagaaga 4500
gaatttaagg accgtaccat cttaacaatt gcacatcgta tcgacactgt attggacagt 4560
gataagataa ttgttcttga ccagggtagt gtgagggaat tcgattcacc ctcgaaattg 4620
ttatccgata aaacgtctat tttttacagt ctttgtgaga aaggtgggta tttgaaataa 4680

<210> SEQ ID NO 22
<211> LENGTH: 4680
<212> TYPE: DNA
<213> ORGANISM: Artificial Sequence
<220> FEATURE:
<223> OTHER INFORMATION: Synthetic: nucleic acid sequence

<400> SEQUENCE: 22

```
atgtcttcac tagaagtggt agatgggtgc ccctatggat accgaccata tccagatagt     60
ggcacaaatg cattaaatcc atgttttata tcagtaatat ccgcctggca agccgtcttt    120
ttcctattga ttggtagcta tcaattgtgg aaactttata agaacaataa agtaccaccc    180
agatttaaga actttcctac attaccaagt aaaatcaaca gtcgacatct aacgcatttg    240
accaatgttt gctttcagtc cacgcttata atttgtgaac tggccttggt atcccaatct    300
agcgataggg tttatccatt tatactaaag aaggctctgt acttgaatct ccttttcaat    360
ttgggtattt ctctccctac tcaatactta gcttatttta aaagtacatt ttcaatgggc    420
aaccagcttt tctattacat gtttcaaatt cttctacagc tcttcttgat attgcagagg    480
tactatcatg gttctagtaa cgaaaggctt actgttatta gcggacaaac tgctatgatt    540
ttagaagtgc tccttctttt caattctgtg gcaattttta tttatgatct atgcattttt    600
gagccaatta acgaattatc tgaatactac aagaaaaatg ggtggtatcc ccccgttcat    660
gtactatcct atattacatt tatctggatg aacaaactga ttgtggaaac ttaccgtaac    720
aagaaaatca aagatcctaa ccagttacca ttgccgccag tagatctgaa tattaagtcg    780
ataagtaagg aatttaaggc taactgggaa ttggaaaaat ggttgaatag aaattctctt    840
tggagggcca tttggaagtc atttggtagg actatttctg tggctatgct gtatgaaacg    900
acatctgatt tactttctgt agtacagccc cagtttctac ggatattcat agatggtttg    960
aacccggaaa catcttctaa atatcctcct ttaaatggtg tatttattgc tctaaccctt   1020
ttcgtaatca gcgtggtttc tgtgttcctc accaatcaat tttatattgg aatttttgag   1080
gctggtttgg ggataagagg ctctttagct tctttagtgt atcagaagtc cttaagattg   1140
acgctagcag agcgtaacga aaaatctact ggtgacatct taaatttgat gtctgtggat   1200
gtgttaagga tccagcggtt tttcgaaaat gcccaaacca ttattggcgc tcctattcag   1260
attattgttg tattaacttc cctgtactgg ttgctaggaa aggctgttat tggagggttg   1320
gttactatgg ctattatgat gcctatcaat gccttcttat ctagaaaggt aaaaaagcta   1380
tcaaaaactc aaatgaagta taaggacatg agaatcaaga ctattacaga gcttttgaat   1440
gctataaaat ctattaaatt atacgcctgg gaggaaccta tgatggcaag attgaatcat   1500
gttcgtaatg atatggagtt gaaaaatttt cggaaaattg gtatagtgag caatctgata   1560
tattttgcgt ggaattgtgt acctttaatg gtgacatgtt ccacatttgg cttattttct   1620
ttatttagtg attctccgtt atctcctgcc attgtcttcc cttcattatc tttatttaat   1680
attttgaaca gtgccatcta ttccgttcca tccatgataa ataccattat agagacaagc   1740
gtttctatgg aaagattaaa gtcattccta cttagtgacg aaattgatga ttcgttcatc   1800
gaacgtattg atccttcagc ggatgaaaga gcgttacctg ctatagagat gaataatatt   1860
acattttat ggaaatcaaa agaagtatta acatctagcc aatctggaga taatttgagg   1920
acagatgaag agtctattat cggatcttct caaattgcgt tgaagaatat cgatcatttt   1980
gaagcaaaaa ggggtgattt agtttgtgtt gttggtcggg taggagctgg taaatcaaca   2040
tttttgaagg caattcttgg tcaacttcct tgcatgagtg gttctaggga ctcgatacca   2100
cctaaactga tcattagatc atcgtctgta gcctactgtt cacaagaatc ctggataatg   2160
aacgcatctg taagagaaaa cattctattt ggtcacaagt tcgaccaaga ttattatgac   2220
ctcactatta aagcatgtca attgctaccc gatttgaaaa tactaccaga tggtgatgaa   2280
actttggtag gtgaaaaggg catttcccta tcaggcggtc agaaggcccg tctttcatta   2340
```

-continued

```
gccagagcgg tgtactcgag agcagatatt tatttgttgg atgacatttt atctgctgtt   2400
gatgcagaag ttagtaaaaa tattattgaa tatgttttga tcggaaagac ggctttatta   2460
aaaaataaaa caattatttt aactaccaat actgtatcaa ttttaaaaca ttcgcagatg   2520
atatatgcgc tagaaaacgg tgaaattgtt gaacaaggga attatgagga tgtaatgaac   2580
cgtaagaaca atacttcaaa actgaaaaaa ttactagagg aatttgattc tccgattgat   2640
aatggaaatg aaagcgatgt ccaaactgaa caccgatccg aaagtgaagt ggatgaacct   2700
ctgcagctta aagtaactga atcagaaact gaggatgagg ttgttactga gagtgaatta   2760
gaactaatca aagccaattc tagaagagct tctctagcta cgctaagacc tagacccttt   2820
gtgggagcac aattggattc cgtgaagaaa acggcgcaaa aggccgagaa gacagaggtg   2880
ggaagagtca aaacaaagat ttatcttgcg tatattaagg cttgtggagt tttaggtgtt   2940
gttttatttt tcttgtttat gatattaaca agggttttcg acttagcaga gaatttttgg   3000
ttaaagtact ggtcagaatc taatgaaaaa aatggttcaa atgaaagggt ttggatgttt   3060
gttggtgtgt attccttaat cggagtagca tcggccgcat tcaataattt acggagtatt   3120
atgatgctac tgtattgttc tattaggggt tctaagaaac tgcatgaaag catggccaaa   3180
tctgtaatta gaagtcctat gactttcttt gagactacac cagttggaag gatcataaac   3240
aggttctcat ctgatatgga tgcagtggac agtaatctac agtacatttt ctcctttttt   3300
ttcaaatcaa tactaaccta tttggttact gttatattag tcgggtacaa tatgccatgg   3360
tttttagtgt tcaatatgtt tttggtggtt atctatattt actatcaaac attttacatt   3420
gtgctatcta gggagctaaa aagattgatc agtatatctt actctccgat tatgtcctta   3480
atgagtgaga gcttgaacgg ttattctatt attgatgcat acgatcattt tgagagattc   3540
atctatctaa attatgaaaa aatccaatac aacgttgatt ttgtcttcaa ctttagatca   3600
acgaatagat ggttatccgt gagattgcaa actattggtg ctacaattgt tttggctact   3660
gcaatcttag cactagcaac aatgaatact aaaaggcaac taagttcggg tatggttggt   3720
ctactaatga gctattcatt agaggttaca ggttcattga cttggattgt aaggacaact   3780
gtgacgattg aaaccaacat tgtatcagtg gagagaattg ttgagtactg cgaattacca   3840
cctgaagcac agtccattaa ccctgaaaag aggccagatg aaaattggcc atcaaagggt   3900
ggtattgaat tcaaaaacta ttccacaaaa tacagagaaa atttggatcc agtgctgaat   3960
aatattaacg tgaagattga gccatgtgaa aaggttggga ttgttggcag aacaggtgca   4020
gggaagtcta cactgagcct ggcattattt agaatactag aacctaccga aggtaaaatt   4080
attattgacg gcattgatat atccgacata ggtctgttcg atttaagaag ccatttggca   4140
attattcctc aggatgcaca agcttttgaa ggtacagtaa agaccaattt ggaccctttc   4200
aatcgttatt cagaagatga acttaaaagg gctgttgagc aggcacattt aaagcctcat   4260
ctggaaaaaa tgctgcacag taaaccaaga ggtgatgatt ctaatgaaga ggatggcaat   4320
gttaatgata ttctggatgt caagattaat gagaacggta gtaacttgtc agtggggcaa   4380
agacaactac tatgtttggc aagagcgctg ctaaaccgtt ccaaaatatt ggtccttgat   4440
gaagcaacgg cttctgtgga tatggaaacc gataaaatta tccaagacac tataagaaga   4500
gaatttaagg accgtaccat cttaacaatt gcacatcgta tcgacactgt attggacagt   4560
gataagataa ttgttcttga ccagggtagt gtgagggaat tcgattcacc ctcgaaattg   4620
ttatccgata aaacgtctat tttttacagt ctttgtgaga aaggtgggta tttgaaataa   4680
```

<210> SEQ ID NO 23
<211> LENGTH: 4680
<212> TYPE: DNA
<213> ORGANISM: Artificial Sequence
<220> FEATURE:
<223> OTHER INFORMATION: Synthetic: nucleic acid sequence

<400> SEQUENCE: 23
atgtcttcac tagaagtggt agatgggtgc ccctatggat accgaccata tccagatagt 60
ggcacaaatg cattaaatcc atgttttata tcagtaatat ccgcctggca agccgtcttt 120
ttcctattga ttggtagcta tcaattgtgg aaactttata agaacaataa agtaccaccc 180
agatttaaga actttcctac attaccaagt aaaatcaaca gtcgacatct aacgcatttg 240
accaatgttt gctttcagtc cacgcttata atttgtgaac tggccttggt atcccaatct 300
agcgataggg tttatccatt tatactaaag aaggctctgt acttgaatct ccttttcaat 360
ttgggtattt ctctccctac tcaatactta gcttatttta aaagtacatt ttcaatgggc 420
aaccagcttt tctattacat gtttcaaatt cttctacagc tcttcttgat attgcagagg 480
tactatcatg gttctagtaa cgaaaggctt actgttatta gcggacaaac tgctatgatt 540
ttagaagtgc tccttctttt caattctgtg gcaattttta tttatgatct atgcattttt 600
gagccaatta acgaattatc tgaatactac aagaaaaatg ggtggtatcc ccccgttcat 660
gtactatcct atattacatt tatctggatg aacaaactga ttgtggaaac ttaccgtaac 720
aagaaaatca aagatcctaa ccagttacca ttgccgccag tagatctgaa tattaagtcg 780
ataagtaagg aatttaaggc taactgggaa ttggaaaaat ggttgaatag aaattctctt 840
tggagggcca tttggaagtc atttggtagg actatttctg tggctatgct gtatgaaacg 900
acatctgatt tactttctgt agtacagccc cagtttctac ggatattcat agatggtttg 960
aacccggaaa catcttctaa atatcctcct ttaaatggtg tatttattgc tctaaccctt 1020
ttcgtaatca gcgtggtttc tgtgttcctc accaatcaat tttatattgg aatttttgag 1080
gctggtttgg ggataagagg ctctttagct tctttagtgt atcagaagtc cttaagattg 1140
acgctagcag agcgtaacga aaaatctact ggtgacatct taaatttgat gtctgtggat 1200
gtgttaagga tccagcggtt tttcgaaaat gcccaaacca ttattggcgc tcctattcag 1260
attattgttg tattaacttc cctgtactgg ttgctaggaa aggctgttat tggagggttg 1320
gttactatgg ctattatgat gcctatcaat gccttcttat ctagaaaggt aaaaaagcta 1380
tcaaaaactc aaatgaagta taaggacatg agaatcaaga ctattacaga gcttttgaat 1440
gctataaaat ctattaaatt atacgcctgg gaggaaccta tgatggcaag attgaatcat 1500
gttcgtaatg atatggagtt gaaaaatttt cggaaaattg gtatagtgag caatctgata 1560
tattttgcgt ggaattgtgt acctttaatg gtgacatgtt ccacatttgg cttattttct 1620
ttatttagtg attctccgtt atctcctgcc attgtcttcc cttcattatc tttatttaat 1680
attttgaaca gtgccatcta ttccgttcca tccatgataa ataccattat agagacaagc 1740
gtttctatgg aaagattaaa gtcattccta cttagtgacg aaattgatga ttcgttcatc 1800
gaacgtattg atccttcagc ggatgaaaga gcgttacctg ctatagagat gaataatatt 1860
acatttttat ggaaatcaaa agaagtatta acatctagcc aatctggaga taatttgagg 1920
acagatgaag agtctattat cggatcttct caaattgcgt tgaagaatat cgatcatttt 1980
gaagcaaaaa ggggtgattt agtttgtgtt gttggtcggg taggagctgg taaatcaaca 2040
tttttgaagg caattcttgg tcaacttcct tgcatgagtg gttctaggga ctcgatacca 2100

-continued

```
cctaaactga tcattagatc atcgtctgta gcctactgtt cacaagaatc ctggataatg   2160
aacgcatctg taagagaaaa cattctattt ggtcacaagt tcgaccaaga ttattatgac   2220
ctcactatta aagcatgtca attgctaccc gatttgaaaa tactaccaga tggtgatgaa   2280
actttggtag gtgaaaaggg catttcccta tcaggcggtc agaaggcccg tctttcatta   2340
gccagagcgg tgtactcgag agcagatatt tatttgttgg atgacatttt atctgctgtt   2400
gatgcagaag ttagtaaaaa tattattgaa tatgttttga tcggaaagac ggctttatta   2460
aaaaataaaa caattatttt aactaccaat actgtatcaa ttttaaaaca ttcgcagatg   2520
atatatgcgc tagaaaacgg tgaaattgtt gaacaaggga attatgagga tgtaatgaac   2580
cgtaagaaca atacttcaaa actgaaaaaa ttactagagg aatttgattc tccgattgat   2640
aatggaaatg aaagcgatgt ccaaactgaa caccgatccg aaagtgaagt ggatgaacct   2700
ctgcagctta aagtaactga atcagaaact gaggatgagg ttgttactga gagtgaatta   2760
gaactaatca aagccaattc tagaagagct tctctagcta cgctaagacc tagacccttt   2820
gtgggagcac aattggattc cgtgaagaaa acggcgcaaa aggccgagaa gacagaggtg   2880
ggaagagtca aaacaaagat ttatcttgcg tatattaagg cttgtggagt tttaggtgtt   2940
gttttatttt tcttgtttat gatattaaca agggttttcg acttagcaga gaatttttgg   3000
ttaaagtact ggtcagaatc taatgaaaaa aatggttcaa atgaaagggt ttggatgttt   3060
gttggtgtgt attccttaat cggagtagca tcggccgcat tcaataattt acggagtatt   3120
atgatgctac tgtattgttc tattaggggt tctaagaaac tgcatgaaag catggccaaa   3180
tctgtaatta gaagtcctat gactttcttt gagactacac cagttggaag gatcataaac   3240
aggttctcat ctgatatgga tgcagtggac agtaatctac agtacatttt ctcctttttt   3300
ttcaaatcaa tactaaccta tttggttact gttatattag tcgggtacaa tatgccatgg   3360
tttttagtgt tcaatatgtt tttggtggtt atctatattt actatcaaac attttacatt   3420
gtgctatcta gggagctaaa aagattgatc agtatatctt actctccgat tatgtcctta   3480
atgagtgaga gcttgaacgg ttattctatt attgatgcat acgatcattt tgagagattc   3540
atctatctaa attatgaaaa aatccaatac aacgttgatt ttgtcttcaa ctttagatca   3600
acgaatagat ggttatccgt gagattgcaa actattggtg ctacaattgt tttggctact   3660
gcaatcttag cactagcaac aatgaatact aaaaggcaac taagttcggg tatggttggt   3720
ctactaatga gctattcatt agaggttaca ggttcattga cttggattgt aaggacaact   3780
gtgacgattg aaaccaacat tgtatcagtg gagagaattg ttgagtactg cgaattacca   3840
cctgaagcac agtccattaa ccctgaaaag aggccagatg aaaattggcc atcaaagggt   3900
ggtattgaat tcaaaaacta ttccacaaaa tacagagaaa atttggatcc agtgctgaat   3960
aatattaacg tgaagattga gccatgtgaa aaggttggga ttgttggcag aacaggtgca   4020
gggaagtcta cactgagcct ggcattattt agaatactag aacctaccga aggtaaaatt   4080
attattgacg gcattgatat atccgacata ggtctgttcg atttaagaag ccatttggca   4140
attattcctc aggatgcaca agcttttgaa ggtacagtaa agaccaattt ggaccctttc   4200
aatcgttatt cagaagatga acttaaaagg gctgttgagc aggcacattt aaagcctcat   4260
ctggaaaaaa tgctgcacag taaaccaaga ggtgatgatt ctaatgaaga ggatggcaat   4320
gttaatgata ttctggatgt caagattaat gagaacggta gtaacttgtc agtggggcaa   4380
agacaactac tatgtttggc aagagcgctg ctaaaccgtt ccaaaatatt ggtccttgat   4440
```

gaagcaacgg cttctgtgga tatggaaacc gataaaatta tccaagacac tataagaaga 4500
gaatttaagg accgtaccat cttaacaatt gcacatcgta tcgacactgt attggacagt 4560
gataagataa ttgttcttga ccagggtagt gtgagggaat tcgattcacc ctcgaaattg 4620
ttatccgata aaacgtctat tttttacagt ctttgtgaga aaggtgggta tttgaaataa 4680

<210> SEQ ID NO 24
<211> LENGTH: 4680
<212> TYPE: DNA
<213> ORGANISM: Artificial Sequence
<220> FEATURE:
<223> OTHER INFORMATION: Synthetic: nucleic acid sequence

<400> SEQUENCE: 24
atgtcttcac tagaagtggt agatgggtgc ccctatggat accgaccata tccagatagt 60
ggcacaaatg cattaaatcc atgttttata tcagtaatat ccgcctggca agccgtcttt 120
ttcctattga ttggtagcta tcaattgtgg aaactttata agaacaataa agtaccaccc 180
agatttaaga actttcctac attaccaagt aaaatcaaca gtcgacatct aacgcatttg 240
accaatgttt gctttcagtc cacgcttata atttgtgaac tggccttggt atcccaatct 300
agcgataggg tttatccatt tatactaaag aaggctctgt acttgaatct ccttttcaat 360
ttgggtattt ctctccctac tcaatactta gcttatttta aaagtacatt ttcaatgggc 420
aaccagcttt tctattacat gtttcaaatt cttctacagc tcttcttgat attgcagagg 480
tactatcatg gttctagtaa cgaaaggctt actgttatta gcggacaaac tgctatgatt 540
ttagaagtgc tccttctttt caattctgtg gcaattttta tttatgatct atgcattttt 600
gagccaatta acgaattatc tgaatactac aagaaaaatg ggtggtatcc ccccgttcat 660
gtactatcct atattacatt tatctggatg aacaaactga ttgtggaaac ttaccgtaac 720
aagaaaatca aagatcctaa ccagttacca ttgccgccag tagatctgaa tattaagtcg 780
ataagtaagg aatttaaggc taactgggaa ttggaaaaat ggttgaatag aaattctctt 840
tggagggcca tttggaagtc atttggtagg actatttctg tggctatgct gtatgaaacg 900
acatctgatt tactttctgt agtacagccc cagtttctac ggatattcat agatggtttg 960
aacccggaaa catcttctaa atatcctcct ttaaatggtg tatttattgc tctaaccctt 1020
ttcgtaatca gcgtggtttc tgtgttcctc accaatcaat tttatattgg aatttttgag 1080
gctggtttgg ggataagagg ctctttagct tctttagtgt atcagaagtc cttaagattg 1140
acgctagcag agcgtaacga aaaatctact ggtgacatct taaatttgat gtctgtggat 1200
gtgttaagga tccagcggtt tttcgaaaat gcccaaacca ttattggcgc tcctattcag 1260
attattgttg tattaacttc cctgtactgg ttgctaggaa aggctgttat tggagggttg 1320
gttactatgg ctattatgat gcctatcaat gccttcttat ctagaaaggt aaaaaagcta 1380
tcaaaaactc aaatgaagta taaggacatg agaatcaaga ctattacaga gcttttgaat 1440
gctataaaat ctattaaatt atacgcctgg gaggaaccta tgatggcaag attgaatcat 1500
gttcgtaatg atatggagtt gaaaaatttt cggaaaattg gtatagtgag caatctgata 1560
tattttgcgt ggaattgtgt acctttaatg gtgacatgtt ccacatttgg cttattttct 1620
ttatttagtg attctccgtt atctcctgcc attgtcttcc cttcattatc tttatttaat 1680
attttgaaca gtgccatcta ttccgttcca tccatgataa ataccattat agagacaagc 1740
gtttctatgg aaagattaaa gtcattccta cttagtgacg aaattgatga ttcgttcatc 1800
gaacgtattg atccttcagc ggatgaaaga gcgttacctg ctatagagat gaataatatt 1860

-continued

```
acatttttat ggaaatcaaa agaagtatta acatctagcc aatctggaga taatttgagg   1920
acagatgaag agtctattat cggatcttct caaattgcgt tgaagaatat cgatcatttt   1980
gaagcaaaaa ggggtgattt agtttgtgtt gttggtcggg taggagctgg taaatcaaca   2040
tttttgaagg caattcttgg tcaacttcct tgcatgagtg gttctaggga ctcgatacca   2100
cctaaactga tcattagatc atcgtctgta gcctactgtt cacaagaatc ctggataatg   2160
aacgcatctg taagagaaaa cattctattt ggtcacaagt tcgaccaaga ttattatgac   2220
ctcactatta aagcatgtca attgctaccc gatttgaaaa tactaccaga tggtgatgaa   2280
actttggtag gtgaaaaggg catttcccta tcaggcggtc agaaggcccg tctttcatta   2340
gccagagcgg tgtactcgag agcagatatt tatttgttgg atgacatttt atctgctgtt   2400
gatgcagaag ttagtaaaaa tattattgaa tatgttttga tcggaaagac ggctttatta   2460
aaaaataaaa caattatttt aactaccaat actgtatcaa ttttaaaaca ttcgcagatg   2520
atatatgcgc tagaaaacgg tgaaattgtt gaacaaggga attatgagga tgtaatgaac   2580
cgtaagaaca atacttcaaa actgaaaaaa ttactagagg aatttgattc tccgattgat   2640
aatggaaatg aaagcgatgt ccaaactgaa caccgatccg aaagtgaagt ggatgaacct   2700
ctgcagctta aagtaactga atcagaaact gaggatgagg ttgttactga gagtgaatta   2760
gaactaatca aagccaattc tagaagagct tctctagcta cgctaagacc tagacccttt   2820
gtgggagcac aattggattc cgtgaagaaa acggcgcaaa aggccgagaa gacagaggtg   2880
ggaagagtca aaacaaagat ttatcttgcg tatattaagg cttgtggagt tttaggtgtt   2940
gttttatttt tcttgtttat gatattaaca agggttttcg acttagcaga gaatttttgg   3000
ttaaagtact ggtcagaatc taatgaaaaa aatggttcaa atgaaagggt ttggatgttt   3060
gttggtgtgt attccttaat cggagtagca tcggccgcat tcaataattt acggagtatt   3120
atgatgctac tgtattgttc tattaggggt tctaagaaac tgcatgaaag catggccaaa   3180
tctgtaatta gaagtcctat gactttcttt gagactacac cagttggaag gatcataaac   3240
aggttctcat ctgatatgga tgcagtggac agtaatctac agtacatttt ctcctttttt   3300
ttcaaatcaa tactaaccta tttggttact gttatattag tcgggtacaa tatgccatgg   3360
tttttagtgt tcaatatgtt tttggtggtt atctatattt actatcaaac attttacatt   3420
gtgctatcta gggagctaaa aagattgatc agtatatctt actctccgat tatgtcctta   3480
atgagtgaga gcttgaacgg ttattctatt attgatgcat acgatcattt tgagagattc   3540
atctatctaa attatgaaaa aatccaatac aacgttgatt ttgtcttcaa ctttagatca   3600
acgaatagat ggttatccgt gagattgcaa actattggtg ctacaattgt tttggctact   3660
gcaatcttag cactagcaac aatgaatact aaaaggcaac taagttcggg tatggttggt   3720
ctactaatga gctattcatt agaggttaca ggttcattga cttggattgt aaggacaact   3780
gtgacgattg aaaccaacat tgtatcagtg gagagaattg ttgagtactg cgaattacca   3840
cctgaagcac agtccattaa ccctgaaaag aggccagatg aaaattggcc atcaaagggt   3900
ggtattgaat tcaaaaacta ttccacaaaa tacagagaaa atttggatcc agtgctgaat   3960
aatattaacg tgaagattga gccatgtgaa aaggttggga ttgttggcag aacaggtgca   4020
gggaagtcta cactgagcct ggcattattt agaatactag aacctaccga aggtaaaatt   4080
attattgacg gcattgatat atccgacata ggtctgttcg atttaagaag ccatttggca   4140
attattcctc aggatgcaca agcttttgaa ggtacagtaa agaccaattt ggaccctttc   4200
```

-continued

```
aatcgttatt cagaagatga acttaaaagg gctgttgagc aggcacattt aaagcctcat   4260
ctggaaaaaa tgctgcacag taaaccaaga ggtgatgatt ctaatgaaga ggatggcaat   4320
gttaatgata ttctggatgt caagattaat gagaacggta gtaacttgtc agtggggcaa   4380
agacaactac tatgtttggc aagagcgctg ctaaaccgtt ccaaaatatt ggtccttgat   4440
gaagcaacgg cttctgtgga tatggaaacc gataaaatta tccaagacac tataagaaga   4500
gaatttaagg accgtaccat cttaacaatt gcacatcgta tcgacactgt attggacagt   4560
gataagataa ttgttcttga ccagggtagt gtgagggaat tcgattcacc ctcgaaattg   4620
ttatccgata aaacgtctat tttttacagt ctttgtgaga aaggtgggta tttgaaataa   4680
```

<210> SEQ ID NO 25
<211> LENGTH: 4680
<212> TYPE: DNA
<213> ORGANISM: Artificial Sequence
<220> FEATURE:
<223> OTHER INFORMATION: Synthetic: nucleic acid sequence

<400> SEQUENCE: 25

```
atgtcttcac tagaagtggt agatgggtgc ccctatggat accgaccata tccagatagt     60
ggcacaaatg cattaaatcc atgttttata tcagtaatat ccgcctggca agccgtcttt    120
ttcctattga ttggtagcta tcaattgtgg aaactttata agaacaataa agtaccaccc    180
agatttaaga actttcctac attaccaagt aaaatcaaca gtcgacatct aacgcatttg    240
accaatgttt gctttcagtc cacgcttata atttgtgaac tggccttggt atcccaatct    300
agcgataggg tttatccatt tatactaaag aaggctctgt acttgaatct ccttttcaat    360
ttgggtattt ctctccctac tcaatactta gcttatttta aaagtacatt ttcaatgggc    420
aaccagcttt tctattacat gtttcaaatt cttctacagc tcttcttgat attgcagagg    480
tactatcatg gttctagtaa cgaaaggctt actgttatta gcggacaaac tgctatgatt    540
ttagaagtgc tccttctttt caattctgtg gcaattttta tttatgatct atgcattttt    600
gagccaatta acgaattatc tgaatactac aagaaaaatg ggtggtatcc ccccgttcat    660
gtactatcct atattacatt tatctggatg aacaaactga ttgtggaaac ttaccgtaac    720
aagaaaatca aagatcctaa ccagttacca ttgccgccag tagatctgaa tattaagtcg    780
ataagtaagg aatttaaggc taactgggaa ttggaaaaat ggttgaatag aaattctctt    840
tggagggcca tttggaagtc atttggtagg actatttctg tggctatgct gtatgaaacg    900
acatctgatt tactttctgt agtacagccc cagtttctac ggatattcat agatggtttg    960
aacccggaaa catcttctaa atatcctcct ttaaatggtg tatttattgc tctaaccctt   1020
ttcgtaatca gcgtggtttc tgtgttcctc accaatcaat tttatattgg aatttttgag   1080
gctggtttgg ggataagagg ctctttagct tctttagtgt atcagaagtc cttaagattg   1140
acgctagcag agcgtaacga aaaatctact ggtgacatct taaatttgat gtctgtggat   1200
gtgttaagga tccagcggtt tttcgaaaat gcccaaacca ttattggcgc tcctattcag   1260
attattgttg tattaacttc cctgtactgg ttgctaggaa aggctgttat tggagggttg   1320
gttactatgg ctattatgat gcctatcaat gccttcttat ctagaaaggt aaaaaagcta   1380
tcaaaaactc aaatgaagta taaggacatg agaatcaaga ctattacaga gcttttgaat   1440
gctataaaat ctattaaatt atacgcctgg gaggaaccta tgatggcaag attgaatcat   1500
gttcgtaatg atatggagtt gaaaaatttt cggaaaattg gtatagtgag caatctgata   1560
tattttgcgt ggaattgtgt acctttaatg gtgacatgtt ccacatttgg cttattttct   1620
```

-continued

```
ttatttagtg attctccgtt atctcctgcc attgtcttcc cttcattatc tttatttaat   1680
attttgaaca gtgccatcta ttccgttcca tccatgataa ataccattat agagacaagc   1740
gtttctatgg aaagattaaa gtcattccta cttagtgacg aaattgatga ttcgttcatc   1800
gaacgtattg atccttcagc ggatgaaaga gcgttacctg ctatagagat gaataatatt   1860
acatttttat ggaaatcaaa agaagtatta acatctagcc aatctggaga taatttgagg   1920
acagatgaag agtctattat cggatcttct caaattgcgt tgaagaatat cgatcatttt   1980
gaagcaaaaa ggggtgattt agtttgtgtt gttggtcggg taggagctgg taaatcaaca   2040
tttttgaagg caattcttgg tcaacttcct tgcatgagtg gttctaggga ctcgatacca   2100
cctaaactga tcattagatc atcgtctgta gcctactgtt cacaagaatc ctggataatg   2160
aacgcatctg taagagaaaa cattctattt ggtcacaagt tcgaccaaga ttattatgac   2220
ctcactatta aagcatgtca attgctaccc gatttgaaaa tactaccaga tggtgatgaa   2280
actttggtag gtgaaaaggg catttcccta tcaggcggtc agaaggcccg tctttcatta   2340
gccagagcgg tgtactcgag agcagatatt tatttgttgg atgacatttt atctgctgtt   2400
gatgcagaag ttagtaaaaa tattattgaa tatgttttga tcggaaagac ggctttatta   2460
aaaaataaaa caattatttt aactaccaat actgtatcaa ttttaaaaca ttcgcagatg   2520
atatatgcgc tagaaaacgg tgaaattgtt gaacaaggga attatgagga tgtaatgaac   2580
cgtaagaaca atacttcaaa actgaaaaaa ttactagagg aatttgattc tccgattgat   2640
aatggaaatg aaagcgatgt ccaaactgaa caccgatccg aaagtgaagt ggatgaacct   2700
ctgcagctta aagtaactga atcagaaact gaggatgagg ttgttactga gagtgaatta   2760
gaactaatca aagccaattc tagaagagct tctctagcta cgctaagacc tagacccttt   2820
gtgggagcac aattggattc cgtgaagaaa acggcgcaaa aggccgagaa gacagaggtg   2880
ggaagagtca aaacaaagat ttatcttgcg tatattaagg cttgtggagt tttaggtgtt   2940
gttttatttt tcttgtttat gatattaaca agggttttcg acttagcaga gaatttttgg   3000
ttaaagtact ggtcagaatc taatgaaaaa aatggttcaa atgaaagggt ttggatgttt   3060
gttggtgtgt attccttaat cggagtagca tcggccgcat tcaataattt acggagtatt   3120
atgatgctac tgtattgttc tattaggggt tctaagaaac tgcatgaaag catggccaaa   3180
tctgtaatta gaagtcctat gactttcttt gagactacac cagttggaag gatcataaac   3240
aggttctcat ctgatatgga tgcagtggac agtaatctac agtacatttt ctccttttt   3300
ttcaaatcaa tactaaccta tttggttact gttatattag tcgggtacaa tatgccatgg   3360
tttttagtgt tcaatatgtt tttggtggtt atctatattt actatcaaac attttacatt   3420
gtgctatcta gggagctaaa aagattgatc agtatatctt actctccgat tatgtcctta   3480
atgagtgaga gcttgaacgg ttattctatt attgatgcat acgatcattt tgagagattc   3540
atctatctaa attatgaaaa aatccaatac aacgttgatt ttgtcttcaa ctttagatca   3600
acgaatagat ggttatccgt gagattgcaa actattggtg ctacaattgt tttggctact   3660
gcaatcttag cactagcaac aatgaatact aaaaggcaac taagttcggg tatggttggt   3720
ctactaatga gctattcatt agaggttaca ggttcattga cttggattgt aaggacaact   3780
gtgacgattg aaaccaacat tgtatcagtg gagagaattg ttgagtactg cgaattacca   3840
cctgaagcac agtccattaa ccctgaaaag aggccagatg aaaattggcc atcaaagggt   3900
ggtattgaat tcaaaaacta ttccacaaaa tacagagaaa atttggatcc agtgctgaat   3960
```

aatattaacg tgaagattga gccatgtgaa aaggttggga ttgttggcag aacaggtgca 4020
gggaagtcta cactgagcct ggcattattt agaatactag aacctaccga aggtaaaatt 4080
attattgacg gcattgatat atccgacata ggtctgttcg atttaagaag ccatttggca 4140
attattcctc aggatgcaca agcttttgaa ggtacagtaa agaccaattt ggaccctttc 4200
aatcgttatt cagaagatga acttaaaagg gctgttgagc aggcacattt aaagcctcat 4260
ctggaaaaaa tgctgcacag taaaccaaga ggtgatgatt ctaatgaaga ggatggcaat 4320
gttaatgata ttctggatgt caagattaat gagaacggta gtaacttgtc agtggggcaa 4380
agacaactac tatgtttggc aagagcgctg ctaaaccgtt ccaaaatatt ggtccttgat 4440
gaagcaacgg cttctgtgga tatggaaacc gataaaatta tccaagacac tataagaaga 4500
gaatttaagg accgtaccat cttaacaatt gcacatcgta tcgacactgt attggacagt 4560
gataagataa ttgttcttga ccagggtagt gtgagggaat tcgattcacc ctcgaaattg 4620
ttatccgata aaacgtctat tttttacagt ctttgtgaga aaggtgggta tttgaaataa 4680

<210> SEQ ID NO 26
<211> LENGTH: 4680
<212> TYPE: DNA
<213> ORGANISM: Artificial Sequence
<220> FEATURE:
<223> OTHER INFORMATION: Synthetic: nucleic acid sequence

<400> SEQUENCE: 26
atgtcttcac tagaagtggt agatgggtgc ccctatggat accgaccata tccagatagt 60
ggcacaaatg cattaaatcc atgttttata tcagtaatat ccgcctggca agccgtcttt 120
ttcctattga ttggtagcta tcaattgtgg aaactttata agaacaataa agtaccaccc 180
agatttaaga actttcctac attaccaagt aaaatcaaca gtcgacatct aacgcatttg 240
accaatgttt gctttcagtc cacgcttata atttgtgaac tggccttggt atcccaatct 300
agcgataggg tttatccatt tatactaaag aaggctctgt acttgaatct ccttttcaat 360
ttgggtattt ctctccctac tcaatactta gcttatttta aaagtacatt ttcaatgggc 420
aaccagcttt tctattacat gtttcaaatt cttctacagc tcttcttgat attgcagagg 480
tactatcatg gttctagtaa cgaaaggctt actgttatta gcggacaaac tgctatgatt 540
ttagaagtgc tccttctttt caattctgtg gcaattttta tttatgatct atgcattttt 600
gagccaatta acgaattatc tgaatactac aagaaaaatg ggtggtatcc ccccgttcat 660
gtactatcct atattacatt tatctggatg aacaaactga ttgtggaaac ttaccgtaac 720
aagaaaatca aagatcctaa ccagttacca ttgccgccag tagatctgaa tattaagtcg 780
ataagtaagg aatttaaggc taactgggaa ttggaaaaat ggttgaatag aaattctctt 840
tggagggcca tttggaagtc atttggtagg actatttctg tggctatgct gtatgaaacg 900
acatctgatt tactttctgt agtacagccc cagtttctac ggatattcat agatggtttg 960
aacccggaaa catcttctaa atatcctcct ttaaatggtg tatttattgc tctaaccctt 1020
ttcgtaatca gcgtggtttc tgtgttcctc accaatcaat tttatattgg aatttttgag 1080
gctggtttgg ggataagagg ctctttagct tctttagtgt atcagaagtc cttaagattg 1140
acgctagcag agcgtaacga aaaatctact ggtgacatct taaatttgat gtctgtggat 1200
gtgttaagga tccagcggtt tttcgaaaat gcccaaacca ttattggcgc tcctattcag 1260
attattgttg tattaacttc cctgtactgg ttgctaggaa aggctgttat tggagggttg 1320
gttactatgg ctattatgat gcctatcaat gccttcttat ctagaaaggt aaaaaagcta 1380

-continued

```
tcaaaaactc aaatgaagta taaggacatg agaatcaaga ctattacaga gcttttgaat   1440
gctataaaat ctattaaatt atacgcctgg gaggaaccta tgatggcaag attgaatcat   1500
gttcgtaatg atatggagtt gaaaaatttt cggaaaattg gtatagtgag caatctgata   1560
tattttgcgt ggaattgtgt acctttaatg gtgacatgtt ccacatttgg cttattttct   1620
ttatttagtg attctccgtt atctcctgcc attgtcttcc cttcattatc tttatttaat   1680
attttgaaca gtgccatcta ttccgttcca tccatgataa ataccattat agagacaagc   1740
gtttctatgg aaagattaaa gtcattccta cttagtgacg aaattgatga ttcgttcatc   1800
gaacgtattg atccttcagc ggatgaaaga gcgttacctg ctatagagat gaataatatt   1860
acatttttat ggaaatcaaa agaagtatta acatctagcc aatctggaga taatttgagg   1920
acagatgaag agtctattat cggatcttct caaattgcgt tgaagaatat cgatcatttt   1980
gaagcaaaaa ggggtgattt agtttgtgtt gttggtcggg taggagctgg taaatcaaca   2040
tttttgaagg caattcttgg tcaacttcct tgcatgagtg gttctaggga ctcgatacca   2100
cctaaactga tcattagatc atcgtctgta gcctactgtt cacaagaatc ctggataatg   2160
aacgcatctg taagagaaaa cattctattt ggtcacaagt tcgaccaaga ttattatgac   2220
ctcactatta aagcatgtca attgctaccc gatttgaaaa tactaccaga tggtgatgaa   2280
actttggtag gtgaaaaggg catttcccta tcaggcggtc agaaggcccg tctttcatta   2340
gccagagcgg tgtactcgag agcagatatt tatttgttgg atgacatttt atctgctgtt   2400
gatgcagaag ttagtaaaaa tattattgaa tatgttttga tcggaaagac ggctttatta   2460
aaaaataaaa caattatttt aactaccaat actgtatcaa ttttaaaaca ttcgcagatg   2520
atatatgcgc tagaaaacgg tgaaattgtt gaacaaggga attatgagga tgtaatgaac   2580
cgtaagaaca atacttcaaa actgaaaaaa ttactagagg aatttgattc tccgattgat   2640
aatggaaatg aaagcgatgt ccaaactgaa caccgatccg aaagtgaagt ggatgaacct   2700
ctgcagctta aagtaactga atcagaaact gaggatgagg ttgttactga gagtgaatta   2760
gaactaatca aagccaattc tagaagagct tctctagcta cgctaagacc tagacccttt   2820
gtgggagcac aattggattc cgtgaagaaa acggcgcaaa aggccgagaa gacagaggtg   2880
ggaagagtca aaacaaagat ttatcttgcg tatattaagg cttgtggagt tttaggtgtt   2940
gttttatttt tcttgtttat gatattaaca agggttttcg acttagcaga gaatttttgg   3000
ttaaagtact ggtcagaatc taatgaaaaa aatggttcaa atgaaagggt ttggatgttt   3060
gttggtgtgt attccttaat cggagtagca tcggccgcat tcaataattt acggagtatt   3120
atgatgctac tgtattgttc tattaggggt tctaagaaac tgcatgaaag catggccaaa   3180
tctgtaatta gaagtcctat gactttcttt gagactacac cagttggaag gatcataaac   3240
aggttctcat ctgatatgga tgcagtggac agtaatctac agtacatttt ctcctttttt   3300
ttcaaatcaa tactaaccta tttggttact gttatattag tcgggtacaa tatgccatgg   3360
tttttagtgt tcaatatgtt tttggtggtt atctatattt actatcaaac attttacatt   3420
gtgctatcta gggagctaaa aagattgatc agtatatctt actctccgat tatgtcctta   3480
atgagtgaga gcttgaacgg ttattctatt attgatgcat acgatcattt tgagagattc   3540
atctatctaa attatgaaaa aatccaatac aacgttgatt ttgtcttcaa ctttagatca   3600
acgaatagat ggttatccgt gagattgcaa actattggtg ctacaattgt tttggctact   3660
gcaatcttag cactagcaac aatgaatact aaaaggcaac taagttcggg tatggttggt   3720
```

```
ctactaatga gctattcatt agaggttaca ggttcattga cttggattgt aaggacaact   3780

gtgacgattg aaaccaacat tgtatcagtg gagagaattg ttgagtactg cgaattacca   3840

cctgaagcac agtccattaa ccctgaaaag aggccagatg aaaattggcc atcaaagggt   3900

ggtattgaat tcaaaaacta ttccacaaaa tacagagaaa atttggatcc agtgctgaat   3960

aatattaacg tgaagattga gccatgtgaa aaggttggga ttgttggcag aacaggtgca   4020

gggaagtcta cactgagcct ggcattattt agaatactag aacctaccga aggtaaaatt   4080

attattgacg gcattgatat atccgacata ggtctgttcg atttaagaag ccatttggca   4140

attattcctc aggatgcaca agcttttgaa ggtacagtaa agaccaattt ggaccctttc   4200

aatcgttatt cagaagatga acttaaaagg gctgttgagc aggcacattt aaagcctcat   4260

ctggaaaaaa tgctgcacag taaaccaaga ggtgatgatt ctaatgaaga ggatggcaat   4320

gttaatgata ttctggatgt caagattaat gagaacggta gtaacttgtc agtggggcaa   4380

agacaactac tatgtttggc aagagcgctg ctaaaccgtt ccaaaatatt ggtccttgat   4440

gaagcaacgg cttctgtgga tatggaaacc gataaaatta tccaagacac tataagaaga   4500

gaatttaagg accgtaccat cttaacaatt gcacatcgta tcgacactgt attggacagt   4560

gataagataa ttgttcttga ccagggtagt gtgagggaat tcgattcacc ctcgaaattg   4620

ttatccgata aaacgtctat tttttacagt ctttgtgaga aaggtgggta tttgaaataa   4680
```

<210> SEQ ID NO 27
<211> LENGTH: 4953
<212> TYPE: DNA
<213> ORGANISM: Artificial Sequence
<220> FEATURE:
<223> OTHER INFORMATION: Synthetic: nucleic acid sequence

<400> SEQUENCE: 27

```
atgtcaggtt caaattcgaa ttcaaatcta gatgcaataa gtgattcatg cccattttgg     60

cgctatgatg atattacaga gtgtggaaga gtgcagtata tcaattacta ccttccaata    120

acattggtag gcgtttctct cttgtattta ttcaaaaacg cgatccaaca ttattacaga    180

aagcctcaag aaattaagcc tagtgttgct tccgaattat tgggctcaaa tctcacagac    240

cttccgaatg aaaacaagcc tttactatcg gagagtacac aagcattata cactaatccg    300

gattcgaata agacaggatt ctctctaaaa gaggagcatt tctctataaa taaagttaca    360

cttacggaaa ttcattccaa taagcatgac gctgtgaaga tcgtaaggag aaactggctt    420

gaaaaattaa gagtgttctt agaatgggtt ctatgcgcct tacaactttg catctacatt    480

tcagtctggt cgaaatacac taatacccaa gaggatttcc caatgcacgc atctatctca    540

ggtctaatgt tatggtctct actcttgtta gtagtgtcat tgaggttggc aaacatcaac    600

cagaatataa gctggatcaa ttcaggaccg ggaaacttat gggccctttc atttgcatgt    660

tatctatcac tattctgcgg atccgttttg ccattgagat ctatctatat cggtcatatc    720

acagatgaaa ttgcatcaac attttataag ttgcaatttt acctaagttt gacactattc    780

ttgttacttt tcacctctca agcgggaaat cggtttgcca ttatctataa aagtacacca    840

gatataacac cgtctcctga acctattgtg tcgattgcaa gttatatcac ttgggcatgg    900

gtagataaat ttctttggaa agcgcatcaa aattatatcg aaatgaaaga tgtttggggt    960

ctaatggtgg aagactattc cattctcgta ataaagagat tcaatcattt tgttcagaat   1020

aaaaccaagt ctaggacatt ttcatttaac ttaatccact tttcatgaa atttatcgcc    1080

attcaaggtg cctgggcaac aatttcgtca gttattagtt ttgttccaac aatgttgctc   1140
```

-continued

```
agacgtattt tggagtatgt tgaagatcaa tcaactgctc cattaaattt ggcttggatg   1200
tatatttttc ttatgttcct tgccagaatt ttaactgcca tatgtgctgc tcaggcgcta   1260
tttttaggga gaagggtttg tatcagaatg aaggctatca taatttctga aatctactcc   1320
aaggctttga gaagaaaaat ttctccaaat tccactaagg agccaactga tgtcgttgat   1380
ccacaggaat taaatgacaa acaacacgtt gatggagatg aagaatcagc aaccactgca   1440
aatcttggtg ctatcattaa tttgatggcg gtggatgctt tcaaagtatc cgaaatatgt   1500
gcgtatttgc actcctttat agaggcgatc atcatgacca ttgttgcatt attcctttta   1560
tatcggttaa taggctggtc tgctttagtt ggtagtgcaa tgattatttg cttcttacca   1620
ttgaacttca aacttgccag cttgttaggg acactccaaa agaaatcctt ggcaatcaca   1680
gataaaagaa ttcagaaact aaacgaagct ttccaggcca ttcgtattat caaattcttc   1740
tcttgggaag agaattttga aaaggacata caaaacacaa gggatgaaga attaaatatg   1800
cttttaaaaa ggtctatcgt ttgggctctt tcttctcttg tttggttcat taccccctct   1860
attgtcacat ccgcttcttt tgcagtctat atttatgtgc aaggccaaac tttaactact   1920
ccggtagcat ttactgcact atctctattt gctctactaa gaaatccgtt agacatgctt   1980
tctgatatgt tgtcttttgt tattcaatcc aaggtctctt tggatagagt ccaagaattt   2040
ttaaatgaag aggagacgaa aaagtatgag caattaaccg tatcaagaaa taaacttggg   2100
ttgcaaaacg ctacttttac atgggataaa aataatcaag atttcaagtt aaaaaaccta   2160
actattgatt tcaaaattgg gaaattaaac gttattgtag gtccaactgg atctggtaaa   2220
acatcattgt taatgggatt attgggtgaa atggagctat tgaacggaaa agttttcgtc   2280
ccttcgctca atcctaggga agagttggtt gtagaggccg atggaatgac taattcaatc   2340
gcgtactgct cccaagctgc ctggttgcta aatgatactg tcaggaacaa tattctattc   2400
aatgcgcctt ataatgagaa tagatataat gccgtcatct ctgcgtgtgg tttgaaacgc   2460
gacttcgaga tcttaagcgc tggtgatcag acagagattg gcgaaaaggg tataacactt   2520
tctggtggtc aaaaacaaag agtctcgttg gccagatcat tgtattcttc atcaagacat   2580
ttgctgttag atgattgttt gagtgccgta gactcgcaca cggccttatg gatctacgaa   2640
aattgtataa caggcccatt aatggaagga agaacatgtg tattggtttc tcacaatgtt   2700
gcattaactt taaaaaatgc agattgggtt atcattatgg aaaatggtag agtaaaagaa   2760
caaggcgaac cagtagaatt gctacagaag gggtcccttg gggatgactc catggtgaaa   2820
tcatcaattt tgtcccgtac ggcgtcctca gttaatattt cagaaactaa cagtaagatt   2880
tctagtggtc cgaaggctcc agcggaatcg gataatgcca atgaggagtc caccacctgt   2940
ggagatcgtt caaagtcaag cggcaagcta atcgctgaag aaacaaaatc aaacggtgtt   3000
gtttccctgg acgtctataa gtggtatgcc gtgtttttcg gtggatggaa gatgatatca   3060
tttttgtgtt tcattttctt gtttgcccaa atgatcagta tttcacaggc ctggtggttg   3120
cgtgcttggg cctccaacaa cactctaaaa gttttctcca accttggatt gcaaacaatg   3180
aggccattcg ctttgtcctt acaaggaaaa gaagcttctc ctgtgactct tagtgctgtt   3240
ttcccaaatg gcagtctaac aacagccacg gaaccaaatc actcgaacgc gtattatcta   3300
tcaatatatt tgggtattgg tgtattccag gctttatgtt catcttcgaa agcaattata   3360
aactttgtgg ccggtattag agcttccagg aaaatattca atttattgtt gaaaaatgtg   3420
ttatacgcca agctgagatt ttttgattct actccaatag gaagaataat gaacagattt   3480
```

-continued

```
tctaaagaca tcgaatcaat agatcaagaa ttgactcctt atatggaagg tgcatttggt   3540
tccttaatac aatgtgtttc cacaattatc gtcattgcat acattactcc ccaatttttg   3600
attgtcgcgg cgattgtcat gttattgttt tattttgttg cctactttta catgtcagga   3660
gcaagagaat taaagcgtct tgaatcgatg tcacgctctc ctattcatca gcacttctct   3720
gagactcttg tgggtatcac gactattcga gcattttctg acgagcggcg ttttctggtt   3780
gataatatga agaaaattga tgataataat aggccttttct tttacttatg ggtctgtaat   3840
agatggctat cttacagaat cgagctgata ggcgccctta ttgttttggc tgcaggtagt   3900
ttcatcttat tgaacataaa atcgatcgat tctggtttgg ccggtatttc attgggtttc   3960
gctatacaat ttaccgatgg tgccctttgg gttgttaggt tatattccaa cgttgaaatg   4020
aatatgaatt ccgtcgaaag gttaaaagag tacaccacca tcgagcaaga accttctaac   4080
gttggtgcct tggtacctcc ttgcgaatgg ccacaaaatg gtaaaatcga agtcaaggat   4140
ttatctttac gctatgcagc tggtctacca aaggttataa aaaatgtcac attcaccgtc   4200
gattcaaagt gtaaagtagg tattgttggc aggactggtg ctggtaaatc tactattatc   4260
acagcccttt tcagattctt agaccctgaa actggttata tcaaaatcga tgacgttgat   4320
ataacaacca ttggtttaaa acgtttgcgc caatctatca ctattattcc acaggaccca   4380
accctttttca ccggtacttt gaaaaccaat ctcgatccat acaacgaata ttcggaagct   4440
gaaattttcg aagctctaaa acgtgtcaac cttgtttcct cagaagaact tggtaatcct   4500
tctacttcgg attcaacctc ggtacattca gcaaatatga ataagttttt ggatttggaa   4560
aatgaagtca gtgaaggtgg ttccaacctc tcacaaggac aacgtcaatt gatatgtttg   4620
gcccgttcat tattgcggtg tccaaaggta attctacttg atgaagccac agcttcaatc   4680
gattataact cagactctaa aatccaggct actataaggg aagaattcag taatagtacc   4740
attctcacga ttgctcatcg tttacgatca attattgatt atgataaaat acttgttatg   4800
gatgctgggg aggttaaaga atatgatcat ccttactcct tattgttgaa tcgtgatagt   4860
atattctatc atatgtgtga agatagtgga gaattagaag tcttgataca attagccaaa   4920
gaatcatttg tcaaaaagct caatgcaaat tga                                4953
```

<210> SEQ ID NO 28
<211> LENGTH: 1381
<212> TYPE: PRT
<213> ORGANISM: Artificial Sequence
<220> FEATURE:
<223> OTHER INFORMATION: Synthetic: Fungal_5_muA

<400> SEQUENCE: 28

```
Met Thr Ser Pro Gly Ser Glu Lys Cys Thr Pro Arg Ser Asp Glu Asp
1               5                   10                  15

Leu Glu Arg Ser Glu Pro Gln Leu Gln Arg Arg Leu Leu Thr Pro Phe
            20                  25                  30

Leu Leu Ser Lys Lys Val Pro Pro Ile Pro Lys Glu Asp Glu Arg Lys
        35                  40                  45

Pro Tyr Pro Tyr Leu Lys Thr Asn Pro Leu Ser Gln Ile Leu Phe Trp
    50                  55                  60

Trp Leu Asn Pro Leu Leu Arg Val Gly Tyr Lys Arg Thr Leu Asp Pro
65                  70                  75                  80

Asn Asp Phe Tyr Tyr Leu Glu His Ser Gln Asp Ile Glu Thr Thr Tyr
                85                  90                  95

Ser Asn Tyr Glu Met His Leu Ala Arg Ile Leu Glu Lys Asp Arg Ala
```

-continued

```
            100                 105                 110

Lys Ala Arg Ala Lys Asp Pro Thr Leu Thr Asp Glu Asp Leu Lys Asn
        115                 120                 125

Arg Glu Tyr Pro Lys Asn Ala Val Ile Lys Ala Leu Phe Leu Thr Phe
    130                 135                 140

Lys Trp Lys Tyr Leu Trp Ser Ile Phe Leu Lys Leu Leu Ser Asp Ile
145                 150                 155                 160

Val Leu Val Leu Asn Pro Leu Leu Ser Lys Ala Leu Ile Asn Phe Val
                165                 170                 175

Asp Glu Lys Met Tyr Asn Pro Asp Met Ser Val Gly Arg Gly Val Gly
            180                 185                 190

Tyr Ala Ile Gly Val Thr Phe Met Leu Gly Thr Ser Gly Ile Leu Ile
        195                 200                 205

Asn His Phe Leu Tyr Leu Ser Leu Thr Val Gly Ala His Cys Lys Ala
    210                 215                 220

Val Leu Thr Thr Ala Ile Met Asn Lys Ser Phe Arg Ala Ser Ala Lys
225                 230                 235                 240

Ser Lys His Glu Tyr Pro Ser Gly Arg Val Thr Ser Leu Met Ser Thr
                245                 250                 255

Asp Leu Ala Arg Ile Asp Leu Ala Ile Gly Phe Gln Pro Phe Ala Ile
            260                 265                 270

Thr Val Pro Val Pro Ile Gly Val Ala Ile Ala Leu Leu Ile Val Asn
        275                 280                 285

Ile Gly Val Ser Ala Leu Ala Gly Ile Ala Val Phe Leu Val Cys Ile
    290                 295                 300

Val Val Ile Ser Ala Ser Ser Lys Ser Leu Leu Lys Met Arg Lys Gly
305                 310                 315                 320

Ala Asn Gln Tyr Thr Asp Ala Arg Ile Ser Tyr Met Arg Glu Ile Leu
                325                 330                 335

Gln Asn Met Arg Ile Ile Lys Phe Tyr Ser Trp Glu Asp Ala Tyr Glu
            340                 345                 350

Lys Ser Val Val Thr Glu Arg Asn Ser Glu Met Ser Ile Ile Leu Lys
        355                 360                 365

Met Gln Ser Ile Arg Asn Phe Leu Leu Ala Leu Ser Leu Ser Leu Pro
    370                 375                 380

Ala Ile Ile Ser Met Val Ala Phe Leu Val Leu Tyr Gly Val Ser Asn
385                 390                 395                 400

Asp Lys Asn Pro Gly Asn Ile Phe Ser Ser Ile Ser Leu Phe Ser Val
                405                 410                 415

Leu Ala Gln Gln Thr Met Met Leu Pro Met Ala Leu Ala Thr Gly Ala
            420                 425                 430

Asp Ala Lys Ile Gly Leu Glu Arg Leu Arg Gln Tyr Leu Gln Ser Gly
        435                 440                 445

Asp Ile Glu Lys Glu Tyr Glu Asp His Glu Lys Pro Gly Asp Arg Asp
    450                 455                 460

Val Val Leu Pro Asp Asn Val Ala Val Glu Leu Asn Asn Ala Ser Phe
465                 470                 475                 480

Ile Trp Glu Lys Phe Asp Asp Ala Asp Asp Asn Asp Gly Asn Ser Glu
                485                 490                 495

Lys Thr Lys Glu Val Val Val Thr Ser Lys Ser Ser Leu Thr Asp Ser
            500                 505                 510

Ser His Ile Asp Lys Ser Thr Asp Ser Ala Asp Gly Glu Tyr Ile Lys
        515                 520                 525
```

-continued

Ser Val Phe Glu Gly Phe Asn Asn Ile Asn Leu Thr Ile Lys Lys Gly
    530                 535                 540

Glu Phe Val Ile Ile Thr Gly Pro Ile Gly Ser Gly Lys Ser Ser Leu
545                 550                 555                 560

Leu Val Ala Leu Ala Gly Phe Met Lys Lys Thr Ser Gly Thr Leu Gly
                565                 570                 575

Val Asn Gly Thr Met Leu Leu Cys Gly Gln Pro Trp Val Gln Asn Cys
            580                 585                 590

Thr Val Arg Asp Asn Ile Leu Phe Gly Leu Glu Tyr Asp Glu Ala Arg
        595                 600                 605

Tyr Asp Arg Val Val Glu Val Cys Ala Leu Gly Asp Asp Leu Lys Met
    610                 615                 620

Phe Thr Ala Gly Asp Gln Thr Glu Ile Gly Glu Arg Gly Ile Thr Leu
625                 630                 635                 640

Ser Gly Gly Gln Lys Ala Arg Ile Asn Leu Ala Arg Ala Val Tyr Ala
                645                 650                 655

Asn Lys Asp Ile Ile Leu Leu Asp Asp Ala Leu Ser Ala Val Asp Ala
            660                 665                 670

Arg Val Gly Lys Leu Ile Val Asp Asp Cys Leu Thr Ser Phe Leu Gly
        675                 680                 685

Asp Lys Thr Arg Ile Leu Ala Thr His Gln Leu Ser Leu Ile Glu Ala
    690                 695                 700

Ala Asp Arg Val Ile Tyr Leu Asn Gly Asp Gly Thr Ile His Ile Gly
705                 710                 715                 720

Thr Val Gln Glu Leu Leu Glu Ser Asn Glu Gly Phe Leu Lys Leu Met
                725                 730                 735

Glu Phe Ser Arg Lys Ser Glu Ser Glu Asp Glu Glu Asp Val Glu Ala
            740                 745                 750

Ala Asn Glu Lys Asp Val Ser Leu Gln Lys Ala Val Ser Val Val Gln
        755                 760                 765

Glu Gln Asp Ala His Ala Gly Val Leu Ile Gly Gln Glu Glu Arg Ala
    770                 775                 780

Val Asn Gly Ile Glu Trp Asp Ile Tyr Lys Glu Tyr Leu His Glu Gly
785                 790                 795                 800

Arg Gly Lys Leu Gly Ile Phe Ala Ile Pro Thr Ile Ile Met Leu Leu
                805                 810                 815

Val Leu Asp Val Phe Thr Ser Ile Phe Val Asn Val Trp Leu Ser Phe
            820                 825                 830

Trp Ile Ser His Lys Phe Lys Ala Arg Ser Asp Gly Phe Tyr Ile Gly
        835                 840                 845

Leu Tyr Val Met Phe Val Ile Leu Ser Val Ile Trp Ile Thr Ala Glu
    850                 855                 860

Phe Val Val Met Gly Asn Phe Ser Ser Thr Ala Ala Arg Arg Leu Asn
865                 870                 875                 880

Leu Lys Ala Met Lys Arg Val Leu His Thr Pro Met His Phe Leu Asp
                885                 890                 895

Val Thr Pro Met Gly Arg Ile Leu Asn Arg Phe Thr Lys Asp Thr Asp
            900                 905                 910

Val Leu Asp Asn Glu Ile Gly Glu Gln Ala Arg Met Phe Leu His Pro
        915                 920                 925

Ala Ala Tyr Val Ile Gly Val Leu Ile Leu Cys Ile Ile Asn Ile Pro
    930                 935                 940

-continued

Trp Phe Ala Ile Ala Ile Pro Pro Leu Ala Ile Pro Phe Thr Phe Ile
945 950 955 960

Thr Asn Phe Tyr Ile Ala Ser Ser Arg Glu Val Lys Arg Ile Glu Ala
965 970 975

Ile Gln Arg Ser Leu Val Tyr Asn Asn Phe Asn Glu Val Leu Asn Gly
980 985 990

Leu Gln Thr Leu Lys Ala Tyr Asn Ala Thr Ser Arg Phe Met Glu Lys
995 1000 1005

Asn Lys Arg Leu Leu Asn Arg Met Asn Glu Ala Tyr Leu Leu Val
1010 1015 1020

Ile Ala Asn Gln Arg Trp Ile Ser Val Asn Leu Asp Leu Val Ser
1025 1030 1035

Cys Cys Phe Val Phe Leu Ile Ser Met Leu Ser Val Phe Arg Val
1040 1045 1050

Phe Asp Ile Asn Ala Ser Ser Val Gly Leu Val Val Thr Ser Val
1055 1060 1065

Leu Gln Ile Gly Gly Leu Met Ser Leu Ile Met Arg Ala Tyr Thr
1070 1075 1080

Thr Val Glu Asn Glu Met Asn Ser Val Glu Arg Leu Cys His Tyr
1085 1090 1095

Ala Asn Lys Leu Glu Gln Glu Ala Pro Tyr Ile Met Asn Glu Thr
1100 1105 1110

Lys Pro Arg Pro Thr Trp Pro Glu His Gly Ala Ile Glu Phe Lys
1115 1120 1125

His Ala Ser Met Arg Tyr Arg Glu Gly Leu Pro Leu Val Leu Lys
1130 1135 1140

Asp Leu Thr Ile Ser Val Lys Gly Gly Glu Lys Ile Gly Ile Cys
1145 1150 1155

Gly Arg Thr Gly Ala Gly Lys Ser Thr Ile Met Asn Ala Leu Tyr
1160 1165 1170

Arg Leu Thr Glu Leu Ala Glu Gly Ser Ile Thr Ile Asp Gly Val
1175 1180 1185

Glu Ile Ser Gln Leu Gly Leu Tyr Asp Leu Arg Ser Lys Leu Ala
1190 1195 1200

Ile Ile Pro Gln Asp Pro Val Leu Phe Arg Gly Thr Ile Arg Lys
1205 1210 1215

Asn Leu Asp Pro Phe Gly Gln Asn Asp Asp Glu Thr Leu Trp Asp
1220 1225 1230

Ala Leu Arg Arg Ser Gly Leu Val Glu Gly Ser Ile Leu Asn Thr
1235 1240 1245

Ile Lys Ser Gln Ser Lys Asp Asp Pro Asn Phe His Lys Phe His
1250 1255 1260

Leu Asp Gln Thr Val Glu Asp Glu Gly Ala Asn Phe Ser Leu Gly
1265 1270 1275

Glu Arg Gln Leu Ile Ala Leu Ala Arg Ala Leu Val Arg Asn Ser
1280 1285 1290

Lys Ile Leu Ile Leu Asp Glu Ala Thr Ser Ser Val Asp Tyr Glu
1295 1300 1305

Thr Asp Ser Lys Ile Gln Lys Thr Ile Ser Thr Val Phe Ser His
1310 1315 1320

Cys Thr Ile Leu Cys Ile Ala His Arg Leu Lys Thr Ile Leu Thr
1325 1330 1335

Tyr Asp Arg Ile Leu Val Leu Glu Lys Gly Glu Val Glu Glu Phe 1340 1345 1350

Asp Thr Pro Arg Val Leu Tyr Ser Lys Asn Gly Val Phe Arg Gln
1355 1360 1365

Met Cys Glu Arg Ser Glu Ile Thr Ser Ala Asp Phe Val
1370 1375 1380

<210> SEQ ID NO 29
<211> LENGTH: 1381
<212> TYPE: PRT
<213> ORGANISM: Artificial Sequence
<220> FEATURE:
<223> OTHER INFORMATION: Synthetic: Fungal_5_muA2

<400> SEQUENCE: 29

Met Thr Ser Pro Gly Ser Glu Lys Cys Thr Pro Arg Ser Asp Glu Asp
1 5 10 15

Leu Glu Arg Ser Glu Pro Gln Leu Gln Arg Arg Leu Leu Thr Pro Phe
20 25 30

Leu Leu Ser Lys Lys Val Pro Pro Ile Pro Lys Glu Asp Glu Arg Lys
35 40 45

Pro Tyr Pro Tyr Leu Lys Thr Asn Pro Leu Ser Gln Ile Leu Phe Trp
50 55 60

Trp Leu Asn Pro Leu Leu Arg Val Gly Tyr Lys Arg Thr Leu Asp Pro
65 70 75 80

Asn Asp Phe Tyr Tyr Leu Glu His Ser Gln Asp Ile Glu Thr Thr Tyr
85 90 95

Ser Asn Tyr Glu Met His Leu Ala Arg Ile Leu Glu Lys Asp Arg Ala
100 105 110

Lys Ala Arg Ala Lys Asp Pro Thr Leu Thr Asp Glu Asp Leu Lys Asn
115 120 125

Arg Glu Tyr Pro Lys Asn Ala Val Ile Lys Ala Leu Phe Leu Thr Phe
130 135 140

Lys Trp Lys Tyr Leu Trp Ser Ile Phe Leu Lys Leu Leu Ser Asp Ile
145 150 155 160

Val Leu Val Leu Asn Pro Leu Leu Ser Lys Ala Leu Ile Asn Phe Val
165 170 175

Asp Glu Lys Met Tyr Asn Pro Asp Met Ser Val Gly Arg Gly Val Gly
180 185 190

Tyr Ala Ile Gly Val Thr Phe Met Leu Gly Thr Ser Gly Ile Leu Ile
195 200 205

Asn His Phe Leu Tyr Leu Ser Leu Thr Val Gly Ala His Cys Lys Ala
210 215 220

Val Leu Thr Thr Ala Ile Met Asn Lys Ser Phe Arg Ala Ser Ala Lys
225 230 235 240

Ser Lys His Glu Tyr Pro Ser Gly Arg Val Thr Ser Leu Met Ser Thr
245 250 255

Asp Leu Ala Arg Ile Asp Leu Ala Ile Gly Phe Gln Pro Phe Ala Ile
260 265 270

Thr Val Pro Val Pro Ile Gly Val Ala Ile Ala Leu Leu Ile Val Asn
275 280 285

Ile Gly Val Ser Ala Leu Ala Gly Ile Ala Val Phe Leu Val Cys Ile
290 295 300

Val Val Ile Ser Ala Ser Ser Lys Ser Leu Leu Lys Met Arg Lys Gly
305 310 315 320

Ala Asn Gln Tyr Thr Asp Ala Arg Ile Ser Tyr Met Arg Glu Ile Leu

-continued

```
                325                 330                 335

Gln Asn Met Arg Ile Ile Lys Phe Tyr Ser Trp Glu Asp Ala Tyr Glu
            340                 345                 350

Lys Ser Val Val Thr Glu Arg Asn Ser Glu Met Ser Ile Ile Leu Lys
        355                 360                 365

Met Gln Ser Ile Arg Asn Phe Leu Leu Ala Leu Ser Leu Ser Leu Pro
    370                 375                 380

Ala Ile Ile Ser Met Val Ala Phe Leu Val Leu Tyr Gly Val Ser Asn
385                 390                 395                 400

Asp Lys Asn Pro Gly Asn Ile Phe Ser Ser Ile Ser Leu Phe Ser Val
                405                 410                 415

Leu Ala Gln Gln Thr Met Met Leu Pro Met Ala Leu Ala Thr Gly Ala
            420                 425                 430

Asp Ala Lys Ile Gly Leu Glu Arg Leu Arg Gln Tyr Leu Gln Ser Gly
        435                 440                 445

Asp Ile Glu Lys Glu Tyr Glu Asp His Glu Lys Pro Gly Asp Arg Asp
    450                 455                 460

Val Val Leu Pro Asp Asn Val Ala Val Glu Leu Asn Asn Ala Ser Phe
465                 470                 475                 480

Ile Trp Glu Lys Phe Asp Asp Ala Asp Asp Asn Asp Gly Asn Ser Glu
                485                 490                 495

Lys Thr Lys Glu Val Val Val Thr Ser Lys Ser Ser Leu Thr Asp Ser
            500                 505                 510

Ser His Ile Asp Lys Ser Thr Asp Ser Ala Asp Gly Glu Tyr Ile Lys
        515                 520                 525

Ser Val Phe Glu Gly Phe Asn Asn Ile Asn Leu Thr Ile Lys Lys Gly
    530                 535                 540

Glu Phe Val Ile Ile Thr Gly Pro Ile Gly Ser Gly Lys Ser Ser Leu
545                 550                 555                 560

Leu Val Ala Leu Ala Gly Phe Met Lys Lys Thr Ser Gly Thr Leu Gly
                565                 570                 575

Val Asn Gly Thr Met Leu Leu Cys Gly Gln Pro Trp Val Gln Asn Cys
            580                 585                 590

Thr Val Arg Asp Asn Ile Leu Phe Gly Leu Glu Tyr Asp Glu Ala Arg
        595                 600                 605

Tyr Asp Arg Val Val Glu Val Cys Ala Leu Gly Asp Asp Leu Lys Met
    610                 615                 620

Phe Thr Ala Gly Asp Gln Thr Glu Ile Gly Glu Arg Gly Ile Thr Leu
625                 630                 635                 640

Ser Gly Gly Gln Lys Ala Arg Ile Asn Leu Ala Arg Ala Val Tyr Ala
                645                 650                 655

Asn Lys Asp Ile Ile Leu Leu Asp Asp Ala Leu Ser Ala Val Asp Ala
            660                 665                 670

Arg Val Gly Lys Leu Ile Val Asp Asp Cys Leu Thr Ser Phe Leu Gly
        675                 680                 685

Asp Lys Thr Arg Ile Leu Ala Thr His Gln Leu Ser Leu Ile Glu Ala
    690                 695                 700

Ala Asp Arg Val Ile Tyr Leu Asn Gly Asp Gly Thr Ile His Ile Gly
705                 710                 715                 720

Thr Val Gln Glu Leu Leu Glu Ser Asn Glu Gly Phe Leu Lys Leu Met
                725                 730                 735

Glu Phe Ser Arg Lys Ser Glu Ser Glu Asp Glu Glu Asp Val Glu Ala
            740                 745                 750
```

-continued

```
Ala Asn Glu Lys Asp Val Ser Leu Gln Lys Ala Val Ser Val Val Gln
      755                 760                 765

Glu Gln Asp Ala His Ala Gly Val Leu Ile Gly Gln Glu Glu Arg Ala
    770                 775                 780

Val Asn Gly Ile Glu Trp Asp Ile Tyr Lys Glu Tyr Leu His Glu Gly
785                 790                 795                 800

Arg Gly Lys Leu Gly Ile Phe Ala Ile Pro Thr Ile Ile Met Leu Leu
                805                 810                 815

Val Leu Asp Val Phe Thr Ser Ile Phe Val Asn Val Trp Leu Ser Phe
            820                 825                 830

Trp Ile Ser His Lys Phe Lys Ala Arg Ser Asp Gly Phe Tyr Ile Gly
      835                 840                 845

Leu Tyr Val Met Phe Val Ile Leu Ser Val Ile Trp Ile Thr Ala Glu
    850                 855                 860

Phe Val Val Met Gly Asn Phe Ser Ser Thr Ala Ala Arg Arg Leu Asn
865                 870                 875                 880

Leu Lys Ala Met Lys Arg Val Leu His Thr Pro Met His Phe Leu Asp
                885                 890                 895

Val Thr Pro Met Gly Arg Ile Leu Asn Arg Phe Thr Lys Asp Thr Asp
            900                 905                 910

Val Leu Asp Asn Glu Ile Gly Glu Gln Ala Arg Met Phe Leu His Pro
      915                 920                 925

Ala Ala Tyr Val Ile Gly Val Leu Ile Leu Cys Ile Ile Asn Ile Pro
    930                 935                 940

Trp Phe Ala Ile Ala Ile Pro Pro Leu Ala Ile Pro Phe Thr Phe Ile
945                 950                 955                 960

Thr Asn Phe Tyr Ile Ala Ser Ser Arg Glu Val Lys Arg Ile Glu Ala
                965                 970                 975

Ile Gln Arg Ser Leu Val Tyr Asn Asn Phe Asn Glu Val Leu Asn Gly
            980                 985                 990

Leu Gln Thr Leu Lys Ala Tyr Asn  Ala Thr Ser Arg Phe  Met Glu Lys
      995                 1000                1005

Asn Lys  Arg Leu Leu Asn Arg  Met Asn Glu Ala Tyr  Leu Leu Val
    1010                 1015                 1020

Ile Ala  Asn Gln Arg Trp Ile  Ser Val Asn Leu Asp  Leu Val Ser
    1025                 1030                 1035

Cys Cys  Phe Val Phe Leu Ile  Ser Met Leu Ser Val  Phe Arg Val
    1040                 1045                 1050

Phe Asp  Ile Asn Ala Ser Ser  Val Gly Leu Val Val  Thr Ser Val
    1055                 1060                 1065

Leu Gln  Ile Gly Gly Leu Met  Ser Leu Ile Met Arg  Ala Tyr Thr
    1070                 1075                 1080

Thr Val  Glu Asn Glu Met Asn  Ser Val Glu Arg Leu  Cys His Tyr
    1085                 1090                 1095

Ala Asn  Lys Leu Glu Gln Glu  Ala Pro Tyr Ile Met  Asn Glu Thr
    1100                 1105                 1110

Lys Pro  Arg Pro Thr Trp Pro  Glu His Gly Ala Ile  Glu Phe Lys
    1115                 1120                 1125

His Ala  Ser Met Arg Tyr Arg  Glu Gly Leu Pro Leu  Val Leu Lys
    1130                 1135                 1140

Asp Leu  Thr Ile Ser Val Lys  Gly Gly Glu Lys Ile  Gly Ile Cys
    1145                 1150                 1155
```

Gly Arg Thr Gly Ala Gly Lys Ser Thr Ile Met Asn Ala Leu Tyr
1160 1165 1170

Arg Leu Thr Glu Leu Ala Glu Gly Ser Ile Thr Ile Asp Gly Val
1175 1180 1185

Glu Ile Ser Gln Leu Gly Leu Tyr Asp Leu Arg Ser Lys Leu Ala
1190 1195 1200

Ile Ile Pro Gln Asp Pro Val Leu Phe Arg Gly Thr Ile Arg Lys
1205 1210 1215

Asn Leu Asp Pro Phe Gly Gln Asn Asp Asp Glu Thr Leu Trp Asp
1220 1225 1230

Ala Leu Arg Arg Ser Gly Leu Val Glu Gly Ser Ile Leu Asn Thr
1235 1240 1245

Ile Lys Ser Gln Ser Lys Asp Asp Pro Asn Phe His Lys Phe His
1250 1255 1260

Leu Asp Gln Thr Val Glu Asp Glu Gly Ala Asn Phe Ser Leu Gly
1265 1270 1275

Glu Arg Gln Leu Ile Ala Leu Ala Arg Ala Leu Val Arg Asn Ser
1280 1285 1290

Lys Ile Leu Ile Leu Asp Glu Ala Thr Ser Ser Val Asp Tyr Glu
1295 1300 1305

Thr Asp Ser Lys Ile Gln Lys Thr Ile Ser Thr Glu Phe Ser His
1310 1315 1320

Cys Thr Ile Leu Cys Ile Ala His Arg Leu Lys Thr Ile Leu Thr
1325 1330 1335

Tyr Asp Arg Ile Leu Val Leu Glu Lys Gly Glu Val Glu Glu Phe
1340 1345 1350

Asp Thr Pro Arg Val Leu Tyr Ser Lys Asn Gly Val Phe Arg Gln
1355 1360 1365

Met Cys Glu Arg Ser Glu Ile Thr Ser Ala Asp Phe Val
1370 1375 1380

<210> SEQ ID NO 30
<211> LENGTH: 1381
<212> TYPE: PRT
<213> ORGANISM: Artificial Sequence
<220> FEATURE:
<223> OTHER INFORMATION: Synthetic: Fungal_5_muA3

<400> SEQUENCE: 30

Met Thr Ser Pro Gly Ser Glu Lys Cys Thr Pro Arg Ser Asp Glu Asp
1 5 10 15

Leu Glu Arg Ser Glu Pro Gln Leu Gln Arg Arg Leu Leu Thr Pro Phe
20 25 30

Leu Leu Ser Lys Lys Val Pro Pro Ile Pro Lys Glu Asp Glu Arg Lys
35 40 45

Pro Tyr Pro Tyr Leu Lys Thr Asn Pro Leu Ser Gln Ile Leu Phe Trp
50 55 60

Trp Leu Asn Pro Leu Leu Arg Val Gly Tyr Lys Arg Thr Leu Asp Pro
65 70 75 80

Asn Asp Phe Tyr Tyr Leu Glu His Ser Gln Asp Ile Glu Thr Thr Tyr
85 90 95

Ser Asn Tyr Glu Met His Leu Ala Arg Ile Leu Glu Lys Asp Arg Ala
100 105 110

Lys Ala Arg Ala Lys Asp Pro Thr Leu Thr Asp Glu Asp Leu Lys Asn
115 120 125

-continued

```
Arg Glu Tyr Pro Lys Asn Ala Val Ile Lys Ala Leu Phe Leu Thr Phe
    130                 135                 140

Lys Trp Lys Tyr Leu Trp Ser Ile Phe Leu Lys Leu Leu Ser Asp Ile
145                 150                 155                 160

Val Leu Val Leu Asn Pro Leu Leu Ser Lys Ala Leu Ile Asn Phe Val
                165                 170                 175

Asp Glu Lys Met Tyr Asn Pro Asp Met Ser Val Gly Arg Gly Val Gly
            180                 185                 190

Tyr Ala Ile Gly Val Thr Phe Met Leu Gly Thr Ser Gly Ile Leu Ile
        195                 200                 205

Asn His Phe Leu Tyr Leu Ser Leu Thr Val Gly Ala His Cys Lys Ala
    210                 215                 220

Val Leu Thr Thr Ala Ile Met Asn Lys Ser Phe Arg Ala Ser Ala Lys
225                 230                 235                 240

Ser Lys His Glu Tyr Pro Ser Gly Arg Val Thr Ser Leu Met Ser Thr
                245                 250                 255

Asp Leu Ala Arg Ile Asp Leu Ala Ile Gly Phe Gln Pro Phe Ala Ile
            260                 265                 270

Thr Val Pro Val Pro Ile Gly Val Ala Ile Ala Leu Leu Ile Val Asn
        275                 280                 285

Ile Gly Val Ser Ala Leu Ala Gly Ile Ala Val Phe Leu Val Cys Ile
    290                 295                 300

Val Val Ile Ser Ala Ser Ser Lys Ser Leu Leu Lys Met Arg Lys Gly
305                 310                 315                 320

Ala Asn Gln Tyr Thr Asp Ala Arg Ile Ser Tyr Met Arg Glu Ile Leu
                325                 330                 335

Gln Asn Met Arg Ile Ile Lys Phe Tyr Ser Trp Glu Asp Ala Tyr Glu
            340                 345                 350

Lys Ser Val Val Thr Glu Arg Asn Ser Glu Met Ser Ile Ile Leu Lys
        355                 360                 365

Met Gln Ser Ile Arg Asn Phe Leu Leu Ala Leu Ser Leu Ser Leu Pro
    370                 375                 380

Ala Ile Ile Ser Met Val Ala Phe Leu Val Leu Tyr Gly Val Ser Asn
385                 390                 395                 400

Asp Lys Asn Pro Gly Asn Ile Phe Ser Ser Ile Ser Leu Phe Ser Val
                405                 410                 415

Leu Ala Gln Gln Thr Met Met Leu Pro Met Ala Leu Ala Thr Gly Ala
            420                 425                 430

Asp Ala Lys Ile Gly Leu Glu Arg Leu Arg Gln Tyr Leu Gln Ser Gly
        435                 440                 445

Asp Ile Glu Lys Glu Tyr Glu Asp His Glu Lys Pro Gly Asp Arg Asp
    450                 455                 460

Val Val Leu Pro Asp Asn Val Ala Val Glu Leu Asn Asn Ala Ser Phe
465                 470                 475                 480

Ile Trp Glu Lys Phe Asp Asp Ala Asp Asp Asn Asp Gly Asn Ser Glu
                485                 490                 495

Lys Thr Lys Glu Val Val Val Thr Ser Lys Ser Ser Leu Thr Asp Ser
            500                 505                 510

Ser His Ile Asp Lys Ser Thr Asp Ser Ala Asp Gly Glu Tyr Ile Lys
        515                 520                 525

Ser Val Phe Glu Gly Phe Asn Asn Ile Asn Leu Thr Ile Lys Lys Gly
    530                 535                 540

Glu Phe Val Ile Ile Thr Gly Pro Ile Gly Ser Gly Lys Ser Ser Leu
```

-continued

```
545                 550                 555                 560

Leu Val Ala Leu Ala Gly Phe Met Lys Lys Thr Ser Gly Thr Leu Gly
                565                 570                 575

Val Asn Gly Thr Met Leu Leu Cys Gly Gln Pro Trp Val Gln Asn Cys
            580                 585                 590

Thr Val Arg Asp Asn Ile Leu Phe Gly Leu Glu Tyr Asp Glu Ala Arg
        595                 600                 605

Tyr Asp Arg Val Val Glu Val Cys Ala Leu Gly Asp Asp Leu Lys Met
    610                 615                 620

Phe Thr Ala Gly Asp Gln Thr Glu Ile Gly Glu Arg Gly Ile Thr Leu
625                 630                 635                 640

Ser Gly Gly Gln Lys Ala Arg Ile Asn Leu Ala Arg Ala Val Tyr Ala
                645                 650                 655

Asn Lys Asp Ile Ile Leu Leu Asp Asp Ala Leu Ser Ala Val Asp Ala
            660                 665                 670

Arg Val Gly Lys Leu Ile Val Asp Asp Cys Leu Thr Ser Phe Leu Gly
        675                 680                 685

Asp Lys Thr Arg Ile Leu Ala Thr His Gln Leu Ser Leu Ile Glu Ala
    690                 695                 700

Ala Asp Arg Val Ile Tyr Leu Asn Gly Asp Gly Thr Ile His Ile Gly
705                 710                 715                 720

Thr Val Gln Glu Leu Leu Glu Ser Asn Glu Gly Phe Leu Lys Leu Met
                725                 730                 735

Glu Phe Ser Arg Lys Ser Glu Ser Glu Asp Glu Glu Asp Val Glu Ala
            740                 745                 750

Ala Asn Glu Lys Asp Val Ser Leu Gln Lys Ala Val Ser Val Val Gln
        755                 760                 765

Glu Gln Asp Ala His Ala Gly Val Leu Ile Gly Gln Glu Glu Arg Ala
    770                 775                 780

Val Asn Gly Ile Glu Trp Asp Ile Tyr Lys Glu Tyr Leu His Glu Gly
785                 790                 795                 800

Arg Gly Lys Leu Gly Ile Phe Ala Ile Pro Thr Ile Ile Met Leu Leu
                805                 810                 815

Val Leu Asp Val Phe Thr Ser Ile Phe Val Asn Val Trp Leu Ser Phe
            820                 825                 830

Trp Ile Ser His Lys Phe Lys Ala Arg Ser Asp Gly Phe Tyr Ile Gly
        835                 840                 845

Leu Tyr Val Met Phe Val Ile Leu Ser Val Ile Trp Ile Thr Ala Glu
    850                 855                 860

Phe Val Val Met Gly Asn Phe Ser Ser Thr Ala Ala Arg Arg Leu Asn
865                 870                 875                 880

Leu Lys Ala Met Lys Arg Val Leu His Thr Pro Met His Phe Leu Asp
                885                 890                 895

Val Thr Pro Met Gly Arg Ile Leu Asn Arg Phe Thr Lys Asp Thr Asp
            900                 905                 910

Val Leu Asp Asn Glu Ile Gly Glu Gln Ala Arg Met Phe Leu His Pro
        915                 920                 925

Ala Ala Tyr Val Ile Gly Val Leu Ile Leu Cys Ile Ile Asn Ile Pro
    930                 935                 940

Trp Phe Ala Ile Ala Ile Pro Pro Leu Ala Ile Leu Phe Thr Phe Ile
945                 950                 955                 960

Thr Asn Phe Tyr Ile Ala Ser Ser Arg Glu Val Lys Arg Ile Glu Ala
                965                 970                 975
```

-continued

```
Ile Gln Arg Ser Leu Val Tyr Asn Asn Phe Asn Glu Val Leu Asn Gly
            980                 985                 990

Leu Gln Thr Leu Lys Ala Tyr Asn  Ala Thr Ser Arg Phe  Met Glu Lys
        995                 1000                1005

Asn Lys  Arg Leu Leu Asn Arg  Met Asn Glu Ala Tyr  Leu Leu Val
    1010                 1015                 1020

Ile Ala  Asn Gln Arg Trp Ile  Ser Val Asn Leu Asp  Leu Val Ser
    1025                 1030                 1035

Cys Cys  Phe Val Phe Leu Ile  Ser Met Leu Ser Val  Phe Arg Val
    1040                 1045                 1050

Phe Asp  Ile Asn Ala Ser Ser  Val Gly Leu Val Val  Thr Ser Val
    1055                 1060                 1065

Leu Gln  Ile Gly Gly Leu Met  Ser Leu Ile Met Arg  Ala Tyr Thr
    1070                 1075                 1080

Thr Val  Glu Asn Glu Met Asn  Ser Val Glu Arg Leu  Cys His Tyr
    1085                 1090                 1095

Ala Asn  Lys Leu Glu Gln Glu  Ala Pro Tyr Ile Met  Asn Glu Thr
    1100                 1105                 1110

Lys Pro  Arg Pro Thr Trp Pro  Glu His Gly Ala Ile  Glu Phe Lys
    1115                 1120                 1125

His Ala  Ser Met Arg Tyr Arg  Glu Gly Leu Pro Leu  Val Leu Lys
    1130                 1135                 1140

Asp Leu  Thr Ile Ser Val Lys  Gly Gly Glu Lys Ile  Gly Ile Cys
    1145                 1150                 1155

Gly Arg  Thr Gly Ala Gly Lys  Ser Thr Ile Met Asn  Ala Leu Tyr
    1160                 1165                 1170

Arg Leu  Thr Glu Leu Ala Glu  Gly Ser Ile Thr Ile  Asp Gly Val
    1175                 1180                 1185

Glu Ile  Ser Gln Leu Gly Leu  Tyr Asp Leu Arg Ser  Lys Leu Ala
    1190                 1195                 1200

Ile Ile  Pro Gln Asp Pro Val  Leu Phe Arg Gly Thr  Ile Arg Lys
    1205                 1210                 1215

Asn Leu  Asp Pro Phe Gly Gln  Asn Asp Asp Glu Thr  Leu Trp Asp
    1220                 1225                 1230

Ala Leu  Arg Arg Ser Gly Leu  Val Glu Gly Ser Ile  Leu Asn Thr
    1235                 1240                 1245

Ile Lys  Ser Gln Ser Lys Asp  Asp Pro Asn Phe His  Lys Phe His
    1250                 1255                 1260

Leu Asp  Gln Thr Val Glu Asp  Glu Gly Ala Asn Phe  Ser Leu Gly
    1265                 1270                 1275

Glu Arg  Gln Leu Ile Ala Leu  Ala Arg Ala Leu Val  Arg Asn Ser
    1280                 1285                 1290

Lys Ile  Leu Ile Leu Asp Glu  Ala Thr Ser Ser Val  Asp Tyr Glu
    1295                 1300                 1305

Thr Asp  Ser Lys Ile Gln Lys  Thr Ile Ser Thr Glu  Phe Ser His
    1310                 1315                 1320

Cys Thr  Ile Leu Cys Ile Ala  His Arg Leu Lys Thr  Ile Leu Thr
    1325                 1330                 1335

Tyr Asp  Arg Ile Leu Val Leu  Glu Lys Gly Glu Val  Glu Glu Phe
    1340                 1345                 1350
```

-continued

```
Asp Thr  Pro Arg Val Leu Tyr  Ser Lys Asn Gly Val  Phe Arg Gln
    1355                 1360                 1365

Met Cys  Glu Arg Ser Glu Ile  Thr Ser Ala Asp Phe  Val
    1370                 1375                 1380
```